US012616372B2

(12) United States Patent
Dacosta et al.

(10) Patent No.: US 12,616,372 B2
(45) Date of Patent: May 5, 2026

(54) DEVICES, METHODS, AND SYSTEMS FOR FLUORESCENCE-BASED IMAGING AND DETECTION OF LOCATION(S) AND/OR SOURCE(S) OF POTENTIAL CONTAMINATION AND/OR POLLUTION

(71) Applicant: UNIVERSITY HEALTH NETWORK, Toronto (CA)

(72) Inventors: Ralph S. Dacosta, Toronto (CA); Brian C. Wilson, Toronto (CA); Kai Zhang, Scarborough (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 896 days.

(21) Appl. No.: 17/408,027

(22) Filed: Aug. 20, 2021

(65) Prior Publication Data

US 2021/0378518 A1 Dec. 9, 2021

Related U.S. Application Data

(63) Continuation of application No. 14/719,493, filed on May 22, 2015, now Pat. No. 11,375,898, which is a
(Continued)

(51) Int. Cl.
*A61B 5/00* (2006.01)
*A61B 5/01* (2006.01)
(Continued)

(52) U.S. Cl.
CPC .......... *A61B 5/0071* (2013.01); *A61B 5/0059* (2013.01); *A61B 5/01* (2013.01);
(Continued)

(58) Field of Classification Search
CPC ....... A61B 5/0071; A61B 5/0059; A61B 5/01; A61B 5/445; A61B 5/0042; A61B 5/4519;
(Continued)

(56) References Cited

U.S. PATENT DOCUMENTS

| 4,556,057 A | 12/1985 | Hiruma et al. |
| 4,740,459 A | 4/1988 | Chen et al. |
| | (Continued) | |

FOREIGN PATENT DOCUMENTS

| CA | 2360229 C | 5/2007 |
| CA | 2231799 C | 7/2007 |
| | (Continued) | |

OTHER PUBLICATIONS

Kang Uk et al., "Fluorescence video dermatoscope," SOI—Korea Center of Korean Electrotechnology Research Institute (KERI), Seoul, Korean Republic, published in J. Opt. Technol. 75 (1), Jan. 2008.

(Continued)

*Primary Examiner* — Serkan Akar
(74) *Attorney, Agent, or Firm* — Jones Robb, PLLC

(57) ABSTRACT

A method for fluorescence-based imaging of a target to detect contamination and/or pollutants is disclosed. The method includes labelling a pre-selected biomarker at the target, illuminating the target with excitation light emitted by an excitation light source and having at least one wavelength or wavelength band causing at least the pre-selected biomarker to fluoresce, detecting fluorescence emissions of at least the pre-selected biomarker with an image detector of a handheld imaging device, and determining the presence, location, and/or quantity of contamination and/or pollutants on and/or in the illuminated target based on the detected fluorescence emissions of at least the pre-selected biomarker.

24 Claims, 53 Drawing Sheets

Related U.S. Application Data continuation of application No. 12/992,040, filed as application No. PCT/CA2009/000680 on May 20, 2009, now Pat. No. 9,042,967.

(60) Provisional application No. 61/054,780, filed on May 20, 2008.

(51) Int. Cl.
*A61B 10/00* (2006.01)
*G01N 21/64* (2006.01)

(52) U.S. Cl.
CPC ................ *A61B 5/445* (2013.01); *A61B 5/72* (2013.01); *A61B 5/742* (2013.01); *G01N 21/6456* (2013.01); *G01N 21/6486* (2013.01); *A61B 5/0042* (2013.01); *A61B 5/4519* (2013.01); *A61B 10/00* (2013.01); *G01N 21/6408* (2013.01); *G01N 2021/6421* (2013.01); *G01N 2021/6471* (2013.01); *G01N 2201/0221* (2013.01); *Y02A 90/10* (2018.01)

(58) Field of Classification Search
CPC ........... G01N 21/6456; G01N 21/6486; G01N 2021/6421
See application file for complete search history.

(56) References Cited

U.S. PATENT DOCUMENTS

| | | | |
|---|---|---|---|
| 4,859,063 A | 8/1989 | Fay et al. |
| 5,306,144 A | 4/1994 | Hibst et al. |
| 5,421,337 A | 6/1995 | Richards-Kortum et al. |
| 5,456,260 A | 10/1995 | Kollias et al. |
| 5,474,910 A | 12/1995 | Alfano |
| 5,482,041 A | 1/1996 | Wilk et al. |
| 5,507,287 A | 4/1996 | Palcic et al. |
| 5,522,868 A | 6/1996 | Buckley et al. |
| 5,533,508 A | 7/1996 | Doiron |
| 5,552,134 A | 9/1996 | Morgan et al. |
| 5,562,100 A | 10/1996 | Kittrell et al. |
| 5,566,673 A | 10/1996 | Shiono et al. |
| 5,569,911 A | 10/1996 | Tomlinson, Jr. et al. |
| 5,572,996 A | 11/1996 | Doiron et al. |
| 5,579,773 A | 12/1996 | Vo-Dinh et al. |
| 5,588,428 A | 12/1996 | Smith et al. |
| 5,590,660 A | 1/1997 | MacAulay et al. |
| 5,605,152 A | 2/1997 | Slate et al. |
| 5,612,540 A | 3/1997 | Richards-Kortum et al. |
| 5,623,932 A | 4/1997 | Ramanujam et al. |
| 5,626,134 A | 5/1997 | Zuckerman |
| 5,628,310 A | 5/1997 | Rao et al. |
| 5,647,368 A | 7/1997 | Zeng et al. |
| 5,687,730 A | 11/1997 | Doiron et al. |
| 5,690,417 A | 11/1997 | Polidor et al. |
| 5,697,373 A | 12/1997 | Richards-Kortum et al. |
| 5,701,902 A | 12/1997 | Vari et al. |
| 5,760,407 A | 6/1998 | Margosiak et al. |
| 5,769,792 A | 6/1998 | Palcic et al. |
| 5,770,454 A | 6/1998 | Essenpreis et al. |
| 5,779,631 A | 7/1998 | Chance |
| 5,813,987 A | 9/1998 | Modell et al. |
| 5,820,558 A | 10/1998 | Chance |
| 5,849,595 A | 12/1998 | Alfano et al. |
| 5,851,181 A | 12/1998 | Talmor |
| 5,865,754 A | 2/1999 | Sevick-Muraca et al. |
| 5,879,294 A | 3/1999 | Anderson et al. |
| 5,935,075 A | 8/1999 | Casscells et al. |
| 5,938,617 A | 8/1999 | Vo-Dinh |
| 5,952,664 A | 9/1999 | Wake et al. |
| 5,981,958 A | 11/1999 | Li et al. |
| 5,986,271 A | 11/1999 | Lazarev et al. |
| 6,002,137 A | 12/1999 | Hayashi |
| 6,008,889 A | 12/1999 | Zeng et al. |
| 6,014,204 A | 1/2000 | Prahl et al. |
| 6,021,344 A | 2/2000 | Lui et al. |
| 6,026,319 A | 2/2000 | Hayashi |
| 6,036,941 A | 3/2000 | Bottiroli et al. |
| 6,055,451 A | 4/2000 | Bambot et al. |
| 6,058,324 A | 5/2000 | Chance |
| 6,061,591 A | 5/2000 | Freitag et al. |
| 6,064,897 A | 5/2000 | Lindberg et al. |
| 6,064,899 A | 5/2000 | Fein et al. |
| 6,069,689 A | 5/2000 | Zeng et al. |
| 6,078,833 A | 6/2000 | Hueber |
| 6,081,612 A | 6/2000 | Gutkowicz-Krusin et al. |
| 6,081,739 A | 6/2000 | Lemchen |
| 6,088,087 A | 7/2000 | Graves et al. |
| 6,088,606 A | 7/2000 | Ignotz et al. |
| 6,091,984 A | 7/2000 | Perelman et al. |
| 6,091,985 A | 7/2000 | Alfano et al. |
| 6,095,982 A | 8/2000 | Richards-Kortum et al. |
| 6,104,939 A | 8/2000 | Groner et al. |
| 6,104,945 A | 8/2000 | Modell et al. |
| 6,122,042 A | 9/2000 | Wunderman et al. |
| 6,122,536 A | 9/2000 | Sun et al. |
| 6,124,597 A | 9/2000 | Shehada et al. |
| 6,128,516 A | 10/2000 | Macfarlane et al. |
| 6,128,525 A | 10/2000 | Zeng et al. |
| 6,129,664 A | 10/2000 | Macfarlane et al. |
| 6,135,965 A | 10/2000 | Tumer et al. |
| 6,142,629 A | 11/2000 | Adel et al. |
| 6,148,227 A | 11/2000 | Wagnieres et al. |
| 6,161,031 A | 12/2000 | Hochman et al. |
| 6,167,297 A | 12/2000 | Benaron |
| 6,192,261 B1 | 2/2001 | Gratton et al. |
| 6,205,354 B1 | 3/2001 | Gellermann et al. |
| 6,208,749 B1 | 3/2001 | Gutkowicz-Krusin et al. |
| 6,212,425 B1 | 4/2001 | Irion et al. |
| 6,219,566 B1 | 4/2001 | Weersink et al. |
| 6,223,071 B1 | 4/2001 | Lundahl et al. |
| 6,236,871 B1 | 5/2001 | Tsuchiya |
| 6,236,881 B1 | 5/2001 | Zahler et al. |
| 6,238,348 B1 | 5/2001 | Crowley et al. |
| 6,241,662 B1 | 6/2001 | Richards-Kortum et al. |
| 6,256,530 B1 | 7/2001 | Wolfe |
| 6,258,576 B1 | 7/2001 | Richards-Kortum et al. |
| 6,272,367 B1 | 8/2001 | Chance |
| 6,272,376 B1 | 8/2001 | Marcu et al. |
| 6,280,386 B1 | 8/2001 | Alfano et al. |
| 6,289,236 B1 | 9/2001 | Koenig et al. |
| 6,304,766 B1 | 10/2001 | Colvin, Jr. |
| 6,317,624 B1 | 11/2001 | Kollias et al. |
| 6,343,227 B1 | 1/2002 | Crowley |
| 6,364,829 B1 | 4/2002 | Fulghum |
| 6,373,568 B1 | 4/2002 | Miller et al. |
| 6,385,484 B2 | 5/2002 | Nordstrom et al. |
| 6,393,315 B1 | 5/2002 | Aprahamian et al. |
| 6,422,994 B1 | 7/2002 | Kaneko et al. |
| 6,427,082 B1 | 7/2002 | Nordstrom et al. |
| 6,436,127 B1 | 8/2002 | Anderson et al. |
| 6,442,416 B1 | 8/2002 | Schultz |
| 6,465,968 B1 | 10/2002 | Sendai |
| 6,473,637 B1 | 10/2002 | Hayashi |
| 6,487,428 B1 | 11/2002 | Culver et al. |
| 6,496,719 B2 | 12/2002 | Hayashi |
| 6,510,338 B1 | 1/2003 | Irion et al. |
| 6,522,911 B1 | 2/2003 | Toida et al. |
| 6,526,309 B1 | 2/2003 | Chance |
| 6,542,772 B1 | 4/2003 | Chance |
| 6,549,801 B1 | 4/2003 | Chen et al. |
| 6,563,105 B2 | 5/2003 | Seibel et al. |
| 6,571,119 B2 | 5/2003 | Hayashi |
| 6,573,513 B2 | 6/2003 | Hayashi |
| 6,574,502 B2 | 6/2003 | Hayashi |
| 6,577,394 B1 | 6/2003 | Zavislan |
| 6,577,884 B1 | 6/2003 | Boas |
| 6,580,941 B2 | 6/2003 | Webb |
| 6,582,363 B2 | 6/2003 | Adachi et al. |
| 6,584,342 B1 | 6/2003 | Trushin et al. |
| 6,590,651 B1 | 7/2003 | Bambot et al. |
| 6,597,932 B2 | 7/2003 | Tian et al. |
| 6,600,947 B2 | 7/2003 | Averback et al. |
| 6,603,126 B2 | 8/2003 | Yamada et al. |

(56) References Cited

U.S. PATENT DOCUMENTS

| | | |
|---|---|---|
| 6,603,552 B1 | 8/2003 | Cline et al. |
| 6,615,063 B1 | 9/2003 | Ntziachristos et al. |
| 6,622,032 B1 | 9/2003 | Robinson et al. |
| 6,631,286 B2 | 10/2003 | Pfeiffer et al. |
| 6,631,289 B2 | 10/2003 | Alfano et al. |
| 6,636,759 B2 | 10/2003 | Robinson |
| 6,639,668 B1 | 10/2003 | Trepagnier |
| 6,640,124 B2 | 10/2003 | Elsner et al. |
| 6,640,130 B1 | 10/2003 | Freeman et al. |
| 6,640,131 B1 | 10/2003 | Irion et al. |
| 6,652,836 B2 | 11/2003 | Luiken |
| 6,665,556 B1 | 12/2003 | Alfano et al. |
| 6,667,803 B1 | 12/2003 | Flessland et al. |
| 6,668,186 B1 | 12/2003 | Zavislan et al. |
| 6,678,398 B2 | 1/2004 | Wolters et al. |
| 6,690,466 B2 | 2/2004 | Miller et al. |
| 6,694,158 B2 | 2/2004 | Polak |
| 6,697,652 B2 | 2/2004 | Georgakoudi et al. |
| 6,697,657 B1 | 2/2004 | Shehada et al. |
| 6,697,666 B1 | 2/2004 | Richards-Kortum et al. |
| 6,701,168 B1 | 3/2004 | Wilson et al. |
| 6,709,446 B2 | 3/2004 | Lundahl et al. |
| 6,711,429 B1 | 3/2004 | Gilboa et al. |
| 6,721,582 B2 | 4/2004 | Trepagnier et al. |
| 6,730,113 B2 | 5/2004 | Eckhardt et al. |
| 6,738,659 B2 | 5/2004 | Hsu |
| 6,748,259 B1 | 6/2004 | Benaron et al. |
| 6,750,964 B2 | 6/2004 | Levenson et al. |
| 6,751,490 B2 | 6/2004 | Esenaliev et al. |
| 6,757,554 B2 | 6/2004 | Rubinstein et al. |
| 6,763,262 B2 | 7/2004 | Hohla et al. |
| 6,766,184 B2 | 7/2004 | Utzinger et al. |
| 6,768,918 B2 | 7/2004 | Zelenchuk |
| 6,778,846 B1 | 8/2004 | Martinez et al. |
| 6,800,057 B2 | 10/2004 | Tsujita et al. |
| 6,806,089 B1 | 10/2004 | Lakowicz et al. |
| 6,818,903 B2 | 11/2004 | Schomacker et al. |
| 6,821,289 B2 | 11/2004 | Bode et al. |
| 6,826,424 B1 | 11/2004 | Zeng et al. |
| 6,865,407 B2 | 3/2005 | Kimball et al. |
| 6,868,285 B2 | 3/2005 | Muller-Dethlefs |
| 6,870,620 B2 | 3/2005 | Faupel et al. |
| 6,873,716 B1 | 3/2005 | Bowker et al. |
| 6,912,412 B2 | 6/2005 | Georgakoudi et al. |
| 6,914,250 B2 | 7/2005 | Seville |
| 6,922,523 B2 | 7/2005 | Merola et al. |
| 6,922,576 B2 | 7/2005 | Raskas |
| 6,930,773 B2 | 8/2005 | Cronin et al. |
| 6,933,154 B2 | 8/2005 | Schomacker et al. |
| 6,936,004 B2 | 8/2005 | Utsui |
| 6,970,729 B2 | 11/2005 | Hartmann |
| 6,975,898 B2 | 12/2005 | Seibel |
| 6,975,899 B2 | 12/2005 | Faupel et al. |
| 6,984,228 B2 | 1/2006 | Anderson et al. |
| 6,992,762 B2 | 1/2006 | Long et al. |
| 7,006,223 B2 | 2/2006 | Mullani |
| 7,016,714 B2 | 3/2006 | Colvin, Jr. |
| 7,016,717 B2 | 3/2006 | Demos et al. |
| 7,027,153 B2 | 4/2006 | Mullani |
| 7,062,311 B1 | 6/2006 | Sendai et al. |
| 7,102,142 B2 | 9/2006 | Sendai |
| 7,103,401 B2 | 9/2006 | Schomacker et al. |
| 7,107,116 B2 | 9/2006 | Geng |
| 7,109,315 B2 | 9/2006 | Bryan et al. |
| 7,113,814 B2 | 9/2006 | Ward et al. |
| 7,127,282 B2 | 10/2006 | Nordstrom et al. |
| 7,130,672 B2 | 10/2006 | Pewzner et al. |
| 7,139,598 B2 | 11/2006 | Hull et al. |
| 7,139,603 B2 | 11/2006 | Chance |
| 7,149,567 B2 | 12/2006 | Demos et al. |
| 7,151,270 B2 | 12/2006 | Birk et al. |
| 7,167,243 B2 | 1/2007 | Mullani |
| 7,167,244 B2 | 1/2007 | Mullani |
| 7,197,355 B2 | 3/2007 | Nelson |
| 7,202,947 B2 | 4/2007 | Liu et al. |
| 7,209,773 B2 | 4/2007 | Iuliano |
| 7,212,848 B1 | 5/2007 | Wake et al. |
| 7,218,822 B2 | 5/2007 | Treado et al. |
| 7,224,468 B2 | 5/2007 | Fouquet |
| RE39,672 E | 6/2007 | Shehada et al. |
| 7,236,815 B2 | 6/2007 | Richards-Kortum et al. |
| 7,242,997 B2 | 7/2007 | Geng |
| 7,248,182 B2 | 7/2007 | Dudda et al. |
| 7,257,437 B2 | 8/2007 | Demos et al. |
| 7,277,210 B2 | 10/2007 | Lipson |
| 7,282,723 B2 | 10/2007 | Schomacker et al. |
| 7,283,858 B2 | 10/2007 | Sendai |
| 7,286,224 B2 | 10/2007 | Curry et al. |
| 7,289,836 B2 | 10/2007 | Colvin, Jr. |
| 7,310,547 B2 | 12/2007 | Zelenchuk |
| 7,317,938 B2 | 1/2008 | Lorenz et al. |
| 7,321,791 B2 | 1/2008 | Levenson et al. |
| 7,324,608 B1 | 1/2008 | Chiodini et al. |
| 7,353,055 B2 | 4/2008 | Hogan |
| 7,359,748 B1 | 4/2008 | Drugge |
| 7,365,844 B2 | 4/2008 | Richards-Kortum et al. |
| 7,366,365 B2 | 4/2008 | Carver |
| 7,368,694 B2 | 5/2008 | Goulas et al. |
| 7,376,346 B2 | 5/2008 | Merola et al. |
| 7,376,451 B2 | 5/2008 | Mahony et al. |
| 7,378,056 B2 | 5/2008 | Black |
| 7,389,132 B2 | 6/2008 | Wang et al. |
| 7,403,812 B2 | 7/2008 | Rice et al. |
| 7,404,929 B2 | 7/2008 | Fulghum, Jr. |
| 7,454,046 B2 | 11/2008 | Chhibber et al. |
| 7,477,393 B2 | 1/2009 | Sendai |
| 7,477,767 B2 | 1/2009 | Chhibber et al. |
| 7,477,931 B2 | 1/2009 | Hoyt |
| 7,479,990 B2 | 1/2009 | Imaizumi et al. |
| 7,491,956 B2 | 2/2009 | Knoche et al. |
| 7,495,233 B2 | 2/2009 | Pfister et al. |
| 7,496,392 B2 | 2/2009 | Alarcon et al. |
| 7,499,161 B2 | 3/2009 | Richards-Kortum et al. |
| 7,505,809 B2 | 3/2009 | Strommer et al. |
| 7,508,524 B2 | 3/2009 | Mahadevan-Jansen et al. |
| 7,510,699 B2 | 3/2009 | Black et al. |
| 7,515,952 B2 | 4/2009 | Balas et al. |
| 7,519,411 B2 | 4/2009 | Long |
| 7,522,797 B2 | 4/2009 | Treado et al. |
| 7,526,329 B2 | 4/2009 | Hogan et al. |
| 7,536,213 B2 | 5/2009 | Lipson et al. |
| 7,539,530 B2 | 5/2009 | Caplan et al. |
| 7,555,332 B2 | 6/2009 | Rice et al. |
| 7,558,619 B2 | 7/2009 | Ferguson et al. |
| 7,564,550 B2 | 7/2009 | Yaroslavsky et al. |
| 7,570,359 B2 | 8/2009 | Fox |
| 7,570,984 B2 | 8/2009 | Katsuda et al. |
| 7,580,185 B2 | 8/2009 | Haisch et al. |
| 7,583,993 B2 | 9/2009 | Sendai |
| 7,587,236 B2 | 9/2009 | Demos et al. |
| 7,590,437 B2 | 9/2009 | Rubinstein et al. |
| 7,598,088 B2 | 10/2009 | Balas |
| 7,599,065 B2 | 10/2009 | Sendai |
| 7,599,731 B2 | 10/2009 | Rice et al. |
| 7,599,732 B2 | 10/2009 | Sevick-Muraca et al. |
| 7,603,031 B1 | 10/2009 | Viaud et al. |
| 7,609,814 B2 | 10/2009 | Baumgart |
| 7,610,082 B2 | 10/2009 | Chance |
| 7,613,504 B2 | 11/2009 | Rowe |
| 7,613,505 B2 | 11/2009 | Mazuir et al. |
| 7,633,621 B2 | 12/2009 | Thornton |
| 7,646,002 B2 | 1/2010 | Sendai |
| 7,652,763 B2 | 1/2010 | Matousek et al. |
| 7,653,424 B2 | 1/2010 | March |
| 7,672,702 B2 | 3/2010 | Hwang et al. |
| 7,697,966 B2 | 4/2010 | Monfre et al. |
| 7,697,975 B2 | 4/2010 | Zeng |
| 7,702,381 B2 | 4/2010 | Gaeta et al. |
| 7,722,537 B2 | 5/2010 | Sterling et al. |
| 7,729,732 B2 | 6/2010 | Ohashi |
| 7,729,749 B2 | 6/2010 | Roessler et al. |
| 7,734,325 B2 | 6/2010 | Vizard et al. |
| 7,738,032 B2 | 6/2010 | Kollias et al. |
| 7,749,217 B2 | 7/2010 | Podhajsky |

(56) References Cited

U.S. PATENT DOCUMENTS

| | | | |
|---|---|---|---|
| 7,761,126 B2 | 7/2010 | Gardner et al. |
| 7,764,303 B2 | 7/2010 | Pote et al. |
| 7,785,277 B2 | 8/2010 | Babaev et al. |
| 7,787,928 B2 | 8/2010 | Frisch et al. |
| 7,794,925 B2 | 9/2010 | Cullen |
| 7,798,955 B2 | 9/2010 | Ishihara et al. |
| 7,804,991 B2 | 9/2010 | Abovitz et al. |
| 7,812,945 B2 | 10/2010 | Fortier et al. |
| 7,817,267 B2 | 10/2010 | Carver |
| 7,821,640 B2 | 10/2010 | Koenig et al. |
| 7,822,450 B2 | 10/2010 | Colvin, Jr. et al. |
| 7,826,878 B2 | 11/2010 | Alfano et al. |
| 7,843,572 B2 | 11/2010 | Tearney et al. |
| 7,860,554 B2 | 12/2010 | Leonardi et al. |
| 7,865,231 B2 | 1/2011 | Tearney et al. |
| 7,872,759 B2 | 1/2011 | Tearney et al. |
| 7,888,659 B2 | 2/2011 | Scholz et al. |
| 7,889,348 B2 | 2/2011 | Tearney et al. |
| 7,899,518 B2 | 3/2011 | Trepagnier et al. |
| 7,899,624 B2 | 3/2011 | Cualing et al. |
| 7,904,140 B2 | 3/2011 | Pilon et al. |
| 7,909,253 B2 | 3/2011 | Sherman |
| 7,912,534 B2 | 3/2011 | Grinvald et al. |
| 7,914,442 B1 | 3/2011 | Gazdzinski |
| 7,916,283 B2 | 3/2011 | Fukutani et al. |
| 7,925,333 B2 | 4/2011 | Weir et al. |
| 7,935,055 B2 | 5/2011 | Burckhardt |
| 7,945,077 B2 | 5/2011 | Demos |
| 7,960,707 B2 | 6/2011 | Hall et al. |
| 7,962,200 B2 | 6/2011 | Nitziachristos et al. |
| 7,966,060 B2 | 6/2011 | Smit et al. |
| 7,973,925 B2 | 7/2011 | Lipson et al. |
| 7,977,650 B2 | 7/2011 | Laidevant et al. |
| 7,979,107 B2 | 7/2011 | Lin et al. |
| 7,983,736 B2 | 7/2011 | Villard et al. |
| 7,983,740 B2 | 7/2011 | Culver et al. |
| 7,986,342 B2 | 7/2011 | Yogesan et al. |
| 7,986,987 B2 | 7/2011 | Bazin et al. |
| 7,996,068 B2 | 8/2011 | Telischak et al. |
| 8,000,775 B2 | 8/2011 | Pogue et al. |
| 8,005,527 B2 | 8/2011 | Zelenchuk |
| 8,026,942 B2 | 9/2011 | Payonk et al. |
| 8,031,924 B2 | 10/2011 | Can et al. |
| 8,039,816 B2 | 10/2011 | Morishita et al. |
| 8,041,162 B2 | 10/2011 | Wang et al. |
| 8,045,153 B2 | 10/2011 | Mimura et al. |
| 8,045,263 B2 | 10/2011 | Yaroslavsky et al. |
| 8,050,735 B2 | 11/2011 | Feke et al. |
| 8,055,035 B2 | 11/2011 | Okugawa et al. |
| 8,078,243 B2 | 12/2011 | Ediger et al. |
| 8,078,263 B2 | 12/2011 | Zeman et al. |
| 8,078,264 B2 | 12/2011 | Basilion |
| 8,078,265 B2 | 12/2011 | Mahmood et al. |
| 8,082,024 B2 | 12/2011 | Alfano et al. |
| 8,107,696 B2 | 1/2012 | Pote et al. |
| 8,108,022 B2 | 1/2012 | Balberg et al. |
| 8,118,206 B2 | 2/2012 | Zand et al. |
| 8,121,671 B2 | 2/2012 | Hull et al. |
| 8,125,623 B2 | 2/2012 | Munger et al. |
| 8,129,105 B2 | 3/2012 | Zuckerman |
| 8,131,332 B2 | 3/2012 | Maynard et al. |
| 8,131,349 B2 | 3/2012 | Okawa et al. |
| 8,135,449 B2 | 3/2012 | Wilson et al. |
| 8,139,211 B2 | 3/2012 | Yaroslavsky et al. |
| 8,140,147 B2 | 3/2012 | Maynard et al. |
| 8,145,295 B2 | 3/2012 | Boyden et al. |
| 8,149,418 B2 | 4/2012 | Tearney et al. |
| 8,157,807 B2 | 4/2012 | Ferren et al. |
| 8,158,919 B2 | 4/2012 | Maeda et al. |
| 8,160,680 B2 | 4/2012 | Boyden et al. |
| 8,180,421 B2 | 5/2012 | Phillips et al. |
| 8,180,436 B2 | 5/2012 | Boyden et al. |
| 8,185,180 B2 | 5/2012 | Diab et al. |
| 8,188,446 B2 | 5/2012 | Ohno |
| 8,189,201 B2 | 5/2012 | Haisch et al. |
| 8,189,887 B2 | 5/2012 | Kollias et al. |
| 8,190,231 B2 | 5/2012 | Miwa et al. |
| 8,190,242 B2 | 5/2012 | Demos et al. |
| 8,204,579 B2 | 6/2012 | Nielsen et al. |
| 8,213,005 B2 | 7/2012 | Masilamani et al. |
| 8,218,143 B2 | 7/2012 | Gupta |
| 8,224,427 B2 | 7/2012 | Kopriva |
| 8,227,766 B2 | 7/2012 | Chapman |
| 8,228,368 B2 | 7/2012 | Zhao et al. |
| 8,229,548 B2 | 7/2012 | Frangioni |
| 8,231,526 B2 | 7/2012 | Yabe et al. |
| 8,238,993 B2 | 8/2012 | Maynard et al. |
| 8,243,269 B2 | 8/2012 | Matousek et al. |
| 8,246,611 B2 | 8/2012 | Paithankar et al. |
| 8,255,040 B2 | 8/2012 | Goldman et al. |
| 8,260,010 B2 | 9/2012 | Chhibber et al. |
| 8,270,689 B2 | 9/2012 | Liang et al. |
| 8,279,275 B2 | 10/2012 | Gono et al. |
| 8,280,140 B2 | 10/2012 | Levenson et al. |
| 8,280,471 B2 | 10/2012 | Rainone et al. |
| 8,285,015 B2 | 10/2012 | Demos |
| 8,285,353 B2 | 10/2012 | Choi et al. |
| 8,289,522 B2 | 10/2012 | Tearney et al. |
| 8,294,081 B2 | 10/2012 | Rosenheimer et al. |
| 8,295,901 B2 | 10/2012 | Tobola et al. |
| 8,311,607 B2 | 11/2012 | Zelenchuk |
| 8,320,650 B2 | 11/2012 | Demos et al. |
| 8,326,404 B2 | 12/2012 | Zeng et al. |
| 8,326,406 B2 | 12/2012 | Ntziachristos et al. |
| 8,330,087 B2 | 12/2012 | Domenicali |
| 8,332,006 B2 | 12/2012 | Naganuma et al. |
| 8,335,550 B2 | 12/2012 | Segman |
| 8,346,329 B2 | 1/2013 | Xu et al. |
| 8,351,026 B2 | 1/2013 | Stern |
| 8,351,041 B2 | 1/2013 | Leveque et al. |
| 8,358,821 B2 | 1/2013 | Yamaguchi et al. |
| 8,380,268 B2 | 2/2013 | Georgakoudi et al. |
| 8,385,615 B2 | 2/2013 | Levenson et al. |
| 8,391,961 B2 | 3/2013 | Levenson et al. |
| 8,403,862 B2 | 3/2013 | Grinvald et al. |
| 8,417,324 B2 | 4/2013 | Mycek et al. |
| 8,423,127 B2 | 4/2013 | Mahmood et al. |
| 8,452,357 B2 | 5/2013 | Rebec et al. |
| 8,452,384 B2 | 5/2013 | Ince |
| 8,463,006 B2 | 6/2013 | Prokoski |
| 8,467,857 B2 | 6/2013 | Kim et al. |
| 8,491,120 B2 | 7/2013 | Kahn et al. |
| 8,496,695 B2 | 7/2013 | Kang et al. |
| 8,498,682 B2 | 7/2013 | Markle et al. |
| 8,504,140 B2 | 8/2013 | Feke et al. |
| 8,521,261 B2 | 8/2013 | Okawa et al. |
| 8,538,195 B2 | 9/2013 | Robinson |
| 8,538,504 B2 | 9/2013 | Kleen et al. |
| 8,540,393 B2 | 9/2013 | Mizuno et al. |
| 8,543,180 B2 | 9/2013 | Bechtel et al. |
| 8,547,425 B2 | 10/2013 | Ishihara |
| 8,562,657 B2 | 10/2013 | Ferren et al. |
| 8,574,859 B2 | 11/2013 | Lin et al. |
| 8,581,970 B2 | 11/2013 | Yamazaki et al. |
| 8,588,893 B2 | 11/2013 | Jaeb et al. |
| 8,593,513 B2 | 11/2013 | Yamaguchi et al. |
| 8,598,540 B2 | 12/2013 | Moy et al. |
| 8,605,974 B2 | 12/2013 | Liang et al. |
| 8,609,358 B2 | 12/2013 | Sebastian et al. |
| 8,617,057 B2 | 12/2013 | Morishita et al. |
| 8,619,257 B2 | 12/2013 | Plowman et al. |
| 8,620,411 B2 | 12/2013 | Stamatas et al. |
| 8,626,271 B2 | 1/2014 | Dunki-Jacobs et al. |
| 8,634,607 B2 | 1/2014 | Levenson et al. |
| 8,639,043 B2 | 1/2014 | Levenson et al. |
| 8,644,663 B2 | 2/2014 | Viellerobe et al. |
| 8,644,900 B2 | 2/2014 | Balberg et al. |
| 8,644,911 B1 | 2/2014 | Panasyuk et al. |
| 8,660,637 B2 | 2/2014 | Crowley |
| 8,676,283 B2 | 3/2014 | Matter et al. |
| 8,676,302 B2 | 3/2014 | Wang et al. |
| 8,705,042 B2 | 4/2014 | Haisch et al. |
| 8,718,737 B2 | 5/2014 | Diab et al. |
| 9,042,967 B2 | 5/2015 | Dacosta et al. |

(56)  References Cited

U.S. PATENT DOCUMENTS

| | | |
|---|---|---|
| 9,675,238 B2 | 6/2017 | Lida et al. |
| 9,696,897 B2 | 7/2017 | Garcia |
| 10,200,625 B2 | 2/2019 | Marcelpoil et al. |
| 10,438,356 B2 | 10/2019 | Dacosta |
| 11,154,198 B2 | 10/2021 | Dacosta et al. |
| 11,266,345 B2 | 3/2022 | Saiko et al. |
| 11,284,800 B2 | 3/2022 | Dacosta et al. |
| 11,375,898 B2 | 7/2022 | Dacosta et al. |
| 12,169,935 B2 | 12/2024 | Dacosta |
| 12,226,186 B2 | 2/2025 | Dacosta et al. |
| 12,251,191 B2 | 3/2025 | Dacosta et al. |
| 12,387,335 B2 | 8/2025 | DaCosta |
| 2001/0034477 A1 | 10/2001 | Mansfield et al. |
| 2001/0047136 A1 | 11/2001 | Domanik et al. |
| 2002/0058864 A1 | 5/2002 | Mansfield et al. |
| 2002/0091324 A1 | 7/2002 | Kollias et al. |
| 2002/0138008 A1 | 9/2002 | Tsujita et al. |
| 2002/0146160 A1 | 10/2002 | Parker et al. |
| 2003/0001104 A1 | 1/2003 | Sendai et al. |
| 2003/0049175 A1 | 3/2003 | Buechler et al. |
| 2003/0055341 A1 | 3/2003 | Banerjee |
| 2003/0068274 A1 | 4/2003 | Jungmann et al. |
| 2003/0082105 A1 | 5/2003 | Fischman et al. |
| 2003/0109787 A1 | 6/2003 | Black |
| 2003/0113934 A1 | 6/2003 | Kwon |
| 2003/0123056 A1 | 7/2003 | Barnes et al. |
| 2003/0135122 A1 | 7/2003 | Bambot et al. |
| 2003/0158470 A1 | 8/2003 | Wolters et al. |
| 2003/0160182 A1 | 8/2003 | Petrich et al. |
| 2003/0173525 A1 | 9/2003 | Seville |
| 2003/0184853 A1 | 10/2003 | Sasaki |
| 2003/0195401 A1 | 10/2003 | Tian et al. |
| 2003/0206301 A1 | 11/2003 | Cline et al. |
| 2003/0216626 A1 | 11/2003 | Tsujita et al. |
| 2004/0006276 A1 | 1/2004 | Demos et al. |
| 2004/0034292 A1 | 2/2004 | Mansfield et al. |
| 2004/0064053 A1 | 4/2004 | Chang et al. |
| 2004/0073120 A1 | 4/2004 | Motz et al. |
| 2004/0077951 A1 | 4/2004 | Lin et al. |
| 2004/0101826 A1 | 5/2004 | Jones et al. |
| 2004/0143190 A1 | 7/2004 | Schnitzer |
| 2004/0147843 A1 | 7/2004 | Bambot et al. |
| 2004/0148141 A1 | 7/2004 | Tsujita et al. |
| 2004/0186382 A1 | 9/2004 | Modell et al. |
| 2004/0186383 A1 | 9/2004 | Rava et al. |
| 2004/0196463 A1 | 10/2004 | Cline et al. |
| 2004/0225222 A1 | 11/2004 | Zeng et al. |
| 2004/0236229 A1 | 11/2004 | Freeman et al. |
| 2004/0260365 A1 | 12/2004 | Groseth et al. |
| 2005/0021235 A1 | 1/2005 | Bar-Or et al. |
| 2005/0064602 A1 | 3/2005 | Kaufman et al. |
| 2005/0119548 A1 | 6/2005 | Lin et al. |
| 2005/0131304 A1 | 6/2005 | Stamatas et al. |
| 2005/0143662 A1 | 6/2005 | Marchitto et al. |
| 2005/0195316 A1 | 9/2005 | Kollias et al. |
| 2006/0004292 A1 | 1/2006 | Beylin |
| 2006/0008866 A1 | 1/2006 | Flick et al. |
| 2006/0013454 A1 | 1/2006 | Flewelling et al. |
| 2006/0030761 A1 | 2/2006 | Raskas |
| 2006/0077581 A1 | 4/2006 | Schwiegerling et al. |
| 2006/0082768 A1 | 4/2006 | Wilson et al. |
| 2006/0089556 A1 | 4/2006 | Bambot et al. |
| 2006/0135869 A1 | 6/2006 | Farina |
| 2006/0151709 A1 | 7/2006 | Hahl |
| 2006/0188389 A1 | 8/2006 | Levy |
| 2006/0241495 A1 | 10/2006 | Kurtz |
| 2006/0241499 A1 | 10/2006 | Irion et al. |
| 2006/0249690 A1 | 11/2006 | Pfister et al. |
| 2006/0253261 A1 | 11/2006 | Maier et al. |
| 2006/0264761 A1 | 11/2006 | Knoche et al. |
| 2006/0270919 A1 | 11/2006 | Brenner |
| 2007/0004972 A1 | 1/2007 | Cole et al. |
| 2007/0015963 A1 | 1/2007 | Fengler et al. |
| 2007/0024946 A1 | 2/2007 | Panasyuk et al. |
| 2007/0038124 A1 | 2/2007 | Fulghum et al. |
| 2007/0038126 A1 | 2/2007 | Pyle et al. |
| 2007/0049809 A1 | 3/2007 | Bechtel et al. |
| 2007/0060804 A1 | 3/2007 | Thompson et al. |
| 2007/0064985 A1 | 3/2007 | Chhibber et al. |
| 2007/0073156 A1 | 3/2007 | Zilberman et al. |
| 2007/0073158 A1 | 3/2007 | Sendai |
| 2007/0080305 A1 | 4/2007 | Maitrejean et al. |
| 2007/0093700 A1 | 4/2007 | Wang et al. |
| 2007/0093703 A1 | 4/2007 | Sievert et al. |
| 2007/0129613 A1 | 6/2007 | Rochester et al. |
| 2007/0129615 A1 | 6/2007 | Backman et al. |
| 2007/0135873 A1 | 6/2007 | Johansson et al. |
| 2007/0149868 A1 | 6/2007 | Blank et al. |
| 2007/0149882 A1 | 6/2007 | Wedel |
| 2007/0156036 A1 | 7/2007 | Pilon et al. |
| 2007/0167836 A1 | 7/2007 | Scepanovic et al. |
| 2007/0167838 A1 | 7/2007 | Hubble et al. |
| 2007/0179366 A1 | 8/2007 | Pewzner et al. |
| 2007/0212038 A1 | 9/2007 | Asai et al. |
| 2007/0213618 A1 | 9/2007 | Li et al. |
| 2007/0223797 A1 | 9/2007 | Kaneko |
| 2007/0239031 A1 | 10/2007 | Lee et al. |
| 2007/0239034 A1 | 10/2007 | Knoche et al. |
| 2007/0244395 A1 | 10/2007 | Wang et al. |
| 2007/0276199 A1 | 11/2007 | Ediger et al. |
| 2008/0013166 A1 | 1/2008 | Haisch et al. |
| 2008/0013960 A1 | 1/2008 | Tearney et al. |
| 2008/0014463 A1 | 1/2008 | Varadarajan et al. |
| 2008/0021329 A1 | 1/2008 | Wood et al. |
| 2008/0045799 A1 | 2/2008 | Whitehead et al. |
| 2008/0051664 A1 | 2/2008 | Demos et al. |
| 2008/0051665 A1 | 2/2008 | Xu et al. |
| 2008/0058587 A1 | 3/2008 | Boyden et al. |
| 2008/0058785 A1 | 3/2008 | Boyden et al. |
| 2008/0058795 A1 | 3/2008 | Boyden et al. |
| 2008/0059070 A1 | 3/2008 | Boyden et al. |
| 2008/0076985 A1 | 3/2008 | Matousek et al. |
| 2008/0082000 A1 | 4/2008 | Thoms |
| 2008/0086038 A1 | 4/2008 | Thornton |
| 2008/0091110 A1 | 4/2008 | Zelenchuk |
| 2008/0097225 A1 | 4/2008 | Tearney et al. |
| 2008/0103355 A1 | 5/2008 | Boyden et al. |
| 2008/0103375 A1 | 5/2008 | Kiani |
| 2008/0103384 A1 | 5/2008 | Pfister |
| 2008/0118886 A1 | 5/2008 | Liang et al. |
| 2008/0119832 A1 | 5/2008 | Cronin |
| 2008/0128505 A1 | 6/2008 | Challa et al. |
| 2008/0132793 A1 | 6/2008 | Kollias et al. |
| 2008/0154102 A1 | 6/2008 | Frangioni et al. |
| 2008/0161699 A1 | 7/2008 | Zeng et al. |
| 2008/0177140 A1 | 7/2008 | Cline et al. |
| 2008/0183059 A1 | 7/2008 | LaPlante et al. |
| 2008/0188727 A1 | 8/2008 | Benaron et al. |
| 2008/0188736 A1 | 8/2008 | Bambot et al. |
| 2008/0194928 A1 | 8/2008 | Bandic et al. |
| 2008/0194968 A1 | 8/2008 | Drugge |
| 2008/0221416 A1 | 9/2008 | Baker |
| 2008/0228037 A1 | 9/2008 | Cline et al. |
| 2008/0228049 A1 | 9/2008 | Black |
| 2008/0249381 A1 | 10/2008 | Muller et al. |
| 2008/0269617 A1 | 10/2008 | Kohler et al. |
| 2008/0300493 A1 | 12/2008 | Gatto et al. |
| 2008/0312540 A1 | 12/2008 | Ntziachristos |
| 2009/0010804 A1 | 1/2009 | Withrow, III et al. |
| 2009/0018418 A1 | 1/2009 | Markle et al. |
| 2009/0043296 A1 | 2/2009 | Foster et al. |
| 2009/0060304 A1 | 3/2009 | Gulfo et al. |
| 2009/0073439 A1 | 3/2009 | Tearney et al. |
| 2009/0075391 A1 | 3/2009 | Fulghum, Jr. |
| 2009/0118600 A1 | 5/2009 | Ortiz et al. |
| 2009/0118622 A1 | 5/2009 | Durkin et al. |
| 2009/0124854 A1 | 5/2009 | Yamaguchi et al. |
| 2009/0131800 A1 | 5/2009 | Liang |
| 2009/0137908 A1 | 5/2009 | Patwardhan |
| 2009/0137952 A1 | 5/2009 | Ramamurthy et al. |
| 2009/0163819 A1 | 6/2009 | De Kok et al. |
| 2009/0180955 A1 | 7/2009 | Stritzker et al. |
| 2009/0187108 A1 | 7/2009 | Tang et al. |
| 2009/0192349 A1 | 7/2009 | Berguer et al. |

(56)                References Cited

U.S. PATENT DOCUMENTS

| | | |
|---|---|---|
| 2009/0209866 A1 | 8/2009 | Abovitz et al. |
| 2009/0234234 A1 | 9/2009 | Machida |
| 2009/0236541 A1 | 9/2009 | Lomnes et al. |
| 2009/0247881 A1 | 10/2009 | Maeda et al. |
| 2009/0249500 A1 | 10/2009 | Zhao et al. |
| 2009/0264772 A1 | 10/2009 | Van Der Brug et al. |
| 2009/0268011 A1 | 10/2009 | Scott et al. |
| 2009/0270702 A1 | 10/2009 | Zeng et al. |
| 2009/0289200 A1 | 11/2009 | Ishii |
| 2009/0299196 A1 | 12/2009 | Bawendi et al. |
| 2010/0010340 A1 | 1/2010 | Godavarty et al. |
| 2010/0016688 A1 | 1/2010 | Debreczeny et al. |
| 2010/0041998 A1 | 2/2010 | Postel |
| 2010/0069758 A1 | 3/2010 | Barnes et al. |
| 2010/0091104 A1 | 4/2010 | Sprigle et al. |
| 2010/0140461 A1 | 6/2010 | Sprigle et al. |
| 2010/0160752 A1 | 6/2010 | Chance |
| 2010/0168586 A1 | 7/2010 | Hillman et al. |
| 2010/0172567 A1 | 7/2010 | Prokoski |
| 2010/0174160 A1 | 7/2010 | Chance |
| 2010/0185099 A1 | 7/2010 | Johansson et al. |
| 2010/0217129 A1 | 8/2010 | El-Deiry et al. |
| 2010/0228183 A1 | 9/2010 | Sunnen |
| 2010/0234739 A1 | 9/2010 | Nakaoka et al. |
| 2010/0234740 A1 | 9/2010 | Roessler et al. |
| 2010/0241055 A1 | 9/2010 | Dacey, Jr. et al. |
| 2010/0256469 A1 | 10/2010 | Cook et al. |
| 2010/0256504 A1 | 10/2010 | Moreau-Gaudry et al. |
| 2010/0268091 A1 | 10/2010 | Takaoka |
| 2010/0331705 A1 | 12/2010 | Het Hooft et al. |
| 2010/0331706 A1 | 12/2010 | Hasegawa |
| 2010/0331707 A1 | 12/2010 | Fukutani et al. |
| 2011/0015591 A1 | 1/2011 | Hanson et al. |
| 2011/0042580 A1 | 2/2011 | Wilson et al. |
| 2011/0063427 A1 | 3/2011 | Fengler et al. |
| 2011/0085714 A1 | 4/2011 | Yan et al. |
| 2011/0087111 A1 | 4/2011 | Ntziachristos |
| 2011/0098575 A1 | 4/2011 | Stamnes et al. |
| 2011/0102566 A1 | 5/2011 | Zakian et al. |
| 2011/0117025 A1 | 5/2011 | Dacosta et al. |
| 2011/0118608 A1 | 5/2011 | Lindner et al. |
| 2011/0124989 A1 | 5/2011 | Edgar et al. |
| 2011/0144504 A1 | 6/2011 | Tearney et al. |
| 2011/0184260 A1 | 7/2011 | Robinson et al. |
| 2011/0201940 A1 | 8/2011 | Wang et al. |
| 2011/0213252 A1 | 9/2011 | Fulghum |
| 2011/0224553 A1 | 9/2011 | Stothers et al. |
| 2011/0237909 A1 | 9/2011 | Black |
| 2011/0275899 A1 | 11/2011 | Tearney et al. |
| 2011/0275900 A1 | 11/2011 | Gilhuly et al. |
| 2011/0295125 A1 | 12/2011 | Lin et al. |
| 2011/0313296 A9 | 12/2011 | Johnson et al. |
| 2012/0004508 A1 | 1/2012 | McDowall et al. |
| 2012/0004557 A1 | 1/2012 | McDowall et al. |
| 2012/0016230 A1 | 1/2012 | Kishima et al. |
| 2012/0029348 A1 | 2/2012 | Yaroslavsky et al. |
| 2012/0053429 A1 | 3/2012 | Trepagnier et al. |
| 2012/0059254 A1 | 3/2012 | Lifan et al. |
| 2012/0065484 A1 | 3/2012 | Hull et al. |
| 2012/0071764 A1 | 3/2012 | Yaroslavsky et al. |
| 2012/0078075 A1 | 3/2012 | Maynard et al. |
| 2012/0089031 A1 | 4/2012 | Ince |
| 2012/0108982 A1 | 5/2012 | Hoyt et al. |
| 2012/0197096 A1 | 8/2012 | Ridder et al. |
| 2012/0197134 A1 | 8/2012 | Okawa et al. |
| 2012/0220880 A1 | 8/2012 | Zuluaga |
| 2012/0226167 A1 | 9/2012 | Zuluaga |
| 2012/0265078 A1 | 10/2012 | Goldman et al. |
| 2012/0277558 A1 | 11/2012 | Barber et al. |
| 2012/0283531 A1 | 11/2012 | Maynard et al. |
| 2012/0302892 A1 | 11/2012 | Lue et al. |
| 2013/0016963 A1 | 1/2013 | Miller |
| 2013/0018236 A1 | 1/2013 | Altshuler et al. |
| 2013/0033589 A1 | 2/2013 | Demos |
| 2013/0066215 A1 | 3/2013 | Tearney et al. |
| 2013/0072769 A1 | 3/2013 | Zuckerman |
| 2013/0100455 A1 | 4/2013 | Tearney et al. |
| 2013/0131488 A1 | 5/2013 | Zeng et al. |
| 2013/0148106 A1 | 6/2013 | Tearney et al. |
| 2013/0217985 A1 | 8/2013 | Dvorsky et al. |
| 2013/0237860 A1 | 9/2013 | Ince |
| 2013/0302746 A1 | 11/2013 | Liang et al. |
| 2014/0031647 A1 | 1/2014 | Lin et al. |
| 2014/0050667 A1 | 2/2014 | Wang et al. |
| 2014/0055605 A1 | 2/2014 | Moy et al. |
| 2014/0058220 A1 | 2/2014 | LeBoeuf et al. |
| 2014/0073885 A1 | 3/2014 | Frangioni |
| 2014/0128730 A1 | 5/2014 | Wang et al. |
| 2014/0158541 A1 | 6/2014 | Beaudet et al. |
| 2014/0207003 A1 | 7/2014 | Gilhuly et al. |
| 2014/0221843 A1 | 8/2014 | You et al. |
| 2014/0271557 A1 | 9/2014 | Lee et al. |
| 2014/0300891 A1 | 10/2014 | Alfano et al. |
| 2015/0042877 A1 | 2/2015 | O'Neill et al. |
| 2015/0145966 A1 | 5/2015 | Krieger et al. |
| 2015/0182196 A1 | 7/2015 | Ninomiya et al. |
| 2015/0192521 A1 | 7/2015 | Lausch et al. |
| 2015/0216418 A1 | 8/2015 | Ammon et al. |
| 2016/0045114 A1 | 2/2016 | Dacosta et al. |
| 2016/0187199 A1 | 6/2016 | Brunk et al. |
| 2016/0289729 A1 | 10/2016 | Richards et al. |
| 2016/0324506 A1 | 11/2016 | Tariyal et al. |
| 2017/0023599 A1 | 1/2017 | Richards et al. |
| 2017/0183705 A1 | 6/2017 | Hicks et al. |
| 2017/0236281 A1 | 8/2017 | Dacosta |
| 2018/0188108 A1 | 7/2018 | Fawzy |
| 2018/0242848 A1 | 8/2018 | Dacosta et al. |
| 2018/0325377 A1 | 11/2018 | Dacosta et al. |
| 2019/0216326 A1 | 7/2019 | Cross et al. |
| 2020/0104998 A1 | 4/2020 | Dacosta et al. |
| 2021/0259552 A1 | 8/2021 | Dacosta et al. |
| 2021/0378518 A1 | 12/2021 | Dacosta et al. |
| 2022/0039656 A1 | 2/2022 | DaCosta et al. |
| 2022/0047164 A1 | 2/2022 | Dacosta et al. |
| 2024/0346658 A1 | 10/2024 | Dacosta |
| 2024/0346659 A1 | 10/2024 | Dacosta |
| 2024/0366090 A1 | 11/2024 | DaCosta et al. |
| 2025/0152010 A1 | 5/2025 | DaCosta et al. |
| 2025/0160648 A1 | 5/2025 | DaCosta et al. |
| 2025/0160649 A1 | 5/2025 | DaCosta et al. |
| 2025/0160650 A1 | 5/2025 | DaCosta et al. |
| 2025/0160651 A1 | 5/2025 | DaCosta et al. |
| 2025/0166198 A1 | 5/2025 | Dacosta |
| 2025/0166199 A1 | 5/2025 | Dacosta |
| 2025/0166200 A1 | 5/2025 | Dacosta |
| 2025/0166201 A1 | 5/2025 | Dacosta |
| 2025/0185914 A1 | 6/2025 | DaCosta et al. |
| 2025/0204785 A1 | 6/2025 | DaCosta et al. |
| 2025/0204786 A1 | 6/2025 | DaCosta et al. |
| 2025/0325187 A1 | 10/2025 | DaCosta et al. |
| 2025/0325188 A1 | 10/2025 | DaCosta et al. |

FOREIGN PATENT DOCUMENTS

| | | |
|---|---|---|
| CA | 2306795 C | 1/2009 |
| CA | 2343401 C | 1/2009 |
| CA | 2305721 C | 2/2009 |
| CA | 2190374 C | 7/2010 |
| CA | 2371886 C | 1/2012 |
| CA | 2544204 C | 7/2013 |
| CA | 2331090 C | 10/2013 |
| CA | 2533621 C | 12/2013 |
| CA | 2489915 C | 1/2014 |
| CA | 2501098 C | 4/2014 |
| CA | 2685000 C | 4/2014 |
| CN | 1623001 A | 6/2005 |
| CN | 1652012 A | 8/2005 |
| CN | 101943661 | 1/2011 |
| CN | 102099671 | 6/2011 |
| EP | 694165 B1 | 3/1998 |
| EP | 930916 B1 | 9/2001 |
| EP | 864864 B1 | 1/2003 |
| EP | 850018 B1 | 4/2003 |
| EP | 779508 B1 | 6/2003 |

(56) References Cited

FOREIGN PATENT DOCUMENTS

| EP | 1239771 B1 | 10/2004 |
| EP | 1089067 B1 | 12/2004 |
| EP | 783867 B1 | 2/2006 |
| EP | 1026999 B1 | 6/2006 |
| EP | 1161924 B1 | 12/2006 |
| EP | 1519769 B1 | 2/2007 |
| EP | 765134 B1 | 7/2007 |
| EP | 1071473 B1 | 10/2007 |
| EP | 1692510 B1 | 1/2008 |
| EP | 1144049 B1 | 3/2008 |
| EP | 1383542 B1 | 4/2008 |
| EP | 1912059 | 4/2008 |
| EP | 1314395 B1 | 6/2008 |
| EP | 1520508 B1 | 11/2008 |
| EP | 1304955 B1 | 12/2008 |
| EP | 1281405 B1 | 1/2009 |
| EP | 1217943 B1 | 4/2009 |
| EP | 1196088 B1 | 9/2009 |
| EP | 1778076 B1 | 9/2009 |
| EP | 1277436 B1 | 12/2009 |
| EP | 1830705 B1 | 12/2010 |
| EP | 2073706 B1 | 10/2011 |
| EP | 1617761 B1 | 1/2012 |
| EP | 1045717 B1 | 3/2012 |
| EP | 2291640 | 12/2012 |
| EP | 1576181 B1 | 8/2013 |
| EP | 3171765 | 5/2018 |
| GB | 2367125 A | 3/2002 |
| JP | 35940830 | 3/1984 |
| JP | H02-195235 | 8/1990 |
| JP | 104127039 | 4/1992 |
| JP | 05337142 | 12/1993 |
| JP | H07-044707 | 2/1995 |
| JP | H08-320321 | 12/1996 |
| JP | H09-173048 | 7/1997 |
| JP | 10096697 A | 4/1998 |
| JP | 0328129 | 12/1998 |
| JP | 2001503645 | 3/2001 |
| JP | 2004127039 A | 4/2004 |
| JP | 2004237081 | 8/2004 |
| JP | 2005233636 A | 9/2005 |
| JP | 2005331889 A | 12/2005 |
| JP | 2006081842 | 3/2006 |
| JP | 2006094761 | 4/2006 |
| JP | 2006-122335 A | 5/2006 |
| JP | 2006515065 | 5/2006 |
| JP | 2006187598 | 7/2006 |
| JP | 2007050010 | 3/2007 |
| JP | 2007151782 | 6/2007 |
| JP | 2007515947 | 6/2007 |
| JP | 2007516009 | 6/2007 |
| JP | 2007198845 | 8/2007 |
| JP | 2007524389 | 8/2007 |
| JP | 2007526478 | 9/2007 |
| JP | 2008304298 | 12/2008 |
| JP | 4475923 | 6/2010 |
| JP | 2011103118 | 5/2011 |
| JP | 2011521237 | 7/2011 |
| JP | 2024037187 | 3/2024 |
| JP | 7482732 | 5/2024 |
| WO | 1994/021816 | 9/1994 |
| WO | 1997015226 | 5/1997 |
| WO | 2000/025114 | 5/2000 |
| WO | 2002/055729 | 7/2002 |
| WO | 02061405 | 8/2002 |
| WO | 03095995 | 11/2003 |
| WO | 2004025556 | 3/2004 |
| WO | 2006/007715 | 1/2006 |
| WO | 2006101736 | 9/2006 |
| WO | 2007035829 | 3/2007 |
| WO | 2008028298 | 3/2008 |
| WO | 2009140757 | 11/2009 |
| WO | 2012075028 | 6/2012 |
| WO | 2012083349 | 6/2012 |
| WO | 2016011534 | 1/2016 |
| WO | 2017079844 | 5/2017 |
| WO | 2019092509 | 5/2019 |

OTHER PUBLICATIONS

Gupta et al., "Wood's lamp," Department of Dermatology, Venereology &Leprology, Dr. S. N. Medical College, Jodhpur,India, published in Indian J Dermatol Venereol Leprol, Mar.-Apr. 2004, vol. 70, Issue 2.
F. Fisher et al., "An Affordable, Portable Fluorescence Imaging Device for Skin Lesion Detection Using a Dual Wavelength Approach for Image Contrast Enhancement and Aminolaevulinic Acid-induced Protoporphyrin IX. Part I. Design, Spectral and Spatial Characteristics," Department of Chemistry and Chemical Engineering, Royal Military College of Canada, published in Lasers Med Sci 2001 16:199-206.
Notice of Allowance in U.S. Appl. No. 16/027,775, dated Oct. 29, 2020.
Office Action in U.S. Appl. No. 14/719,493, dated Dec. 22, 2020.
JP Office Action dated Feb. 9, 2021 for JP Application No. 2019-102705.
CN Office Action dated Dec. 28, 2020 in related CN Application No. 2015102835236.
Notice of Allowance in U.S. Appl. No. 16/027,775, dated Mar. 2, 2021.
U.S. Appl. No. 17/193,318, filed Mar. 5, 2021.
Final Office Action dated Jun. 14, 2021 in related U.S. Appl. No. 14/719,493, 28 pages.
Office Action dated Jun. 29, 2021 in related U.S. Appl. No. 15/965,462, 16 pages.
U.S. Appl. No. 17/407,870, filed Aug. 20, 2021.
Office Action from U.S. Appl. No. 16/027,775, dated Feb. 5, 2019.
Partial European Search Report from European Application No. 18205726.5, dated May 14, 2019.
European Search Report from European Application No. 18205726.5, dated Sep. 12, 2019.
Office Action from U.S. Appl. No. 16/027,775, dated Sep. 12, 2019.
Office Action from Chinese Patent Application No. 2015-10283523.6, dated Aug. 8, 2019.
Notice of Allowance from U.S. Appl. No. 16/027,775, dated Nov. 22, 2019.
First Office Action in JP Application No. 2019-102705, dated Jul. 14, 2020.
Grossweiner, "PDT light dosimetry revisited," Journal of Photochemistry and Photobiology B:Biology 38, 1997:258-268 ;11 pages).
Tonnesen et al., "Angiogenesis in Wound Healing," The Society for Investigative Dermatology, Inc. 2000; 5(1):40-46 (7 pages).
Chwirot et al., "Detection of Melanomas by Digital Imaging of Spectrally Resolved Ultraviolet Light-induced Autofluorescence of Human Skin," European Journal of Cancer, vol. 34, No. 11:1730-1734, 1998 (5 pages).
Bishop, "Burn wound assessment and surgical management." Crit Care Nurs Clin North Am. 2004; 16(1):145-177 Abstract 1 page).
Charles, "Radon exposure of the skin: II. Estimation of the attributable risk for skin cancer incidence," Journal of Radiological Protection 2007, 27(3):253-274 (23 pages).
Prettry, "Caries detection and diagnosis: Novel technologies," Journal of Dentistry 2006, 34(10):727-739 (13 pages).
Kois et al., "Detecting oral cancer: a new technique and case reports." Dent Today, Oct. 2006; 25(10):94 and 36-97 (Abstract 1 page).
Bogaards et al., "Increased Brain Tumor Resection Using Fluorescence Image Guidance in a Preclinical Model," Lasers in Surgery and Medicine 2004; 35:181-190 (10 pages).
Kingsley, "The Wound Infection Continuum and its Application to Clinical Practice," Ostomy Wound Management, Jul. 2003, 49(7A Suppl):1-7 (8 pages).
Sibbald et al., "Increased Bacterial Burden and Infection: The Story of Nerds and Stones," Advances in Skin & Wound Care, Oct. 2006; 19:447-461 (15 pages).

(56)     References Cited

OTHER PUBLICATIONS

Bauer et al., "Angiogensis, Vasculogenesis, and Induction of Healing in Chronic Wounds," Vascular and Endovascular Surgery vol. 39, No. 4, 2005:293-306 (14 pages).

Brem et al., "Cellular and molecular basis of wound healing in diabetes," The Journal of Clinical Investigation, May 2007, vol. 117, No. 5:1219-1222 (4 pages).

Badiavas et al., "Treatment of Chronic Wounds With Bone Marrow-Derived Cells," Arch Dermatol, Apr. 2003, vol. 139 A):510-516 (7 pages).

Phillips, "Biologic skin substitutes." J Dermatol Surg Oncol. Aug. 1993, 19(8):794-800 (Abstract 1 page).

Falanga et al., Wounding of Bioengineered Skin: Cellular and Molecular Aspects After Injury, J. Invest Dermatol 2002, 119(3):653-660 (8 pages).

Culting et al., Journal of Wound Care 1994, 3:198-201.

Dow G. In: Krasner et al. eds. "Chronic Wound Care: A Clinical Source Book for Healthcare Professionals," 3rd ed. Wayne Pa: HMP Communications 2001:343-356.

Physiological basis of wound healing in Developments in wound care, PJB Publications Ltd., 5-17, 1994.

Cooper et al., Wound Infection and Microbiology. Medical Communications (UK) Ltd for Johnson & Johnson Medical, 2003.

Mortimer PS. In: Doyle et al. editors. Oxford Textbook of Palliative Medicine (2nd ed). Oxford: Oxford University Press, 1998, 617-627.

Englund F. RCN Contact 1993.

Galpin et al., "Sepsis Associated with Decubitus Ulcers," The American Journal of Medicine, Sep. 1976, vol. 61 pp. 346-350 (5 pages).

Ayton M., "Wound Care: wounds that won't heal," Nurs Times Nov. 1985; 81(46): suppl 16-19 (1 page).

Grocott P., "The palliative management of fungating malignant wounds.", J Wound Care May 1995, 4(5);240-242 (1 page).

Collier M., The assessment of patients with malignant fungating wounds—a holistic approach: Part 1., Nurs Times Oct. 29-Nov. 4, 1997; 93(44): suppl 1-4 (1 page).

Grocott P., "The management of fungating wounds." J Wound Care May 1999; 8(5):232-234 (1 page).

Young T., "The challenge of managing fungating wounds." Oct. 1997; 3(9): 41-44 (1 page).

Website http://www.iec.ch/online news/etech/arch_2006/etech_0906/focus.htm.

Office Action in JP Application No. 2011-509825, dated Jun. 3, 2014.

Communication in EP Application No. 15 824 466.5 dated Apr. 19, 2018.

Office Action in CA Application No. 2,891,990, dated Jun. 30, 2017.

Notice of Grounds of Rejection in JP Application No. 2011-509826, dated Oct. 8, 2013.

Notification of the First Office Action in CN Application No. 2015102835236, dated Apr. 14, 2017.

Office Action in CA Application No. 2,724,973, dated Jun. 25, 2014.

Examination Report in IN Application No. 9067/DELNP/2010, dated May 29, 2018.

Notice of Grounds of Rejection in JP Application No. 2017-098103, dated May 29, 2018.

Treuillet, S. et al. "Three-Dimensional Assessment of Skin Wounds Using a Standard Digital Camera", IEEE Transactions on Medical Imaging, May 2009, vol. 28, No. 5, pp. 752-762.

Office Action in CN Application No. 200980128426.2, dated Dec. 24, 2012.

Notice of Grounds of Rejection in JP Application No. 2014-207852, dated Sep. 20, 2016.

Notice of Reexamination in CN Application No. 2009-80128426, dated Jul. 8, 2014.

Communication in EP Application No. 09749361.3, dated Nov. 11, 2015.

Final Decision for Rejection in JP Application No. 2011-509826, dated Jun. 10, 2014.

Examination Report in CA Application No. 2,891,990, dated Jul. 5, 2016.

Final Office Action dated Aug. 31, 2022 in related U.S. Appl. No. 17/193,318, 35 pages.

Office Action dated Sep. 13, 2022 in related JP Application No. 2019-102705.

Final Additional Submission in reply to statement filed Jun. 15, 2022 related to pre-grant opposition Indian Patent Application No. 9067/DELNP/2010, 417 pages.

*Adiuvo Diagnostics Private Limited* Vs. *University Health Network*, Evidence by way of an Affidavit on behalf of the opponent, 13 pages.

Hiram C. Polk, Jr "Early Detection of Pseudomonas Burn Infection", Clinical Experience with Wood's Light Fluorescence, Arch Surg/vol. 98, Mar. 1969, 3 pages.

S Veeranna, "Wood's lamp: A modified method of examination" Indian J Dermatol Venereol Leprol Sep.-Oct. 2005 vol. 71 Issue 5, 2 pages.

Ev Vogeley, MD, JD, "Experience With Wood Lamp Illumination and Digital Photography in the Documentation of Bruises on Human Skin", vol. 156, Mar. 2002, www.archpediatrics.com, 4 pages.

Adiuvo Diagnostics private limited Pre-grant opposition filed Jan. 3, 2021 for Pre-grant Opposition Indian patent Application: 9067/DELNP/2010, 640 pages.

Office Action dated Sep. 13, 2022 in related CA Application No. 3,162,577.

Non Final Office Action in U.S. Appl. No. 14/719,493, dated Nov. 7, 2018.

Non Final Office Action in U.S. Appl. No. 16/027,775, dated Feb. 5, 2019.

Decision of Rejection in JP Application No. 2019-102705 dated Sep. 28, 2021, 6 pages.

Office Action dated Oct. 5, 2021 in related U.S. Appl. No. 17/193,318, 24 pp.

Wieringa, F. P., Mastik, F., Cate, F. J., Neumann, H. A., & van der Steen, A. F. (2006). Remote non-invasive stereoscopic imaging of blood vessels: first in-vivo results of a new multispectral contrast enhancement technology. Annals of biomedical engineering, 34(12), 1870-1878. (Year: 2006).

U.S. Appl. No. 17/509,914, filed Oct. 25, 2021.

Office Action dated Nov. 3, 2021 for U.S. Appl. No. 16/593,174, 16 Pp.

Notice of Allowance dated Nov. 12, 2021 for U.S. Appl. No. 15/965,462, 15 pp.

Notice of Allowance dated Nov. 26, 2021 for U.S. Appl. No. 14/719,493.

First Examination Report for Indian Application No. 202018049911, dated Nov. 30, 2021.

International Search Report in PCT/CA2015/000444 mailed Oct. 30, 2015.

Office Action in CN Appln No. 201510283523.6 dated Apr. 14, 2017.

Office Action in JP Appln No. 2014-207852 dated Oct. 27, 2015.

Office Action in JP Appln No. 2011-509826 dated Oct. 8, 2013.

Office Action in CA Appln No. 2,724,973 dated Jun. 25, 2014.

Communication in EP Appln No. 09749361.3 dated Nov. 6, 2012.

Extended European Search Report in PCT/CA2009/000680 dated Nov. 6, 2012.

Notification of Reexamination in CN Appln No. 200980128426.2 dated Jul. 8, 2014.

Extended Supplementary European Search Report in EP Appln No. 09 74 9361, dated Oct. 25, 2012.

Non-Final Office Action in U.S. Appl. No. 15/328,214, dated Apr. 3, 2018.

Non-Final Office Action in U.S. Appl. No. 12/992,040, dated Jun. 25, 2014.

Final Office Action in U.S. Appl. No. 12/992,040, dated Dec. 29, 2014.

Notice of Allowance in U.S. Appl. No. 12/992,040, dated Jan. 23, 2015.

Notification of Second Office Action in CN Appln No. 200980128426.2, mailed Dec. 24, 2012.

(56) References Cited

OTHER PUBLICATIONS

Chinese Office Action for Chinese Patent Application No. CN100098 dated Feb. 1, 2012 (6 pages).
A Thesis: Non-invasive Optical Technologies to Monitor Wound Healing, Zhu, Drexel University, Dec. 2007 (189 pages).
In vivo fluorescence imaging for tissue diagnostics, Andersson-Engels et al., Phys. Med. Biol. 42 (1997):815-824 (10 pages).
International Search Report dated Sep. 24, 2009 for International Application No. PCT/CA2009/000680 (3 pages).
Broer et al. "Laserinduced Fluorescence Spectroscopy for Real-Time Tissue Differentiation", Medical Laser Application 19:45-53, 2004 (9 pages).
DaCosta, et al., "Autofluorescence characterisation of isolated whole crypts and primary cultured human epithelial cells from normal, hyperplastic, and adenomatous colonic mucosa", J Clin Pathol 2005; 58:766-774 (10 pages).
Jacques et al., "PDT with ALA/PPIX is enhanced by prolonged light exposure putatively by targeting mitochondria." SPIE Proceedings, vol. 2972, Optical Methods for Tumor Treatment and Detection, ed T. Dougherty, San Jose, Feb. 1997 (5 pages).
Bowler et al., "Wound Microbiology and Associated Approaches to Wound Management," Clinical Microbiology Reviews 2001, 14:244-269 (27 pages).
Dow et al., "Infection in chronic wounds: controversies in diagnosis and treatment.", Ostomy/VVound Management 1999, 45:23-40 (Abstract—1 page).
Winter, "Formation of the Scab and the Rate of Epithelization of Superficial Wounds in the Skin of the Young Domestic Pig," Nature, Jan. 20, 1962, 193:293-294 (2 pages).
Perednia, "What dermatologists should know about digital imaging," J Am Acad Dermatol 1991, 25:89-108 (20 pages).
Serena et al., "The Lack of Reliability of Clinical Examination in the Diagnosis of Wound Infection: Preliminary Communication," The International Journal of Lower Extremity Wounds, V7(1); Mar. 2008:32-35 (4 pages).
Gardner et al., "Diagnostic Validity of Semiquantitative Swab Cultures," Wounds Feb. 2007; vol. 19, Issue 2:31-38 (8 pages).
Falanga et al., "Workshop on the Pathogenesis of Chronic Wounds," J. Invest Dermatol 1994, 102(1):125-127 (4 pages).
Kingsley et al., "A proactive approach to wound infection", Nursing Standard Apr. 2001; 15(30): 50-54, 56 & 58 (6 pages).
DaCosta et al., "Molecular Fluorescence Excitation-Emission Matrices Relevant to Tissue Spectroscopy", Photochemistry and Photobiology Oct. 2003, 78(4):384-392 (9 pages).
DaCosta et al., "New optical technologies for earlier endoscopic diagnosis of premalignant gastrointestinal lesions", Journal of Gastroenterology and Hepatology (2002) 17 (Suppl.) S85-S104 (20 pages).
Poh et al., "Direct Fluorescence Visualization of Clinically Occult High-Risk Oral Premalignant Disease Using a Simple Hand-Held Device", Head & Neck—DOI, Jan. 2007; 29(1):71-76 (6 pages).
Hanibuchi et al., "Autofluorescence bronchoscopy, a novel modality for the early detection of bronchial premalignant and malignant lesions", The Journal of Medical Investigation 2007, vol. 54:261-266 (6 pages).
D'Hallewin et al., "Fluorescence Detection of Bladder Cancer: A Review", European Urology 2002, 42(5):417-425 (9 pages).
Rotomskis et al., "Spectroscopic studies of photobleaching and photoproduct formation of porphyrins used in tumor therapy," Journal of Photochemistry and Photobiology B:Biology 33, 1996:61-67 (7 pages).
Yasui et al., "Determination of collagen fiber orientation in human tissue by use of polariztation measurement of molecular second-harmonic-generation light", Applied Optics May 10, 2004; vol. 43, No. 14:2861-2867 (7 pages).
Dietel et al., "5-Aminolaevulinic acid (ALA) induced formation of different fluorescent porphyrins: A study of the biosynthesis of porphyrins by bacteria of the human digestive tract", Journal of Photochemistry and Photobiology B: Biology 86:77-86, (2007) (10 pages).

Bissonette et al., "Current status of photodynamic therapy in dermatology." Dermatol Clin. Jul. 1997, 15(3):507-519 (Abstract 1 page).
Carruth, "Clinical applications of photodynamic therapy.", Int. J. Clin. Pract. Jan.-Feb. 1998; 52(1):39-42 (Abstract 1 page).
Dougherty et al. "Photodynamic Therapy", Journal of the National Cancer Institute, vol. 90, No. 12, Jun. 17, 1998:889-905 (17 pages).
Jori et al., "Photodynamic Therapy in the Treatment of Microbial Infections: Basic Principles and Perspective Applications", Lasers in Surgery and Medicine Jun. 2006, 38(5):468-481 (14 pages).
Hamblin et al., "Photodynamic therapy: a new antimicrobial approach to infectious disease?", Photochem Photobiol Sci. May 2004; 3(5):436-450 (30 pages).
Gudgin et al., "On the role of protoporphyrin IX photoproducts in photodynamic therapy," Journal of Photochemistry and Photobiology B: Biology 29; 1995:91-93 (3 pages).
Konig et al., "In vivo photoproduct formation during PDT with ALA-induced endogenous porphyrins," J. Photochem. Photobiol. B: Biol., 18 (1993):287-290 (4 pages).
Georgakoudi et al., "The Mechanism of Photofrin Photobleaching and Its Consequences for Photodynamic Dosimetry," Photochemistry and Photobiology, 1997, 65(1):135-144 (10 pages).
Grossweiner, "Optical Dosimetry in Photodynamic Therapy," Lasers in Surgery and Medicine, 1986; 6:462-466 (5 pages).
Jongen et al., "Mathematical description of photobleaching in vivo describing the influence of tissue optics on measured fluorescence signals", Phys. Med. Biol. 42, 1997:1701-1716 (17 pages).
Rhodes et al., "Iontophoretic Delivery of ALA Provides a Quantitative Model for ALA Pharmacokinetics and PpIX Phototoxicity in Human Skin," The Society for Investigative Dermatology, Inc. 1997; 108:87-91 (6 pages).
Robinson et al., "Fluorescence Photobleaching of ALA-induced Protoporphyrin IX during Photodynamic Therapy of Normal Hairless Mouse Skin: The Effect of Light Dose and Irradiance and the Resulting Biological Effect," Photochemistry and Photobiology, 1998, 67(1):140-149 (10 pages).
Song, et al., "Pork Freshness Detecting Method Based on the Change of Germ Area," Journal of Agricultural Mechanization Research, May 31, 2009.
Second Office Action in CN Application No. 2015102835236, dated Mar. 5, 2018.
Office Action dated May 13, 2022 in related U.S. Appl. No. 17/193,318, 34 pages.
Specification and Drawings filed Jul. 1, 2022 in U.S. Appl. No. 17/856,487.
Examination Report dated Mar. 10, 2022 in EP 18205726.5.
First Examination Report for IN App No. 202018050052 dated Dec. 1, 2021.
Office Action dated Jan. 27, 2022 in related U.S. Appl. No. 17/193,318.
Notice of Allowance dated Jan. 24, 2022 in CA Application No. 2891990.
Office Action dated Dec. 20, 2022 in related JP Appliation No. 2022-011965.
Priority U.S. Appl. No. 62/584,404, filed Nov. 10, 2017.
Ferenczi., Web archive from the Wayback machine—"Camera review: Google turns its attention to imaging on new Nexus 5", Digital Photography review, Nov. 29, 2013.
Petitioner's Opposition to Patent Owner's Motion to Amend filed Apr. 27, 2023 in U.S. Pat. No. 11,266,345.
Office Action dated Aug. 11, 2023 in related U.S. Appl. No. 17/193,318.
Office Action dated Sep. 12, 2023 in related JP Application No. 2022-011965.
Office Action dated Oct. 2, 2023 received in related U.S. Appl. No. 17/856,487, 7 pages.
Office Action dated Oct. 23, 2023 received in related U.S. Appl. No. 18/334,133, 18 pages.
Notice of Allowance dated Dec. 6, 2023 in related U.S. Appl. No. 18/148,861.
Notice of Allowance dated Dec. 12, 2023 in related U.S. Appl. No. 18/334,123, 8 pages.

(56) References Cited

OTHER PUBLICATIONS

Notice of Allowance dated Feb. 7, 2024 in related U.S. Appl. No. 18/334,133, 9 pages.
Final Office Action dated Mar. 6, 2024 in related U.S. Appl. No. 17/193,318, 34 pp.
Application and Drawings filed Apr. 8, 2024 in related U.S. Appl. No. 18/629,603.
Application and Drawings filed Apr. 15, 2024 in related U.S. Appl. No. 18/635,677.
Notice of Allowance dated Mar. 19, 2024 in U.S. Appl. No. 18/334,123, 2 pages.
Application and Drawings filed May 13, 2024 in related U.S. Appl. No. 18/662,583.
Application and Drawings filed May 13, 2024 in related U.S. Appl. No. 18/662,750.
Office Action dated May 23, 2024 in related U.S. Appl. No. 17/509,914, 15 pp.
Godse et al_Mobile Camera Microphotography: A Simple but Elegant Technique for Telediagnosis of Malaria, JK Science, vol. 10 No. 3, Jul.-Sep. 2008.
Office Action dated Mar. 1, 2023 in related U.S. Appl. No. 17/193,318, 33 pp.
Office Action dated Aug. 1, 2024 in related U.S. Appl. No. 17/407,870.
Office Action dated Aug. 23, 2024 received in related U.S. Appl. No. 18/662,583.
Office Action dated Sep. 3, 2024 in related CA Application No. 3,194,784.
Office Action dated Sep. 16, 2024 in related U.S. Appl. No. 18/662,750, 24 pages.
Notice of Allowance dated Oct. 17, 2024 in related U.S. Appl. No. 17/193,318.
Office Action dated Oct. 29, 2024 received in related U.S. Appl. No. 18/629,603, 10 pp.
Notice of Allowance dated Oct. 24, 2024 recived in related U.S. Appl. No. 17/856,487, 13 pp.
Office Action dated Dec. 6, 2024 received in related U.S. Appl. No. 18/635,677, 13 pp.
Corrected Notice of Allowability dated Dec. 11, 2024 in related U.S. Appl. No. 17/856,487.
Final Office Action dated Dec. 11, 2024 received in related U.S. Appl. No. 18/662,583.
Final Office Action dated Jan. 2, 2025 received in related U.S. Appl. No. 18/662,750.
Corrected Notice of Allowability dated Jan. 3, 2025 received in related U.S. Appl. No. 17/193,318.
Application and Drawings filed Jan. 16, 2025 in related U.S. Appl. No. 19/025,073.
Application and Drawings filed Jan. 16, 2025 in related U.S. Appl. No. 19/025,440.
Application and Drawings filed Jan. 16, 2025 in related U.S. Appl. No. 19/025,446.
Application and Drawings filed Jan. 16, 2025 in related U.S. Appl. No. 19/025,507.
Application and Drawings filed Jan. 16, 2025 in related U.S. Appl. No. 19/024,995.
Application and Drawings filed Jan. 16, 2025 in related U.S. Appl. No. 19/025,038.
Application and Drawings filed Jan. 17, 2025 in related U.S. Appl. No. 19/027,622.
Application and Drawings filed Jan. 17, 2025 in related U.S. Appl. No. 19/027,127.
Application and Drawings filed Jan. 17, 2025 in related U.S. Appl. No. 19/027,145.

Application and Drawings filed Jan. 17, 2025 in related U.S. Appl. No. 19/028,009.
Application and Drawings filed Jan. 17, 2025 in related U.S. Appl. No. 19/027,847.
Application and Drawings filed Jan. 17, 2025 in related U.S. Appl. No. 19/027,884.
Application and Drawings filed Jan. 17, 2025 in related U.S. Appl. No. 19/027,928.
Application and Drawings filed Jan. 17, 2025 in related U.S. Appl. No. 19/028,076.
Final Office Action dated Jul. 23, 2025 received in U.S. Appl. No. 18/635,677, 13 pp.
Office Action dated Sep. 8, 2025 in U.S. Appl. No. 17/407,870.
Final Office Action dated Feb. 11, 2025 received in U.S. Appl. No. 17/509,914.
Christoph Ebner, et al., "Mobile teledermatology: a feasibility study of 58 subjects using mobile phones," Journal of Telemedicine and Telecare 2008; 14: 2-7.
Final Office Action dated Feb. 12, 2025 in U.S. Appl. No. 17/407,870.
Office Action dated Mar. 4, 2025 in JP Application No. 2022-011965.
Office Action dated Feb. 20, 2025 in CA Application No. 3,194,784.
Office Action dated Mar. 12, 2025 in U.S. Appl. No. 19/028,076.
Office Action dated Mar. 12, 2025 in U.S. Appl. No. 19/027,847.
Application and Drawings filed Mar. 17, 2025 in related U.S. Appl. No. 19/081,680.
Office Action dated Mar. 20, 2025 in U.S. Appl. No. 19/027,884.
Office Action dated Mar. 21, 2025 in U.S. Appl. No. 19/027,928.
Office Action dated Mar. 26, 2025 in U.S. Appl. No. 19/025,446.
Office Action dated Mar. 26, 2025 in U.S. Appl. No. 19/025,440.
Office Action dated Mar. 26, 2025 in U.S. Appl. No. 19/024,995.
Office Action dated Mar. 28, 2025 in U.S. Appl. No. 19/025,507.
Office Action dated Mar. 28, 2025 in U.S. Appl. No. 19/025,038.
Office Action dated Apr. 10, 2025 in U.S. Appl. No. 19/027,622.
Duckworth et al ("A clinically affordable non-contact wound measurement device." Proceedings of Rehab Engineering Society of North America (RESNA) 2007).
Office Action dated Apr. 10, 2025 in U.S. Appl. No. 18/662,583.
Notice of Allowance dated Apr. 9, 2025 in U.S. Appl. No. 18/629,603.
Notice of Allowance dated Jul. 1, 2025 in U.S. Appl. No. 19/027,847.
Final Office Action dated Jul. 1, 2025 in U.S. Appl. No. 19/028,076.
Final Office Action dated Jul. 8, 2025 in U.S. Appl. No. 19/024,995.
Final Office Action dated Jul. 9, 2025 in U.S. Appl. No. 19/025,440.
Final Office Action dated Jul. 10, 2025 in U.S. Appl. No. 19/025,446.
Final Office Action dated Jul. 11, 2025 in U.S. Appl. No. 19/027,928.
Final Office Action dated Jul. 21, 2025 in U.S. Appl. No. 19/025,507.
Final Office Action dated Jul. 25, 2025 in U.S. Appl. No. 19/027,622.
Final Office Action dated Jul. 29, 2025 in U.S. Appl. No. 19/027,884.
Final Office Action dated Aug. 4, 2025 received in U.S. Appl. No. 18/662,583.
Office Action dated Aug. 4, 2025 received in U.S. Appl. No. 18/662,750.
Application and Drawings filed Aug. 6, 2025 in U.S. Appl. No. 19/292,051.
Office Action dated Sep. 22, 2025 received in U.S. Appl. No. 17/509,914.
Notice of Allowance dated Sep. 23, 2025 in U.S. Appl. No. 19/027,928.
Corrected Notice of Allowance dated Sep. 30, 2025 in U.S. Appl. No. 19/027,928.
Final Office Action dated Oct. 7, 2025 in U.S. Appl. No. 19/025,038.
Notice of Allowance dated Oct. 8, 2025 in U.S. Appl. No. 19/028,076.
Corrected Notice of Allowance dated Oct. 30, 2025 in U.S. Appl. No. 19/027,928.

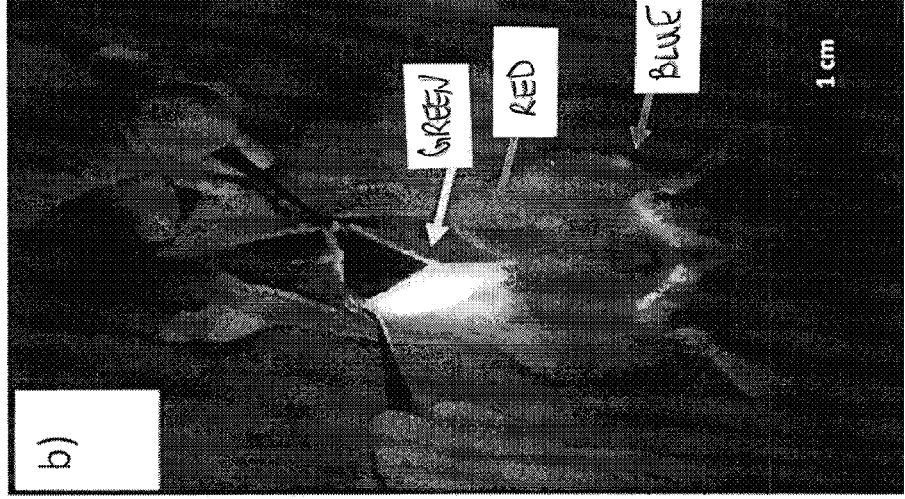
Figure 14

| | Chronic wound in diabetic patient | Wound in diabetic mouse/rat |
|---|---|---|
| Macromolecular | | |
| Nerve count | ↓ | ↓ |
| Angiogenesis | ↓ | ↓ |
| Granulation tissue formation | ↓ | ↓ |
| Collagen content | ↓ | ↓ |
| Enzyme activity | | |
| NEP | ↑ | ↑ |
| NOS | ↑ | ↓ |
| Arginase | ↑ | ↑ (mouse, chronic) ↓ (rat) |
| MMPs | ↑ | ↑ |
| TIMP concentration | ↓ | ---- |
| Neutrophil elastase | ↑ | ---- |
| Cathepsin G | ↑ | ---- |
| Growth factors and receptors | | |
| IGF-1 | ↓ | ↓ |
| IGF-2 | ↑ | ↑ (mRNA) |
| IGF-R1 (mRNA) | ---- | ↓ |
| TGF-β1 | ↓ | ↓ |
| TGF-β2 | ↑ | ---- |
| TGF-β3 | ↑ | ---- |
| TGF-βR1 and -R2 | ↓ | ---- |
| PDGF | ↓ | ↓ |
| PDGF-R | ---- | ↓ |
| KGF (mRNA) | ---- | ↓ |
| aFGF (mRNA) | ---- | ↓ |
| bFGF (mRNA) | ---- | ↓ |
| FGF-R1, -2, -3 (mRNA) | ---- | ↓ |
| IL-6 | ---- | ↓ |
| VEGF | ---- | ↓ |
| NGF | ---- | ↓ |
| MIP-2 | ---- | ↑ |
| MCP-1 | ---- | ↑ |
| TNFα (mRNA) | ---- | ↑ |
| IL-1β (mRNA) | ---- | ↑ |
| Other | | |
| GSH | ↓ | ↓ |

FIGURE 22

Red                    Green                    Blue

DEVICES, METHODS, AND SYSTEMS FOR FLUORESCENCE-BASED IMAGING AND DETECTION OF LOCATION(S) AND/OR SOURCE(S) OF POTENTIAL CONTAMINATION AND/OR POLLUTION

This is application is a continuation application of U.S. application Ser. No. 14/719,493, filed May 22, 2015, which is a continuation application of U.S. application Ser. No. 12/992,040, filed on Feb. 7, 2011, now U.S. Pat. No. 9,042,967, which is a national stage application of PCT/CA2009/000680, filed internationally on May 20, 2009, which claims benefit to U.S. Provisional Application No. 61/054,780, filed May 20, 2008, the entire content of each of which is incorporated by reference herein.

TECHNICAL FIELD

A device and method for fluorescence-based imaging and monitoring is disclosed. In particular, the device and method may be suitable for monitoring biochemical and/or biological and non-biological substances, such as for the detection of bacteria.

BACKGROUND

Wound care is a major clinical challenge. Healing and chronic non-healing wounds are associated with a number of biological tissue changes including inflammation, proliferation, remodeling of connective tissues and, a common major concern, bacterial infection. A proportion of wound infections are not clinically apparent and contribute to the growing economic burden associated with wound care, especially in aging populations. Currently, the gold-standard wound assessment includes direct visual inspection of the wound site under white light combined with indiscriminate collection of bacterial swabs and tissue biopsies resulting in delayed, costly and often insensitive bacteriological results. This may affect the timing and effectiveness of treatment. Qualitative and subjective visual assessment only provides a gross view of the wound site, but does not provide information about underlying biological and molecular changes that are occurring at the tissue and cellular level. A relatively simple and complementary method that exploits 'biological and molecular' information to improve the early identification of such occult change is desirable in clinical wound management. Early recognition of high-risk wounds may guide therapeutic intervention and provide response monitoring over time, thus greatly reducing both morbidity and mortality due especially to chronic wounds.

Wound care and management is major clinical challenge that presents a significant burden and challenge to health care globally [Bowler et al., Clin Microbiol Rev. 2001, 14:244-269; Cutting et al., Journal of Wound Care. 1994, 3:198-201; Dow et al., Ostomy/Wound Management. 1999, 45:23-40]. Wounds are generally classified as, wounds without tissue loss (e.g. in surgery), and wounds with tissue loss, such as burn wounds, wounds caused as a result of trauma, abrasions or as secondary events in chronic ailments (e.g., venous stasis, diabetic ulcers or pressure sores and iatrogenic wounds such as skin graft donor sites and dermabrasions, pilonidal sinuses, non-healing surgical wounds and chronic cavity wounds). Wounds are also classified by the layers involved; superficial wounds involve only the epidermis, partial thickness wounds involve only epidermis and dermis, and full thickness wounds involve the subcutaneous fat or deeper tissue. Although restoration of tissue continuity after injury is a natural phenomenon, infection, quality of healing, speed of healing, fluid loss and other complications that enhance the healing time represents a major clinical challenge. The majority of wounds heal without any complication. However, chronic non-healing wounds involving progressively more tissue loss result in a large challenge for wound-care practitioners and researchers. Unlike surgical incisions where there is relatively little tissue loss and wounds generally heal without significant complications, chronic wounds disrupt the normal process of healing which is often not sufficient in itself to effect repair. Delayed healing is generally a result of compromised wound physiology [Winter (1962) Nature. 193:293-294] and typically occurs with venous stasis and diabetic ulcers, or prolonged local pressure as in immuno-suppressed and immobilized elderly individuals. These chronic conditions increase the cost of care and reduce the patient's quality of life. As these groups are growing in number, the need for advanced wound care products will increase.

Conventional clinical assessment methods of acute and chronic wounds continue to be suboptimal. They are usually based on a complete patient history, qualitative and subjective clinical assessment with simple visual appraisal using ambient white light and the 'naked eye', and can sometimes involve the use of color photography to capture the general appearance of a wound under white light illumination [Perednia (1991) J Am Acad Dermatol. 25: 89-108]. Regular re-assessment of progress toward healing and appropriate modification of the intervention is also necessary. Wound assessment terminology is non-uniform, many questions surrounding wound assessment remain unanswered, agreement has yet to be reached on the key wound parameters to measure in clinical practice, and the accuracy and reliability of available wound assessment techniques vary. Visual assessment is frequently combined with swabbing and/or tissue biopsies for bacteriological culture for diagnosis. Bacterial swabs are collected at the time of wound examination and have the noted advantage of providing identification of specific bacterial/microbial species [Bowler, 2001; Cutting, 1994; Dow, 1999; Dow G. In: Krasner et al. eds. Chronic Wound Care: A Clinical Source Book for Healthcare Professionals, 3rd ed. Wayne Pa.: HMP Communications. 2001:343-356]. However, often, multiple swabs and/or biopsies are collected randomly from the wound site, and some swabbing techniques may in fact spread the microorganisms around with the wound during the collection process thus affecting patient healing time and morbidity [Dow, 1999]. This may be a problem especially with large chronic (non-healing) wounds where the detection yield for bacterial presence using current swabbing and biopsy protocols is suboptimal (diagnostically insensitive), despite many swabs being collected. Thus, current methods for obtaining swabs or tissue biopsies from the wound site for subsequent bacteriological culture are based on a non-targeted or 'blind' swabbing or punch biopsy approach, and have not been optimized to minimize trauma to the wound or to maximize the diagnostic yield of the bacteriology tests. In addition, obtaining swabs and biopsy samples for bacteriology can be laborious, invasive, painful, costly, and more importantly, bacteriological culture results often take about 2-3 days to come back from the laboratory and can be inconclusive [Serena et al. (2008) Int J Low Extrem Wounds. 7(1):32-5.; Gardner et al., (2007) WOUNDS. 19(2):31-38], thus delaying accurate diagnosis and treatment [Dow, 1999]. Thus, bacterial swabs do not provide real-time detection of infectious status of wounds. Although wound swabbing appears to be straightforward, it can lead to inappropriate treatment, patient morbidity and increased hospital stays if not performed correctly [Bowler, 2001; Cutting, 1994; Dow, 1999; Dow, 2001]. The lack of a non-invasive imaging method to objectively and rapidly evaluate wound repair at a biological level (which may be at greater detail than simply appearance or morphology based), and to aid in targeting of the collection of swab and tissue biopsy samples for bacteriology is a major obstacle in clinical wound assessment and treatment. An alternative method is highly desirable.

As wounds (chronic and acute) heal, a number of key biological changes occur at the wound site at the tissue and cellular level [Cutting, 1994]. Wound healing involves a complex and dynamic interaction of biological processes divided into four overlapping phases—haemostasis, inflammation, cellular proliferation, and maturation or remodeling of connective tissues—which affect the pathophysiology of wound healing [Physiological basis of wound healing, in Developments in wound care, PJB Publications Ltd., 5-17, 1994]. A common major complication arising during the wound healing process, which can range from days to months, is infection caused by bacteria and other microorganisms [Cutting, 1994; Dow, 1999]. This can result in a serious impediment to the healing process and lead to significant complications. All wounds contain bacteria at levels ranging from contamination, through colonization, critical colonization to infection, and diagnosis of bacterial infection is based on clinical symptoms and signs (e.g., visual and odorous cues).

The most commonly used terms for wound infection have included wound contamination, wound colonisation, wound infection and, more recently, critical colonisation. Wound contamination refers to the presence of bacteria within a wound without any host reaction [Ayton M. *Nurs Times* 1985, 81(46): suppl 16-19], wound colonisation refers to the presence of bacteria within the wound which do multiply or initiate a host reaction [Ayton, 1985], Critical colonisation refers to multiplication of bacteria causing a delay in wound healing, usually associated with an exacerbation of pain not previously reported but still with no overt host reaction [Falanga et al., *J Invest Dermatol* 1994, 102(1): 125-27; Kingsley A, *Nurs Stand* 2001, 15(30): 50-54, 56, 58]. Wound infection refers to the deposition and multiplication of bacteria in tissue with an associated host reaction [Ayton, 1985]. In practice the term 'critical colonisation' can be used to describe wounds that are considered to be moving from colonisation to local infection. The challenge within the clinical setting, however, is to ensure that this situation is quickly recognized with confidence and for the bacterial bioburden to be reduced as soon as possible, perhaps through the use of topical antimicrobials. Potential wound pathogens can be categorised into different groups, such as, bacteria, fungi, spores, protozoa and viruses depending on their structure and metabolic capabilities [Cooper et al., *Wound Infection and Microbiology*.: Medical Communications (UK) Ltd for Johnson & Johnson Medical, 2003]. Although viruses do not generally cause wound infections, bacteria can infect skin lesions formed during the course of certain viral diseases. Such infections can occur in several settings including in health-care settings (hospitals, clinics) and at home or chronic care facilities. The control of wound infections is increasingly complicated, yet treatment is not always guided by microbiological diagnosis. The diversity of micro-organisms and the high incidence of polymicrobic flora in most chronic and acute wounds gives credence to the value of identifying one or more bacterial pathogens from wound cultures. The early recognition of causative agents of wound infections can assist wound care practitioners in taking appropriate measures. Furthermore, faulty collagen formation arises from increased bacterial burden and results in over-vascularized friable loose granulation tissue that usually leads to wound breakdown [Sapico et al. (1986) Diagn Microbiol Infect Dis. 5:31-38].

Accurate and clinically relevant wound assessment is an important clinical tool, but this process currently remains a substantial challenge. Current visual assessment in clinical practice only provides a gross view of the wound site (e.g., presence of purulent material and crusting). Current best clinical practice fails to adequately use the critically important objective information about underlying key biological changes that are occurring at the tissue and cellular level (e.g., contamination, colonization, infection, matrix remodeling, inflammation, bacterial/microbial infection, and necrosis) since such indices are i) not easily available at the time of the wound examination and ii) they are not currently integrated into the conventional wound management process. Direct visual assessment of wound health status using white light relies on detection of color and topographical/textural changes in and around the wound, and thus may be incapable and unreliable in detecting subtle changes in tissue remodeling. More importantly, direct visual assessment of wounds often fails to detect the presence of bacterial infection, since bacteria are occult under white light illumination. Infection is diagnosed clinically with microbiological tests used to identify organisms and their antibiotic susceptibility. Although the physical indications of bacterial infection can be readily observed in most wounds using white light (e.g., purulent exudate, crusting, swelling, erythema), this is often significantly delayed and the patient is already at increased risk of morbidity (and other complications associated with infection) and mortality. Therefore, standard white light direct visualization fails to detect the early presence of the bacteria themselves or identify the types of bacteria within the wound.

Implantation and grafting of stem cells have recently become of interest, such as for wound care and treatment. However, it is currently challenging to track the proliferation of stem cells after implantation or grafting. Tracking and identifying cancer cells have also been challenging. It would be desirable if such cells could be monitored in a minimally-invasive or non-invasive way.

It is also useful to provide a way for detecting contamination of other target surfaces, including non-biological targets.

SUMMARY

A device and method for fluorescence-based monitoring is disclosed. In some aspects, the device comprises an optical (e.g., fluorescence and/or reflectance) device for real-time, non-invasive imaging of biochemical and/or organic substances, for example wounds. This device may be compact, portable, and/or hand-held, and may provide high-resolution and/or high-contrast images. Such a device may be easily integrated into current wound care practice. This imaging device may rapidly and conveniently provide the clinician/health care worker with valuable biological information of a wound: including imaging of connective tissue changes, early detection of bacterial contamination/infection. The device may also facilitate wound margin delineation, image-guided collection of bacterial swab/biopsy samples, imaging of exogenous molecular biomarker-targeted and activated optical (e.g., absorption, scattering, fluorescence, reflectance) contrast agents, and may permit longitudinal monitoring of therapeutic response for adaptive intervention in wound management. By exploiting wireless capabilities with dedicated image analysis and diagnostic algorithms, the device may be integrated seamlessly into telemedicine (e.g., E-health) infrastructure for remote-access to specialists in wound care. Such a device may also have applications outside wound care, including early detection of cancers, monitoring of emerging photodynamic therapies, detection and monitoring of stem cells, and as an instrument in the dermatology and cosmetology clinics, in addition to detecting bacteria or contamination for other applications.

In some aspects, a method of detecting potential infection, contamination, and/or pollution sources in and/or on a target is provided. The method includes applying an exogenous, contrast agent to a target to be screened, the contrast agent configured to make bacteria, micro-organisms, and/or pathogens visible. The target to which the contrast agent has been applied is illuminated with excitation light emitted by at least one light excitation light source of a handheld device, the at least one excitation light source emitting at least one wavelength or wavelength band causing at least one biomarker on and/or in the illuminated target to fluoresce. With at least one optical filter of the handheld device, optical signals responsive to illumination of the target including the contrast agent with the excitation light are filtered, the at least one optical filter being configured to enable optical signals having a wavelength corresponding to fluorescence of the at least one biomarker to pass through the filter. Biomarker fluorescence data regarding the illuminated target is collected with an image sensor of the handheld device, wherein the collected biomarker fluorescence data comprises at least one image containing data relating to exogenous fluorescence of bacteria, micro-organisms, and/or pathogens responsive to illumination of the target. And, in real-time, based on at least the collected biomarker fluorescence data, the presence and/or location of sources of potential infection, contamination, and/or pollution on and/or in the illuminated target are determined.

In some aspects, a method for fluorescence-based imaging of a target to detect contamination and/or pollutants is provided. The method includes labelling a pre-selected biomarker at the target with at least one fluorescing contrast agent. The target is illuminated with excitation light emitted by an excitation light source and having at least one wavelength or wavelength band causing at least the pre-selected biomarker to fluoresce. Fluorescence emissions of at least the pre-selected biomarker are detected with an image detector of a handheld imaging device. And the presence, location, and/or quantity of contamination and/or pollutants on and/or in the illuminated target is determined based on the detected fluorescence emissions of at least the pre-selected biomarker.

BRIEF DESCRIPTION OF DRAWINGS

FIG. 22 is a table showing examples of tissue, cellular and molecular biomarkers known to be associated with wound healing;

DETAILED DESCRIPTION

Figure 1:
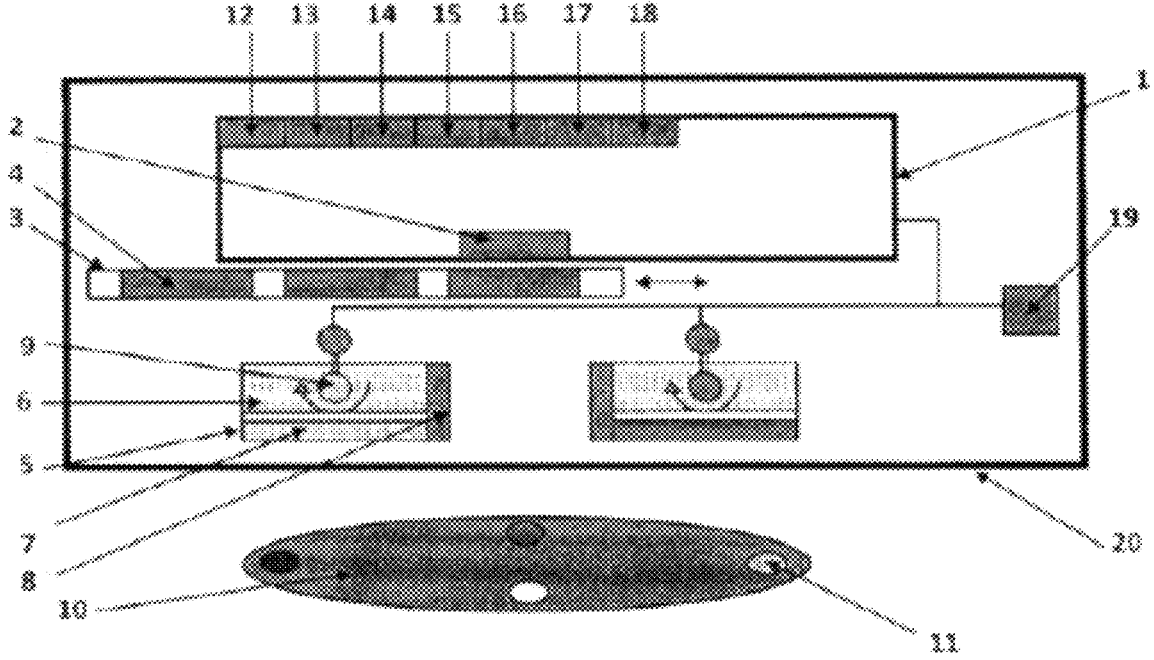
FIG. 1 is a schematic diagram of a device for fluorescence-based monitoring.
Figure 1B:
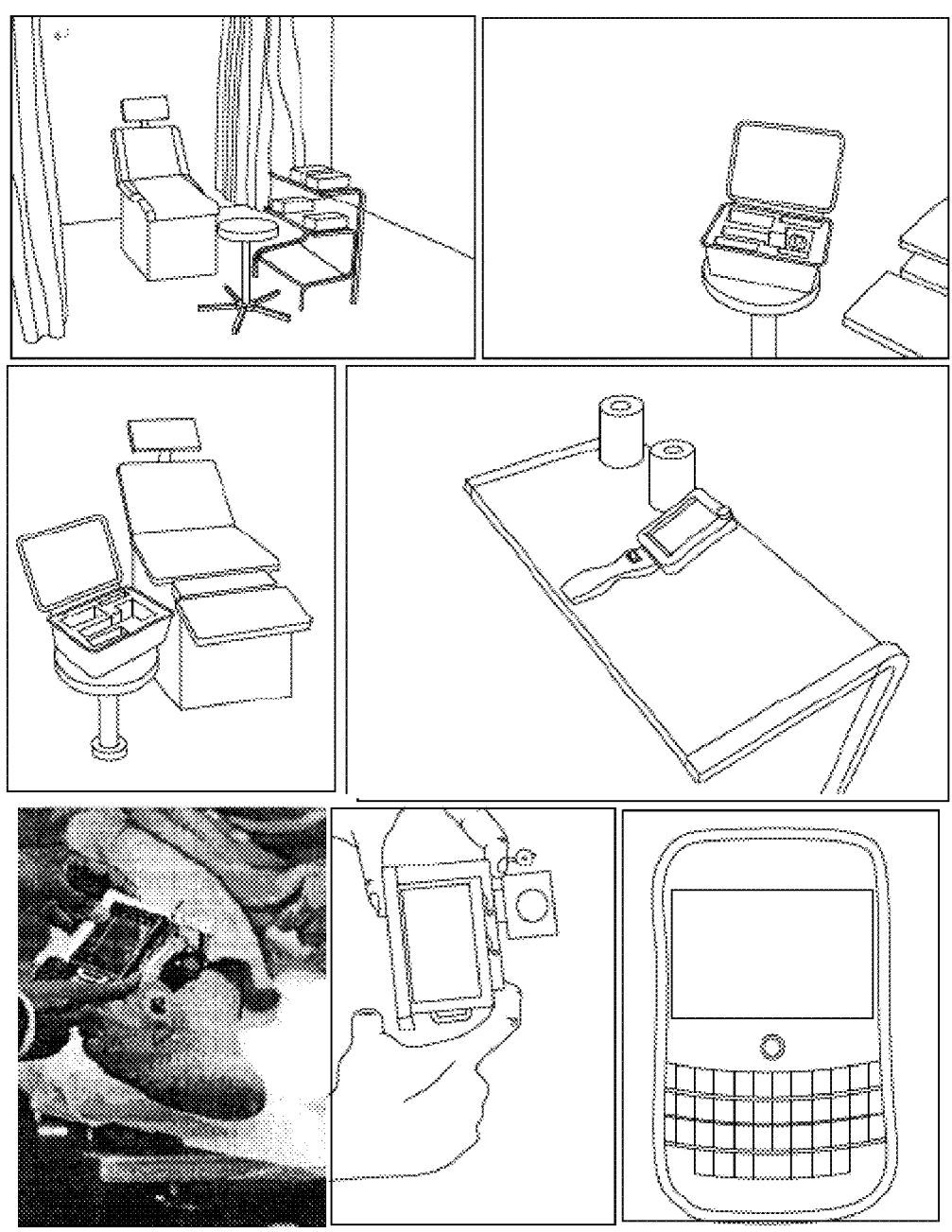
FIG. 1b shows an example of a clinical wound care facility using a device for fluorescence-based monitoring.

Wound progression is currently monitored manually. The National Pressure Ulcer Advisory Panel (NPUAP) developed the Pressure Ulcer Scale for Healing (PUSH) tool that outlines a five-step method of characterizing pressure ulcers. This tool uses three parameters to determine a quantitative score that is then used to monitor the pressure ulcer over time. The qualitative parameters include wound dimensions, tissue type, and the amount of exudate or discharge, and thermal readings present after the dressing is removed. A wound can be further characterized by its odor and color. Such an assessment of wounds currently does not include critical biological and molecular information about the wound. Therefore, all descriptions of wounds are somewhat subjective and noted by hand by either the attending physician or the nurse.

What is desirable is a robust, cost-effective non-invasive and rapid imaging-based method or device for objectively assessing wounds for changes at the biological, biochemical and cellular levels and for rapidly, sensitively and non-invasively detecting the earliest presence of bacteria/microorganisms within wounds. Such a method or device for detection of critical biological tissue changes in wounds may serve an adjunctive role with conventional clinical wound management methods in order to guide key clinico-pathological decisions in patient care. Such a device may be compact, portable and capable of real-time non-invasive and/or non-contact interrogation of wounds in a safe and convenient manner, which may allow it to fit seamlessly into routine wound management practice and user friendly to the clinician, nurse and wound specialist. This may also include use of this device in the home-care environment (including self-use by a patient), as well as in military battlefield environments. In addition, such an image-based device may provide an ability to monitor wound treatment response and healing in real-time by incorporating valuable 'biologically-informed' image-guidance into the clinical wound assessment process. This may ultimately lead to potential new diagnosis, treatment planning, treatment response monitoring and thus 'adaptive' intervention strategies which may permit enhancement of wound-healing response at the individual patient level. Precise identification of the systemic, local, and molecular factors underlying the wound healing problem in individual patients may allow better tailored treatment.

A number of imaging technologies have become available that offer the potential to satisfy the requirements for improved clinical diagnosis and treatment of disease. Of these, fluorescence imaging appears to be promising for improving clinical wound assessment and management. When excited by short wavelength light (e.g., ultraviolet or short visible wavelengths), most endogenous biological components of tissues (e.g., connective tissues such collagen and elastins, metabolic co-enzymes, proteins, etc.) produce fluorescence of a longer wavelength, in the ultraviolet, visible, near-infrared and infrared wavelength ranges [DaCosta et al., Photochem Photobiol. 2003 October, 78(4):384-92]. The most clinically mature of emerging optically-based imaging technologies, tissue autofluorescence imaging has been used to improve the endoscopic detection of early cancers and other diseases in the gastrointestinal tract [Dacosta (2002) J Gastroenterol Hepatol. Suppl:S85-104], the oral cavity [Poh et al., Head Neck. 2007 January, 29(1):71-6], and lungs [Hanibuchi et al., (2007) J Med Invest. 54:261-6] and bladder [D'Hallewin et al. (2002) Eur Urol. 42(5):417-25] in a minimally-invasive manner.

Tissue autofluorescence imaging provides a unique means of obtaining biologically relevant information of normal and diseased tissues in real-time, thus allowing differentiation between normal and diseased tissue states [DaCosta, 2003; DaCosta et al. J Clin Pathol. 2005, 58(7):766-74]. This is based, in part, on the inherently different light-tissue interactions (e.g., absption and scattering of light) that occur at the bulk tissue and cellular levels, changes in the tissue morphology and alterations in the blood content of the tissues. In tissues, blood is a major light absorbing tissue component (i.e., a chromophore). This type of technology is suited for imaging disease in hollow organs (e.g., GI tract, oral cavity, lungs, bladder) or exposed tissue surfaces (e.g., skin) Despite this indication, current endoscopic fluorescence imaging systems are large, involve complex diagnostic algorithms and expensive, and to date, such instruments are mainly found in large clinical centers and very few systems are commercially available. Currently, no such optical or fluorescence-based imaging device exists for wound imaging. However, since wounds are readily accessible, an autofluorescence imaging device may be useful for rapid, non-invasive and non-contact real-time imaging of wounds, to detect and exploit the rich biological information of the wound to overcome current limitations and improve clinical care and management.

A method and device for fluorescence-based imaging and monitoring is disclosed. One embodiment of the device is a portable optical digital imaging device. The device may utilize a combination of white light, tissue fluorescence and reflectance imaging, and may provide real-time wound imaging, assessment, recording/documenting, monitoring and/or care management. The device may be hand-held, compact and/or light-weight. This device and method may be suitable for monitoring of wounds in humans and animals.

Other uses for the device may include:

Clinically- and research-based imaging of small and large (e.g., veterinary) animals.

Detection and monitoring of contamination (e.g., bacterial contamination) in food/animal product preparation in the meat, poultry, dairy, fish, agricultural industries.

Detection of 'surface contamination' (e.g., bacterial or biological contamination) in public (e.g., health care) and private settings.

Multi-spectral imaging and detection of cancers in human and/or veterinary patients.

As a research tool for multi-spectral imaging and monitoring of cancers in experimental animal models of human diseases (e.g., wound and cancers).

Forensic detection, for example of latent finger prints and biological fluids on non-biological surfaces.

Imaging and monitoring of dental plaques, carries and cancers in the oral cavity.

Imaging and monitoring device in clinical microbiology laboratories.

Testing anti-bacterial (e.g., antibiotic), disinfectant agents.

The device may generally comprise: i) one or more excitation/illumination light sources and ii) a detector device (e.g., a digital imaging detector device), which may be combined with one or more optical emission filters, or spectral filtering mechanisms, and which may have a view/control screen (e.g., a touch-sensitive screen), image capture and zoom controls. The device may also have: iii) a wired and/or wireless data transfer port/module, iv) an electrical power source and power/control switches, and/or v) an enclosure, which may be compact and/or light weight, and which may have a mechanism for attachment of the detector device and/or a handle grip. The excitation/illumination light sources may be LED arrays emitting light at about 405 nm (e.g., +/−5 nm), and may be coupled with additional band-pass filters centered at about 405 nm to remove/minimize the side spectral bands of light from the LED array output so as not to cause light leakage into the imaging detector with its own optical filters. The digital imaging detector device may be a digital camera, for example having at least an ISO800 sensitivity, but more preferably an ISO3200 sensitivity, and may be combined with one or more optical emission filters, or other equally effective (e.g., miniaturized) mechanized spectral filtering mechanisms (e.g., acousto-optical tunable filter or liquid crystal tunable filter). The digital imaging detector device may have a touch-sensitive viewing and/or control screen, image capture and zoom controls. The enclosure may be an outer hard plastic or polymer shell, enclosing the digital imaging detector device, with buttons such that all necessary device controls may be accessed easily and manipulated by the user. Miniature heat sinks or small mechanical fans, or other heat dissipating devices may be imbedded in the device to allow excess heat to be removed from the excitation light sources if required. The complete device, including all its embedded accessories and attachments, may be powered using standard AC/DC power and/or by rechargeable battery pack. The complete device may also be attached or mounted to an external mechanical apparatus (e.g., tripod, or movable stand with pivoting arm) allowing mobility of the device within a clinical room with hands-free operation of the device. Alternatively, the device may be provided with a mobile frame such that it is portable. The device may be cleaned using moist gauze wet with water, while the handle may be cleansed with moist gauze wet with alcohol. The device may include software allowing a user to control the device, including control of imaging parameters, visualization of images, storage of image data and user information, transfer of images and/or associated data, and/or relevant image analysis (e.g., diagnostic algorithms).

A schematic diagram of an example of the device is shown in FIG. 1. The device is shown positioned to image a target object 10 or target surface. In the example shown, the device has a digital image acquisition device 1, such as digital camera, video recorder, camcorder, cellular telephone with built-in digital camera, 'Smart' phone with a digital camera, personal digital assistant (PDA), laptop/PC with a digital camera, or a webcam. The digital image acquisition device 1 has a lens 2, which may be aligned to point at the target object 10 and may detect the optical signal that emanates from the object 10 or surface. The device has an optical filter holder 3 which may accommodate one or more optical filters 4. Each optical filter 4 may have different discrete spectral bandwidths and may be band-pass filters. These optical filters 4 may be selected and moved in from of the digital camera lens to selectively detect specific optical signals based on the wavelength of light. The device may include light sources 5 that produce excitation light to illuminate the object 10 in order to elicit an optical signal (e.g., fluorescence) to be imaged with, for example, blue light (e.g., 400-450 nm), or any other combination of single or multiple wavelengths (e.g., wavelengths in the ultraviolet/visible/near infrared/infrared ranges). The light source 5 may comprise a LED array, laser diode and/or filtered lights arranged in a variety of geometries. The device may include a method or apparatus 6 (e.g., a heatsink or a cooling fan) to dissipate heat and cool the illumination light sources 5. The device may include a method or apparatus 7 (e.g., an optical band-pass filter) to remove any undesirable wavelengths of light from the light sources 5 used to illuminate the object 10 being imaged. The device may include a method or apparatus 8 to use an optical means (e.g., use of compact miniature laser diodes that emit a collimated light beam) to measure and determine the distance between the imaging device and the object 10. For example, the device may use two light sources, such as two laser diodes, as part of a triangulation apparatus to maintain a constant distance between the device and the object 10. Other light sources may be possible. The device may also use ultrasound, or a physical measure, such as a ruler, to determine a constant distance to maintain. The device may also include a method or apparatus 9 (e.g., a pivot) to permit the manipulation and orientation of the excitation light sources 5, 8 so as to manoeuvre these sources 5,8 to change the illumination angle of the light striking the object 10 for varying distances.

The target object 10 may be marked with a mark 11 to allow for multiple images to be taken of the object and then being co-registered for analysis. The mark 11 may involve, for example, the use of exogenous fluorescence dyes of different colours which may produce multiple distinct optical signals when illuminated by the light sources 5 and be detectable within the image of the object 10 and thus may permit orientation of multiple images (e.g., taken over time) of the same region of interest by co-registering the different colours and the distances between them. The digital image acquisition device 1 may include one or more of: an interface 12 for a head-mounted display; an interface 13 for an external printer; an interface 14 for a tablet computer, laptop computer, desk top computer or other computer device; an interface 15 for the device to permit wired or wireless transfer of imaging data to a remote site or another device; an interface 16 for a global positioning system (GPS) device; an interface 17 for a device allowing the use of extra memory; and an interface 18 for a microphone.

The device may include a power supply 19 such as an AC/DC power supply, a compact battery bank, or a rechargeable battery pack. Alternatively, the device may be adapted for connecting to an external power supply. The device may have a housing 20 that houses all the components in one entity. The housing 20 may be equipped with a means of securing any digital imaging device within it. The housing 20 may be designed to be hand-held, compact, and/or portable. The housing 20 may be one or more enclosures.

Referring still to FIG. 1, b) shows an example of the device in a typical wound care facility. a) shows a typical clinical wound care facility, showing the examination chair and accessory table. b-c) An example of the device is shown in its hard-case container. The device may be integrated into the routine wound care practice allowing real-time imaging of the patient. d) An example of the device (arrow) is shown placed on the "wound care cart" to illustrate the size of the device. e) The device may be used to image under white light illumination, while f) shows the device being used to take fluorescence images of a wound under dimmed room lights. g) The device may be used in telemedicine/telehealth infrastructures, for example fluorescence images of a patient's wounds may be sent by email to a wound care specialist via a wireless communication device, such as a Smartphone at another hospital using a wireless/WiFi internet connection. Using this device, high-resolution fluorescence images may be sent as email attachments to wound care specialists from remote wound care sites for immediate consultation with clinical experts, microbiologists, etc. at specialized clinical wound care and management centers.

EXAMPLES

An example of a device for fluorescence-based monitoring is described below. All examples are provided for the purpose of illustration only and are not intended to be limiting. Parameters such as wavelengths, dimensions, and incubation time described in the examples may be approximate and are provided as examples only.

In this example, the devices uses two violet/blue light (e.g., 405 nm+/−10 nm emission, narrow emission spectrum) LED arrays (Opto Diode Corporation, Newbury Park, California), each situated on either side of the imaging detector assembly as the excitation or illumination light sources. These arrays have an output power of approximately 1 Watt each, emanating from a 2.5×2.5 cm², with a 70-degree illuminating beam angle. The LED arrays may be used to illuminate the tissue surface from a distance of about 10 cm, which means that the total optical power density on the skin surface is about 0.08 W/cm². At such low powers, there is no known potential harm to either the target wound or skin surface, or the eyes from the excitation light. However, it may be inadvisable to point the light directly at any individual's eyes during imaging procedures. It should also be noted that 405 nm light does not pose a risk to health according to international standards formulated by the International Electrotechnical Commission (IEC), as further detailed on the website:

http://www.iec.ch/onlinenews/etech/arch_2006/ etech_0906/focus.htm

The one or more light sources may be articulated (e.g., manually) to vary the illumination angle and spot size on the imaged surface, for example by using a built in pivot, and are powered for example through an electrical connection to a wall outlet and/or a separate portable rechargeable battery pack. Excitation/illumination light may be produced by sources including, but not limited to, individual or multiple light-emitting diodes (LEDs) in any arrangement including in ring or array formats, wavelength-filtered light bulbs, or lasers. Selected single and multiple excitation/illumination light sources with specific wavelength characteristics in the ultraviolet (UV), visible (VIS), far-red, near infrared (NIR) and infrared (IR) ranges may also be used, and may be composed of a LED array, organic LED, laser diode, or filtered lights arranged in a variety of geometries. Excitation/illumination light sources may be 'tuned' to allow the light intensity emanating from the device to be adjusted while imaging. The light intensity may be variable. The LED arrays may be attached to individual cooling fans or heat sinks to dissipate heat produced during their operation. The LED arrays may emit narrow 405 nm light, which may be spectrally filtered using a commercially available band-pass filter (Chroma Technology Corp, Rockingham, VT, USA) to reduce potential 'leakage' of emitted light into the detector optics. When the device is held above a tissue surface (e.g., a wound) to be imaged, the illuminating light sources may shine a narrow-bandwidth or broad-bandwidth violet/blue wavelength or other wavelength or wavelength band of light onto the tissue/wound surface thereby producing a flat and homogeneous field within the region-of-interest. The light may also illuminate or excite the tissue down to a certain shallow depth. This excitation/illumination light interacts with the normal and diseased tissues and may cause an optical signal (e.g., absorption, fluorescence and/or reflectance) to be generated within the tissue.

By changing the excitation and emission wavelengths accordingly, the imaging device may interrogate tissue components (e.g., connective tissues and bacteria in a wound) at the surface and at certain depths within the tissue (e.g., a wound). For example, by changing from violet/blue (~400-500 nm) to green (~500-540 nm) wavelength light, excitation of deeper tissue/bacterial fluorescent sources may be achieved, for example in a wound. Similarly, by detecting longer wavelengths, fluorescence emission from tissue and/or bacterial sources deeper in the tissue may be detected at the tissue surface. For wound assessment, the ability to interrogate surface and/or sub-surface fluorescence may be useful, for example in detection and potential identification of bacterial contamination, colonization, critical colonization and/or infection, which may occur at the surface and often at depth within a wound (e.g., in chronic non-healing wounds). In one example, Referring to FIG. 6, c) shows the detection of bacteria below the skin surface (i.e., at depth) after wound cleaning. This use of the device for detecting bacteria at the surface and at depth within a wound and surrounding tissue may be assessed in the context of other clinical signs and symptoms used conventionally in wound care centers.

Figure 2:
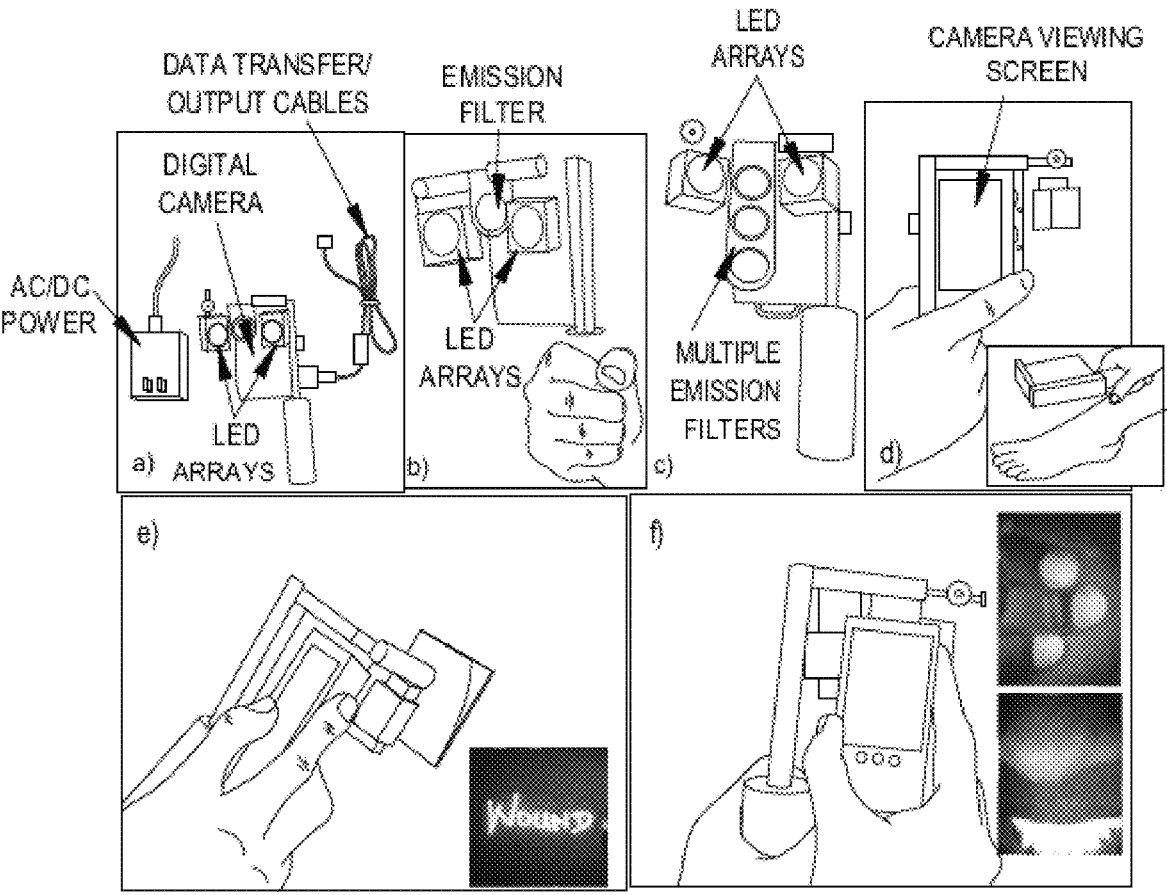
FIG. 2 shows images of a hand-held embodiment of a device for fluorescence-based monitoring.

Example embodiments of the device are shown in FIG. 2. The device may be used with any standard compact digital imaging device (e.g., a charge-coupled device (CCD) or complementary metal-oxide-semiconductor (CMOS) sensors) as the image acquisition device. The example device shown in a) has an external electrical power source, the two LED arrays for illuminating the object/surface to be imaged, and a commercially available digital camera securely fixed to light-weight metal frame equipped with a convenient handle for imaging. A multi-band filter is held in front of the digital camera to allow wavelength filtering of the detected optical signal emanating from the object/surface being imaged. The camera's video/USB output cables allow transfer of imaging data to a computer for storage and subsequent analysis. This example uses a commercially-available 8.1-megapixel Sony digital camera (Sony Cybershot DSC-T200 Digital Camera, Sony Corporation, North America). This camera may be suitable because of i) its slim vertical design which may be easily integrated into the enclosure frame, ii) its large 3.5-inch widescreen touch-panel LCD for ease of control, iii) its Carl Zeiss 5× optical zoom lens, and iv) its use in low light (e.g., ISO 3200). The device may have a built-in flash which allows for standard white light imaging (e.g., high-definition still or video with sound recording output). Camera interface ports may support both wired (e.g., USB) or wireless (e.g., Bluetooth, WiFi, and similar modalities) data transfer or $3^{rd}$ party add-on modules to a variety of external devices, such as: a head-mounted display, an external printer, a tablet computer, laptop computer, personal desk top computer, a wireless device to permit transfer of imaging data to a remote site/other device, a global positioning system (GPS) device, a device allowing the use of extra memory, and a microphone. The digital camera is powered by rechargeable batteries, or AC/DC powered supply. The digital imaging device may include, but is not limited to, digital cameras, webcams, digital SLR cameras, camcorders/video recorders, cellular telephones with embedded digital cameras, Smartphones™, personal digital assistants (PDAs), and laptop computers/tablet PCs, or personal desk-top computers, all of which contain/or are connected to a digital imaging detector/sensor.

This light signal produced by the excitation/illumination light sources may be detected by the imaging device using optical filter(s) (e.g., those available from Chroma Technology Corp, Rockingham, VT, USA) that reject the excitation light but allow selected wavelengths of emitted light from the tissue to be detected, thus forming an image on the display. There is an optical filter holder attached to the enclosure frame in from of the digital camera lens which may accommodate one or more optical filters with different discrete spectral bandwidths, as shown in b) and c) of FIG. 2. b) shows the device with the LED arrays turned on to emit bright violet/blue light, with a single emission filter in place. c) shows the device using a multiple-optical filter holder used to select the appropriate filter for desired wavelength-specific imaging. d) shows the device being held in one hand while imaging the skin surface of a foot.

These band-pass filters may be selected and aligned in front of the digital camera lens to selectively detect specific optical signals from the tissue/wound surface based on the wavelength of light desired. Spectral filtering of the detected optical signal (e.g., absorption, fluorescence, reflectance) may also be achieved, for example, using a liquid crystal tunable filter (LCTF), or an acousto-optic tunable filter (AOTF) which is a solid-state electronically tunable spectral band-pass filter. Spectral filtering may also involve the use of continuous variable filters, and/or manual band-pass optical filters. These devices may be placed in front of the imaging detector to produce multispectral, hyperspectral, and/or wavelength-selective imaging of tissues.

The device may be modified by using optical or variably oriented polarization filters (e.g., linear or circular combined with the use of optical wave plates) attached in a reasonable manner to the excitation/illumination light sources and the imaging detector device. In this way, the device may be used to image the tissue surface with polarized light illumination and non-polarized light detection or vice versa, or polarized light illumination and polarized light detection, with either white light reflectance and/or fluorescence imaging. This may permit imaging of wounds with minimized specular reflections (e.g., glare from white light imaging), as well as enable imaging of fluorescence polarization and/or anisotropy-dependent changes in connective tissues (e.g., collagens and elastin) within the wound and surrounding normal tissues. This may yield useful information about the spatial orientation and organization of connective tissue fibers associated with wound remodeling during healing [Yasui et al., (2004) Appl. Opt. 43: 2861-2867].

All components of the imaging device may be integrated into a single structure, such as an ergonomically designed enclosed structure with a handle, allowing it to be comfortably held with one or both hands. The device may also be provided without any handle. The device may be light weight, portable, and may enable real-time digital imaging (e.g., still and/or video) of any target surface (for example, the skin and/or oral cavity, which is also accessible) using white light, fluorescence and/or reflectance imaging modes. The device may be scanned across the body surface for imaging by holding it at variable distances from the surface, and may be used in a lit environment/room to image white light reflectance/fluorescence. The device may be used in a dim or dark environment/room to optimize the tissue fluorescence signals, and minimize background signals from room lights. The device may be used for direct (e.g., with the unaided eye) or indirect (e.g., via the viewing screen of the digital imaging device) visualization of wounds and surrounding normal tissues.

The device may also be embodied as not being hand-held or portable, for example as being attached to a mounting mechanism (e.g., a tripod or stand) for use as a relatively stationary optical imaging device for white light, fluorescence and reflectance imaging of objects, materials, and surfaces (e.g., a body). This may allow the device to be used on a desk or table or for 'assembly line' imaging of objects, materials and surfaces. In some embodiments, the mounting mechanism may be mobile.

Other features of this device may include the capability of digital image and video recording, possibly with audio, methods for documentation (e.g., with image storage and analysis software), and wired or wireless data transmission for remote telemedicine/E-health needs. For example, e) and f) of FIG. 2 show an embodiment of the device where the image acquisition device is a mobile communication device such as a cellular telephone. The cellular telephone used in this example is a Samsung Model A-900, which is equipped with a 1.3 megapixel digital camera. The telephone is fitted into the holding frame for convenient imaging. e) shows the use of the device to image a piece of paper with fluorescent ink showing the word "Wound". f) shows imaging of fluorescent ink stained fingers, and detection of the common skin bacteria P. Acnes. The images from the cellular telephone may be sent wirelessly to another cellular telephone, or wirelessly (e.g., via Bluetooth connectivity) to a personal computer for image storage and analysis. This demonstrates the capability of the device to perform real-time hand-held fluorescence imaging and wireless transmission to a remote site/person as part of a telemedicine/E-health wound care infrastructure.

In order to demonstrate the capabilities of the imaging device in wound care and other relevant applications, a number of feasibility experiments were conducted using the particular example described. It should be noted that during all fluorescence imaging experiments, the Sony camera (Sony Cybershot DSC-T200 Digital Camera, Sony Corporation, North America) settings were set so that images were captured without a flash, and with the 'Macro' imaging mode set. Images were captured at 8 megapixels. The flash was used to capture white light reflectance images. All images were stored on the xD memory card for subsequent transfer to a personal computer for long-term storage and image analysis.

All white light reflectance and fluorescence images/movies captured with the device were imported into Adobe Photoshop for image analysis. However, image analysis software was designed using MatLab™ (Mathworks) to allow a variety of image-based spectral algorithms (e.g., red-to-green fluorescence ratios, etc.) to be used to extract pertinent image data (e.g., spatial and spectral data) for quantitative detection/diagnostic value. Image post-processing also included mathematical manipulation of the images. Imaging of Bacteriological Samples The imaging device may be useful for imaging and/or monitoring in clinical microbiology laboratories. The device may be used for quantitative imaging of bacterial colonies and quantifying colony growth in common microbiology assays. Fluorescence imaging of bacterial colonies may be used to determine growth kinetics. Software may be used to provide automatic counting of bacterial colonies.

To demonstration the utility of the device in a bacteriology/culture laboratory, live bacterial cultures were grown on sheep's blood agar plates. Bacterial species included *Streptococcus pyogenes, Serratia marcescens, Staphylococcus aureus, Staphylococcus epidermidis, Escherichia coli*, and *Pseudomonas aeruginosa* (American Type Culture Collection, ATCC). These were grown and maintained under standard incubation conditions at 37° C. and used for experimentation when during 'exponential growth phase'. Once colonies were detected in the plates (~24 h after inoculation), the device was used to image agar plates containing individual bacterial species in a darkened room. Using violet/blue (about 405 nm) excitation light, the device was used to image both combined green and red autofluorescence (about 490-550 nm and about 610-640 nm emission) and only red autofluorescence (about 635+/−10 nm, the peak emission wavelength for fluorescent endogenous porphyrins) of each agar plate. Fluorescence images were taken of each bacterial species over time for comparison and to monitor colony growth.

Figure 3:
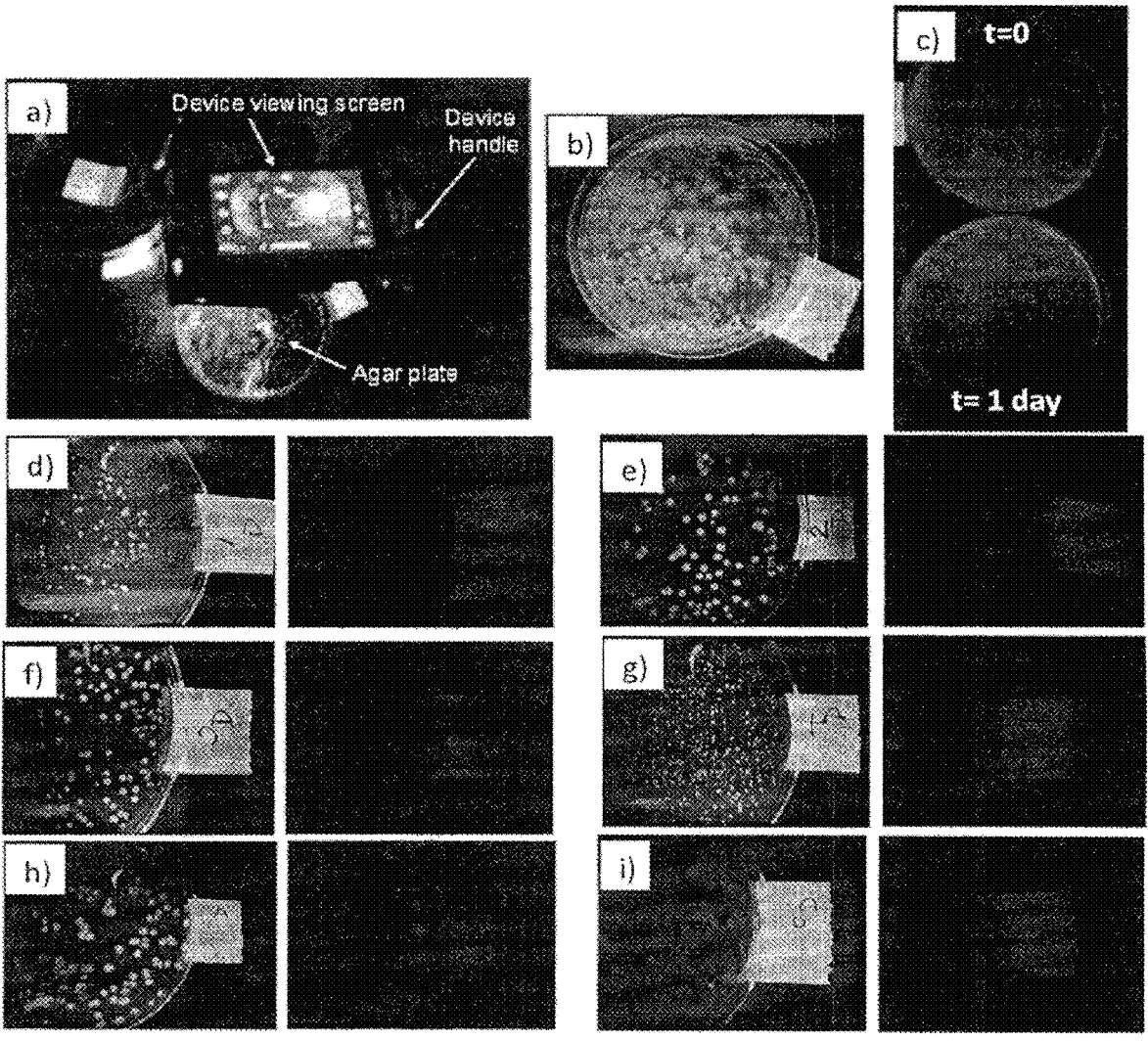
FIG. 3 shows images of live bacterial cultures captured using a device for fluorescence-based monitoring.

Reference is now made to FIG. 3. a) shows the device being used to image live bacterial cultures growing on sheep's blood agar plates to detect bacterial autofluorescence. b) shows the image of autofluorescence emitted by *Pseudomonas aeruginosa*. The device may also be used to detect, quantify and/or monitor bacterial colony growth over time using fluorescence, as demonstrated in c) with fluorescence imaging of the growth of autofluorescent *Staphylococcus aureus* on an agar plate 24 hours after inoculation. Note the presence of distinct single bacterial colonies in the lower image. Using violet/blue (e.g., 405 nm) excitation light, the device was used to detect both combined green and red (e.g., 490-550 nm+610-640 nm) and only red (e.g., 635+/−10 nm, the peak emission wavelength for fluorescent endogenous porphyrins) emission autofluorescence from several live bacterial species including *Streptococcus pyogenes*, shown in d); *Serratia marcescens*, shown in e); *Staphylococcus aureus*, shown in f); *Staphylococcus epidermidis*, shown in g); *Escherichia coli*, shown in h); and *Pseudomonas aeruginosa*, shown in i). Note that the autofluorescence images obtained by the device of the bacterial colonies may provide useful image contrast for simple longitudinal quantitative measurements of bacterial colonization and growth kinetics, as well as a means of potentially monitoring response to therapeutic intervention, with antibiotics, photodynamic therapy (PDT), low level light therapy, hyperbaric oxygen therapy (HOT), or advanced wound care products, as examples.

High spatial resolution of the camera detector combined with significant bacterial autofluorescence signal-to-noise imaging with the device allowed detection of very small (e.g., <1 mm diameter) colonies. The device provided a portable and sensitive means of imaging individual bacterial colonies growing in standard agar plates. This provided a means to quantify and monitor bacterial colony growth kinetics, as seen in c), as well as potentially monitoring response to therapeutic intervention, with antibiotics or photodynamic therapy (PDT) as examples, over time using fluorescence. Therefore, the device may serve as a useful tool in the microbiology laboratory.

Figure 3J:
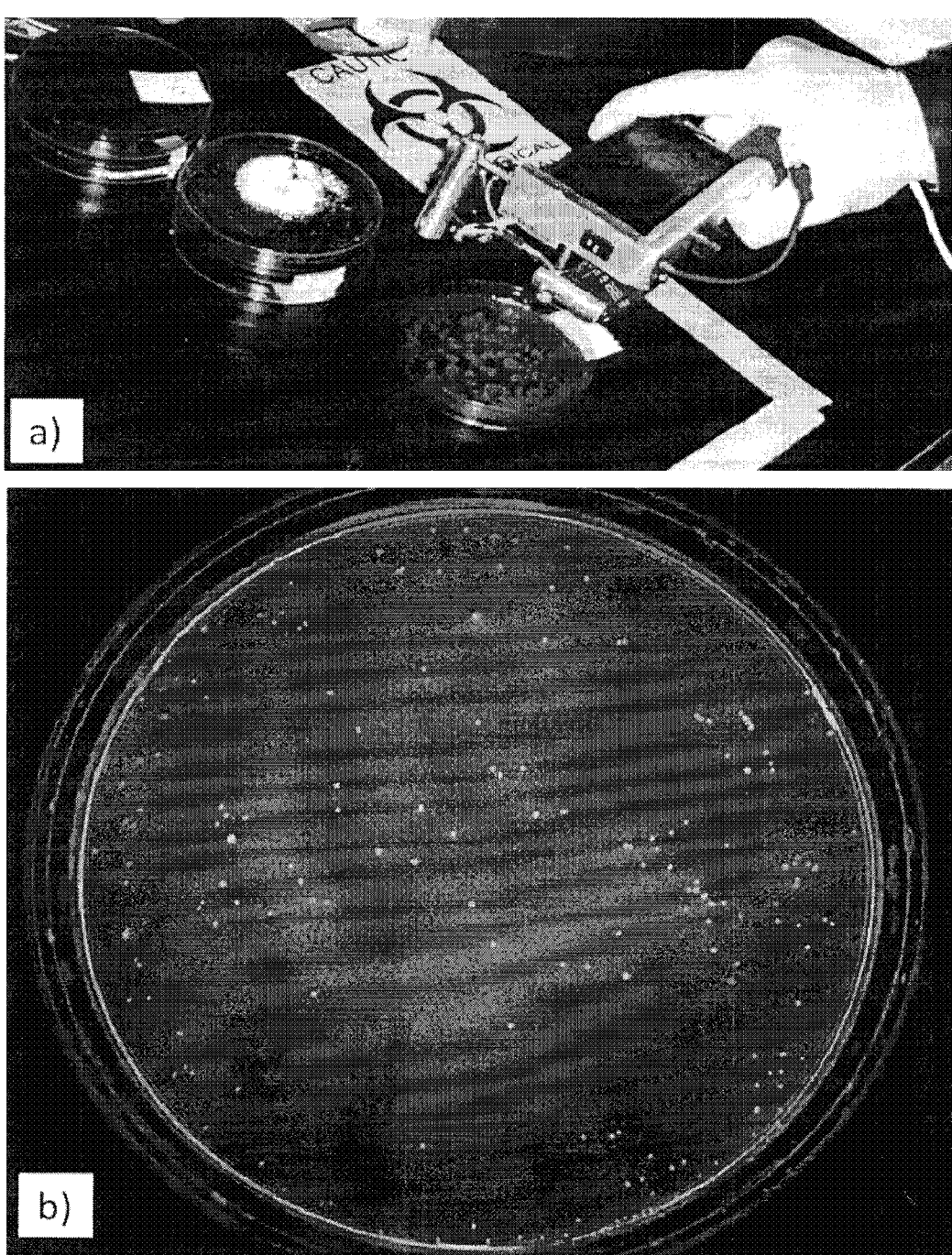
FIG. 3J shows an example of bacterial monitoring using a device for fluorescence-based monitoring.

FIG. 3J shows an example of the use of the imaging device in a) standard bacteriology laboratory practice. b) Here, fluorescence imaging of a Petri dish containing *Staphylococcus aureus* combined with custom proprietary image analysis software allows bacterial colonies to be counted rapidly, and here the fluorescence image of the culture dish shows ~182 (+/−3) colonies (bright bluish-green spots) growing on agar at 37° C. (about 405 nm excitation, about 500-550 nm emission (green), about >600 nm emission (red)).

In addition to providing detecting of bacterial strains, the device may be used for differentiating the presence and/or location of different bacterial strains (e.g., *Staphylococcus aureus* or *Pseudomonas aeruginosa*), for example in wounds and surrounding tissues. This may be based on the different autofluorescence emission signatures of different bacterial strains, including those within the 490-550 nm and 610-640 nm emission wavelength bands when excited by violet/blue light, such as light around 405 nm. Other combinations of wavelengths may be used to distinguish between other species on the images. This information may be used to select appropriate treatment, such as choice of antibiotic.

Such imaging of bacteriology samples may be applicable to monitoring of wound care.
Use in Monitoring of Wound Healing The device may be scanned above any wound (e.g., on the body surface) such that the excitation light may illuminate the wound area. The wound may then be inspected using the device such that the operator may view the wound in real-time, for example, via a viewer on the imaging device or via an external display device (e.g., heads-up display, a television display, a computer monitor, LCD projector or a head-mounted display). It may also be possible to transmit the images obtained from the device in real-time (e.g., via wireless communication) to a remote viewing site, for example for telemedicine purposes, or send the images directly to a printer or a computer memory storage. Imaging may be performed within the routine clinical assessment of patient with a wound.

Prior to imaging, fiduciary markers (e.g., using an indelible fluorescent ink pen) may be placed on the surface of the skin near the wound edges or perimeter. For example, four spots, each of a different fluorescent ink color from separate indelible fluorescent ink pens, which may be provided as a kit to the clinical operator, may be placed near the wound margin or boundary on the normal skin surface. These colors may be imaged by the device using the excitation light and a multispectral band filter that matches the emission wavelength of the four ink spots. Image analysis may then be performed, by co-registering the fiduciary markers for inter-image alignment. Thus, the user may not have to align the imaging device between different imaging sessions. This technique may facilitate longitudinal (i.e., over time) imaging of wounds, and the clinical operator may therefore be able to image a wound over time without need for aligning the imaging device during every image acquisition.

In addition, to aid in intensity calibration of the fluorescence images, a disposable simple fluorescent standard 'strip' may be placed into the field of view during wound imaging (e.g., by using a mild adhesive that sticks the strip to the skin temporarily). The strip may be impregnated with one or several different fluorescent dyes of varying concentrations which may produce pre-determined and calibrated fluorescence intensities when illuminated by the excitation light source, which may have single (e.g., 405 nm) or multiple fluorescence emission wavelengths or wavelength bands for image intensity calibration. The disposable strip may also have the four spots as described above (e.g., each of different diameters or sizes and each of a different fluorescent ink color with a unique black dot placed next to it) from separate indelible fluorescent ink pens. With the strip placed near the wound margin or boundary on the normal skin surface, the device may be used to take white light and fluorescence images. The strip may offer a convenient way to take multiple images over time of a given wound and then align the images using image analysis. Also, the fluorescent 'intensity calibration' strip may also contain an added linear measuring apparatus, such as a ruler of fixed length to aid in spatial distance measurements of the wounds. Such a strip may be an example of a calibration target which may be used with the device to aid in calibration or measuring of image parameters (e.g., wound size, fluorescence intensity, etc.), and other similar calibration target may be used.

It may be desirable to increase the consistency of imaging results and to reproduce the distance between the device and the wound surface, since tissue fluorescence intensity may vary slightly if the distance changes during multiple imaging sessions. Therefore, in an embodiment, the device may have two light sources, such as low power laser beams, which may be used to triangulate individual beams onto the surface of the skin in order to determine a fixed or variable distance between the device and the wound surface. This may be done using a simply geometric arrangement between the laser light sources, and may permit the clinical operator to easily visualize the laser targeting spots on the skin surface and adjust the distance of the device from the wound during multiple imaging sessions. Other methods of maintaining a constant distance may include the use of ultrasound, or the use of a physical measure, such as a ruler.

Use in White Light Imaging

The device may be used to take white light images of the total wound with normal surrounding normal tissues using a measuring apparatus (e.g., a ruler) placed within the imaging field of view. This may allow visual assessment of the wound and calculation/determination of quantitative parameters such as the wound area, circumference, diameter, and topographic profile. Wound healing may be assessed by planimetric measurements of the wound area at multiple time points (e.g., at clinical visits) until wound healing. The time course of wound healing may be compared to the expected healing time calculated by the multiple time point measurements of wound radius reduction using the equation $R=\sqrt{A/\pi}$ (R, radius; A, planimetric wound area; $\pi$, constant 3.14). This quantitative information about the wound may be used to track and monitor changes in the wound appearance over time, in order to evaluate and determine the degree of wound healing caused by natural means or by any therapeutic intervention. This data may be stored electronically in the health record of the patient for future reference. White light imaging may be performed during the initial clinical assessment of the patient by the operator.

Use in Autofluorescence Imaging

The device may be designed to detect all or a majority of tissue autofluorescence (AF). For example, using a multi-spectral band filter, the device may image tissue autofluorescence emanating from the following tissue biomolecules, as well as blood-associated optical absorption, for example under 405 nm excitation: collagen (Types I, II, III, IV, V and others) which appear green, elastin which appears greenish-yellow-orange, reduced nicotinamide adenine dinucleotide (NADH), flavin adenine dinucleotide (FAD), which emit a blue-green autofluorescence signal, and bacteria/microorganisms, most of which appear to have a broad (e.g., green and red) autofluorescence emission.

Image analysis may include calculating a ratio of red-to-green AF in the image. Intensity calculations may be obtained from regions of interest within the wound images. Pseudo-coloured images may be mapped onto the white light images of the wound.

Examples in Wound Healing

Figure 4:
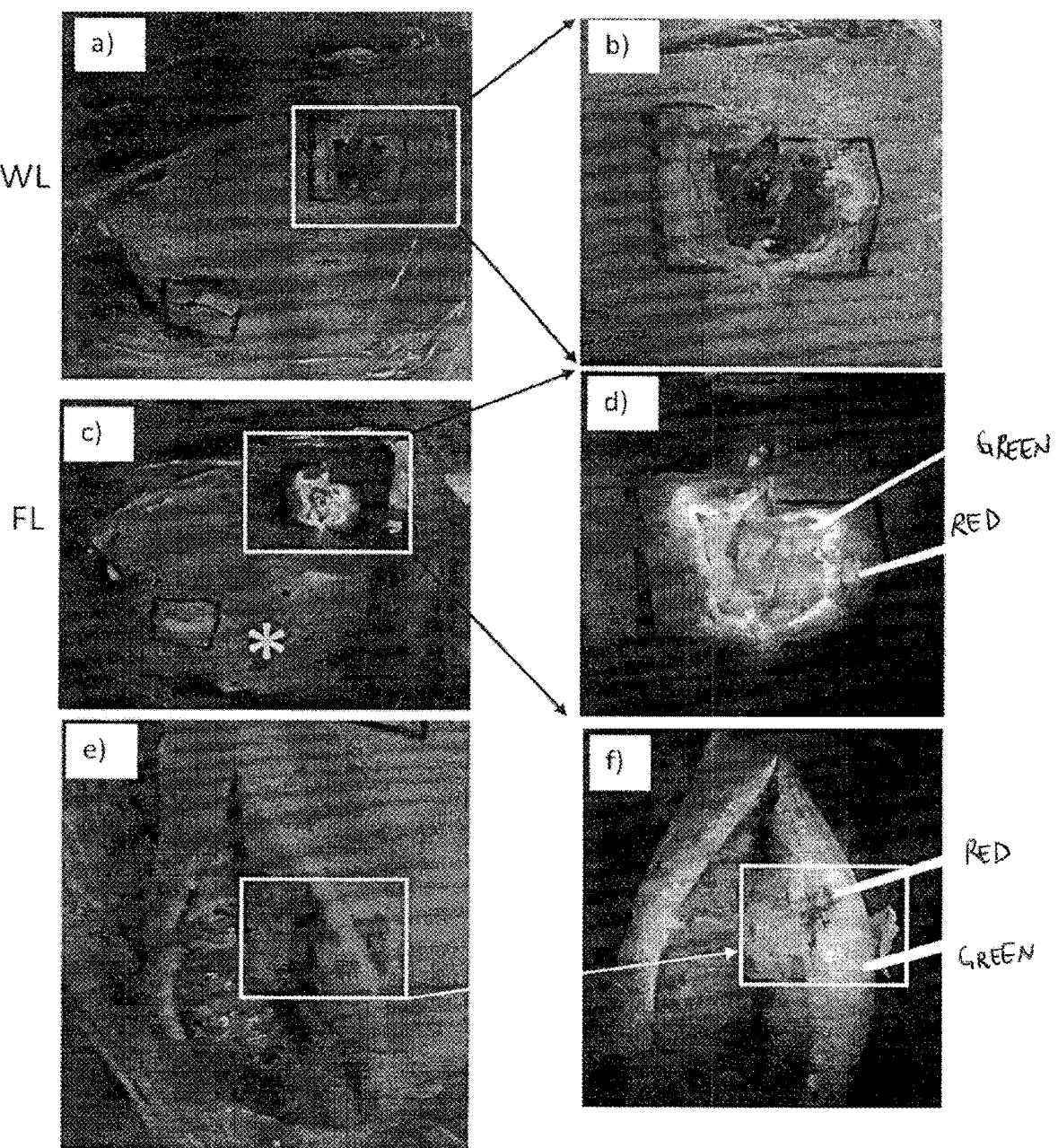
FIG. 4 shows images of a simulated animal wound model, demonstrating non-invasive autofluorescence detection of bacteria using a device for fluorescence-based monitoring.

Reference is now made to FIG. 4. The device was tested in model of wounds contaminated with bacteria. For this, pig meat, with skin, was purchased from a butcher. To simulate wounds, a scalpel was used to make incisions, ranging in size from 1.5 cm$^2$ to 4 cm$^2$ in the skin, and deep enough to see the muscle layer. The device was used to image some meat samples without addition of bacteria to the simulated wounds. For this, the meat sample was left at room temperature for 24 h in order for bacteria on the meat to grow, and then imaging was performed with the device using both white light reflectance and autofluorescence, for comparison.

To test the ability of the device to detect connective tissues and several common bacteria present in typical wounds, a sample of pig meat with simulated wounds was prepared by applying six bacterial species to each of six small 1.5 cm$^2$ wound incision sites on the skin surface: *Streptococcus pyogenes, Serratia marcescens, Staphylococcus aureus, Staphylococcus epidermidis, Escherichia coli,* and *Pseudomonas aeruginosa*. An additional small incision was made in the meat skin, where no bacteria were added, to serve as a control. However, it was expected that bacteria from the other six incisions sites would perhaps contaminate this site in time. The device was used to image the bacteria-laden meat sample using white light reflectance and violet/blue light-induced tissue autofluorescence emission, using both a dual emission band (450-505 nm and 590-650 nm) emission filter and a single band (635+/−10 nm) emission filter, on the left and a single band filter over the course of three days, at 24 h time intervals, during which the meat sample was maintained at 37° C. Imaging was also performed on the styrofoam container on which the meat sample was stored during the three days.

FIG. 4 shows the results of the device being used for non-invasive autofluorescence detection of bacteria in a simulated animal wound model. Under standard white light imaging, bacteria were occult within the wound site, as shown in a) and magnified in b). However, under violet/blue excitation light, the device was capable of allowing identification of the presence of bacteria within the wound site based on the dramatic increase in red fluorescence from bacterial porphyrins against a bright green fluorescence background from connective tissue (e.g., collagen and elastins) as seen in c) and magnified in d). Comparison of b) and d) shows a dramatic increase in red fluorescence from bacterial porphyrins against a bright green fluorescence background from connective tissue (e.g., collagen and elastins). It was noted that with autofluorescence, bacterial colonies were also detected on the skin surface based on their green fluorescence emission causing individual colonies to appear as punctuate green spots on the skin. These were not seen under white light examination. Fluorescence imaging of connective tissues aided in determining the wound margins as seen in e) and f), and some areas of the skin (marked '*' in c) appeared more red fluorescent than other areas, potentially indicating subcutaneous infection of porphyrin-producing bacteria. e) and f) also show the device detecting red fluorescent bacteria within the surgical wound, which are occult under white light imaging.

The device mapped biodistribution of bacteria within the wound site and on the surrounding skin and thus may aid in targeting specific tissue areas requiring swabbing or biopsy for microbiological testing. Furthermore, using the imaging device may permit the monitoring of the response of the bacterially-infected tissues to a variety of medical treatments, including the use of antibiotics and other therapies, such as photodynamic therapy (PDT), hyperbaric oxygen therapy (HOT), low level light therapy, or anti-Matrix Metalloproteinase (MMP). The device may be useful for visualization of bacterial biodistribution at the surface as well as within the tissue depth of the wound, and also for surrounding normal tissues. The device may thus be useful for indicating the spatial distribution of an infection.

Use of Device with Contrast Agents in Monitoring Wounds

The device may be used with exogenous contrast agents, for example the pro-drug aminolaevulinic acid (ALA) at a low dose. ALA may be topically administered to the wound, and imaging may be performed 1-3 hours later for enhanced red fluorescence of wound bacteria.

The pro-drug aminolaevulinic acid (ALA) induces porphyrin formation in almost all living cells. Many bacteria species exposed to ALA are able to induce protoporphyrin IX (PpIX) fluorescence. The use of ultra-low dose ALA may induce PpIX formation in the bacteria and hence may increase the red fluorescence emission, which may enhance the red-to-green fluorescence contrast of the bacteria imaged with the device. ALA is non-fluorescent by itself, but PpIX is fluorescent at around 630 nm, 680 and 710 nm, with the 630 nm emission being the strongest. The imaging device may then be used to image the green and red fluorescence from the wound and the surrounding tissues. The time needed to obtain significant/appreciable increase in red (e.g., peak at 630 nm) fluorescence using the imaging device after the ALA (~20 µg/mL) was applied to the wound ranges from 10-30 mins, but this time can be optimized, and depends also on the ALA dose which can also be optimized.

Thus, a clinical operator can premix the ALA, which is usually provided commercially in lyophilized form with physiological saline or other type of commercially available cream/ointment/hydrogel/dressing etc., at a given dose and administer the agent topically by spraying it, pouring it, or carefully applying the agent to the wound area prior to imaging. Approximately 10-30 mins afterwards, although this time may vary, fluorescence imaging may be performed in a dimly lit or dark room. Bacteria occult under white light and perhaps poorly autofluorescent may appear as bright red fluorescent areas in and around the wound. The fluorescence images may be used to direct targeted swabbing, biopsy and/or fine needle aspirates of the wound for bacterial culturing based on the unique bacterial fluorescence signal, and this may be done at different depths, for superficial and deep wounds.

The device may also be used in conjunction with exogenous 'pro-drug' agents, including, but not limited to, ALA which is FDA approved for clinical therapeutic indications, to increase the endogenous production of porphyrins in bacteria/microorganisms and thereby increase the intensities of unique 'porphyrin' fluorescence signals emanating from these bacteria to improve the detection sensitivity and specificity of the device. Thus, the device may be used to conveniently image photosensitizer-induced fluorescence (e.g., PpIX) in bacteria, growing in culture or in patients' wounds for subsequent image-guided targeted swabbing/ biopsy or treatment, for example using photodynamic therapy (PDT) or hyperbaric oxygen therapy (HOT). The device when used with for example consumable, commercially available fluorescence contrast agents has the ability to increase the signal-to-background for sensitive detection of bacteria, in and around wounds. It should be noted that ALA is commercially available.

In one example, the device was used to image live bacterial culture (*Staphylococcus aureus*, grown on agar plates for 24 h prior to imaging) using violet/blue excitation light. After 30 mins of incubation of *Staphylococcus aureus*~20 µg/mL of ALA at 37° C., a significant increase in red fluorescence from the bacteria was detected, compared with those colonies that did not receive any ALA. Thus, the device may exploit the use of contrast agent strategies to increase the signal-to-background for sensitive detection of bacteria, in wounds for example. The time needed for the ALA to increase the PpIX fluorescence of bacteria in culture to significant levels was approximately 0.5 h which suggests that this approach may be clinically practical. Tests on simulated bacterially-contaminated meat samples revealed similar results to those obtained from bacterial culture. Topical application of 0.2 µg/mL ALA by spraying onto wounds on pig skin resulted in a dramatic increase of bacterial porphyrin red fluorescence contrast approximately 2 h after ALA administration. This demonstrates that the device may allow for detection of bacterial contamination with fluorescence imaging within the wound sites and elsewhere on the skin surface, which was previously occult under white light imaging.

Use with Exogenous Molecular-Targeted and Activated Imaging Agents

The availability of commercially available fluorescence molecular bacteriological detection and viability kits may offer another use for the device in wound care. Such kits may be used to rapidly quantitatively distinguish live and dead bacteria, even in a mixed population containing a range of bacterial types. Conventional direct-count assays of bacterial viability are typically based on metabolic characteristics or membrane integrity. However, methods relying on metabolic characteristics often only work for a limited subset of bacterial groups, and methods for assessing bacterial membrane integrity commonly have high levels of background fluorescence. Both types of determinations also suffer from being very sensitive to growth and staining conditions.

Suitable exogenous optical molecular targeting probes may be prepared using commercially available fluorescence labeling kits, such as the Alexa Fluor active esters and kits (e.g., Zenon Antibody Labeling Kits and or EnzChek Protease Assay Kits, Invitrogen) for labeling proteins, monoclonal antibodies, nucleic acids and oligonucleotides (Invitrogen). For example, these fluorescent dye bioconjugates cover the following wavelength ranges: Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700 and Alexa Fluor 750 dyes, where the number stated refers to the excitation wavelength of the dye. These kits may offer well-differentiated fluorescence emission spectra, providing many options for multicolor fluorescence detection and fluorescence resonance energy transfer, based on the appropriate selection of fluorescence emission filters with the imaging device. The fluorescence dyes offer high absorbance at wavelengths of maximal output of common excitation sources, they are bright and unusually photostable fluorescence of their bioconjugates, and offer good water solubility of the reactive dyes for ease of conjugation within the clinical exam room and resistance of the conjugates to precipitation and aggregation. The dyes' fluorescence spectra are insensitive to pH over a broad range, which makes them particularly useful for wound imaging, since wound pH can vary. In addition, other commercial or non-commercial fluorescent agents exist which may be appropriate for biological imaging of wounds and may be combined with the described device, including fluorescent blood pooling agents and various wound-enzyme or protease activated probes from VisEn Medical (Boston, Mass., USA), for example.

These targeting fluorescent bioconjugates may be prepared using such labeling kits prior to the clinical exam of the wound using the imaging device in fluorescence mode, and may be stored in light-tight containers to avoid photobleaching. Such fluorescence bioconjugates may be prepared in solution at a known and appropriate concentration prior to fluorescence imaging of the wound using the device, and then administered/applied directly to the wound and surrounding normal tissues either topically (e.g., via aerosol/spray, lavage techniques), or given orally in a drink or systemically via intravenous injection. Such dyes may target specific biological components depending on the targeting moiety, and may include: bacteria, fungi, yeast, spores, virus, microbes, parasites, exudates, pH, blood vessels, reduced nicotinamide adenine dinucleotide (NADH), Flavin adenine dinucleotide (FAD), microorganisms, specific types of connective tissues (e.g., collagens, elastin), tissue components, vascular endothelial growth factor (VEGF), endothelial growth factor (EGF), epithelial growth factor, epithelial cell membrane antigen (ECMA), hypoxia inducible factor (HIF-1), carbonic anhydrase IX (CAIX), laminin, fibrin, fibronectin, fibroblast growth factor, transforming growth factors (TGF), fibroblast activation protein (FAP), enzymes (e.g., caspases, matrix metalloproteinases (MMPs), etc.), tissue inhibitors of metalloproteinases (e.g., TIMPs), nitric oxide synthase (NOS), inducible and endothelial NOS, lysosomes in cells, macrophages, neutrophils, lymphocytes, hepatocyte growth factor (HGF), anti-neuropeptides, neutral endopeptidase (NEP), granulocyte-macrophage colony stimulating factor (GM-CSF), neutrophil elastases, cathepsins, arginases, fibroblasts, endothelial cells and keratinocytes, keratinocyte growth factor (KGF), macrophage inflammatory protein-2 (MIP-2), macrophage inflammatory protein-2 (MIP-2), and macrophage chemoattractant protein-1 (MCP-1), polymorphonuclear neutrophils (PMN) and macrophages, myofibroblasts, interleukin-1 (IL-1) and tumour necrosis factor (TNF), nitric oxide (NO) (Kit from Calbiochem, Model DAF-2 DA), and c-myc and beta-catenin, circulating endothelial progenitor cells (EPCs) from the bone marrow. Exogenous optical agents may include, but are not limited to, any of the following: activated molecular beacons (e.g., targeted), nanoparticles having fluorescent agents (e.g., labeled on the surface and/or containing or carrying fluorescent agents), and scattering or absorbing nanoparticles (e.g., gold, silver).

The LIVE/DEAD BacLight™ Bacterial Viability Kits (from Invitrogen, Molecular Probes) assay utilizes mixtures of SYTO® 9 green fluorescent nucleic acid stain and the red fluorescent nucleic acid stain, propidium iodide, although these fluorescent dyes may be exchanged for other existing or emerging fluorescent agents. These stains differ both in their spectral characteristics and in their ability to penetrate healthy bacterial cells. When used alone, the SYTO 9 stain labels bacteria with both intact and damaged membranes. In contrast, propidium iodide penetrates only bacteria with damaged membranes, competing with the SYTO 9 stain for nucleic acid binding sites when both dyes are present. When mixed in recommended proportions, SYTO 9 stain and propidium iodide produce green fluorescent staining of bacteria with intact cell membranes and red fluorescent staining of bacteria with damaged membranes. Thus, live bacteria with intact membranes fluoresce green, while dead bacteria with damaged membranes fluoresce red. The background remains virtually non-fluorescent. Consequently, the ratio of green to red fluorescence intensities may provide a quantitative index of bacterial viability.

Live and dead bacteria may be viewed separately or simultaneously by the imaging device with suitable optical filter sets. As well, similar fluorescence assay kits are available for Gram sign (i.e., positive/negative) identification of bacteria, which is a useful parameter in wound treatment planning, and may be used in conjunction with the imaging device. Such fluorescence agents are general and applicable to most bacteria types, and may be used to determine bacterial viability and/or Gram sign either directly on/within the wound or on ex vivo swab- or tissue biopsy-derived culture samples obtained from the wound site (e.g., superficially or at depth) for real-time quantitative assessment using the imaging device. Such fluorescence fluorescent agents may be prepared in solution in advance at a known and appropriate concentration prior to fluorescence imaging of the wound using the device, and then administered/applied directly to the wound and surrounding normal tissues either topically (e.g., via aerosol/spray, lavage techniques), or perhaps systemically via intravenous injection. Imaging may then be performed accordingly after a defined time for the agents to react with the targets. A washing off of unlabeled agents may be required prior to imaging with the device. For this, physiological saline may be used. Target-bound fluorescent agent may remain within the wound and surrounding tissues for fluorescence imaging.

Therefore, when used with fluorescent reporter systems the imaging device may provide a relatively rapid means of assessing bacterial viability following exposure to antimicrobial agents. The ability to repeatedly measure the same patients or animals may reduce variability within the treatment experiments and allowed equal or greater confidence in determining treatment efficacy. This non-invasive and portable imaging technology may reduce the number of animals used during such studies and has applications for the evaluation of test compounds during drug discovery.

A number of commercially available organic fluorophores have properties that are dependent on hydrogen ion concentration, rendering them useful as probes for measuring pH, and they typically have pH sensitive UV/visible absorption properties. The majority of commercially available pH sensitive fluorescent dyes employed in intracellular studies provide a reduced fluorescent signal in acidic media or alternatively the pKa of the dye is outside the critical intracellular pH window of between 5-8 pH units. However, other pH-sensitive fluorescent agents respond by increasing their fluorescence intensities. For example, Invitrogen/Molecular Probes offers a variety of fluorescent pH indicators, their conjugates and other reagents for pH measurements in biological systems. Among these are several probes with unique optical response and specialized localization characteristics: for example, visible light-excitable SNARF pH indicators enable researchers to determine intracellular pH in the physiological range using dual-emission or dual-excitation ratiometric techniques, thus providing useful tools for confocal laser-scanning microscopy and flow cytometry. LysoSensor probes, as well as indicators based on the Oregon Green fluorophore, may be used to estimate the pH in a cell's acidic organelles. There are also fluorescent pH indicators coupled to dextrans which may be used. Following loading into cells, indicator dextrans may be well retained, may not bind to cellular proteins and may have a reduced tendency to compartmentalize. Again, such fluorescent agents may be prepared in solution in advance at a known and appropriate concentration prior to fluorescence imaging of the wound using the device, and then administered/applied directly to the wound and surrounding normal tissues either topically (e.g., via aerosol/spray, lavage techniques), systemically or for example, via intravenous injection, or orally.

EXAMPLES

Figure 24:
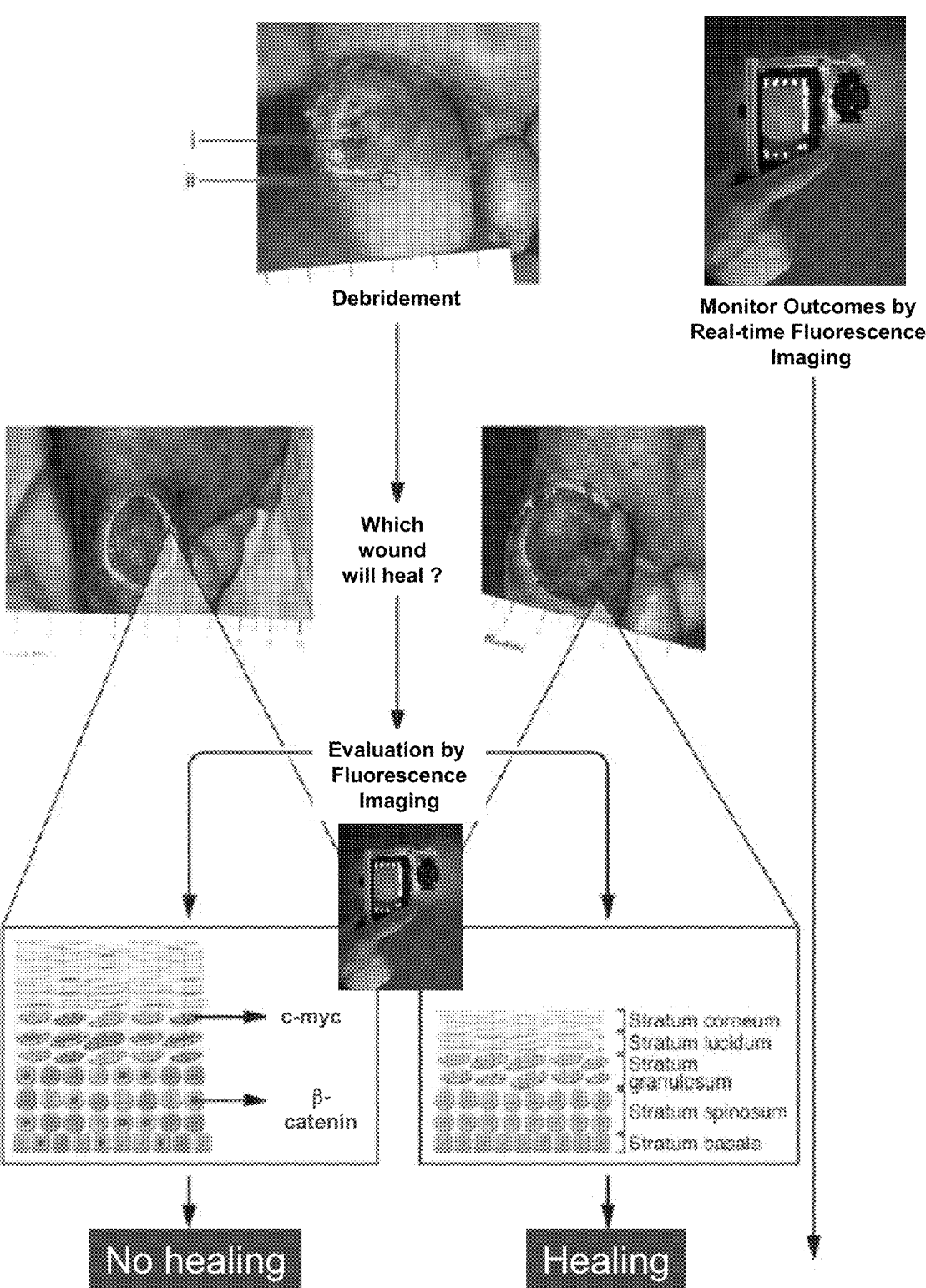
FIG. 24 illustrates an example of monitoring of a chronic wound.

Reference is now made to FIG. 24. As an example, the imaging device may be used clinically to determine the healing status of a chronic wound and the success of wound debridement. For example, a typical foot ulcer in a person with diabetes is shown in the figure, with (i) the nonhealing edge (i.e., callus) containing ulcerogenic cells with molecular markers indicative of healing impairment and (ii) phenotypically normal but physiologically impaired cells, which can be stimulated to heal. Despite a wound's appearance after debridement, it may not be healing and may need to be evaluated for the presence of specific molecular markers of inhibition and/or hyperkeratotic tissue (e.g., c-myc and β-catenin). Using the imaging device in combination with exogenous fluorescently labeled molecular probes against such molecular targets, the clinician may be able to determine the in situ expression of molecular biomarkers. With the device, once a wound is debrided, fluorescence imaging of the wound area and image analyses may allow biopsy targeting for subsequent immunohistochemistry and this may determine whether the extent of debridement was sufficient. If the extent of debridement was insufficient, as shown in the lower left diagram, cells positive for c-myc (which appears green) and nuclear β-catenin (which appears purple) may be found based on their fluorescence, indicating the presence of ulcerogenic cells, which may prevent the wound from healing properly and indicate that additional debridement is necessary. Lack of healing may also be demarcated by a thicker epidermis, thicker cornified layer, and presence of nuclei in the cornified layer. If the debridement was successful, as in the lower right lower diagram, no staining for c-myc or β-catenin may be found, indicating an absence of ulcerogenic cells and successful debridement. These markers of inhibition may be useful, but the goal is actual healing as defined by the appearance of new epithelium, decreased area of the wound, and no drainage. This information may be collected using the fluorescence imaging device and stored electronically in the patient's medical record, which may provide an objective analysis coupled with pathology and microbiology reports. By comparing expected healing time with actual healing (i.e., healing progress) time using the imaging device, adaptive treatment strategies may be implemented on a per-patient basis.

Figure 24B:
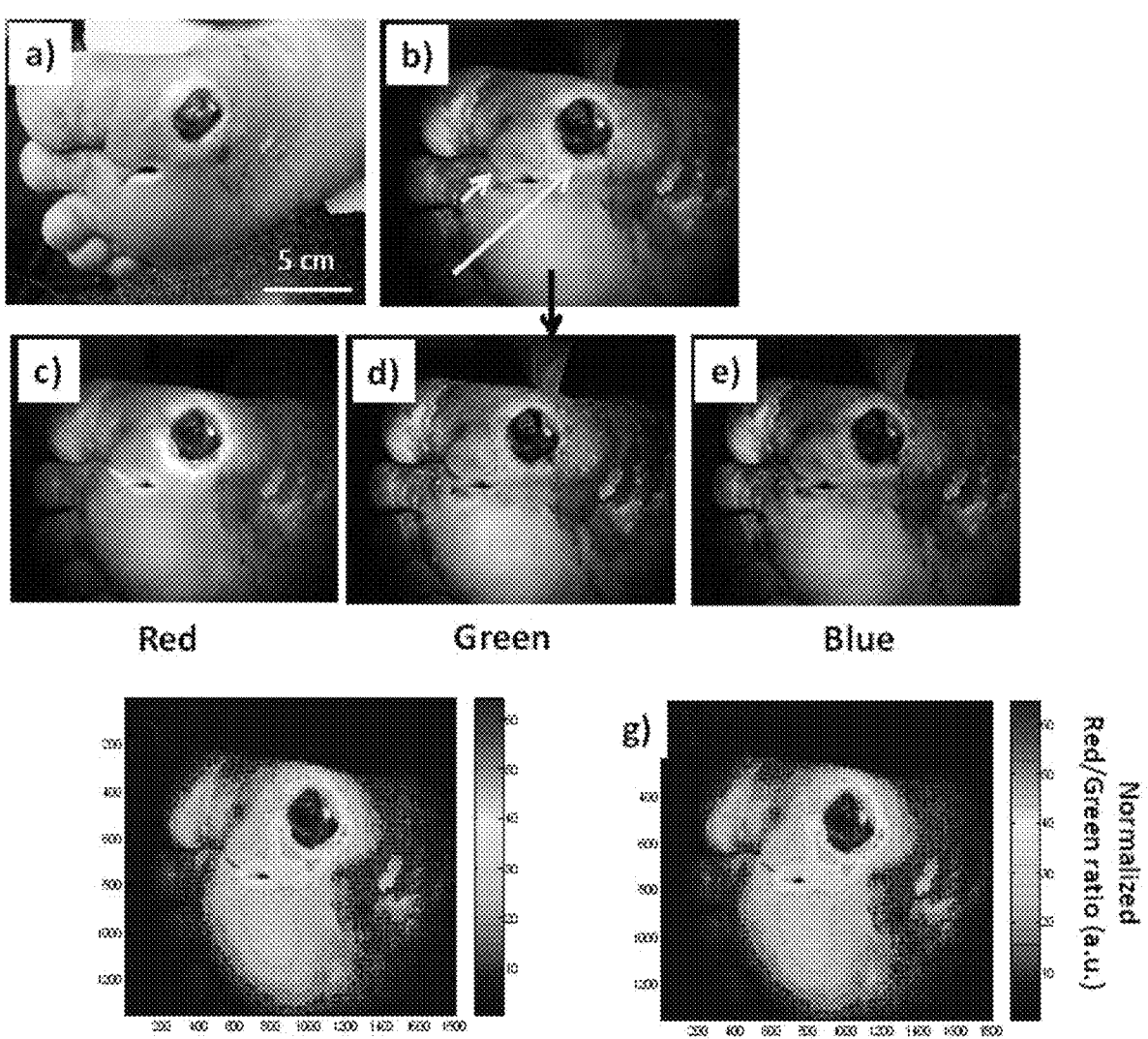
FIGS. 24B-24P show examples of the use of a device for fluorescence-based monitoring for imaging wounds and conditions in clinical patients.

FIG. 24B shows an example of the use of the device for imaging wound healing of a pressure ulcer. a) White light image taken with the device of the right foot of a diabetic patient with a pressure ulcer is shown. b) Corresponding fluorescence image shows the bright red fluorescence of bacteria (bacteriology results confirmed presence of heavy growth of Staphylococcus aureus) which are invisible under standard white light examination (yellow arrows). Note the heavy growth of Staphylococcus aureus bacteria around the periphery of the non-healing wound (long yellow arrow). c-d) Show the spectrally-separated (unmixed) red-green-blue images of the raw fluorescence image in b), which are used to produce spectrally-encoded image maps of the green (e.g. collagen) and red (e.g. bacteria) fluorescence intensities calculated using mathematical algorithms and displayed in false color with color scale. f-g) show examples of image-processing methods used enhance the contrast of the endogenous bacterial autofluorescence signal by calculating the red/green fluorescence intensity ratio to reveal the presence and biodistribution of bacteria (red-orange-yellow) within and around the open wound. These data illustrate the ability to use custom or commercially-available image-analysis software to mathematically analyze the fluorescence images obtained by the device and display them in a meaningful way for clinical use, and this may be done in real-time. (Scale bar 1 cm).

Figure 24C:
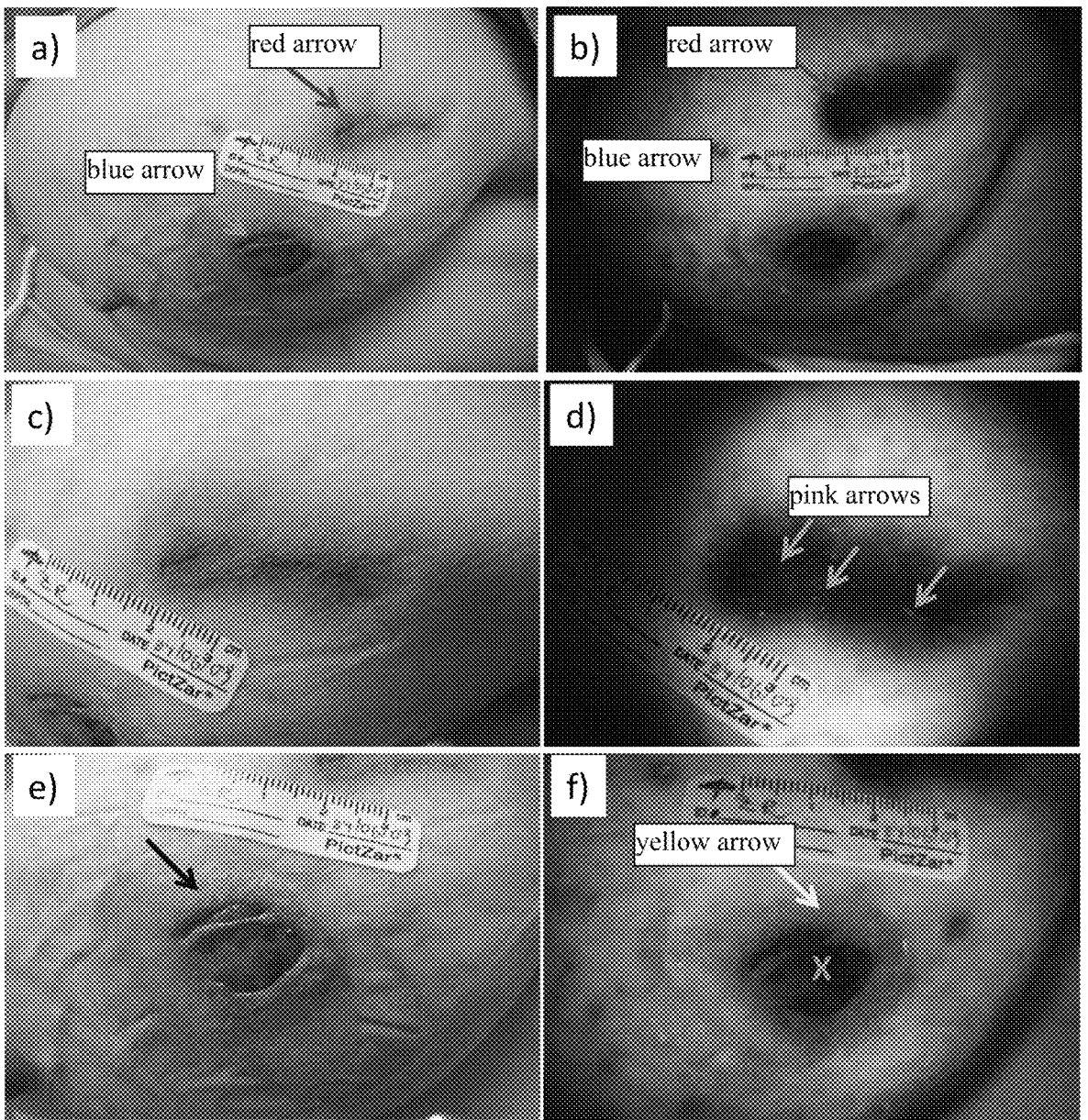
FIG. 24Q shows an example of the use of a device for fluorescence-based monitoring for imaging bacterial response to photodynamic therapy.
FIG. 24R shows an example of the use of a device for fluorescence-based monitoring for imaging tissue.

FIG. 24C shows an example of the use of the device for imaging a chronic non-healing wound. a) White light image taken with the device of the left breast of a female patient with Pyoderma gangrenosum, shows a chronic non-healing wound (blue arrow) and a healed wound (red arrow). Bacteria typically cannot be visualized by standard white light visualization used in conventional clinical examination of the wounds. b) Corresponding fluorescence image of the same wounds (in this example, using 405 nm excitation, 500-550 nm emission (green), >600 nm emission (red)) is shown. Note that the non-healed wound appears dark colored under fluorescence (mainly due to blood absorption of the excitation and fluorescence emission light), while bacteria appear as punctuate bright red spots in the healed wound (red arrow). Under fluorescence, normal surrounding skin appears cyan-green due to endogenous collagen fluorescence (405 nm excitation). By contrast, the non-healed wound (blue arrow) appears to have a band of very bright red fluorescence around the wound border, confirmed with swab cultures (bacteriology) to contain a heavy growth of Staphylococcus aureus (with few Gram positive bacilli and rare Gram positive cocci, confirmed by microscopy). c) White light image of the healed wound in a), b) and d) corresponding fluorescence image showing bright red fluorescence from bacteria (pink arrows), which are occult under white light. e) White light and f) corresponding fluorescence images of the non-healed breast wound. Note that bacteria (Staphylococcus aureus) appear to be mainly localized around the edge/boundary of the wound (yellow arrow), while less bacteria are located within the wound (X), determined by the biodistribution of bacteria directly visualized using fluorescence imaging, but invisible under white light (black arrow, e). (Scale bar in cm).

Figure 24D:
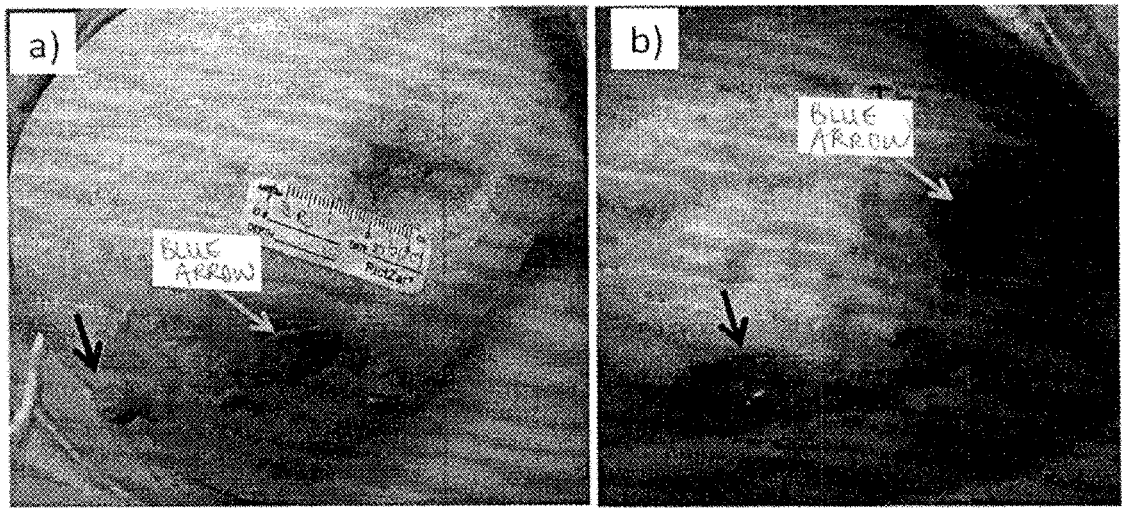

FIG. 24D further illustrates imaging of a chronic non-healing wound using an example of the imaging device. a) White light image taken with the device of left breast of female patient with *Pyoderma gangrenosum*, showing chronic non-healing wound (blue arrow) and healed wound (blue arrow). Bacteria cannot be visualized by standard white light visualization used in clinical examination of the wounds. b) Corresponding fluorescence image of the same wounds (405 nm excitation, 500-550 nm emission (green), >600 nm emission (red)). While the nipple appears to be normal under white without obvious contamination of bacteria, fluorescence imaging shows the presence of bacteria emanating from the nipple ducts. Swabs of the nipple showed bacteria were *Staphylococcus epidermidis* (Occasional growth found on culture). (Scale bar in cm)

Figure 24E:
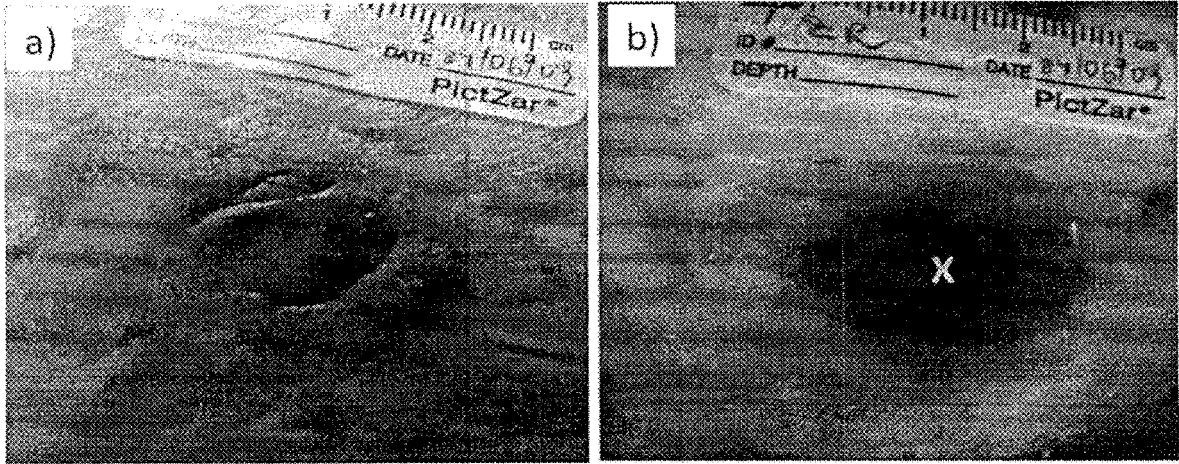

FIG. 24E shows a central area and border of a chronic non-healing wound imaged using the imaging device. a) White light image taken with the device of left breast of female patient with *Pyoderma gangrenosum*, showing the central area and border of a chronic non-healing wound. a) White light and b) corresponding fluorescence images of the non-healed breast wound (405 nm excitation, 500-550 nm emission (green), >600 nm emission (red)). Note that bacteria (*Staphylococcus aureus*; shown by bacterial swabbing) appear to be mainly localized around the edge/boundary of the wound, while less bacteria are located within the wound (X), determined by the biodistribution of bacteria directly visualized using fluorescence imaging, but invisible under white light. (Scale bar in cm).

Figure 24F:
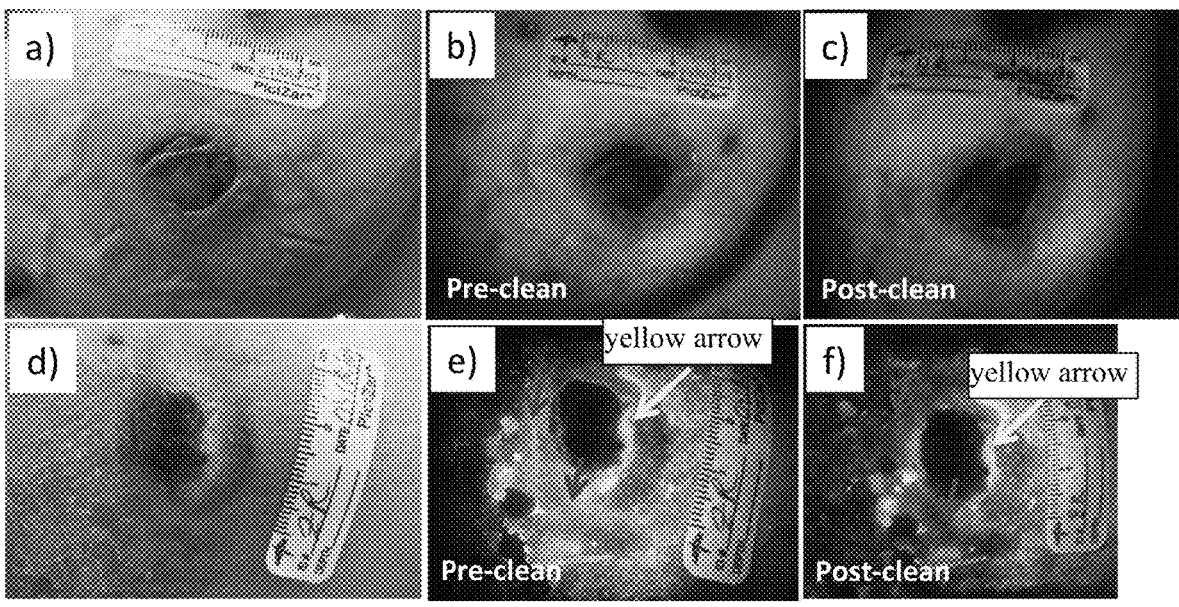

FIG. 24F shows further images of a chronic non-healing wound using the imaging device. a) White light image taken with the device of left breast of female patient with *Pyoderma gangrenosum*, showing chronic non-healing wound. Bacteria cannot be visualized by standard white light visualization used in clinical examination of the wounds. b) Corresponding fluorescence image of the same wound (405 nm excitation, 500-550 nm emission (green), >600 nm emission (red)). Fluorescence imaging shows the presence of bacteria around the wound edge/border pre-cleaning (b) and post-cleaning (c). In this example, cleaning involved the use of standard gauze and phosphate buffered saline to wipe the surface the wound (within and without) for 5 minutes. After cleaning, the red fluorescence of the bacteria is appreciably decreased indicating that some of the red fluorescent bacteria may reside below the tissue surface around the edge of the wound. Small amounts of bacteria (red fluorescent) remained within the wound center after cleaning. This illustrates the use of the imaging device to monitor the effects of wound cleaning in real-time. As an additional example, d) shows a white light image of a chronic non-healing wound in the same patient located on the left calf. e) Shows the corresponding fluorescence images pre-cleaning (e) and post-cleaning (f). Swabbing of the central area of the wound revealed the occasional growth of *Staphylococcus aureus*, with a heavy growth of *Staphylococcus aureus* at the edge (yellow arrow). Cleaning resulted in a reduction of the fluorescent bacteria (*Staphylococcus aureus*) on the wound surface as determined using the handheld optical imaging device. The use of the imaging device resulted in the real-time detection of white light-occult bacteria and this allowed an alteration in the way the patient was treated such that, following fluorescence imaging, wounds and surrounding (bacteria contaminated) were either re-cleaned thoroughly or cleaned for the first time because of de novo detection of bacteria. Also, note the use of a disposable adhesive measurement-calibration 'strip' for aiding in imaging-focusing and this "strip" may be adhered to any part of the body surface (e.g., near a wound) to allow wound spatial measurements. The calibration strip may also be distinctly fluorescent and may be used to add patient-specific information to the images, including the use of multiple exogenous fluorescent dyes for "barcoding" purposes—the information of which can be integrated directly into the fluorescence images of wounds. (Scale bar in cm).

Figure 24G:
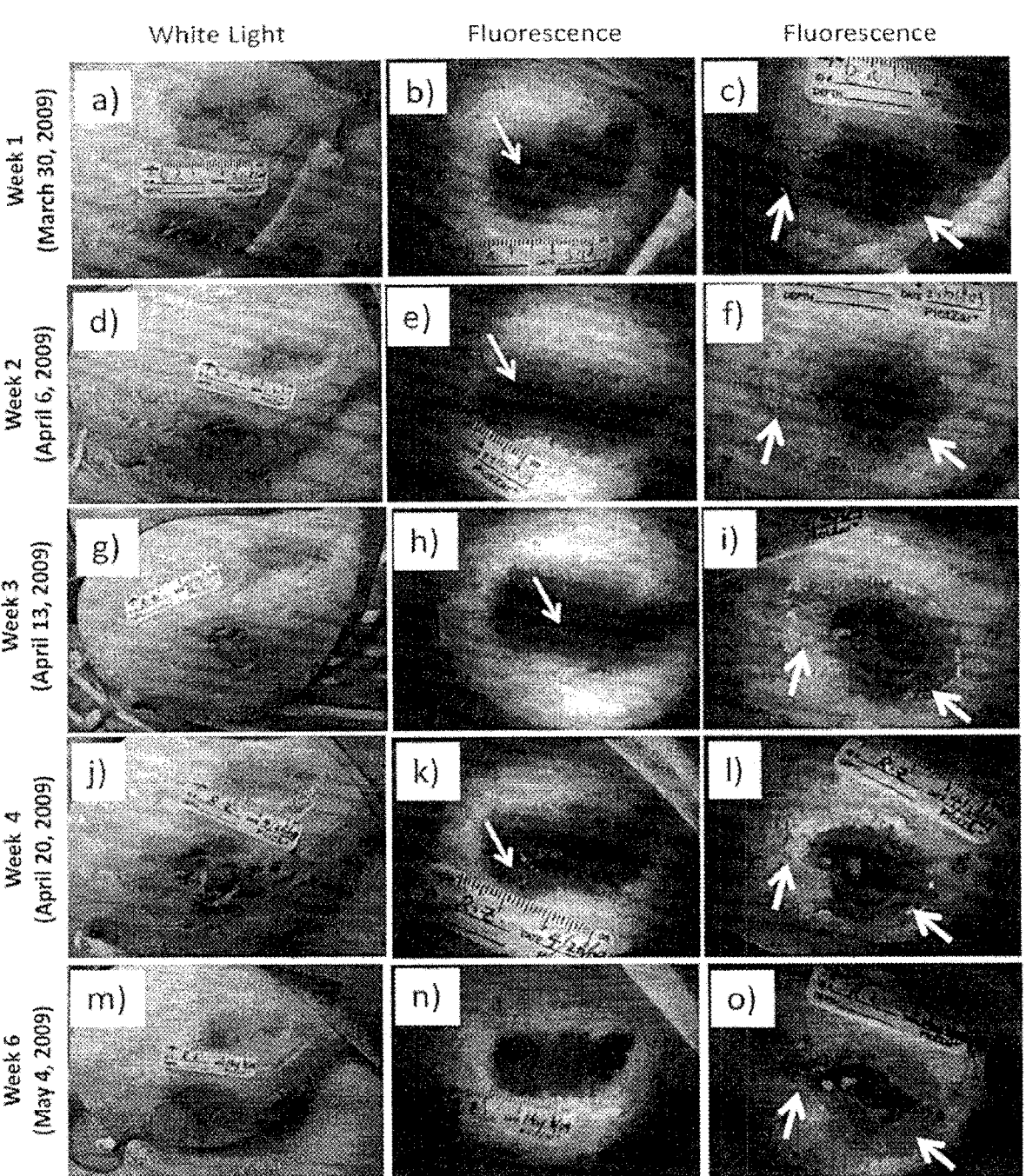

FIG. 24G illustrates use of the imaging device for monitoring wound healing over time. The imaging device is used for tracking changes in the healing status and bacterial biodistribution (e.g. contamination) of a non-healing chronic wound from the left breast of female patient with *Pyoderma gangrenosum*. White light images (a-m) and corresponding fluorescence images of the (b-n) healed wound and of the (c-o) chronic non-healing wound are shown over the course of six weeks. (405 nm excitation, 500-550 nm emission (green), >600 nm emission (red)), taken using the imaging device under both white light and fluorescence modes. In b-n), the presence of small bright red fluorescence bacterial colonies are detected (yellow arrows), and their localization changes over time within the healed wound. Bacterial swabs confirmed that no bacteria were detected on microscopy and no bacterial growth was observed in culture. In c-o), by contrast, the non-healed wound has a band of very bright red fluorescence around the wound border, confirmed with swab cultures (bacteriology) to contain a heavy growth of *Staphylococcus aureus* (with few Gram positive bacilli and rare Gram positive cocci, confirmed by microscopy), which changes in biodistribution over time (i.e., c-o). These data demonstrate that the imaging device may yield real-time biological and molecular information as well as be used to monitor morphological and molecular changes in wounds over time.

Figure 24H:
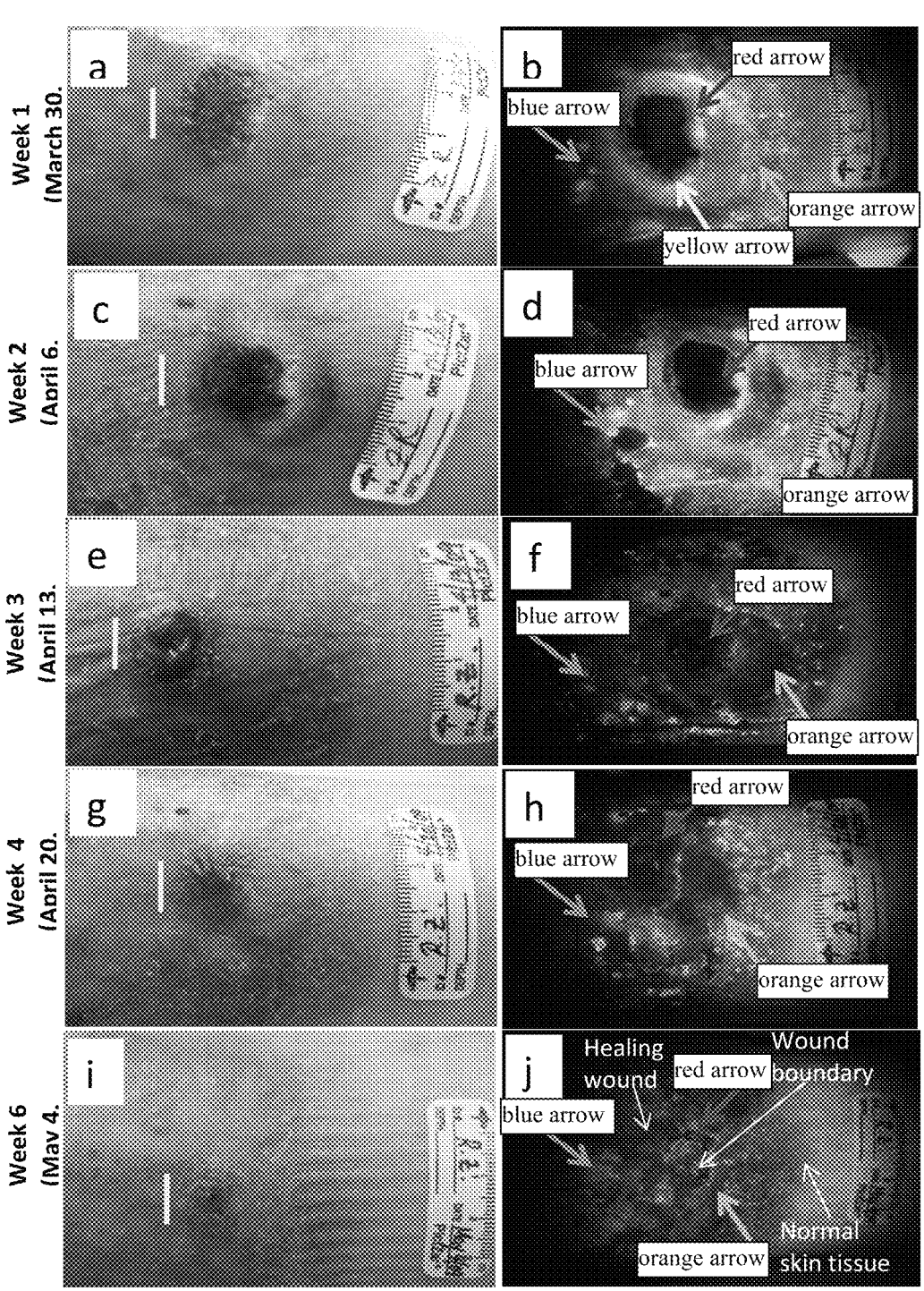

FIG. 24H shows another example of the use of the device for monitoring wound status over time. The imaging device is used tracking changes in the healing status and bacterial biodistribution (e.g. contamination) of a wound from the left calf of 21 year old female patient with *Pyoderma gangrenosum*. White light images (a-i) and corresponding fluorescence images of a (b-j) wound being treated using hyperbaric oxygen therapy (HOT) are shown over the course of six weeks. (Fluorescence parameters: 405 nm excitation, 500-550 nm emission (green), >600 nm emission (red)). a-i) White light images reveal distinct macroscopic changes in the wound as it heals, indicated by the reduction in size over time (e.g. closure) from week 1 (~2 cm long diameter diameter) through to week 6 (~0.75 cm long axis diameter). In b-j), the real-time fluorescence imaging of endogenous bacterial fluorescence (autofluorescence) in and around the wound can be tracked over time, and correlated with the white light images and wound closure measurements (a-i). b) shows a distinct green band of fluorescence at the immediate boundary of the wound (yellow arrow; shown to be contaminated heavy growth of *Staphylococcus aureus*), and this band changes over time as the wound heals. Red fluorescence bacteria are also seen further away from the wound (orange arrow), and their biodistribution changes over time (b-j). The wound-to-periwound-to-normal tissue boundaries can be seen clearly by fluorescence in image j). Connective tissue (in this example, collagens) in normal skin appear as pale green fluorescence (j) and connective tissue remodeling during wound healing can be monitored over time, during various wound treatments including, as is the case here, hyperbaric oxygen therapy of chronic wounds.

Figure 24I:
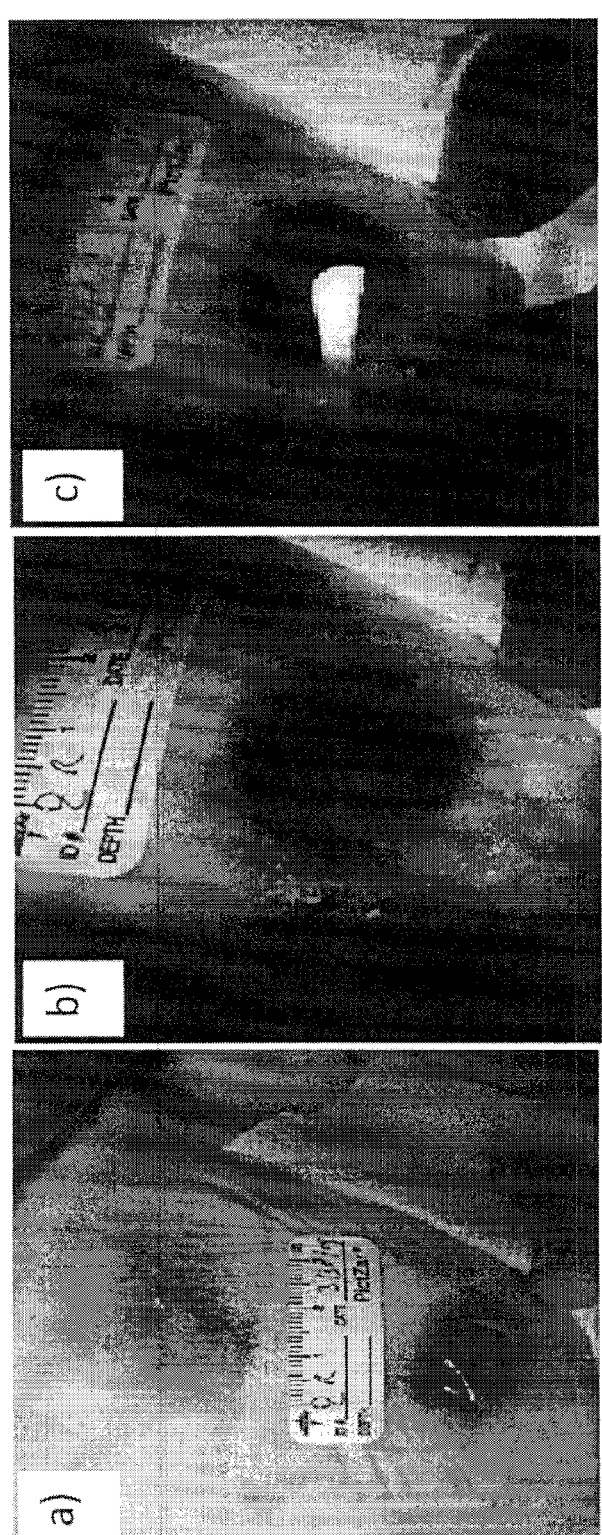

FIG. 24I illustrates use of the imaging device for targeting bacterial swabs during routine wound assessment in the clinic. Under fluorescence imaging, the swab can be directed or targeted to specific areas of bacterial contamination/infection using fluorescence image-guidance in real-time. This may decrease the potential for contamination of non-infected tissues by reducing the spread of bacteria during routine swabbing procedures, which may be a problem in conventional wound swabbing methods. Swab results from this sample were determined to be *Staphylococcus aureus* (with few Gram positive bacilli and rare Gram positive cocci, confirmed by microscopy).

Figure 24J:
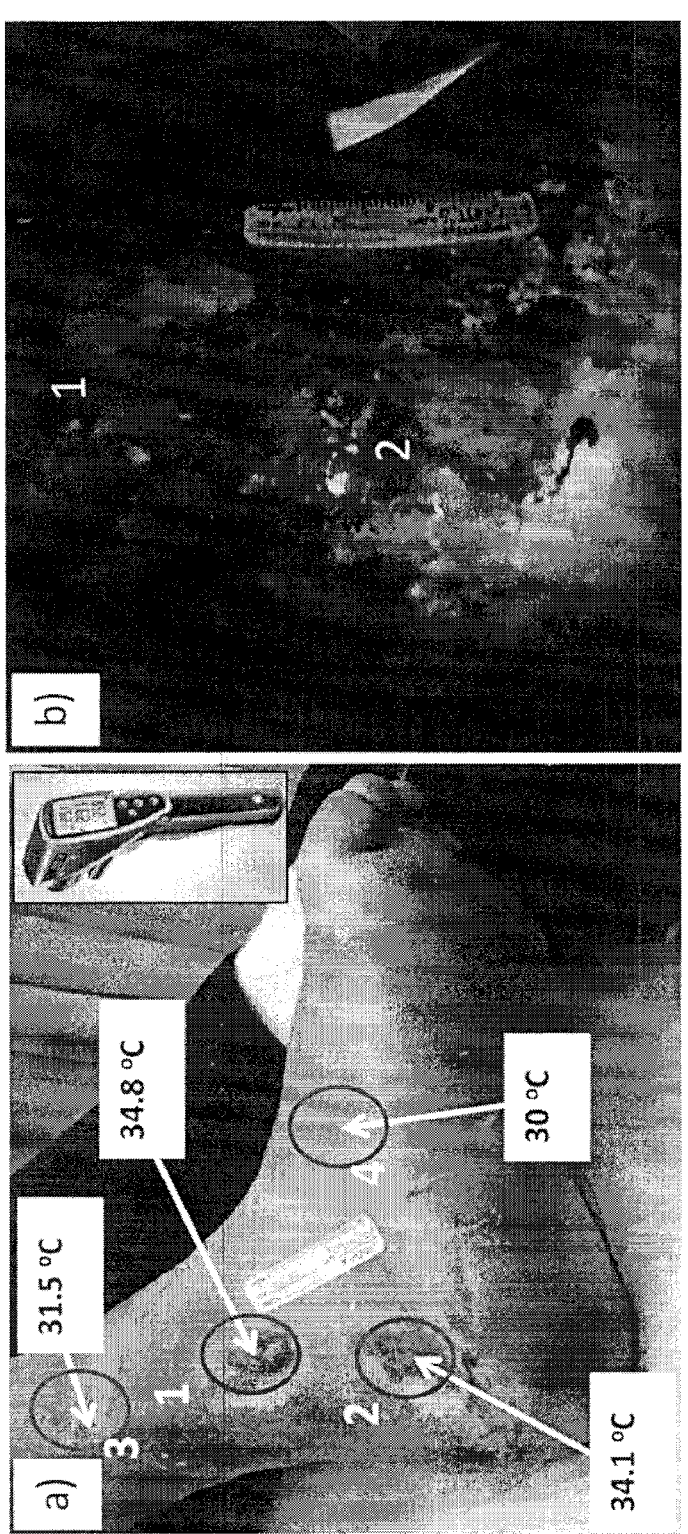

FIG. 24J shows an example of the co-registration of a) white light and b) corresponding fluorescence images made with the imaging device in a patient with diabetes-associated non-healing foot ulcers. Using a non-contact temperature measuring probe (inset in a) with cross-laser sighting, direct temperature measurements were made on normal skin (yellow "3 and 4") and within the foot ulcers (yellow "1 and 2") (infected with *Pseudomonas aeruginosa*, as confirmed by bacteriological culture), indicating the ability to add temperature-based information to the wound assessment during the clinical examination. Infected wounds have elevated temperatures, as seen by the average 34.45° C. in the infected wounds compared with the 30.75° C. on the normal skin surface, and these data illustrate the possibility of multimodality measurements which include white light, fluorescence and thermal information for wound health/infectious assessment in real-time. Note that both non-healing wounds on this patient's right foot contained heavy growth of *Pseudomonas aeruginosa* (in addition to Gram positive cocci and Gram negative bacilli), which in this example appear as bright green fluorescent areas within the wound (b).

Figure 24K:
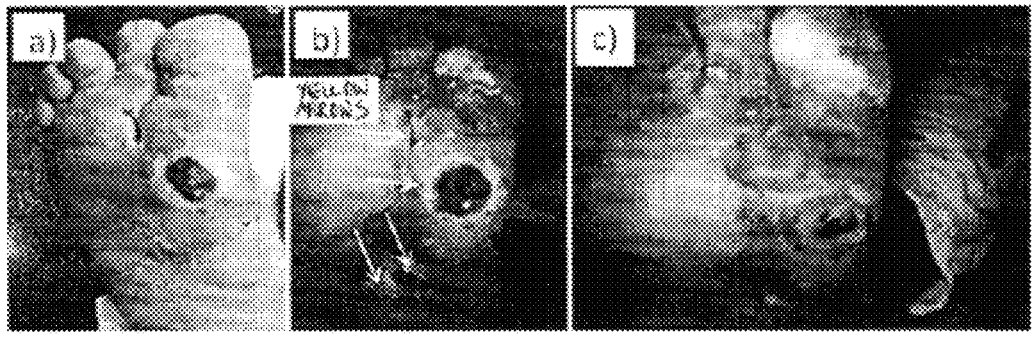

FIG. 24K shows an example of the use of the imaging device for monitoring a pressure ulcer. a) White light image taken with the imaging device of the right foot of a Caucasian diabetic patient with a pressure ulcer is shown. b) Corresponding fluorescence image shows the bright red fluorescence of bacteria (bacteriology results confirmed presence of heavy growth of *Staphylococcus aureus*) which are invisible under standard white light examination (yellow arrows). Dead skin appears as a white/pale light green color (white arrows). Note the heavy growth of *Staphylococcus aureus* bacteria around the periphery of the non-healing open wounds (yellow arrows). c) Shows the fluorescence imaging of a topically applied silver antimicrobial dressing. The imaging device may be used to detect the endogenous fluorescence signal from advanced wound care products (e.g., hydrogels, wound dressings, etc.) or the fluorescence signals from such products which have been prepared with a fluorescent dye with an emission wavelength within the detection sensitivity of the imaging detector on the device. The device may be used for image-guided delivery/application of advanced wound care treatment products and to subsequently monitor their distribution and clearance over time.

Figure 24L:
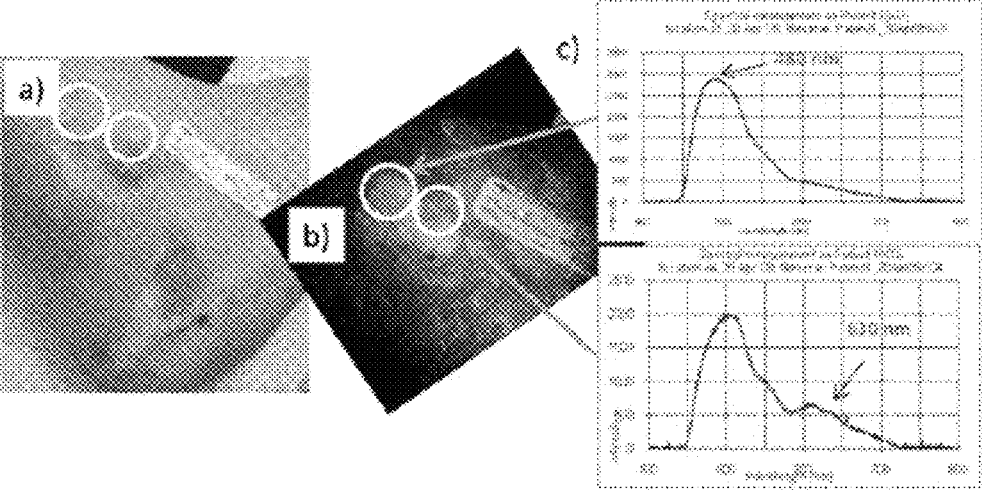

FIG. 24L shows an example of the use of the device for monitoring a pressure ulcer. a) White light image taken with the device of the right foot of a Caucasian diabetic patient with a pressure ulcer. b) Corresponding fluorescence image shows the bright red fluorescent area of bacteria (bacteriology results confirmed presence of heavy growth of *Staphylococcus aureus*, SA) at the wound edge and bright green fluorescent bacteria (bacteriology results confirmed presence of heavy growth of *Pseudomonas aeruginosa*, PA) which are both invisible under standard white light examination. c) Fluorescence spectroscopy taken of the wound revealed unique spectral differences between these two bacterial species: SA has a characteristic red (about 630 nm)

autofluorescence emission peak, while PA lacks the red fluorescence but has a strong green autofluorescence peak at around 480 nm.

Figure 24M:
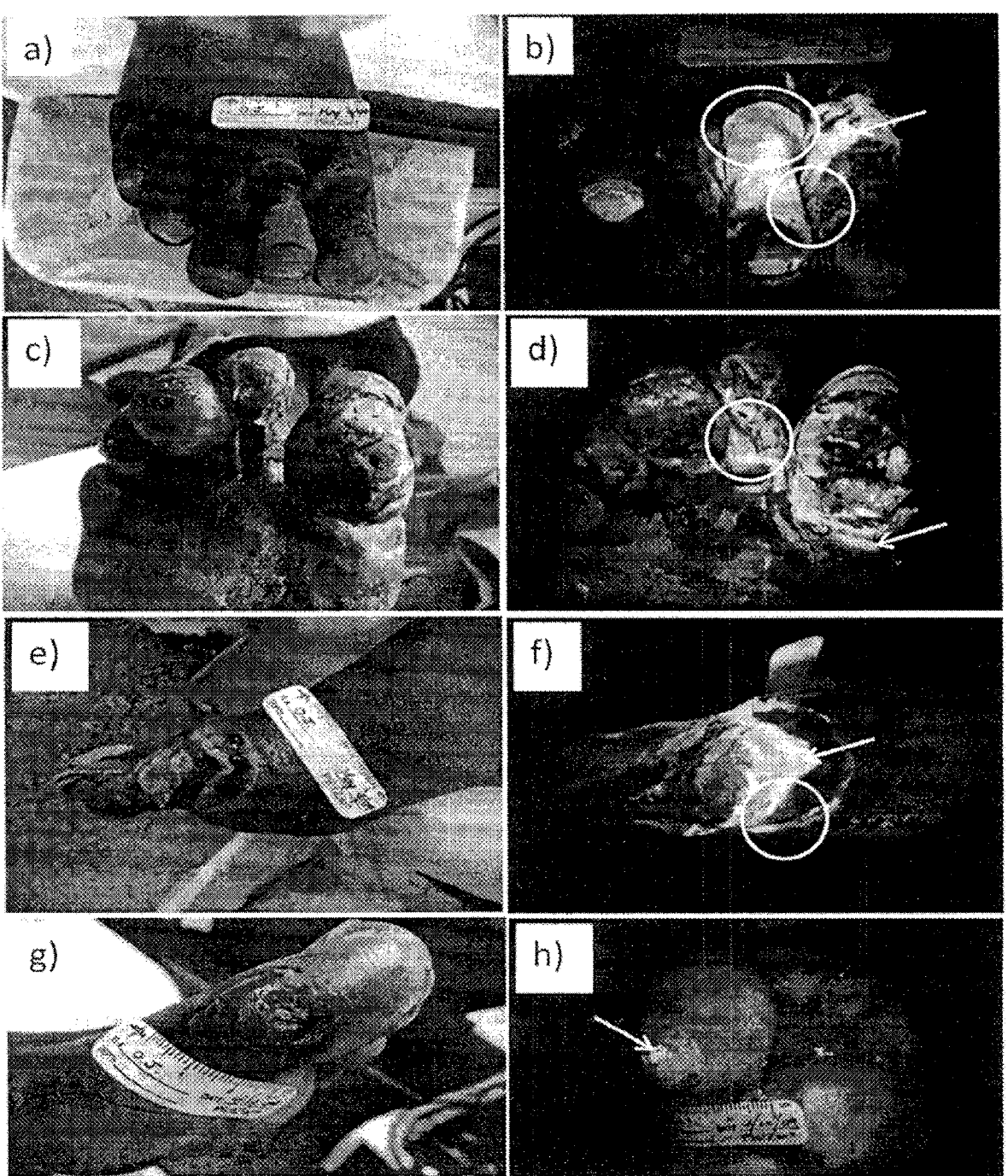

FIG. 24M shows an example of the use of the device for monitoring a chronic non-healing wound. a) White light image taken with the imaging device of chronic non-healing wounds in 44 year old black male patient with Type II diabetes is shown. Bacteria cannot be visualized by standard white light visualization (a-g) used in conventional clinical examination of the wounds. b-h) Corresponding fluorescence image of the same wounds (405 nm excitation, 500-550 nm emission (green), >600 nm emission (red)). This patient presented with multiple open non-healing wounds. Swab cultures taken from each wound area using the fluorescence image-guidance revealed the heavy growths of *Pseudomonas aeruginosa* (yellow arrow) which appear bright green fluorescent, and *Serratia marcescens* (circles) which appear red fluorescent. (Scale bar in cm).

Figure 24N:
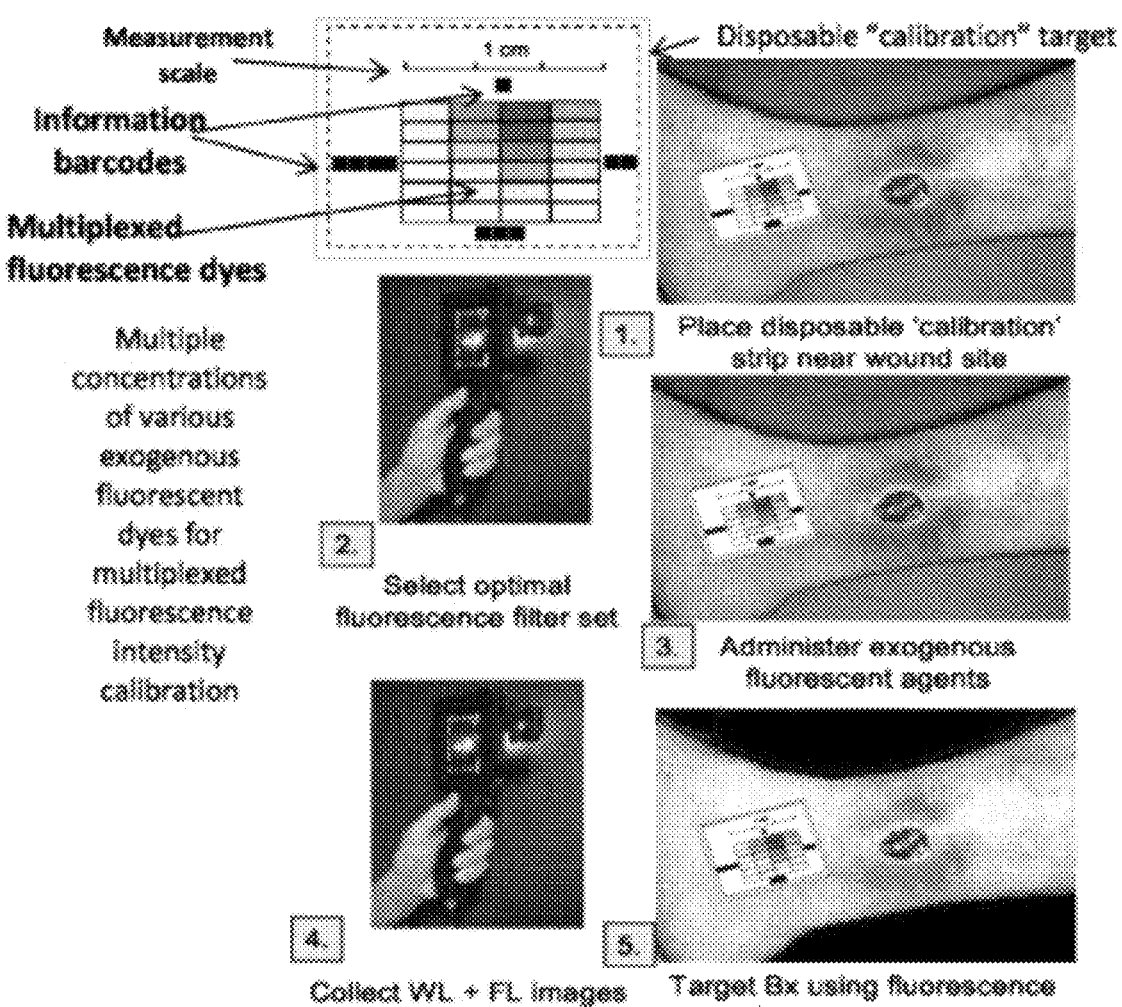

FIG. 24N is a schematic diagram illustrating an example of a use of "calibration" targets, which may be custom-designed, multi-purpose, and/or disposable, for use during wound imaging with the imaging device. The strip, which in this example is adhesive, may contain a combination of one or more of: spatial measurement tools (e.g., length scale), information barcode for integrating patient-specific medical information, and impregnated concentration-gradients of fluorescent dyes for real-time fluorescence image calibration during imaging. For the latter, multiple concentrations of various exogenous fluorescent dyes or other fluorescence agents (e.g., quantum dots) may be used for multiplexed fluorescence intensity calibration, for example when more than one exogenous fluorescently-labeled probe is used for tissue/cell/molecular-targeted molecular imaging of wounds in vivo.

Figure 24O:
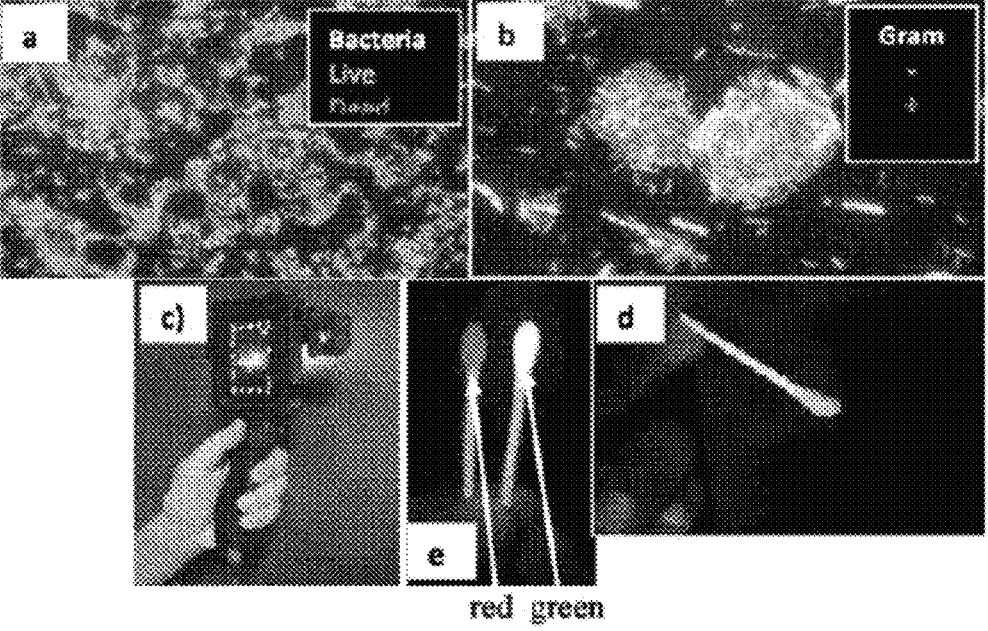

FIG. 24O shows an example of the use of an embodiment of the imaging device for monitoring bacteria, for example for monitoring a treatment response. a) Fluorescence microscopy image of a live/dead bacteria stain sold by Invitrogen Corp. (i.e., BacLight product). b) Fluorescence microscopy image of a Gram staining bacteria labeling stain sold by Invitrogen Corp. Using the imaging device (c) with such products, live (green) and dead (red) bacteria (e) may be distinguished in real-time ex vivo (e.g., on the swab or tissue biopsy) following bacterial swabbing of a wound, or other body surface, for example, in the swabbing of the oral buccal cheek, as in d). This real-time bacterial Gram staining or live/dead image-based assessment may be useful for real-time or relatively rapid bacteriology results that may be used for refining treatments, such as antibiotic or other disinfective treatments, or for monitoring treatment response.

Figure 24P:
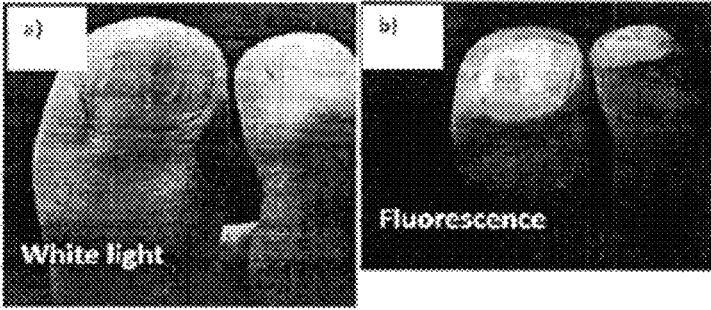

FIG. 24P shows an example of the use of the device used for imaging of toe nail infection. a) White light and b) corresponding autofluorescence of the right toe of a subject demonstrating the enhanced contrast of the infection that fluorescence imaging provides compared to white light visualization (405 nm excitation, 500-550 nm emission (green), >600 nm emission (red)).

Figure 24Q:
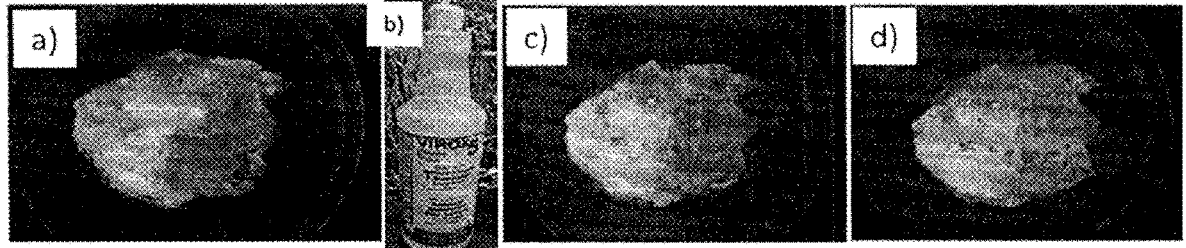

FIG. 24Q shows and example of imaging using the device for monitoring the response of meat-infected with bacteria to a disinfectant (e.g. hydrogen peroxide (Virox5TM)). a) An ex vivo porcine tissue sample was prepared in Petri dishes and contaminated with *Staphylococcus aureus* prior to topical administration of b) Virox5TM and fluorescence imaging (with handheld device), c). Breakdown of the tissue begins to occur rapidly, caused by the disinfectant, while a change in the fluorescence characteristics of the bacteria becomes apparent (e.g. red fluorescence color begins to change to orange fluorescence color, as seen in d), especially after gentle agitation of the sample and over time, here about 5 minutes incubation with the Virox5TM solution. These data suggest the use of the device for monitoring bacterial disinfection, for example in clinical and non-clinical settings (405 nm excitation; 490-550 nm and >600 nm emission).

In addition to fluorescence-enhancing pro-drugs, advances in medicine have enabled widespread use of fluorescent biomarkers to diagnose disease on a molecular level. The accurate measurement of the fluorescent biomarker signal in biological tissues may be a critical parameter towards gaining biomolecular information about disease progression and treatment response, but has historically posed a significant challenge. To date, this type of advanced molecular imaging has not been reported for wound care.

The device described herein may also be used in combination with fluorescent, light-scattering, or light-absorbing exogenous fluorescence contrast agents that can be used passively and/or targeted to unique and specific molecular targets within the wound to improve the detection and diagnosis of wound infection. These targets may be any biological and/or molecular component in the wound or normal surrounding tissues that have a known detection and/or diagnostic value (e.g., normal tissue and wound biomarkers). All exogenous agents may be delivered to the wound either topically and/or systemically, and may include, but are not limited to, any exogenous agent/drug (e.g., encapsulated liposomes, beads or other biocompatible carrier agents) that can be coupled/conjugated with an appropriate wavelength-selected fluorescent/scattering moiety (e.g., organic fluorescent dyes, quantum dots and other fluorescent semi-conductor nano-particles, colloidal metals (e.g., gold, silver, etc.)). Fluorescent and/or light scattering agents/probes, and/or chromogenic (i.e., absorption) agents/dyes may be prepared using standard bioconjugation techniques to include moieties for targeting specific biomarkers. Such moieties may include monoclonal antibodies (e.g., whole and/or fragments), and other tissue-specific moieties (including, but not limited to, peptides, oligomers, aptamers, receptor-binding molecules, enzyme inhibitors, toxins, etc.). The device may also be used for imaging in situ activatable promoter-controlled expression of light generating proteins in preclinical wound models. Furthermore, wound infections may also be detected using the imaging device and then treated using photothermal therapies, such as light-absorbing gold nanoparticles conjugated with specific antibodies which specifically target bacteria.

Figure 24R:
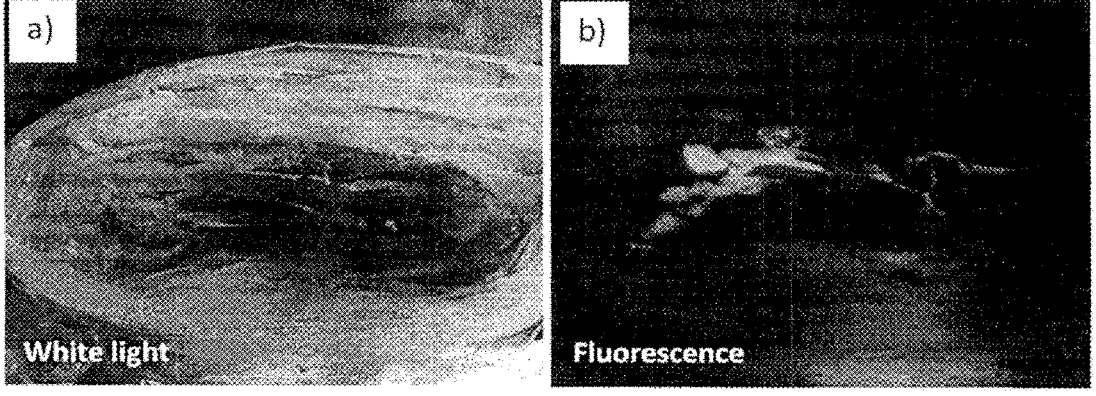

FIG. 24R shows an example of use of the imaging device used for imaging of fluorescent dyes/probes/agents on biological tissues. a) White light imaging of a piece of meat (ex vivo) does not reveal the presence of a fluorescent dye, whereas in b) the device allows accurate fluorescence detection and monitoring of the biodistribution of the fluorescent dye. Although shown for ex vivo tissue, these capabilities may be translated to in vivo applications including but not limited to, for example, imaging the biodistribution of fluorescent photosensitizers within tissues for photodynamic therapy (PDT) of wounds, cancer, infection, or other diseases. White light imaging may provide anatomical context for the fluorescence imaging. These capabilities may also be used to monitor photobleaching of fluorescent agents (including photosensitizers) as well as for image-guided delivery of multiple PDT treatments (405 nm excitation, 500-550 nm emission (green), >600 nm emission (red)). The device may provide for monitoring of pharmocokinetics, biodistribution, and/or photobleaching in PDT. Similarly, the device may be useful for monitoring of low level light therapies.

The device may also be used with other molecular-sensing agents, such as 'molecular beacons' or "smart probes", which produce fluorescence only in the presence of unique and specific biological targets (e.g., enzymes associated with wound health). Such probes may be useful for identifying specific bacterial species or GRAM signing, for example. For example, cutaneous wound healing is a highly complex process involving five overlapping phases (inflammation, granulation tissue formation, epithelialization, matrix production, and remodeling) associated with a number of migratory and remodeling events that are believed to require the action of matrix metalloproteinases (MMPs) and their inhibitors, TIMPs. In vivo analyses of human acute and chronic wounds as well as of a variety of different wound healing models have implicated a functional role of MMPs and TIMPs during normal wound repair, whereas deregulation of their activity is thought to contribute to impaired wound healing. Degradation of extracellular matrices is needed to remove damaged tissue and provisional matrices and to permit vessel formation and re-epithelialization. In contrast, in chronic or non-healing wounds over-expression of proteinases in their inactive form is thought to contribute to the underlying pathology and to inhibit normal tissue repair processes. Molecular beacons are activatable fluorescent reporters that use the fluorescence resonance energy transfer (FRET) principle to control fluorescence emission in response to specific biological stimuli. They usually comprise a disease-specific linker that brings a quencher close to a fluorophore to silence its fluorescence. Upon specific linker-target interactions (e.g., nucleic acid hybridization, protease-specific peptide cleavage, phospholipase-specific phospholipids cleavage), the quencher is removed from the vicinity of the fluorophore to restore its fluorescence. These smart probes may offer several orders of magnitude sensitivity than targeted probes because of the built-in high degree of signal amplification from nonfluorescent to highly fluorescent. Depending on their specific linker-target interactions, they may also be capable of interrogating specific molecular abnormality at the protein or gene expression levels. Because of these advantages, the smart probes have been recently hailed as "a quantum leap" over traditional probes for early cancer detection. Such exogenous agents may be used, for example, for relatively rapid, non-invasive, sensitive and specific optical detection of wound infections, to identify specific bacterial/microorganism species present and in situ microbial diagnosis, to monitor the health status of the wound, and to report in real-time on the effectiveness of treatment and care.

In addition, when used in combination with exogenous optical agents, the device may be used to identity patients minimally responsive to various established and experimental treatments, enabling rapid non-invasive or non-contact visual quantitative assessment of treatment response to make timely changes in therapy in order to optimize treatment outcomes.

Furthermore, real-time monitoring of antimicrobial effects in vitro and within animal model test systems using the imaging device may enhance basic understanding of the action of antibiotics and facilitate unique studies of disease in vivo.

EXAMPLES

Figure 5:
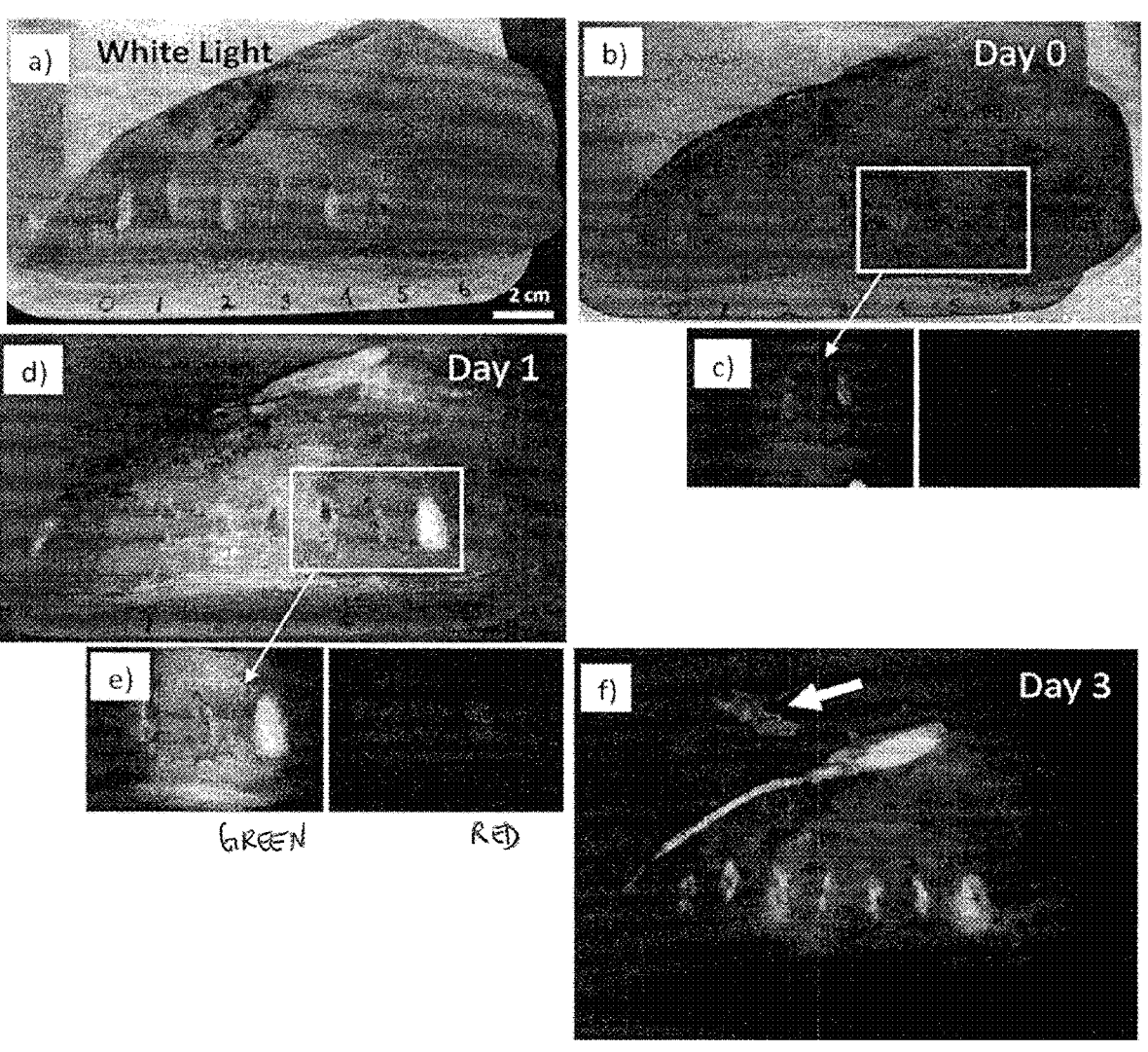
FIG. 5 shows images of a skin surface of a pig meat sample, demonstrating non-invasive autofluorescence detection of collagen and various bacterial species using a device for fluorescence-based monitoring.

FIG. 5 shows an example of the device being used for non-invasive autofluorescence detection of collagen and varies bacterial species on the skin surface of a pig meat sample. In contrast to white light imaging, autofluorescence imaging was able to detect the presence of several bacterial species 24 h after they were topically applied to small incisions made in the skin (i.e., *Streptococcus pyogenes, Serratia marcescens, Staphylococcus aureus, Staphylococcus epidermidis, Escherichia coli*, and *pseudomonas aeruginosa*). a) shows white light images of pig meat used for testing. Several bacterial species were applied to small incisions made in the skin at Day 0, and were labelled as follows: 1) *Streptococcus pyogenes,* 2) *Serratia marcescens,* 3) *Staphylococcus aureus,* 4) *Staphylococcus epidermidis,* 5) *Escherichia coli,* and 6) *Pseudomonas aeruginosa.* The imaging device was used to detect collagen and bacterial autofluorescence over time. Connective tissue fluorescence was intense and easily detected as well. Some bacterial species (e.g., *Pseudomonas aeruginosa*) produces significant green autofluorescence (450-505 nm) which saturated the device's camera. b) shows autofluorescence image at Day 0, magnified in c).

The device was also able to detect spreading of the bacteria over the surface of the meat over time. d) shows an image at Day 1, and f) shows an image at Day 3, as the meat sample was maintained at 37° C. Red fluorescence can be seen in some of the wound sites (5, 6) in c). As shown in d) and magnified in e), after 24 h, the device detects a dramatic increase in bacterial autofluorescence from wound site 5) *Escherichia coli* and 6) *Pseudomonas aeruginosa*, with the latter producing significant green and red autofluorescence. c) and e) show the device detecting fluorescence using a dual band (450-505 nm green and 590-650 nm) on the left and a single band filter (635+/−10 nm) on the right, of the wound surface. As shown in f), by Day 3, the device detects the significant increase in bacterial autofluorescence (in green and red) from the other wound sites, as well as the bacterial contamination (indicated by the arrow in f) on the styrofoam container in which the meat sample was kept. The device was also able to detect spreading of the bacteria over the surface of the meat. This demonstrates the real-time detection of bacterial species on simulated wounds, the growth of those bacteria over time, and the capability of the device to provide longitudinal monitoring of bacterial growth in wounds. The device may provide critical information on the biodistribution of the bacteria on the wound surface which may be useful for targeting bacterial swabbing and tissue biopsies. Note, in d) and f), the intense green fluorescence signal from endogenous collagen at the edge of the pig meat sample.

This example demonstrates the use of the device for real-time detection of biological changes in connective tissue and bacterial growth based on autofluorescence alone, suggesting a practical capability of the device to provide longitudinal monitoring of bacterial growth in wounds.

Figure 6:
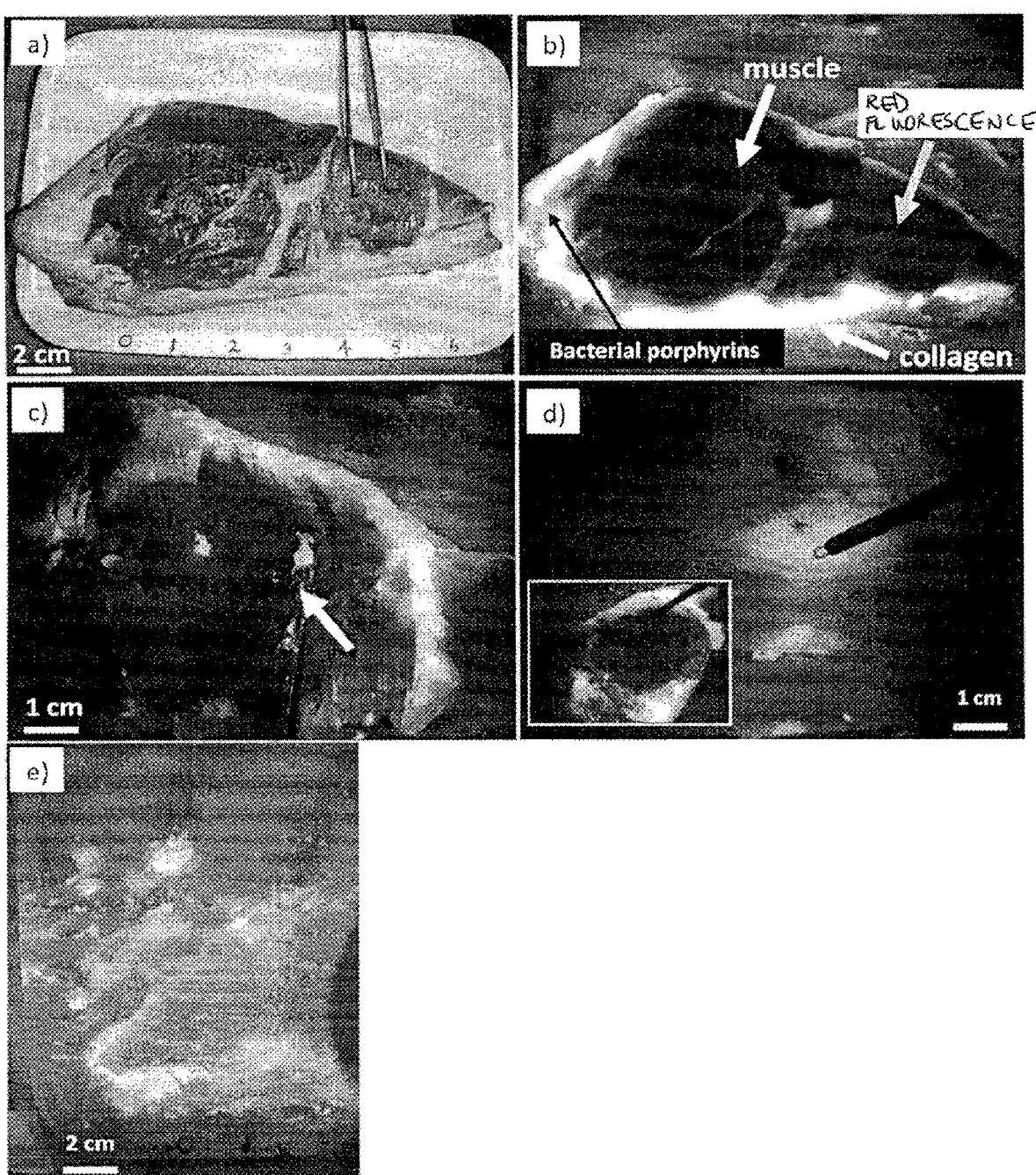
FIG. 6 shows images of a muscle surface of a pig meat sample, demonstrating the use of a device for fluorescence-based monitoring for autofluorescence detection of connective tissues and bacteria.

Reference is now made to FIG. 6, which shows examples of the device used for autofluorescence detection of connective tissues (e.g., collagen, elastin) and bacteria on the muscle surface of a pig meat sample. a) shows that white light image of pig meat used for testing shows no obvious signs of bacterial/microbial contamination or spoilage. However, as seen in b), imaging of the same area with the device under blue/violet light excitation revealed a bright red fluorescent area of the muscle indicating the potential for bacterial contamination compared with the adjacent side of muscle. Extremely bright green autofluorescence of collagen can also be seen at the edge of the skin. In c), the device was used to surgically interrogate suspicious red fluorescence further to provide a targeted biopsy for subsequent pathology or bacteriology. Note also the capability of the device to detect by fluorescence the contamination (arrow) of the surgical instrument (e.g., forceps) during surgery. In d), the device was used to target the collection of fluorescence spectroscopy using a fibre optic probe of an area suspected to be infected by bacteria (inset shows the device being used to target the spectroscopy probe in the same area of red fluorescent muscle in b, c). e) shows an example of the device being used to detect contamination by various thin films of bacteria on the surface of the Styrofoam container on which the meat sample was kept. Autofluorescence of the bacteria appears as streaks of green and red fluorescence under violet/blue excitation light from the various bacterial species previously applied to the meat. Thus, the device is capable of detecting bacteria on non-biological surfaces where they are occult under standard white light viewing (as in a).

In addition to detection of bacteria in wounds and on the skin surface, the device was also able to identify suspicious areas of muscle tissue, which may then be interrogated further by surgery or targeted biopsy for pathological verification, or by other optical means such as fluorescence spectroscopy using a fiber optic probe. Also, it detected contamination by various bacteria on the surface of the Styrofoam container on which the meat sample was kept. Autofluorescence of the bacteria appears as streaks of green and red fluorescence under violet/blue excitation light from the various bacterial species previously applied to the meat.

Figure 7:
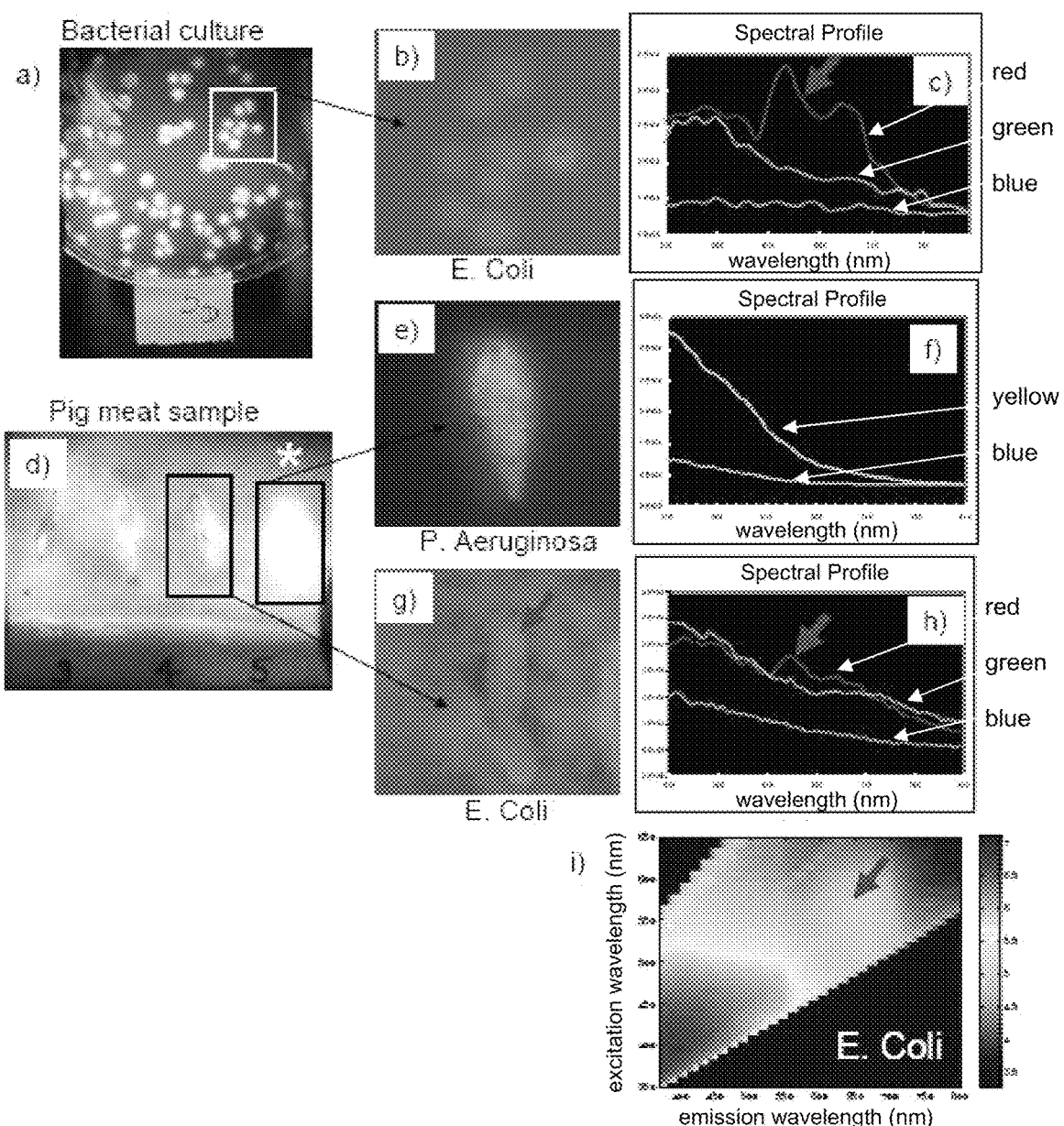
FIG. 7 shows images and spectral plots demonstrating the use of a device for fluorescence-based monitoring to detect fluorescence from bacteria growing in agar plates and on the surface a simulated wound on pig meat.

In order to determine the autofluorescence characteristics of bacteria growing in culture and in the simulated skin wounds, hyperspectral/multispectral fluorescence imaging was used to quantitatively measure the fluorescence intensity spectra from the bacteria under violet/blue light excitation. Reference is now made to FIG. 7. In FIG. 7, the device was used to detect fluorescence from bacteria growing in agar plates and on the surface of a simulated wound on pig meat, as discussed above for FIGS. 4 and 5. Bacterial autofluorescence was detected in the green and red wavelength ranges using the device in the culture (a) and meat samples (d). Hyperspectral/multispectral imaging was used to image the bacteria (*E. Coli*) in culture (b) and to measure the quantitative fluorescence intensity spectra from the bacteria (red line—porphyrins, green—cytoplasm, blue—agar background) (c). The red arrow shows the 635 nm peak of porphyrin fluorescence detected in the bacteria. Hyperspectral/multispectral imaging also confirmed the strong green fluorescence (*, right square in d) from *P. aeruginosa* (with little porphyrin fluorescence, yellow line in f) compared to *E. coli* (left square in d) where significant porphyrin red fluorescence was detected. e) and g) show the color-coded hyperspectral/multispectral images corresponding to *P. aeruginosa* and *E. coli*, respectively, from the meat surface after 2 days of growth (incubated at 37° C.); and f) and h) show the corresponding color-coded fluorescence spectroscopy. In i), excitation-emission matrices (EEM) were also measured for the various bacterial species in solution, demonstrating the ability to select the optimum excitation and emission wavelength bandwidths for use with optical filters in the imaging device. The EEM for *E. coli* shows strong green fluorescence as well as significant red fluorescence from endogenous bacterial porphyrins (arrow).

This example shows that bacteria emit green and red autofluorescence, with some species (e.g., *Pseudomonas aeruginosa*) producing more of the former. *Escherichia coli* produced significant red autofluorescence from endogenous porphyrins. Such intrinsic spectral differences between bacterial species are significant because it may provide a means of differentiating between different bacterial species using autofluorescence alone. Excitation-emission matrices (EEMs) were also measured for each of the bacterial species used in these pilot studies, which confirmed that under violet/blue light excitation, all species produced significant green and/or red fluorescence, the latter being produced by porphyrins. Spectral information derived from excitation-emission matrices may aid in optimizing the selection of excitation and emission wavelength bandwidths for use with optical filters in the imaging device to permit inter-bacterial-species differentiating ex vivo and in vivo. In this way, the device may be used to detect subtle changes in the presence and amount of endogenous connective tissues (e.g. collagens and elastins) as well as bacteria and/or other microorganisms, such as yeast, fungus and mold within wounds and surrounding normal tissues, based on unique autofluorescence signatures of these biological components.

In addition to fluorescence-enhancing pro-drugs, advances in medicine have enabled widespread use of fluorescent biomarkers to diagnose disease on a molecular level. The accurate measurement of the fluorescent biomarker signal in biological tissues may be a critical parameter towards gaining biomolecular information about disease progression and treatment response, but has historically posed a significant challenge. To date, this type of advanced molecular imaging has not been reported for wound care. With the use of the device described here, imaging and monitoring of such biomarkers for diagnosis purposes may be possible.

Imaging of Wound Models Using Exogenous Contrast Agents

When used to assess wounds, tissue autofluorescence imaging may detect relative changes in connective tissue remodeling during wound healing as well as the early presence of bacteria either contaminating, colonizing and/or infecting wounds (including, but not limited to, bacterially-induced production of wound exudate and inflammation). When most wounds are illuminated by violet/blue light, endogenous tissues in the connective tissue matrix (e.g., collagen and elastin) emit a characteristic strong green fluorescent signal, while endogenous bacteria emit a unique red fluorescence signal due to the production of endogenous porphyrins. These bacteria include, but are not limited to, common species typically found at wound sites (e.g., *staphylococcus, streptococcus, e. coli,* and *pseudomonas* species). By using autofluorescence, critical wound information is obtained in real-time to provide a means of early detection of key biological determinants of wound health status, which may aid in stratifyng patients for optimized wound care and treatment.

Figure 8:
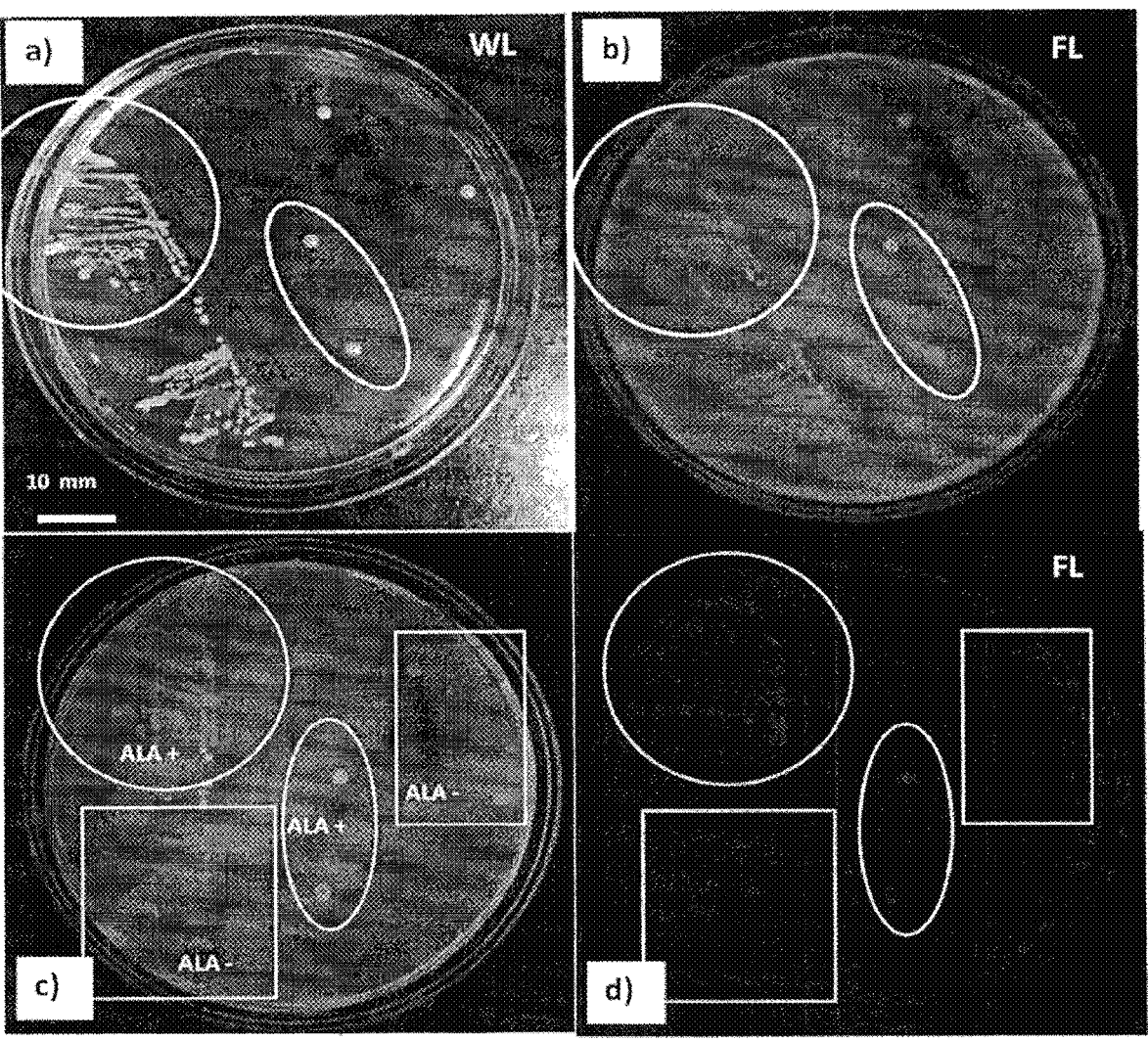
FIG. 8 shows images of bacterial cultures demonstrating of a device for fluorescence-based monitoring, with and without contrast agents.

The pro-drug aminolaevulinic acid (ALA) induces porphyrin formation in almost all living cells. Many bacteria species exposed to ALA are able to induce protoporphyrin IX (PpIX) fluorescence [Dietel et al., (2007). Journal of Photochemistry and Photobiology B: Biology. 86: 77-86]. The use of ultra-low dose ALA to induce PpIX formation in the bacteria and hence increase the red fluorescence emission was investigated, in order to enhance the red-to-green fluorescence contrast of the bacteria with the imaging device. The device was used to image live bacterial culture (*Staphylococcus aureus,* grown on agar plates for 24 h prior to imaging) using violet/blue excitation light, as seen in FIG. 8, which demonstrates the device being used in a bacteriology/culture laboratory.

In a), the device was used to image live bacterial culture (*Staphylococcus aureus,* grown on agar plates for 24 h prior to imaging) under white light (circles). In b), violet/blue excitation light reveals the bacterial red autofluorescence, which is discernable from the background weak green autofluorescence from the agar growth medium. In c), to increase the red-to-green fluorescence contrast of the *Staphylococcus aureus* against the background agar, an ultra-low dose (~20 μg/mL) of the photosensitizer aminolevulinic acid (ALA, in phosphate buffered saline) commonly used in photodynamic therapy (PDT) was added topically to some of the colonies in the agar plate (noted as 'ALA+' in the circles), while the rest of the agar plate was ALA-negative. After 30 mins of incubation at 37° C., the device was again used to image the agar plate under violet/blue light excitation, thus revealing a significant increase in red fluorescence (from ALA-induced protoporphyrin IX, PpIX) from the *Staphylococcus aureus* bacteria, compared with those colonies (square) that did not receive any ALA. Comparing b) with c) shows that the addition of ALA may be beneficial for increased bacterial fluorescence. d) shows the RBG image from c) with the green fluorescence from the agar plate removed, thus revealing the increased red bacterial fluorescence in the *S. aureus* colonies treated with ALA. This demonstrates the ability of the device to exploit the use of contrast agent strategies to increase the signal-to-background for sensitive detection of bacteria, in wounds for example. The time needed for the ALA to increase the PpIX fluorescence to detectable levels was 30 mins which suggests that this technical approach may also be clinically practical. Furthermore, this also demonstrates that the device may be used to conveniently image photosensitizer fluorescence (e.g., PpIX) in bacteria, growing in culture or in patients' wounds for subsequent treatment using PDT.

After 30 mins of incubation of *Staphylococcus aureus* ~20 μg/mL of ALA at 37° C., a significant increase in red fluorescence from the bacteria was detected, compared with those colonies (square) that did not receive any ALA. This demonstrates the ability of the device to exploit the use of contrast agent strategies to increase the signal-to-background for sensitive detection of bacteria, in wounds for example. The time needed for the ALA to increase the PpIX fluorescence of bacteria in culture to significant levels was approximately 0.5 h which suggests that this technical approach may also be clinically practical. Tests on simulated bacterially-contaminated meat samples revealed similar results to those obtained from bacterial culture. Topical application of 0.2 μg/mL ALA by spraying onto wounds on pig skin resulted in a dramatic increase of bacterial porphyrin red fluorescence contrast approximately 2 h after ALA administration. This may allow detection of bacterial contamination with fluorescence imaging within the wound sites and elsewhere on the skin surface, which was previously occult under white light imaging, as demonstrated with reference to FIGS. 9 and 10.

Figure 9:
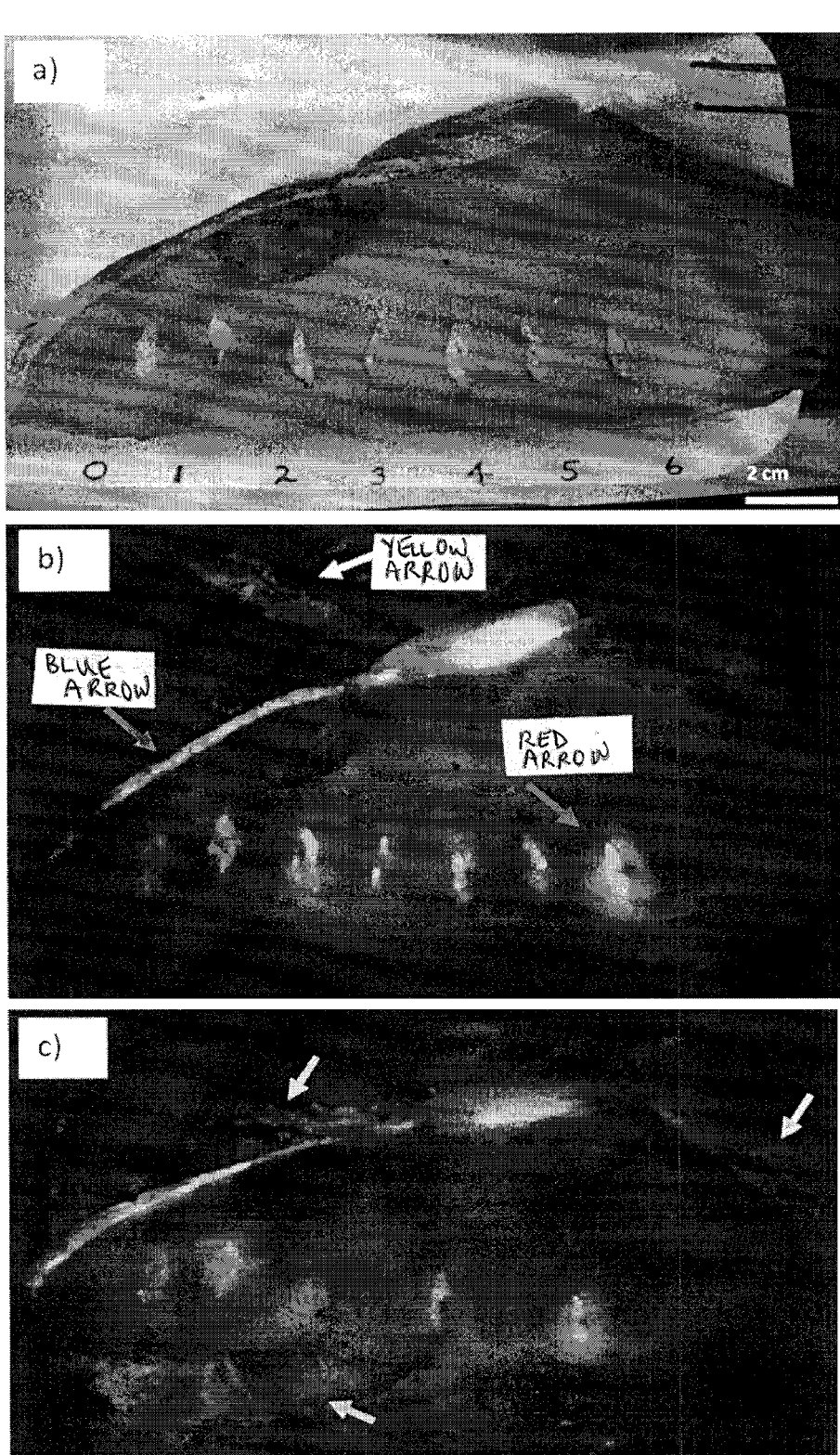
FIG. 9 shows images demonstrating the use of a device for fluorescence-based monitoring for autofluorescence detection of connective tissues and various bacterial species on the skin surface of a pig meat sample.

FIG. 9 shows examples of use of the device for autofluorescence detection of connective tissues and varies bacterial species on the skin surface of a pig meat sample. To determine if the intensity of the bacterial fluorescence may be enhanced for imaging with the device, the non-toxic pro-drug aminolevulinic acid (ALA) (~0.2 mg/mL PBS) was applied topically to the skin surface by spraying using a common atomizer bottle. The meat sample was then placed in a light tight incubator at 37° C. for approximately 3-4 h until white light and fluorescence imaging was performed using the imaging device.

Referring to FIG. 9, a) shows white light images of pig meat used for testing. In b), several bacterial species were applied to small incisions made in the skin [(1) *Streptococcus pyogenes,* 2) *Serratia marcescens,* 3) *Staphylococcus*

*aureus,* 4) *Staphylococcus epidermidis,* 5) *Escherichia coli,* and 6) *Pseudomonas aeruginosa*)]. Under violet/blue excitation light, the device shows bacterial autofluorescence (green and red fluorescence in the wound sites). The presence of endogenous porphyrin red fluorescence can be seen in other areas of the skin surface as well (red arrow). Bright collagen fluorescence can also be seen at the edge of the sample (blue arrow). Bacteria on the surface of the styrofoam container holding the meat sample, also are detected by autofluorescence with the device, but are occult under white light (left panel). This indicates that the device may be used for detecting and imaging of the presence of bacteria or microbes and other pathogens on a variety of surfaces, materials, instruments (e.g., surgical instruments) in hospitals, chronic care facilities, old age homes, and other health care settings where contamination may be the leading source of infection. The device may be used in conjunction with standard detection, identification and enumeration of indicator organisms and pathogens strategies.

In c), the non-toxic pro-drug aminolevulinic acid (ALA) (0.2 mg/mL) was applied topically to the skin surface in order to determine if bacterial fluorescence may be enhanced. The result, approximately 1 h after ALA administration, was a dramatic increase in bacterial porphyrin fluorescence (bright red fluorescence) both on the skin tissue and wound sites, as well as on the surface of the styrofoam container on which the meat sample was kept (arrows). This illustrates the possibilities for biopsytargeting by fluorescence image-guidance, and the use of the device for detection and subsequent treatment of infected areas using PDT, for example.

Figure 10:
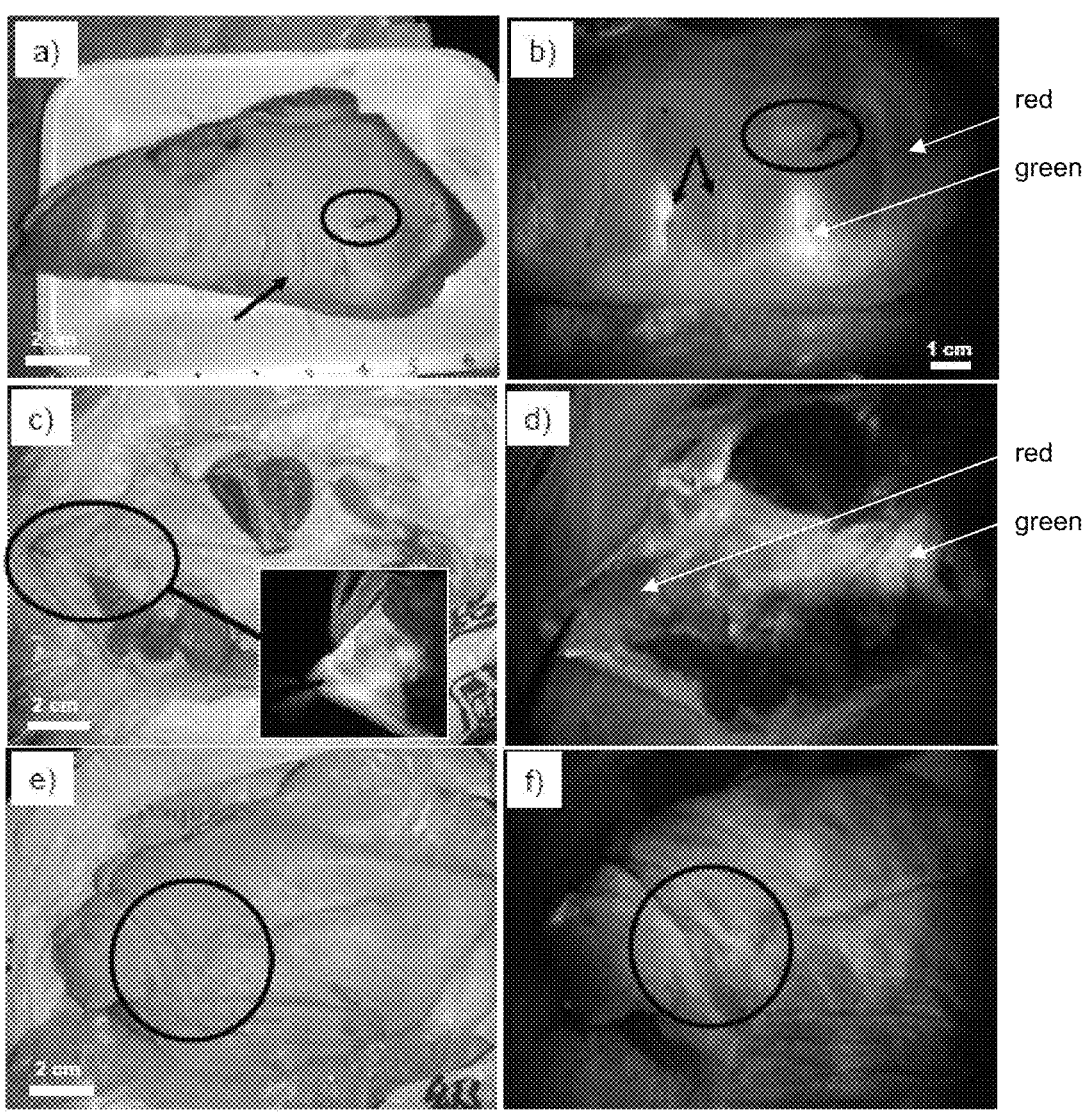
FIG. 10 shows images demonstrating use of a device for fluorescence-based monitoring for fluorescence contrast-enhanced detection of bacterial infection in a pig meat sample.

FIG. 10 shows examples of the use of the device for fluorescence contrast-enhanced detection of bacterial infection in a pig meat sample. a) shows white light image of the pig meat. Several bacterial species were applied to small incisions made in the skin (arrow). In b), the non-toxic pro-drug aminolevulinic acid (ALA) (0.2 µg/mL) was applied topically to the skin surface by spraying using an common atomizer bottle and the imaging device was used to image the resulting ALA-induced protoporphyrin IX (PpIX) red fluorescence. Images of the skin surface (~2 h after ALA administration) using violet/blue light (405 nm), resulted in a dramatic increase of bacterial porphyrin red fluorescence contrast indicating the detection of the presence of bacterial contamination with fluorescence imaging within the simulated surgical wound incisions (arrows) and elsewhere on the skin surface, which was previously occult under white light imaging (circle in a and b). Note that some areas of the skin surface which were not exposed to oxygen because the sample was placed 'skin down' in the container do not emit bright red fluorescence, possibly due to the suspected dependence on oxygen for bacterial production of PpIX. Some bacteria produce a bright green autofluorescence signals which is also detected by the device. In c), in another pig meat sample, bacteria occult under white light imaging (circle) are easily detected using autofluorescence imaging alone (inset). However, as shown in d) the topical application of low dose ALA caused a dramatic increase in bacterial fluorescence after 2 h, demonstrating the utility of exogenous pro-drugs as fluorescence imaging contrast enhancing agents for improved detection of bacterial contamination. Note the bright green autofluorescence of endogenous collagen and elastins in the connective tissues in the sample. In e) and f), ALA-induced fluorescence allowed detection of occult bacteria on the skin surface (circles) offering the possibility of image-guided biopsy-targeting, and use of the device for detection and subsequent treatment of infected areas using PDT, for example.

The device may also be used in conjunction with exogenous 'pro-drug' agents, including, but not limited to, ALA which is FDA approved for clinical therapeutic indications, to increase the endogenous production of porphyrins in bacteria/microorganisms and thereby increase the intensities of unique 'porphyrin' fluorescence signals emanating from these bacteria to improve the detection sensitivity and specificity of the device. Thus, the device may be used to conveniently image photosensitizer-induced fluorescence (e.g., PpIX) in bacteria, growing in culture or in patients' wounds for subsequent image-guided targeted swabbing or biopsy, or treatment using photodynamic therapy (PDT) [Jori et al. Lasers Surg. Med. 2006 June; 38(5):468-81; Dougherty et al. (1998) J. Natl. Cancer Inst. 90, 889-905; Carruth (1998) Int. J. Clin. Pract. 52, 39-42; Bissonnette et al. (1997) Dermatol. Clin. 15, 507-519]. PDT may provide an adjunct to current antibiotic treatment or an alternative where antibiotics no longer are working (e.g., drug-resistant strains). The available evidence suggests that multi-antibiotic resistant strains are as easily killed by PDT as naive strains, and that bacteria may not readily develop resistance to PDT. This may be vital for treating wounds in patients undergoing cancer therapy, HIV patients who demonstrate resistance to antibiotics and the elderly with persistent oral infections [Hamblin et al. (2004) Photochem Photobiol Sci. 3:436-50].

The device may be used to detect bacteria or microorganisms in the wound and surrounding normal tissues using low power excitation/illumination blue/violet light, but may also be used immediately afterwards for destroying them, for example using PDT or other therapies. By using high-power red excitation/illumination light, endogenous porphyrins in bacteria or microorganisms can be destroyed within the wound site by PDT. Therefore, this device may have the capability to serve as an all-in-one non-invasive or non-contact 'find and treat' instrument for clinical wound care. Furthermore, once bacteria or microorganisms are detected, the device may be used to treat and/or disinfect the wound site with PDT, and then the site may be re-imaged soon afterwards to determine the effectiveness of the PDT treatment. In some embodiments, the device may be used only for detection/diagnostic purposes only and may not perform any therapeutic treatment itself. The device may be used continuously until the entire wound and surrounding normal tissue have been disinfected, and the wound may be monitored thereafter in a longitudinal manner as part of standard clinical follow up. Fluorescence images from the device may be used to determine the biodistribution of the PDT photosensitizer or photoproducts [Gudgin et al. (1995) J. Photochem. Photobiol. B: Biol. 29, 91-93; Konig et al. (1993) J. Photochem. Photobiol. B: Biol. 18, 287-290], since most of these are intrinsically fluorescent, and thus the device may serve as a means to target the PDT treatment light. The device may therefore guide, via imaging, the completeness of the PDT treatment. Similarly, the device may be used to guide other therapies.

Since some photosensitizers are known to photobleach [Jongen et al. (1997) Phys. Med. Biol. 42, 1701-1716; Georgakoudi et al. (1997) Photochem. Photobiol. 65, 135-144; Rhodes et al. (1997) J. Investig. Dermatol. 108, 87-91; Grossweiner (1986) Lasers Surg. Med. 6, 462-466; Robinson et al. (1998) Photochem. Photobiol. 67. 140-149; Rotomskis et al. (1996) J. Photochem. Photobiol. B: Biol. 33, 61-67] the fluorescence imaging capability of the device may be used to determine the extent or rate of photobleaching of the photosensitizer. This information may be useful for optimizing PDT dosimetry [Grossweiner (1997) J. Photochem. Photobiol. B: Biol. 38, 258-268] in order to ensure adequate treatment of the disease, while at the same time minimizing damage to surrounding normal tissues. The device, with excitation light sources which may be selected for specific excitation wavelengths and intensities, in an embodiment, may be used to also deliver the light for PDT combined with any commercially available and/or experimental PDT photosensitizers. Therefore, it may have utility in existing clinical PDT indications (e.g., for the skin surface or hollow organs) and/or within the arena of commercial/academic research and development of future PDT photosensitive agents, both pre-clinically and clinically.

Figure 10G:
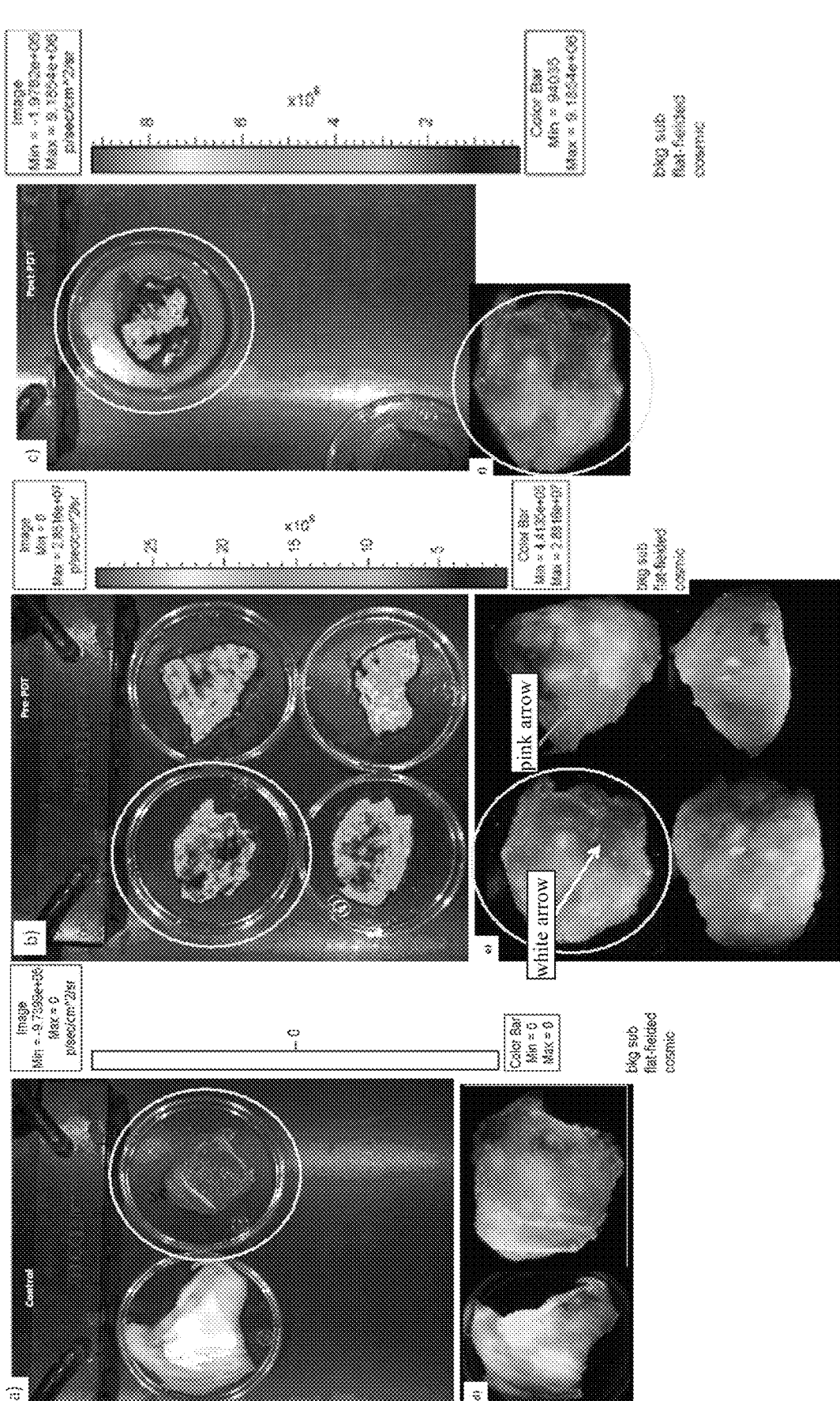
FIG. 10G shows an example of use of a device for fluorescence-based monitoring for monitoring effectiveness of a photodynamic treatment.

FIG. 10G shows an example of the use of the device for monitoring the response of bacteria to photodynamic therapy (PDT). Ex vivo porcine tissues were prepared in Petri dishes and contaminated with bioluminescent (BL) *Staphylococcus aureus* 24 h prior to BL and fluorescence imaging of samples using the device. Bioluminescent and corresponding fluorescence imaging was performed on a), d) non-contaminated, and b), e) SA-contaminated muscle tissues pre- and post PDT. Note, *Staphylococcus aureus* produced red fluorescence color (white arrow in e). PDT was performed on the bacterially-contaminated meat sample (marked by a yellow circle) by incubating the sample with a common photosensitizer called methylene blue (MB) for about 30 mins, followed by removal of excess MB (and rinsing with PBS) and subsequent exposure to about 670 nm light source (here an LED array) for about 10 mins at ~10 $J/cm^2$ in order to cause the photodynamic treatment. Comparing the BL intensity scales in b) and c) shows a marked decrease in BL intensity in the treated meat sample following PDT (e.g., PDT has killed a measureable proportion of the bioluminescent bacteria, thus decreasing the BL signal intensity), and changes in the fluorescence characteristics (e.g., intensity and biodistribution) of the *Staphylococcus aureus* bacteria (red color) can be seen using the handheld imaging device following PDT. Note that the intense green fluorescence on the meat sample (pink arrow in e) was caused by unintentional cross-contamination of the meat sample by non-BL *Pseudomonas aeruginosa* during the experiment (confirmed by bacteriology), and the device detected this. These data suggest the use of the device for monitoring the use of PDT for treatment of bacterial contamination in biological (and non-biological) samples. (405 nm excitation; 490-550 nm and >600 nm emission).

This device may be used as an imaging and/or monitoring device in clinical microbiology laboratories. For example, the device may be used for quantitative imaging of bacterial colonies and quantifying colony growth in common microbiology assays. Fluorescence imaging of bacterial colonies may be used to determine growth kinetics.

Imaging of Blood in Wounds

Angiogenesis, the growth of new blood vessels, is an important natural process required for healing wounds and for restoring blood flow to tissues after injury or insult. Angiogenesis therapies, which are designed to "turn on" new capillary growth, are revolutionizing medicine by providing a unified approach for treating crippling and life-threatening conditions. Angiogenesis is a physiological process required for wound healing Immediately following injury, angiogenesis is initiated by multiple molecular signals, including hemostatic factors, inflammation, cytokine growth factors, and cell-matrix interactions. New capillaries proliferate via a cascade of biological events to form granulation tissue in the wound bed. This process may be sustained until the terminal stages of healing, when angiogenesis is halted by diminished levels of growth factors, resolution of inflammation, stabilized tissue matrix, and endogenous inhibitors of angiogenesis. Defects in the angiogenesis pathway impair granulation and delay healing, and these are evident in chronic wounds [Tonnesen et al. (2000) J Investig Dermatol Symp Proc. 5(1):40-6]. By illuminating the tissue surface with selected narrow wavelength bands (e.g., blue, green and red components) of light or detecting the reflectance of white light within several narrow bandwidths of the visible spectrum (e.g., selected wavelengths of peak absorption from the blood absorption spectrum of white light), the device may also be used to image the presence of blood and microvascular networks within and around the wound, including the surrounding normal tissue, thus also revealing areas of erythema and inflammation.

Figure 11:
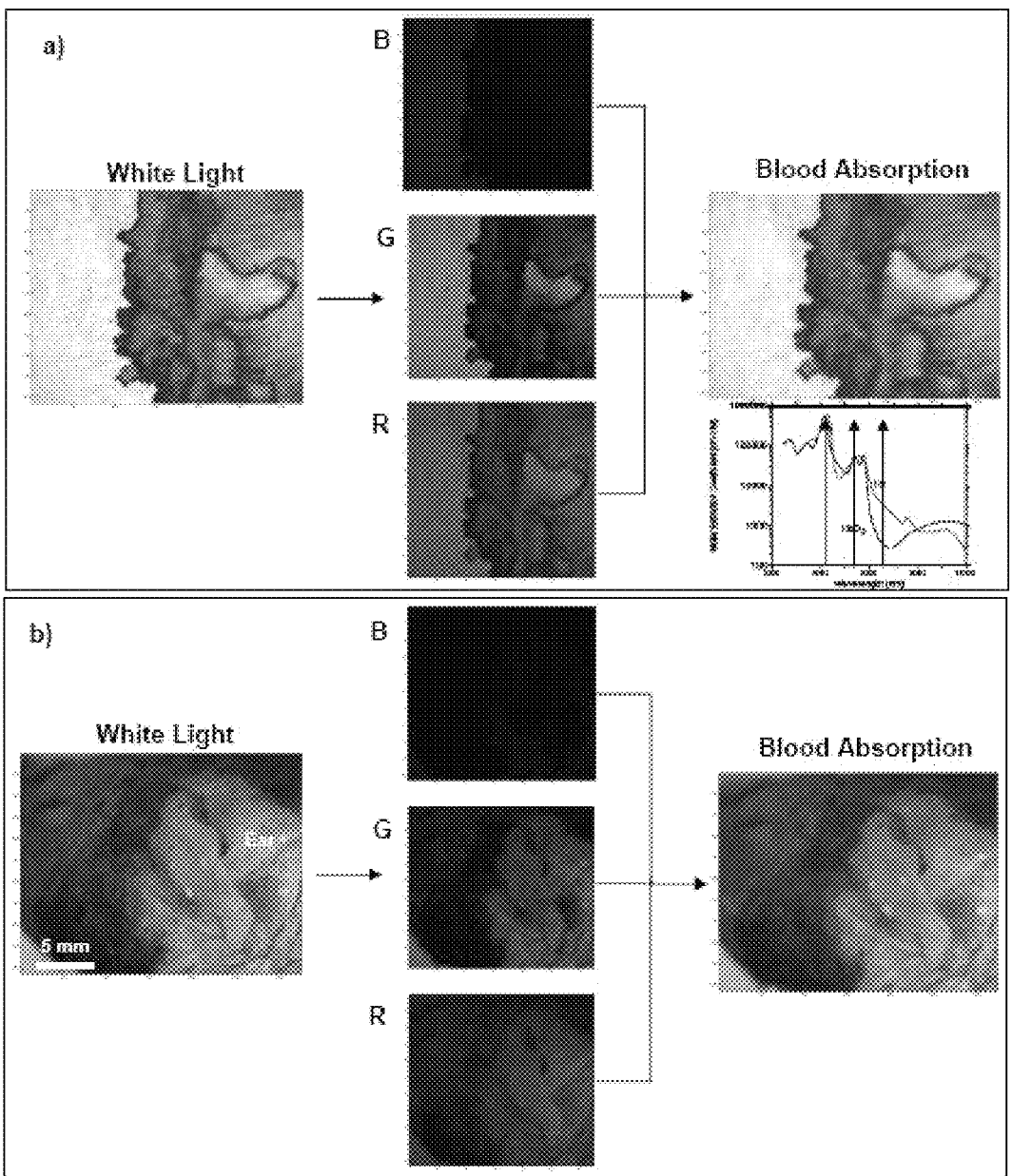
FIG. 11 shows images demonstrating use of a device for fluorescence-based monitoring for imaging of blood and microvasculature.

Reference is now made to FIG. 11. The device may use individual optical filters (e.g., 405 nm, 546 nm, 600 nm, +/−25 nm each) in order to demonstrate the possibility of imaging blood and microvasculature in wounds. White light images of a wound may be collected with the device and then the device, equipped with a triple band-pass filter (e.g., 405 nm, 546 nm, 600 nm, +/−25 nm each), placed in front of the imaging detector may image the separate narrow bandwidths of blue (B), green (G), and red (R) reflected light components from the wound. These wavelength bands may be selected based on the peak absorption wavelengths of blood, containing both oxygenated and deoxygenated hemoglobin, in the visible light wavelength range. The resulting images may yield the relative absorption, and thus reflectance, of visible light by blood in the field of view. The resulting 'blood absorption' image yields a high contrast image of the presence of blood and/or microvascular networks in the wound and surrounding normal tissues. The clinician may select the appropriate optical filter set for use with the device to obtain images of blood and/or microvascular distribution within the wound and the combine this information with one or both of autofluorescence imaging and imaging with exogenous contrast agents. This may provide a comprehensive information set of the wound and surrounding normal tissues at the morphological, topographical, anatomical, physiological, biological and molecular levels, which currently may not be possible within conventional wound care practice.

FIG. 11 shows examples of the device used for imaging of blood and microvasculature in wounds. The device was used to image a piece of filter paper stained with blood (a) and the ear of a mouse during surgery (b). White light images were collected of each specimen using the imaging device, in non-fluorescence mode, and then the device was equipped with a triple band-pass filter placed in front of the imaging detector (405 nm, 546 nm, 600 nm, +/−25 nm each) to image the separate narrow bandwidths of blue (B), green (G), and red (R) reflected light components from the specimens. These wavelength bands were selected based on the peak absorption wavelengths of blood in the visible light wavelength range (inset in a) shows the absorption spectral profile for oxy- and deoxygenated hemoglobin in blood. This shows that using a simple multiband transmission filter, it is possible to combine the three B, G, R images into a single 'white light equivalent' image that measures the relative absorption of light by blood in the field of view. The resulting 'blood absorption' image yields a high contrast image of the presence of blood containing both oxy- and deoxygenated hemoglobin. The device may be used with narrower bandwidth filters to yield higher contrast images of blood absorption in wounds, for example.

The regulation of angiogenesis over time during wound repair in vivo has been largely unexplored, due to difficulties in observing events within blood vessels. Although initial tests of the imaging device were exploratory, simple modification of the existing prototype device may allow longitudinal imaging of dynamic changes in blood supply and microvascular networks during the wound healing process in vivo.

Imaging of Skin and Oral Cavity

This device may be suitable for imaging the skin, the mouth and the oral cavity. The device may allow for detection of connective tissue changes due to minor cutaneous injuries (e.g., cuts, abrasions) and endogenous bacteria found commonly on normal skin (e.g., *Propionibacterium acnes*, or *P. acnes*).

This device may also be suitable for multi-spectral imaging and/or monitoring of dental plaques, carries and/or cancers in the oral cavity. The device may be used to detect the presence of plaques, periodontal diseases, carries and cancers, as well as local oral infections, based on the presence of unique autofluorescence signatures in abnormal or cancerous tissues. The device may use white light, fluorescence, with or without autofluorescence or exogenous fluorescent agents, and reflectance imaging to provide real-time detection and diagnosis of periodontal disease, plaques, and carries and cancers in the oral cavity. The device may record the images for medical record cataloguing. Unlike the direct (i.e., naked eye) viewing approach used by an existing product such as the VELscope System, by Vancouver-based company LED Medical Diagnostics Inc. (LED-MD), the present device may provide digital imaging and recording of tissue white light, fluorescence and reflectance information.

In dermatology, the device may be used to detect bacteria on normal skin. For example, FIG. 12 demonstrates the high-resolution autofluorescence imaging of the normal skin of patients faces in which distinct red fluorescence from the common bacterium *Propionibacterium acnes* is detected.

Figure 12:
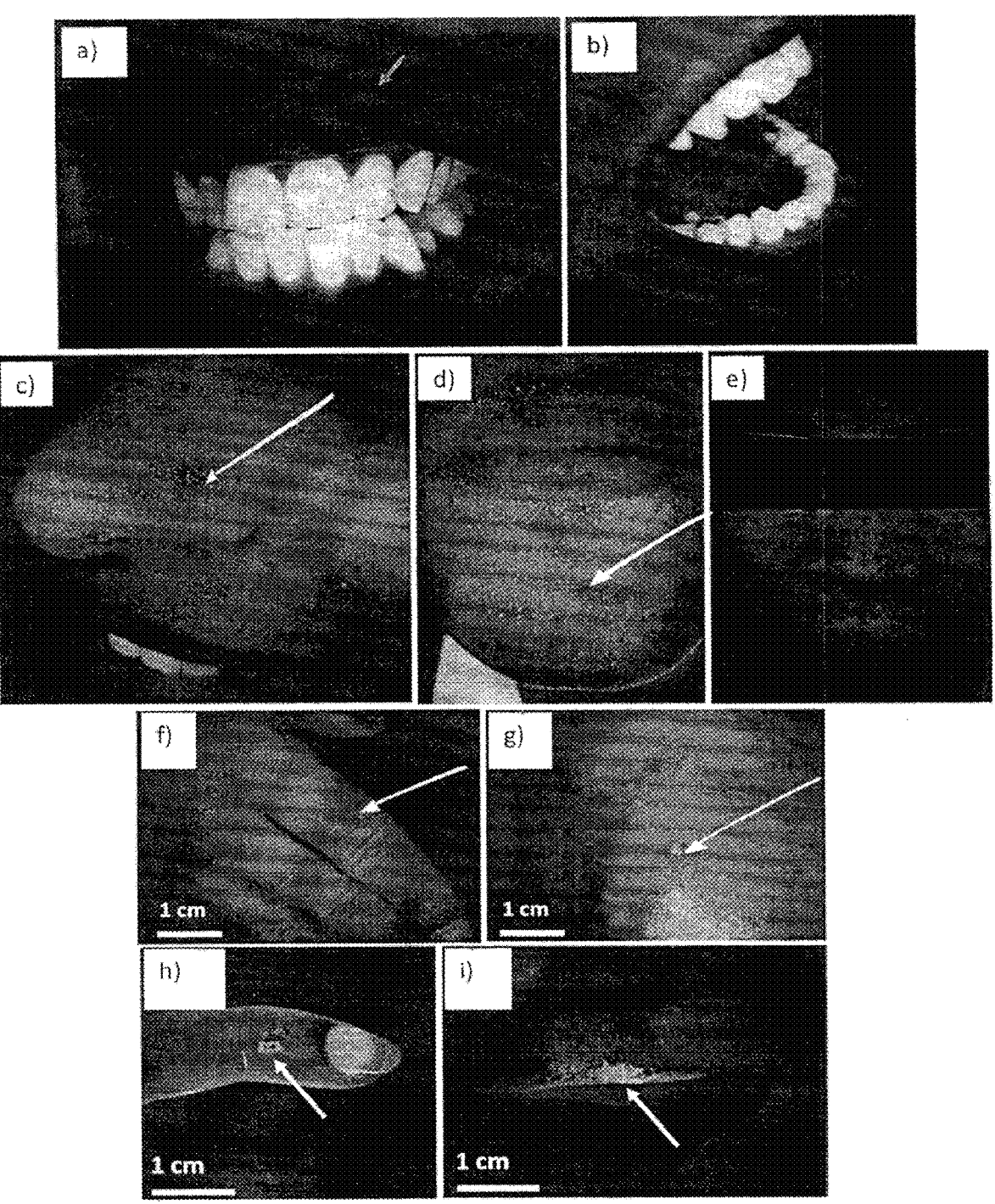
FIG. 12 shows images demonstrating use of a device for fluorescence-based monitoring for imaging of the oral cavity and the skin surface.

FIG. 12 shows examples of the use of the device for non-invasive high-resolution digital still or video imaging of the oral cavity and the skin surface in patients. As shown in a), the device may be used for imaging of the mouth and oral cavity. Violet/blue light excitation excites autofluorescence from the teeth, which appear as an intense green fluorescence, compared to the blood rich gums. Periodontal disease and caries may be easily detected based on the autofluorescence of the teeth and gum tissues using this device. Red fluorescence at the edge of the lips is detected from *Propionibacterium acnes* (*P. acnes*) commonly found within skin pores. The red fluorescence is produced by endogenous bacterial porphyrins. Note the detection of *P. acnes* in individual pores (red arrow) on the lip. Similarly, in b), red fluorescence from endogenous porphyrins in the normal bacteria fauna of the tongue is easily detected as a bright red fluorescent 'blanket' on the tongue surface. The device may also be used to detect early cancers in the oral cavity based on differences in optical properties (e.g., absorption, scattering, autofluorescence) between normal and pre- and neoplastic tissues. The device may be used to 'scan' the oral cavity of mucosal cancers, or determine the effects of anticancer therapeutics such as PDT, or other techniques. The device may also be used to image the skin surface. In c)-e), the device images the skin on patients' faces by detecting autofluorescence produced by violet/blue light excitation of the skin surface. Red fluorescence from *P. acnes* may easily be detected in regions of the face (e). The device may be used to image and/or monitor the potential effects of dermatological interventions (e.g., topical creams, drugs and other antibiotics, etc.) on patients' skin. In f) and g), the device was also used to image minor cuts (arrow, h), scrapes and abrasions on patients' skin, as well as psoriasis on a finger (arrow, i). Under violet/blue light, the device detected tissue autofluorescence from connective tissue components (e.g., collagen and elastin) from the wound site and surrounding normal skin to yield high-resolution images of subtle cutaneous lesions. *P. acnes* is the causative agent of acne vulgaris (i.e., pimples) and is a common resident of the pilosebaceous glands of the human skin, and is occult under white light visualization. These autofluorescent images were obtained without the need of exogenous agents/drugs and demonstrate the capability of the device to detect bacteria porphyrin fluorescence in single skin pores.

Figure 12J:
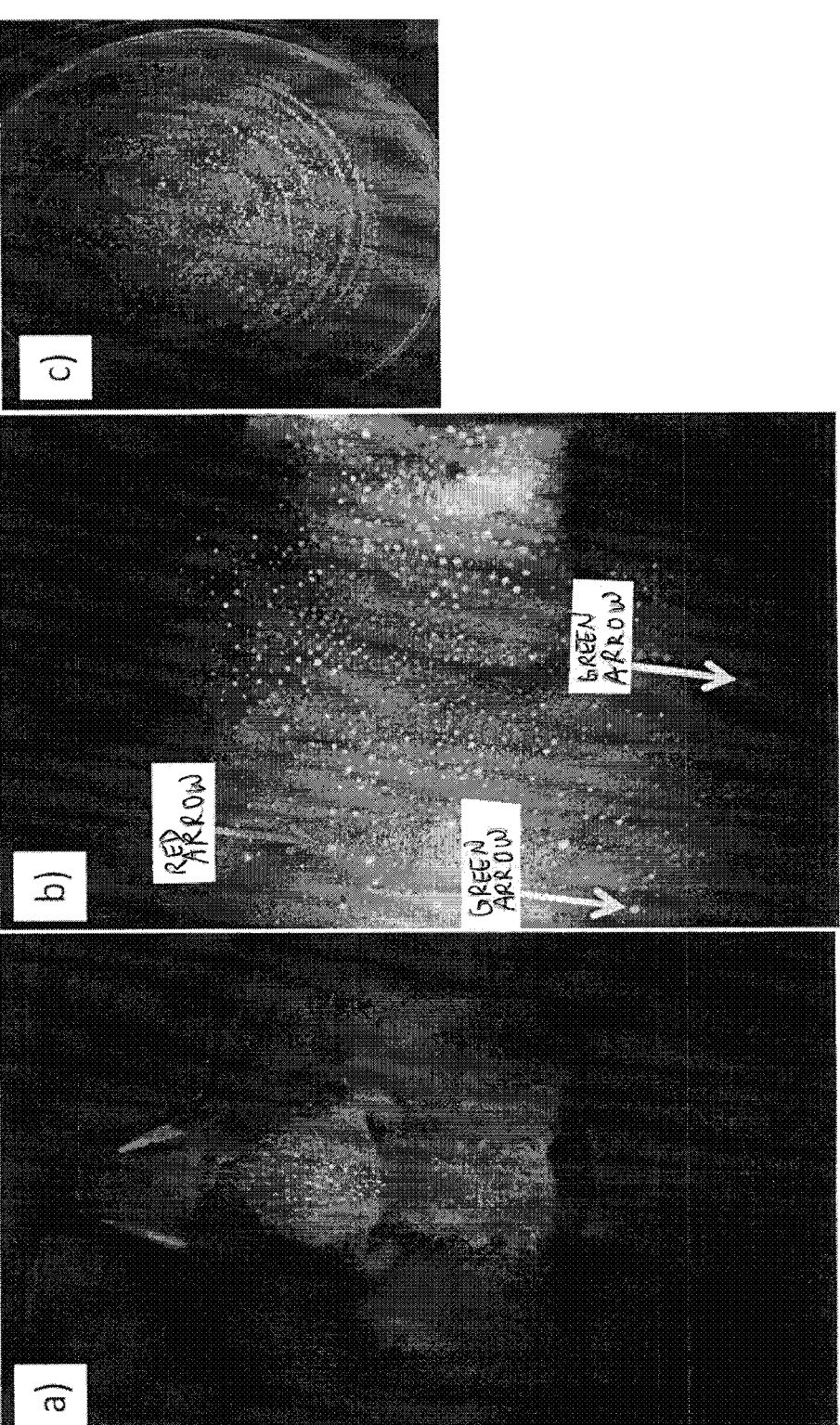
FIG. 12J shows an example of the use of a device for fluorescence-based monitoring for imaging a skin surface.

FIG. 12J shows an example of the use of the imaging device for real-time fluorescence detection of common bacterial flora on skin. a) Red fluorescence on and around the nose is detected from *Propionibacterium acnes* (*P. acnes*) commonly found within skin pores. b) Fluorescence imaging may also be used to detect and monitor more than one bacterial species on the skin at the same time, for example *Propionibacterium acnes* appear as red fluorescent (red arrow) while *Pseudomonas Aeruginosa* appear bright green (green arrows). These data suggest the use of the device for distinguishing relative concentrations/levels of various bacterial species, determining their biodistributions on body surface, and monitoring response to anti-bacterial treatments in dermatology and cosmetology applications. c) Shows an example of a fluorescence image of a culture grown on agar from a swab taken from normal skin on the nose of a healthy volunteer. Bacteriology results showed the presence of *Pseudomonas aeruginosa*.

Such a capability to image and document the presence and biodistribution of bacteria on the skin surface makes the device potentially useful in the dermatology and cosmetology fields. For example, fluorescence imaging may be performed prior to, during and after application of dermatological treatment and/or pharmaceutical/cosmetic formulations (e.g., topical creams, drugs and other antibiotics, skin disinfecting agents, acne treatments, etc.) to the normal and abnormal skin conditions, including but not limited to scarring, hyper-pigmentation, acne, psoriasis, eczema, rashes, etc. Fluorescence/reflectance image-guided tattoo removal (e.g., using surgery or available laser treatments) may also be an option with the device. The device was also used to image minor cuts, scrapes and abrasions on patients skin and under violet/blue light, tissue autofluorescence from connective tissue components (e.g., collagen and elastin) from the wound site and surrounding normal skin aided in detecting white light-occult changes in connective tissues during minor cutaneous wound healing (as seen in FIG. 12*h, i*). In addition, the device may also serve as a practical, cost-effective and sensitive image-based tool for early detection of occult skin cancers and non-cancerous (i.e., benign) lesions in a non-invasive manner [Chwirot et al. (1998) Eur J Cancer. 34(11):1730-4]. The device may then be used to provide image-guidance for surgical excision of the lesions or for PDT. For the latter, fluorescence imaging may monitor PDT response and determine completeness of treatment over-time with multiple longitudinal image scans of the affected area. The device may be used in real-time for determining PDT photosensitizer localization and biodistribution and photobleaching, and this may be mapped onto the white light image of the area to be treated for anatomical comparison. Changes in the optical properties between normal and diseases or burned tissues may be detected using both then white light and fluorescence imaging capabilities of the device. The device may also be used to image, assess and longitudinally monitor the healing process in burns or the determine response of skin grafts or temporary skin substitutes in treatment of burn patients [Bishop (2004) Crit Care Nurs Clin North Am. 200416(1):145-77]. The device may also serve to detect and monitor late radiation-induced skin damage during treatment of patients with ionizing radiation [Charles (2007) J Radiol Prot. 27(3):253-74].

In addition, the device may be used to image the mouth and oral cavity, particularly in the embodiment where the device is small and compact. Pilot imaging studies showed that the device may detect endogenous bacteria in the oral cavity (e.g., on the tongue surface and between teeth on the gum line), suggesting a use in clinical detection of caries and periodontal disease [Pretty (2006) J Dent. 34(10):727-39]. Additionally, tissue autofluorescence has been shown to be useful in detecting oral cancers [Kois et al. (2006) Dent Today. 25(10):94, 96-7]. The device may be used to detect early cancers in the oral cavity based on differences in optical properties (e.g., absorption, scattering, autofluorescence) between normal, pre- and neoplastic oral tissues. In addition, the device may be used to 'scan' the oral cavity for mucosal cancers, and monitor the response to therapy.

In general, the device may be used to image and/or monitor targets such as a skin target, an oral target, an ear-nose-throat target, an ocular target, a genital target, an anal target, and any other suitable targets on a subject.

Use in Malignant Wounds

A malignant wound is also known as tumor necrosis, a fungating wound, ulcerating cancerous wound, or malignant cutaneous wound. A malignant wound can be an emotional and physical challenge for patients, families and even for the experienced clinician. Fungating and ulcerating wounds can be unsightly, malodorous and painful. These wounds may be indicators of disease progression, and may become infected leading to delayed/impeded healing and associated morbidity and thus, reduced quality of life for patients.

Many cancer patients live with the knowledge that their disease is both progressive and incurable. For a significant minority of these people this reality may be present in the form of a malodorous, exuding, necrotic skin lesion, which can be a constant physical reminder of disease progression (Mortimer P S. In: Doyle et al. editors. *Oxford Textbook of Palliative Medicine* (2nd ed). Oxford: Oxford University Press, 1998, 617-27; Englund F. *RCN Contact* 1993; Winter: 2-3). These lesions are commonly known as 'fungating wounds', the term 'fungating' referring to a malignant process of both ulcerating and proliferative growth (Grocott P. *J Wound Care* 1995; 4(5): 240-2). Lesions that have a predominantly proliferative growth pattern may develop into a nodular 'fungus' or 'cauliflower' shaped lesion, whereas a lesion that is ulcerating will produce a wound with a crater-like appearance (Grocott P. *J Wound Care* 1999, 8(5): 232-4; Collier M. *Nurs Times* 1997; 93(44): suppl 1-4). Such lesions may also present with a mixed appearance of both proliferating and ulcerating areas (Young T. *Community Nurse* 1997; 3(9): 41-4).

A malignant wound may develop in one of the following ways:

As a result of a primary skin tumour such as squamous cell carcinoma or melanoma.

Through direct invasion of the structures of the skin by an underlying tumour, for example breast cancer, or haematological malignancy such as cutaneous T-cell lymphoma (mycosis fungoides).

From metastatic spread of a distant tumour. Metastasis may occur along tissue planes, capillaries or lymph vessels.

Malignant wounds are often difficult to manage related to their location, odor, excessive exudates, and propensity for bleeding. Every malignant wound may be unique in its appearance and presenting symptoms. The common symptoms associated with malignant wounds include malodor, excessive exudates, infection, bleeding, maceration and excoriation of peri wound skin, pruritis, pain, poor aesthetics and cosmetic effects of dressings. Currently, the approach to care is mainly holistic and primarily palliative with the aim to control symptoms at the wound site and reduce the impact of the wound on the patient's daily life, primarily by identifying bacterial/microbial infection(s) and monitoring for signs of healing. Unless the pathology is controlled these wounds are not expected to heal.

The described device may be useful for performing clinical assessment of such wounds (e.g., physical and biological examination). The device may provide: a means of thorough image-based wound assessment at baseline and at regular intervals throughout treatment (i.e., longitudinal monitoring), wound assessment including location, size of wound, color, type and amount of any discharge or drainage, serial white light (e.g., for color changes) and fluorescence (e.g., for tissue structural, cellular, biological, and molecular changes) images of chronic malignant wounds, and may provide assessment of any signs and symptoms of infection in real-time, that would affect treatment planning and efficacy. The device may be integrated into the current clinical practice for assessment and care of such malignant wounds.

Imaging of Exogenous Fluorescence Contrast Agents

The development of highly efficient analytical methods capable of probing biological systems at system level is an important task that is required in order to meet the requirements of the emerging field of systems biology. Optical molecular imaging is a very powerful tool for studying the temporal and spatial dynamics of specific biomolecules and their interactions in real time in vivo. Several recent advances in optical molecular imaging have occurred, such as the development of molecular probes that make imaging brighter, more stable and more biologically informative (e.g., FPs and semiconductor nanocrystals, also referred to as quantum dots), the development of imaging approaches that provide higher resolution and greater tissue penetration, and applications for measuring biological events from molecule to organism level. These advances may also be applied to disease diagnosis (e.g., wound care) and pharmaceutical screening. However, current fluorescence imaging devices are large, complicated and involve expensive optical components and very sensitive camera detectors which makes such systems extremely expensive. The device developed here offers an alternative to these cost-limiting systems for preclinical or research studies as well as possible clinical translation of such methods.

Figure 13:
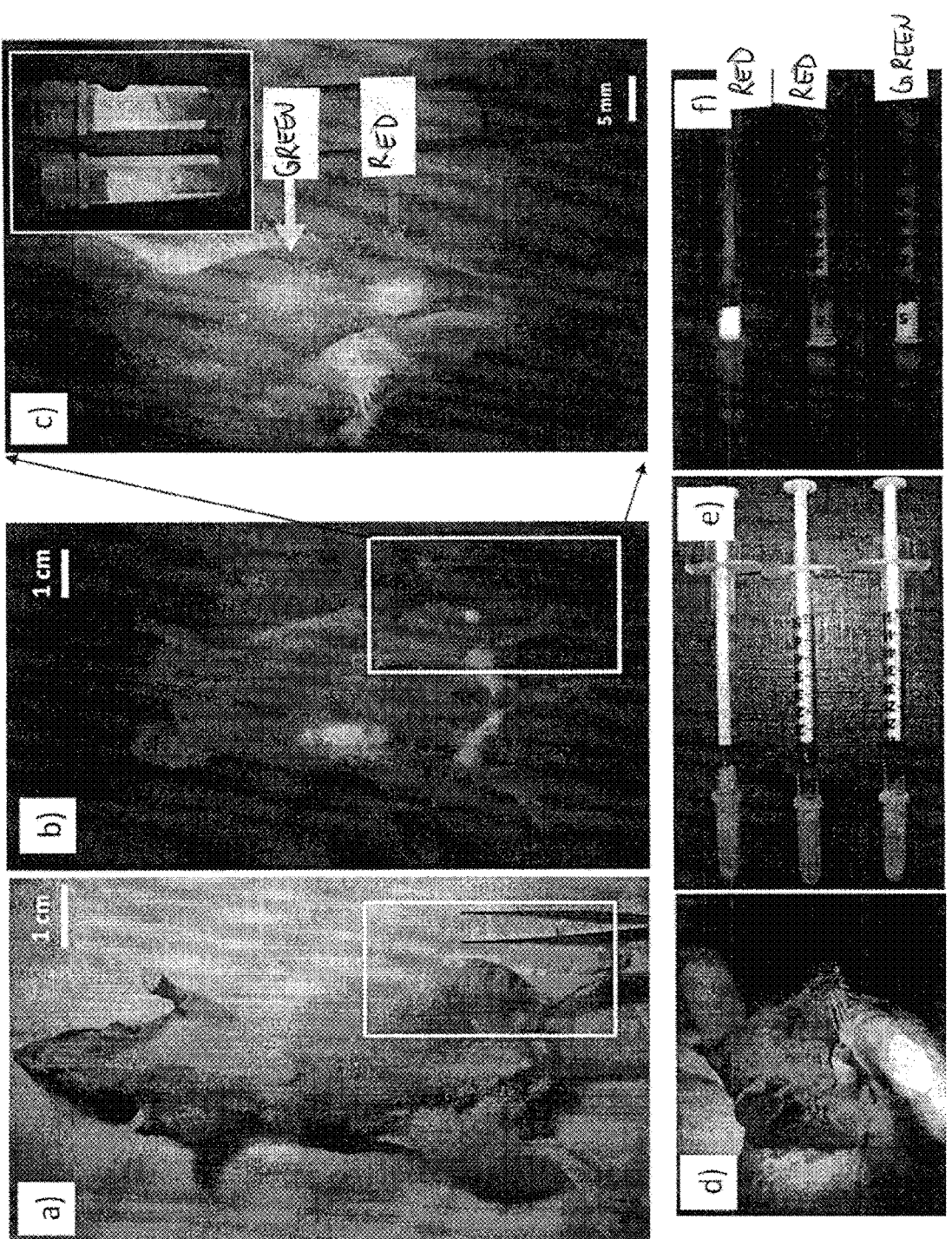
FIG. 13 shows images demonstrating use of a device for fluorescence-based monitoring for detection of exogenous fluorescence contrast agents in vivo.

Reference is now made to FIG. 13. The device was also used to image the animal for general observation under fluorescence to determine the extent of fluorescence from the BPD photosensitizer throughout the skin surface. FIG. 13 demonstrates utility of the device in for real-time imaging and sensitive detection of exogenous fluorescence contrast agents in vivo (e.g., quantum dots, QDots). In a), the device was used to image exogenous fluorescence contrast agents in a sacrificed rat bearing human breast tumor cells metastasized to the bone in the hind leg. The rat was previously injected with a fluorescence photosensitizer called benzoporphyrin derivative (BPD) for an unrelated photodynamic therapy experiment. The rat was administered two separate fluorescent semiconductor nanoparticle solutions (here, QDots), each emitting fluorescence at 540 (+/−15) nm and 600 (+/−15) nm solutions via subcutaneous injection in the left hind leg. Injections were approximately 1 cm apart. The device was then used to image the whole body of the rat using violet/blue excitation light. The rate skin appeared red, and this was likely due to the combination of the fluorescence from the benzo-porphyrin derivative (BPD) photosensitizer administered to the rat prior to the experiment, which was for subsequent PDT, as well as dust and food contamination from the cage in which rat was housed.

Referring still to FIG. 13, in b) the fluorescence from the green and red QDots (inset) was easily detected beneath the skin at the site of the injection, with the red QDots emitting the brighter signal, due to greater tissue penetration of red light. c) shows a magnified image of the hind leg shown in b). The device was capable of detecting multiple fluorescence contrast agent simultaneously along with background tissue autofluorescence with sufficient signal-to-noise (green and red arrows) so as to permit its use in preclinical and expected clinical fluorescence imaging of multiplexed molecularly-targeted fluorescence contrast agents in vivo. Note the green fluorescence is weaker than the red because both the violet/blue excitation light and the subsequent green QDot fluorescence are preferentially absorbed by blood and red QDot fluorescence light has a greater penetration depth through tissue. In d), the device was also used to image the animal for general observation under fluorescence to determine the extent of fluorescence from the BPD photosensitizer throughout the skin surface. The device may also be useful for guiding intravenous injections using needles by detecting surface blood vessels beneath the skin. The device may thus be used to detect fluorescent tumors, such as those that are transfected with fluorescent proteins and grown subcutaneously in a xenograft or orthotopic model. Thus, the device may be used for visualizing multiple wound healing and/or infectious biomarkers using multiplexed exogenous fluorescent molecular targeting agents (e.g., for in situ image-based bacteriology).

To improve the use of fluorescence contrast agents in preclinical research and eventually for clinical translation of optical molecular imaging technologies, it is desirable to be able to relatively rapidly differentiate and identify various fluorescent agents. In e) and f), the device was also used as a means of relatively rapidly identifying which fluorescence contrast agents were in the syringes prior to injection, which was not possible under standard white light, demonstrating the utility of the device as a cost-effective fluorescence-image guided technology for providing useful information quickly during fluorescence-image guided surgical and/or PDT procedures, where fluorescent compounds are commonly used, possibly even in emerging wound care techniques.

Fluorescence-Image Guided Surgery

An emerging area is the use of fluorescence imaging for diagnostic screening and image-guided surgery. Overcoming limitations of standard surgery using white light, fluorescence images may be used to aid in surgical resection of tumors in vivo based on fluorescence (e.g., either autofluorescence or fluorescence from exogenous targeted/non-targeted contrast agents) as well as checking for completeness of tumor removal (e.g., clear margins). Fluorescence-image guided surgery has demonstrated improvements in survival, pre-clinically and clinically [Bogaards et al. (2004) Lasers Surg Med. 35:181-90]. For example, during exploratory surgery on a rat, the device may provide standard white light imaging of the surgical field.

Figure 14:
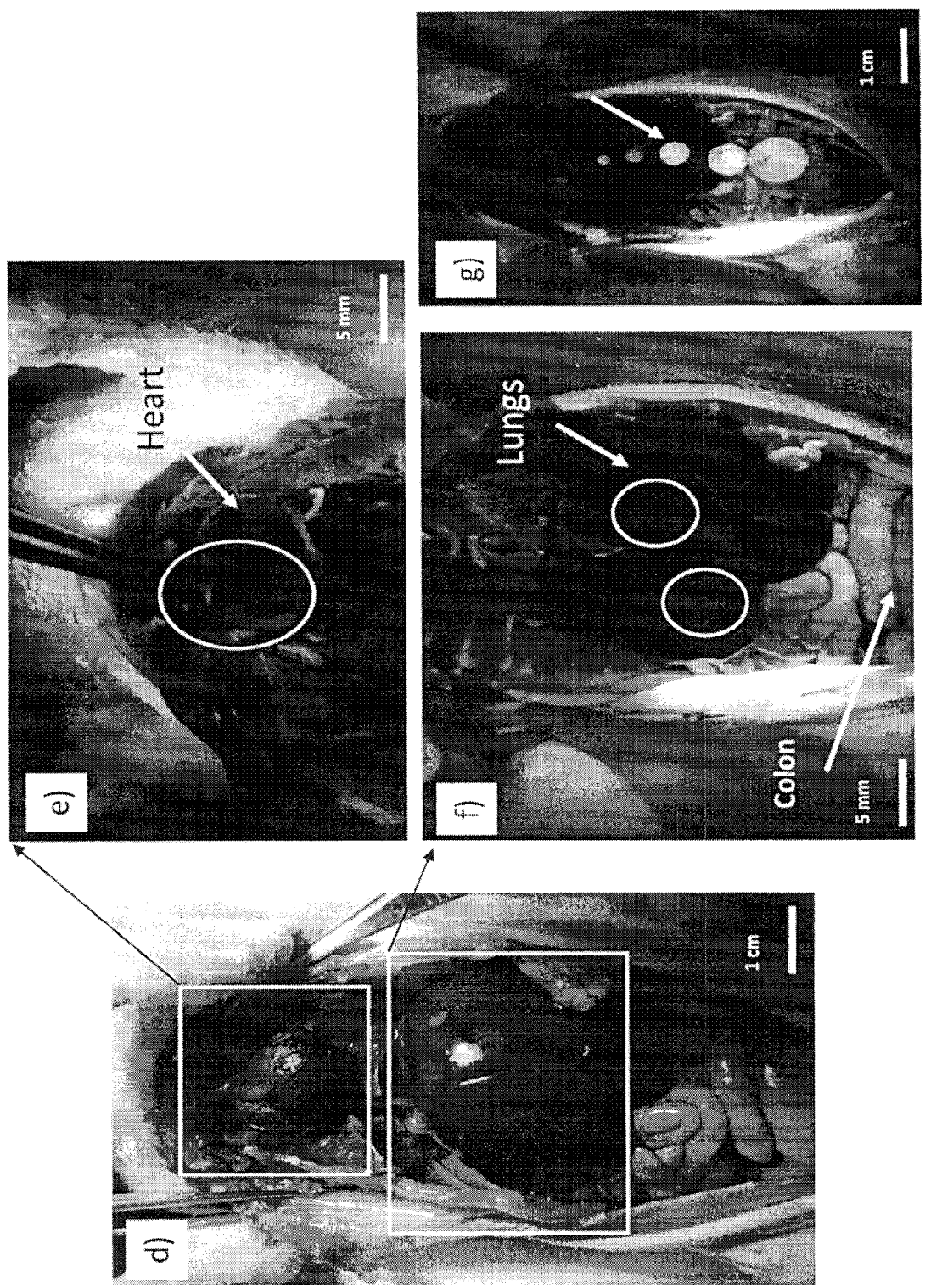
FIG. 14 shows images demonstrating use of a device for fluorescence-based monitoring for fluorescence-image guided surgery using imaging contrast agents.

Reference is now made to FIG. 14. Several tests were conducted to demonstrate the utility of the device for fluorescence-image guided surgery in small animals. Exploratory surgery was performed on a euthanized female rat using the imaging device. FIG. 14 shows examples of the use of the device for fluorescence-image guided surgery using imaging contrast agents. During exploratory surgery, the device provided standard white light imaging of the surgical field, here, the abdomen of a female rat (a). The surgeon used the viewing screen of the device to guide the procedure, switching easily and rapidly between white light and fluorescence mode. In b), using violet/blue excitation light, the device provided added contrast between different types of tissues, which was not possible during white light imaging. For example, connective tissues in the appeared bright green fluorescent (green arrow), while the skin surface (with the red fluorescent photosensitizer BPD) appeared red (red arrow), and the QDots previously injected into the hind leg appeared a bright red (blue arrow). Fluorescence imaging was used to detect contamination of surgical instruments and equipment (e.g., gauze, tape, blankets, etc.) during the surgical procedure. In c), the device also demonstrated utility by detecting soiled/contaminated surgical gauze during the procedure. Compared with standard white light under which all gauze appeared clean, the gauze used to clean the skin and the surgical field during surgery appeared red fluorescent (left) compared with clean gauze (right).

The device was also used for real-time detection of exogenous fluorescent contrast agents (e.g., for labeled cell tracking and fate in vivo experiments, for tissue engineering studies in regenerative medicine, etc.) in an animal model. For this, during surgery, the device was used in fluorescence mode to image the presence of red fluorescent QDots injected within the heart muscle and lungs of the rat (d). Under violet/blue excitation light, the red QDots can be easily detected within the heart (e) and the lungs (f), which appear dark due to the high concentration of blood in these organs, demonstrating the utility of the device for guiding and targeting biopsies or microsurgical procedures, especially those aimed at detection and removal of cancers (e.g., using autofluorescence or fluorescence contrast enhancement). Note the bright red autofluorescence detected by the device from digested food material in the colon. In g), the device demonstrated its utility in imaging fluorescent tumor phantoms commonly used in small animal imaging research. Solid spherical polymer tumor phantoms doped with fluorescent dye were prepared in varying sizes and placed within the surgical field to demonstrate the capability of the device in providing rapid 'high contrast' fluorescence imaging in small animal cancer models.

These results show that the device may be useful in detecting sub-mm sized lesions with fluorescence guidance, which may be useful for targeting biopsies or microsurgical procedures, especially those aimed at detection and removal of cancers (e.g., using autofluorescence or fluorescence contrast enhancement). The device also may have utility in imaging fluorescent tumor phantoms commonly used in small animal imaging research.

Figure 15:
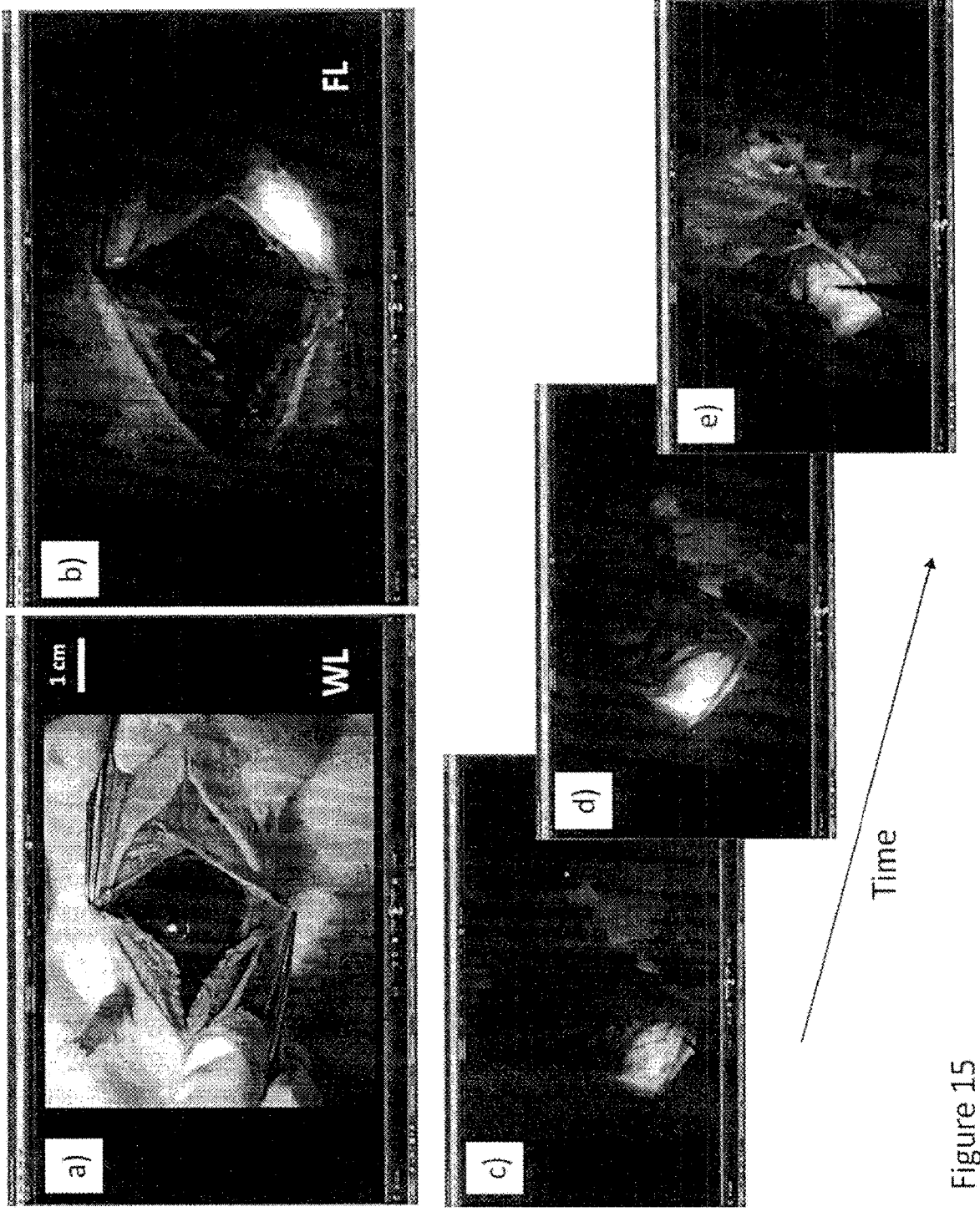
FIG. 15 shows images demonstrating use of a device for fluorescence-based monitoring for video recording of fluorescence-image guided surgery.

FIG. 15 shows examples of the device being used for video recording of high-resolution fluorescence-image guided surgery of the rat in FIG. 9. The device may be capable of providing both still digital images and movies taken with standard white light (WL) (a) and fluorescence (FL) (b), which may be switched between easily. Here, the device was used to capture digital movies of a surgical procedure on a rat using both white light and fluorescence imaging. The surgeon used the digital display screen of the device to guide the complete surgical procedure using fluorescence where white light failed to provide adequate information. In c)-e), for example, under violet/blue light excitation, fluorescence imaging provided the surgeon with significant image contrast between different types of tissues. Blood vessels can be seen clearly under fluorescence, and connective tissues can be discerned from the gastrointestinal tract. Digested food material can also be distinguished. The device may provide a real-time imaging solution for image-guided surgical intervention or biopsy allowing the surgeon to make critical judgments during the procedure. Digital still and/or movie capture of the surgery may allow retrospective analysis of the procedure for patient health records and future skills training of medical personnel. The device may also record audio during the surgical procedure thus allowing a complete record to be collected of each procedure. The utility of the device was also demonstrated as a highly useful tool for image-guided minimally-invasive micro-surgery in animals, and potentially in human procedures.

Figure 16:
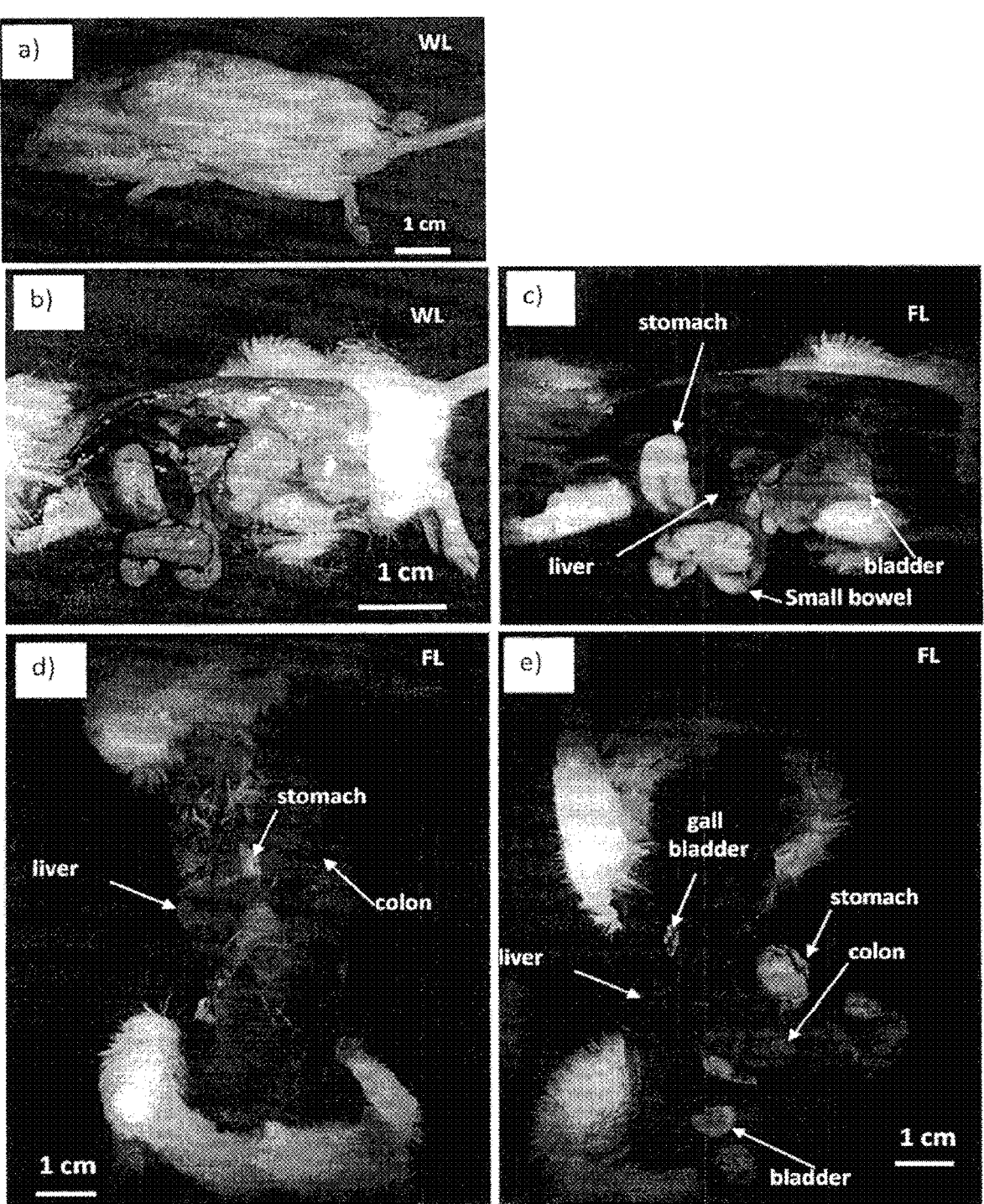
FIG. 16 shows images demonstrating use of a device for fluorescence-based monitoring for autofluorescence-image guided surgical resections of tissues in a mouse cardiac infarction model.

FIG. 16 shows examples of the device being used for autofluorescence-image guided surgical resections of tissues in a mouse cardiac infarction model (a). During exploratory surgery, the device provided standard white light (WL) imaging of the open surgical field, here, the abdomen of the mouse (b). The surgeon used the viewing screen of the device to guide the procedure, switching easily and rapidly between white light and fluorescence mode. Using violet/blue excitation light, the device provided high-contrast between different types of tissues, which was not possible during white light imaging (c). For example, various internal organs were visualized using high-resolution autofluorescence imaging. In d), the intact animal can be imaged with fluorescence prior to and during surgery (e).

Figure 17:
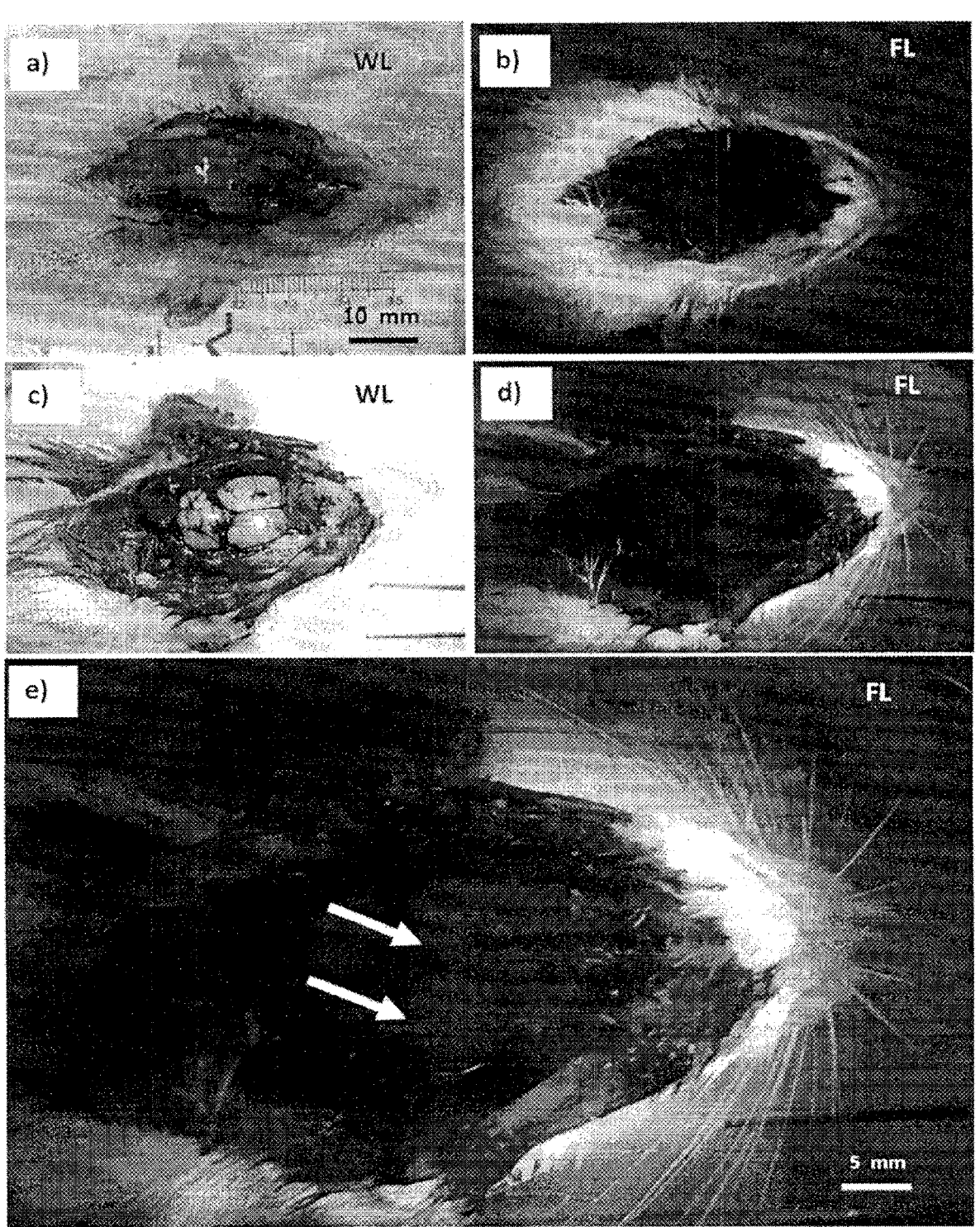
FIG. 17 shows images demonstrating use of a device for fluorescence-based monitoring for autofluorescence-image guided surgery of a mouse brain.

FIG. 17 shows examples of the device being used for non-invasive real-time autofluorescence-image guided surgery of a mouse brain. During exploratory surgery, the device provided standard white light (WL) imaging of the open surgical field (a), here, the skull of the mouse can be seen. The surgeon used the viewing screen of the device to guide the surgical procedure, switching easily and rapidly between WL and fluorescence (FL) mode. b) shows the view of the surgical field (here, skull intact) provided by the imaging device under tissue autofluorescence. Note the surgical area is dark, mainly due to absorption of the violet/blue excitation light and the resulting autofluorescence caused by blood. The snout and eyes appear bright red fluorescent compared to the bright green fluorescence from the fur. c) shows the surgical field with the skull cap removed under WL, while d) shows the autofluorescence image of the brain surface using the imaging device with violet/blue excitation light. Injection of an exogenous contrast agent (here, red fluorescent quantum dots) directly into the right hemisphere of the brain produces a bright red fluorescence (arrows) (e). This demonstrates the utility of the device for imaging fluorescence contrast agents, specifically for high-resolution fluorescence-image guided surgery.

Use in Clinical Care

Although current wound management practice aims to decrease the morbidity and mortality of wounds in patients, a limitation is the availability of health care resources. The potential of incorporating the technology of telemedicine into wound care needs is currently being explored. Wound care is a representation of the care of chronic and debilitating conditions that require long-term specialized care. The major effect of improved living conditions and advances in health care globally has led to people living longer. Therefore, the percentage of worlds' elderly and those with chronic medical conditions that would require medical attention is rising. With the escalating costs of health care, and the push of the industry towards outpatient care, this is a part of the health care crisis that is demanding immediate attention.

The present device may provide biologically-relevant information about wounds and may exploit the emerging telemedicine (e.g., E-health) infrastructure to provide a solution for mobile wound care technology and may greatly impact wound health care treatment. Wound care accounts for a large percentage of home visits conducted by nurses and health care workers. Despite best practices some wounds do not heal as expected and require the services of a clinical specialist. The device described here may enable access to specialized clinical resources to help treat wounds from the convenience of the patient's home or chronic care facility, which decreases travel time for clients, increases availability to clinical wound specialists, and may reduce costs to the health care system.

Different uses of the imaging device have been discussed for wound assessment, monitoring and care management. The device may be used to detect and monitor changes in connective tissues (e.g., collagen, elastin) and blood/vascular supply during the wound healing process, monitor tissue necrosis and exudate in wounds based on fluorescence, detect and diagnose wound infections including potentially indicating critical 'clinically significant' categories of the presence of bacteria or micro-organisms (e.g., for detecting contamination, colonization, critical colonization and infection) at the surface and deep within wounds [Kingsley, Ostomy Wound Manage. 2003 July; 49(7A Suppl):1-7], provide topographic information of the wound, and identify wound margins and surrounding normal tissues. Tissue fluorescence and reflectance imaging data may be 'mapped' onto the white light images of the wound thereby permitting visualization within the wound and the surrounding normal tissues of essential wound biochemical and photobiological (e.g., fluorescence) information, which has not been possible to date. Real-time imaging of wounds may be performed over time to monitoring changes in wound healing, and to potentially monitor the effectiveness of treatments by providing useful information about underlying biological changes that are occurring at the tissue/cellular level (e.g., matrix remodeling, inflammation, infection and necrosis). This may provide quantitative and objective wound information for detection, diagnosis and treatment monitoring in patients. In particular, the device may be used to monitor and/or track the effectiveness of therapy at a biological level (e.g., on a bacterial level), which may provide more information than monitoring only the macroscopic/morphological appearance using white light.

The device may provide real-time non-invasive image-guided biopsy targeting, clinical procedural guidance, tissue characterization, and may enable image-guided treatment using conventional and emerging modalities (e.g., PDT). In addition, use of the imaging device may be used to correlate critical biological and molecular wound information obtained by fluorescence (e.g., endogenous tissue autofluorescence and/or administration of exogenous molecular-biomarker targeted fluorescence contrast agents) with existing and emerging clinical wound care assessment and treatment guides, such as the NERDS and STONES guidelines proposed by Sibbald et al. (Sibbald et al. Increased Bacterial Burden and Infection: The Story of NERDS and STONES. ADV SKIN WOUND CARE 2006; 19:447-61). The fluorescence imaging data obtained with the device may be used to characterize, spatially and spectrally, bacterial balance and burden at the superficial and deep levels of wounds. The device may provide real-time non-invasive image-guided biopsy targeting, clinical procedural guidance, tissue characterization, and may enable image-guided treatment using conventional and emerging modalities (e.g., photodynamic therapy, PDT). The device may be used within the clinical setting and integrated into conventional clinical wound care regimens, and may have a distinct role in areas of infectious diseases. It should be noted as well that this device may also be used for real-time analysis, monitoring and care for chronic and acute wounds in animals and pets, via conventional veterinary care.

This device may allow real-time wound healing assessment for a large patient cohort base. In particular, elderly people, diabetics, immuno-suppressed and immobilized individuals have an increased incidence of chronic wounds and other dermal afflictions that result from poor circulation and immobility, e.g. pressure ulcers such as bed sores, venous stasis ulcers, and diabetic ulcers. These chronic conditions greatly increase the cost of care and reduce the patient's quality of life. As these groups are growing in number, the need for advanced wound care products will increase. This device may impact patient care by allowing a cost-effective means of monitoring chronic and acute wounds in a number of settings, including hospitals, ambulatory clinics, chronic care facilities, in-home-visit health care, emergency rooms and other critical areas in health care facilities. Further, such a 'hand-held' and portable imaging device may be easily carried and used by nursing and ambulance staff. Early identification of scarring, which is related to connective tissue production and re-modeling of the wound, and bacterial infections may be detected and treated appropriately, something that is currently difficult. In addition, recent developments in advanced wound-care products including multiple dressing types (e.g., film, hydro-colloid, foam, anti-microbial, alginate, non-adherent, impregnated), hydrogels, wound cleansers and debriding agents, tissue engineered products (e.g., skin replacements, substitutes, and tissue-engineered products such as synthetic polymer-based biological tissue and growth factors), wound cleansers, pharmacological products, and physical therapies may also benefit from the device developed here as it may allow image-based longitudinal monitoring of the effectiveness of such treatments. Physical therapies may include hydrotherapy, electrical stimulation, electromagnetic stimulation devices, ultraviolet therapy, hyperbaric oxygen therapy, ultrasound devices, laser/light emitting diode (LED) devices, and wound imaging/documentation.

Wound tissue analysis is typically required for the assessment of the healing of skin wounds. Percentage of the granulation tissue, fibrin and necrosis in the wound, and their change during treatment may provide useful information that may guide wound treatment. Image analysis may include advanced statistical pattern recognition and classification algorithms to identify individual pixels within the fluorescence wound images collected with the device based on the optical information of the wound and surrounding normal tissue. Thus, image analysis may allow wound images to be mapped into various components of the wound, including total wound area, epithelialization, granulation, slough, necrotic, hypergranulation, infected, undermining, and surrounding tissue margins. This has an added advantage of providing relatively rapid determination of wound healing rates, as well as informing guide patient management decisions.

Figure 25:
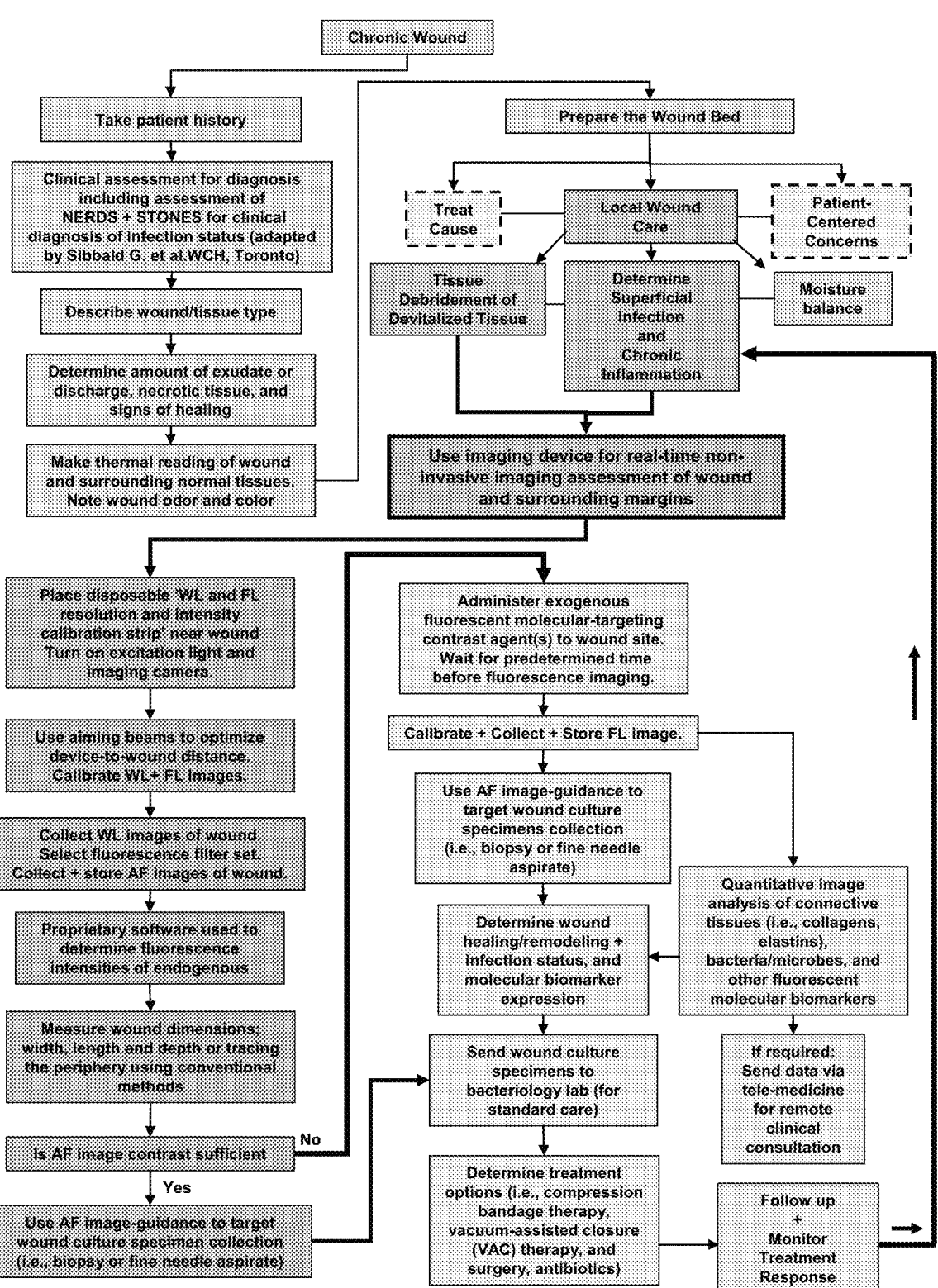
FIG. 25 is a flowchart illustrating the management of a chronic wound using a device for fluorescence-based monitoring.

FIG. 25 illustrates the projected management workflow for the imaging device in a clinical wound care setting. The device may be easily integrated into routine wound assessment, diagnosis, treatment and longitudinal monitoring of response, and may provide critical biological and molecular information of the wound in real-time for rapid decision-making during adaptive interventions.

This device may be easily integrated into existing healthcare computer infrastructures (e.g., desktop and pocket PCs used by a growing number of physicians or other health care professionals) for longitudinal image cataloguing for patient wound management within the conventional clinical environment. The wireless receiving and transmission of data capabilities of the device may allow monitoring of wound care and healing remotely through existing and future wireless telemedicine infrastructure. The device may be used to transfer essential medical data (e.g., wound health status) via the internet or over wireless services, such as cellular telephone, PDA or Smartphone services, to remote sites which may permit remote medical interventions, with a further utility in military medical applications for battlefield wound management. The device may allow real-time surface imaging of wound sites and may be easily carried by point-of-care personnel in clinical settings. Using cost-effective highly sensitive commercially available digital imaging devices, such as digital cameras, cellular phones, PDAs, laptop computers, tablet PCs, webcams, and Smart phones, etc. as the image capture or recording component, the device may offer image-based documentation of wound healing and tracking of treatment effectiveness. Also, this technology may be adapted to also function in 'wireless' mode to permit remote medical interventions by potentially adapting it for use with high-resolution digital cameras embedded in commercially-available cellular telephones.

By using web-based telemedicine and remote medical monitoring infrastructure, the imaging device may be integrated into a 'store-and-forward' concept of wound assessment systems. In addition to providing digital images, such a system may present a comprehensive set of clinical data that meet the recommendations of clinical practice guidelines. The presently-disclosed device may integrate into a computer-based wound assessment system (e.g., with image analysis software) to be used by a health care facility to enhance existing clinical databases and support the implementation of evidence—based practice guidelines. Such an integrated telemedicine infrastructure may be used for monitoring patients at home or in long-term-care facilities, who may benefit from routine monitoring by qualified clinicians but currently do not have access to this care. This device may be further developed into a portable handheld point-of-care diagnostic system, which may represent a major advance in detecting, monitoring, treating, and preventing infectious disease spread in the developed and developing worlds. This knowledge may significantly improve the diagnostic tools available to practitioners who treat chronic wounds in settings where quantitative cultures are inaccessible.

Figure 21:
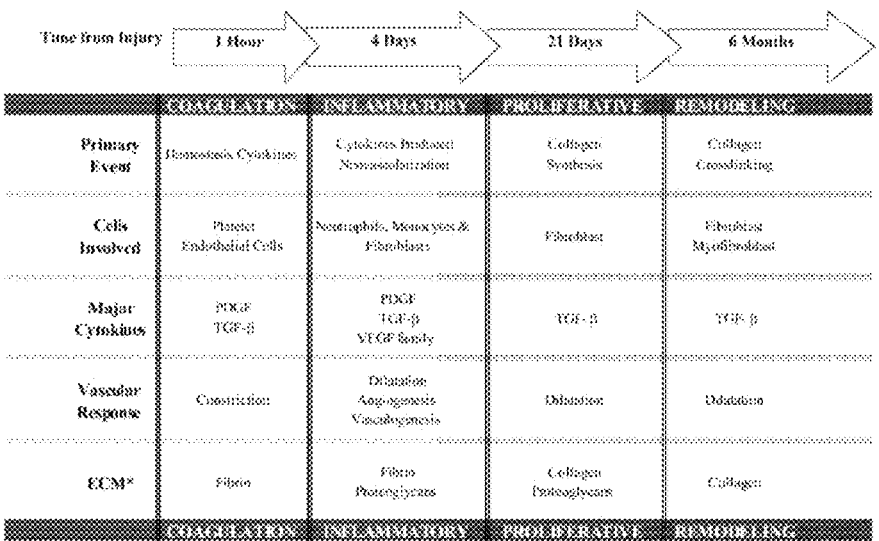
FIG. 21 illustrates the phases of wound healing with time.

The device may allow digital imaging with optical and digital zooming capabilities (e.g., those embedded in commonly available digital imaging devices). Still or video image quality may be in 'high-definition' format to achieve high spatial resolution imaging of the tissue surface. Images may be recorded as still/freeze frame and/or in video/movie format and printed using standard imaging printing protocols which do (e.g., connected via USB) or do not (e.g., PictBridge) require a personal computer. The images/video data may be transferred to a personal computer for data archival storage and/or image viewing and/or analysis/manipulation. The device may also transfer data to a printer or personal computer using wired or wireless capabilities (e.g., Bluetooth). Visualization may be performed on the handheld device screen and/or in addition to simultaneous viewing on a video screen/monitor (e.g., head-mounted displays and glasses) using standard output video cables. This device may display, in combination or separately, optical wavelength and fluorescence/reflectance intensity information with spatial dimensions of the imaged scene to allow quantitative measurements of distances (e.g., monitoring changes tissue morphology/topography) over time. The device may also allow digital image/video storage/cataloguing of images and related patient medical data, for example using dedicated software with imaging analysis capabilities and/or diagnostic algorithms Image Analysis Image analysis may be used together with the device to quantitatively measure fluorescence intensities and relative changes in multiple fluorescence spectra (e.g., multiplexed imaging) of the exogenous optical molecular targeting probes in the wound and surrounding normal tissues. The biodistributions of the fluorescent probes may be determined based on the fluorescence images collected and these may be monitored over time between individual clinical wound imaging sessions for change. By determining the presence and relative changes in abundance quantitatively, using the device, of each and all of the spectrally-unique fluorescent probes, the clinical operator may determine in real-time or near real-time the health and/or healing status and response to treatment over time of a given wound, for example by using a look-up table in which specific tissue, cellular and molecular signals are displayed in correlation to wound health, healing and response status, an example of which is shown in FIG. 21 (adapted from Bauer et al., *Vasc & Endovasc Surg* 2005, 39:4). This may permit the clinician to determine whether a wound is healing based on biological and molecular information which may not be possible otherwise with existing technologies. Furthermore, the presence and abundance of bacteria/microorganisms and their response to treatment may offer a means to adapt the therapy in real-time instead of incurring delays in response assessment with conventional bacteriological testing of wound cultures.

Image analysis techniques may be used to calibrate the initial or first images of the wound using a portable fluorescent standard placed within the field of view during imaging with the device. The image analysis may also permit false or pseudo color display on a monitor for differentiating different biological (e.g., tissue, cellular, and molecular) components of the wound and surrounding normal tissues including those biomarkers identified by autofluorescence and those identified by the use of exogenous targeted or untargeted fluorescence/absorption contrast agents.

Figure 23:
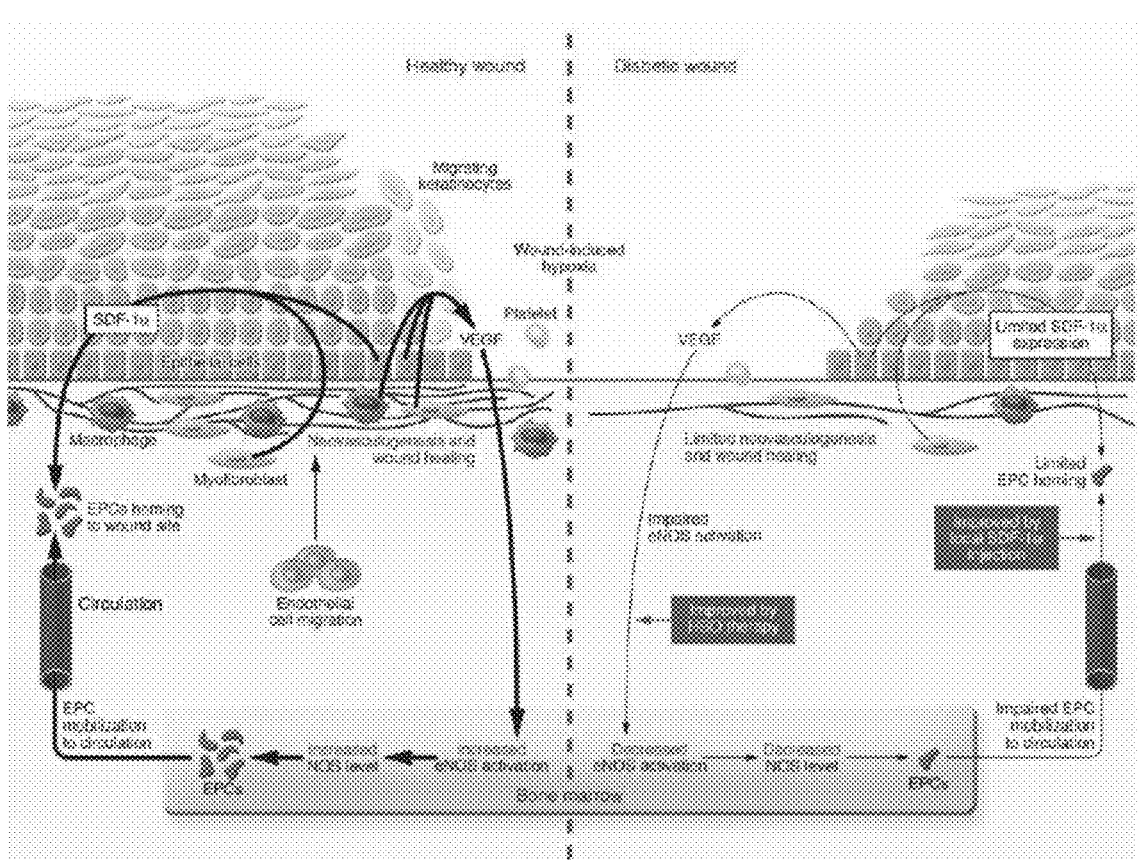
FIG. 23 is a diagram comparing a healthy wound to a chronic wound.

Examples of such biomarkers are listed in FIG. 22 (adapted from Brem et al. *Journal of Clinical Investigation,* 117:5, 2007) and illustrated in FIG. 23. In FIG. 23, the diagram shows mechanisms of wound healing in healthy people versus people with diabetic wounds. In healthy individuals (left), the acute wound healing process is guided and maintained through integration of multiple molecular signals (e.g., in the form of cytokines and chemokines) released by keratinocytes, fibroblasts, endothelial cells, macrophages, and platelets. During wound-induced hypoxia, vascular endothelial growth factor (VEGF) released by macrophages, fibroblasts, and epithelial cells induces the phosphorylation and activation of eNOS in the bone marrow, resulting in an increase in NO levels, which triggers the mobilization of bone marrow EPCs to the circulation. For example, the chemokine SDF-1α □promotes the homing of these EPCs to the site of injury, where they participate in neovasculogenesis. In a murine model of diabetes (right), eNOS phosphorylation in the bone marrow is impaired, which directly limits EPC mobilization from the bone marrow into the circulation. SDF-la expression is decreased in epithelial cells and myofibroblasts in the diabetic wound, which prevents EPC homing to wounds and therefore limits wound healing. It has been shown that establishing hyperoxia in wound tissue (e.g., via HBO therapy) activated many NOS isoforms, increased NO levels, and enhanced EPC mobilization to the circulation. However, local administration of SDF-1α □ was required to trigger homing of these cells to the wound site. These results suggest that HBO therapy combined with SDF-1α□administration may be a potential therapeutic option to accelerate diabetic wound healing alone or in combination with existing clinical protocols.

Pre-assigned color maps may be used to display simultaneously the biological components of the wound and surrounding normal tissues including connective tissues, blood, microvascularity, bacteria, microorganisms, etc. as well as fluorescently labeled drugs/pharmacological agents. This may permit visualization in real-time or near real-time (e.g., less than 1 minute) of the health, healing and infectious status of the wound area.

The image analysis algorithms may provide one or more of the following features:

Patient Digital Image Management

Integration of a variety of image acquisition devices

Records all imaging parameters including all exogenous fluorescence contrast agents Multiple scale and calibrations settings Built-in spectral image un-mixing and calculation algorithms for quantitative determination of tissue/bacterial autofluorescence and exogenous agent fluorescence signals Convenient annotation tools Digital archiving Web publishing Basic Image Processing and Analysis Complete suite of image processing and quantitative analysis functions Image stitching algorithms will allow stitching of a series of panoramic or partially overlapping images of a wound into a single image, either in automated or manual mode.

Easy to use measurement tools

Intuitive set up of processing parameters

Convenient manual editor

Report Generation

Powerful image report generator with professional templates which may be integrated into existing clinical report infrastructures, or telemedicine/e-health patient medical data infrastructures. Reports may be exported to PDF, Word, Excel, for example.

Large Library of Automated Solutions

Customized automated solutions for various areas of wound assessment including quantitative image analysis.

Although image analysis algorithm, techniques, or software have been described, this description also extends to a computing device, a system, and a method for carrying out this image analysis.

Stem Cell Therapy and Cancer Monitoring

The device may be used for imaging and detection of cancers in humans and/or animals. The device may be used to detect cancers based on inherent differences in the fluorescence characteristics between such cancers and surrounding normal tissues in patients. This device may also be used for image-based detection of cancers in pets, for example within veterinary settings.

The device may also be used as a research tool for multi-spectral imaging and monitoring of cancers in experimental animal models of human diseases (e.g., wound or cancers). The device may be used to detect and/or image the presence of cancers and track tumor growth in animals models of cancer, particularly using fluorescent (e.g., in the visible and NIR wavelength ranges) protein transfected tumor cell lines.

The imaging device may be used in conjunction with both existing and emerging cell therapies useful for reconditioning of chronic wounds and accelerating their healing. For this, fluorescently labeled stem cells may be administered to the wound site prior to imaging with the device. Pluripotential stem cells (PSCs), the precursors to all more specialized stem cells, are capable of differentiating into a variety of cell types, including fibroblasts, endothelial cells and keratinocytes, all of which are critical cellular components for healing. A recent report on an uncontrolled clinical trial suggests that direct application of autologous bone marrow and its cultured cells may accelerate the healing of non-healing chronic wounds (Badiavas et al. *Arch Dermatol* 2003; 139(4): 510-16). Considering the pathophysiological abnormalities present in chronic wounds there is the potential that stem cells may reconstitute dermal, vascular and other components required for optimal healing. The device may be used to visualize and track the labeled stem cells at the wound site over time, and determine their biodistribution and therapeutic effect. Using exogenous fluorescence molecular-targeted agents, for example as described above, may confirm differentiation of the stem cells in vivo and may also aid in determining the response of the wound to this treatment.

For example, this device may be used to identify, track and/or monitor cancer tumor stem cells and stem cells in general (e.g., in preclinical small animal experimental models of cancers and other clinical models). An example is shown in the Figures. The device may also be useful for imaging of clinical cell therapies, including treatment of diseases using stem cells.

Figure 18:
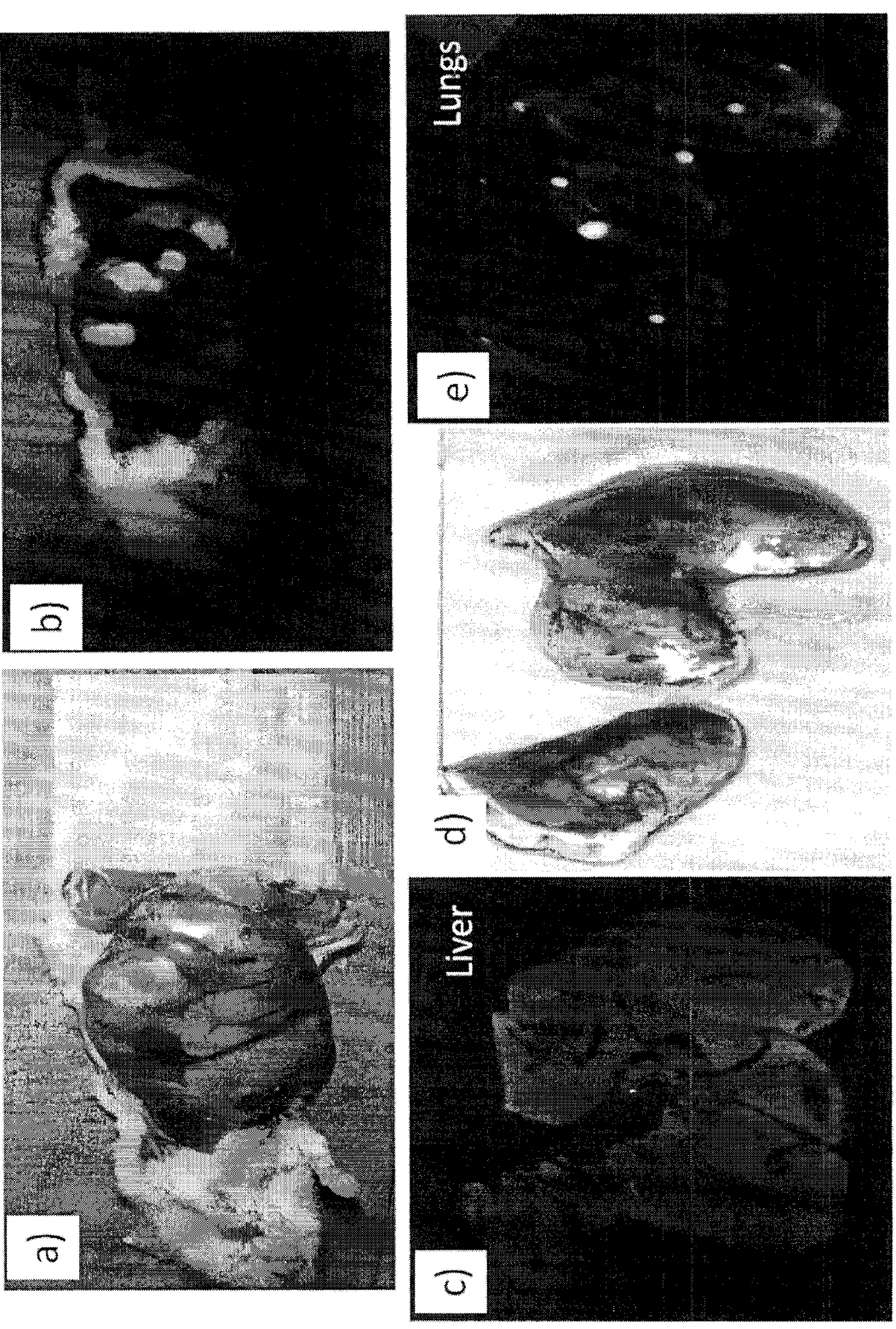
FIG. 18 shows images demonstrating the use of a device for fluorescence-based monitoring in imaging cancer stem cells in a mouse.

Reference is now made to FIG. 18. In a), a mouse model is shown using white light. In b), the individual organs of the mouse are clearly seen using the fluorescence imaging device. c) shows the liver of the mouse imaged with the device, and not fluorescence is seen. d) shows the lungs of the mouse in white light. e) shows the lungs of the mouse imaged with the device, with the cancer tumor stem cells clearly seen as bright fluorescent spots.

Figure 19:
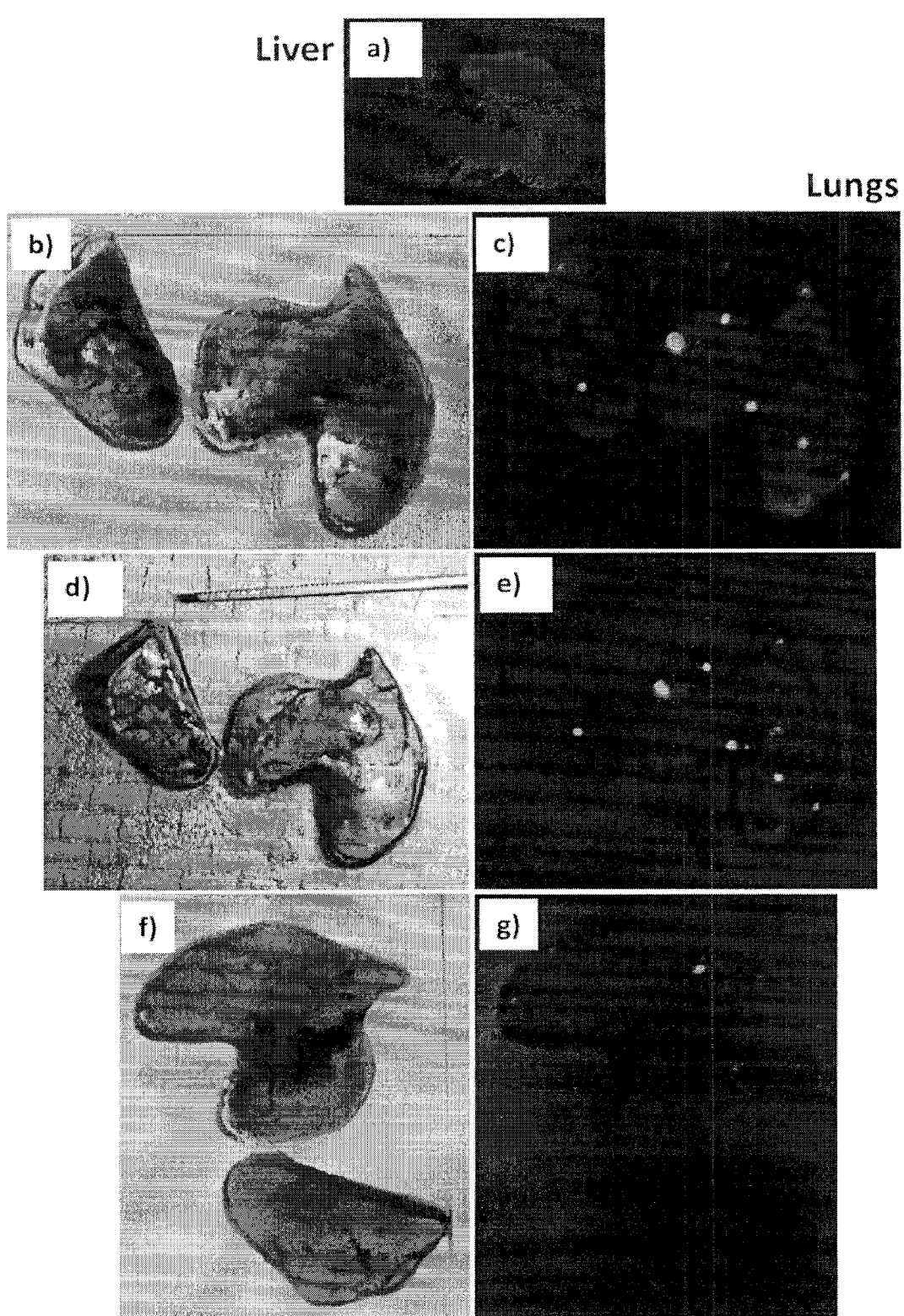
FIG. 19 shows images demonstrating the use of a device for fluorescence-based monitoring in imaging cancer stem cells in a liver and a lung.

Referring now to FIG. 19, in a), the liver of the mouse model of FIG. 18 is not visible under fluorescence imaging. b), d) and f) show different views of the mouse lungs under white light. c), e) and g) show corresponding view of the mouse lungs imaged using the device, clearly showing cancer tumor stem cells as bright fluorescent spots.

Figure 19H:
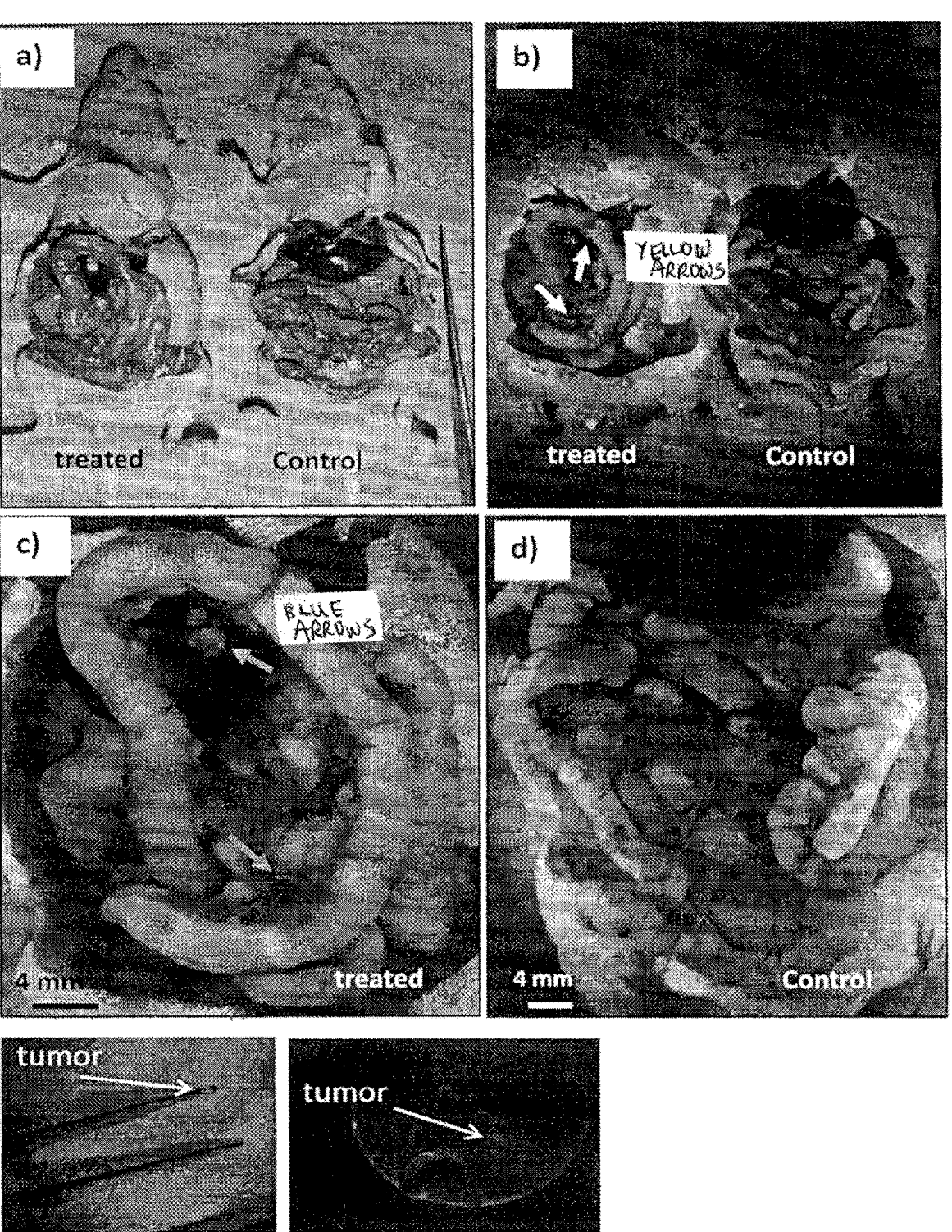
FIGS. 19H and 19I show examples of the use of a device for fluorescence-based monitoring for imaging tumours.

FIG. 19H shows an example of the use of the device for detection of human ovarian tumor-bearing nude mice. a)

White light image of virus-treated and non-treated control mice, showing open abdominal cavity. b) Corresponding, fluorescence image of treated and control mice shows orange-red fluorescence from the optically-labeled virus in tumor nodules in the messentary (yellow arrows), compared with control. c) Shows a magnified view of the messentaries, illustrating the biodistribution of the virus optical probe within the tumor nodules, as well as the capability to detect sub-millimeter tumor nodules (blue arrow), compared with d) control mouse. Note, that probe-fluorescence may be differentiated from background intestinal tissue autofluorescence. These data illustrate the potential use of the device for imaging treatment response including, but not limited to, for examples, virotherapies and cell therapies, as well as for image-guided surgical resection of fluorescent tumor samples (c; insets) (405 nm excitation, 500-550 nm emission (green), >600 nm emission (red)).

Figure 19I:
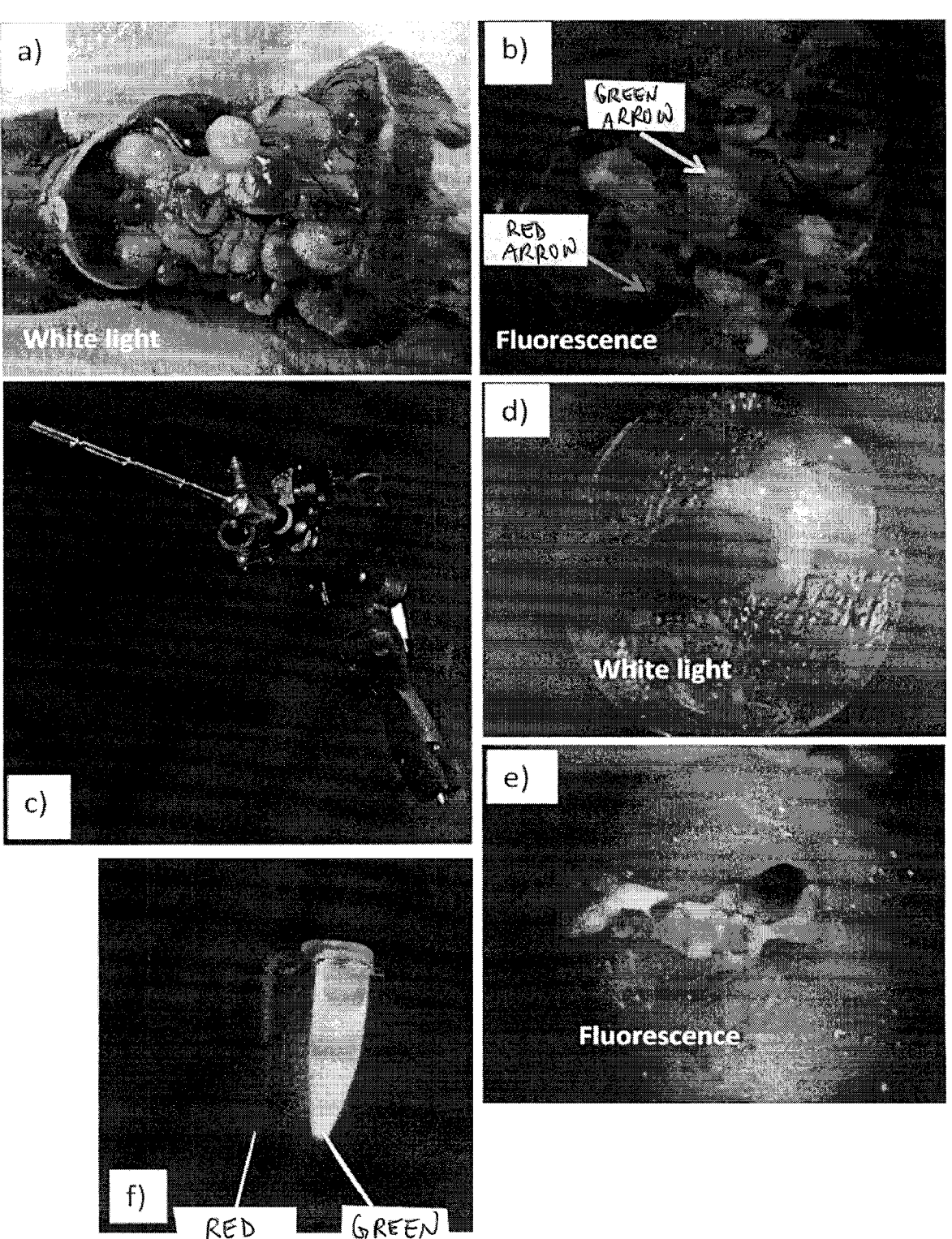

FIG. 19I shows an example of the use of the device for detection/visualization in mouse colon tumor-bearing nude mice administered a fluorescent cocktail of separate exogenous green and red tumor cell-targeting probes post-operatively. a) White light and b) corresponding multispectral fluorescence image of the open abdominal cavity showing simultaneous detection of both the green (green arrow) and red (red arrow) molecular probes, which may be analyzed with spectral un-mixing software. The device may be modified to permit endoscopic imaging as well. In this example, c) a rigid endoscopic probe was attached to the handheld imaging device and d) white light and e) fluorescence images were obtained of tissue surgically resected from the mouse in image a), b). These data suggest the use of the device with endoscopic probe accessories for portable endoscopic real-time fluorescence imaging in vivo in human and veterinary patients for a variety of detection, diagnostic or treatment monitoring applications (clinical- and research-based). f) The device (e.g., with endoscopic capabilities) may be capable of fluorescence imaging of multiple spectrally-unique "probes" which may be used in vivo (405 nm excitation; 490-550 nm and >600 nm emission channels).

This device may be used for multi-spectral imaging and detection of cancers in humans and animals. This device may be also used to detect cancers based on inherent differences in the fluorescence characteristics between such cancers and surrounding normal tissues in patients. This device may also be used for image-based detection of cancers in animals such as pets or livestock, for example within veterinary settings.

This device may also be suitable as a research tool for multi-spectral imaging and monitoring of cancers in experimental animal models of human diseases (e.g., wound and cancers). The device may be used to detect and/or image the presence of cancers and may be used to track tumor growth in animals models of cancer, particularly using fluorescent (e.g., in the visible and NIR wavelength ranges) protein transfected tumor cell lines.

Image-Guidance

The device may also be useful for providing fluorescent image-guidance, for example in surgical procedures, even without the use of dyes or markers. Certain tissues and/or organs may have different fluorescent spectra (e.g., endogenous fluorescence) when viewed using the imaging device, or example under certain excitation light conditions.

Figure 20:
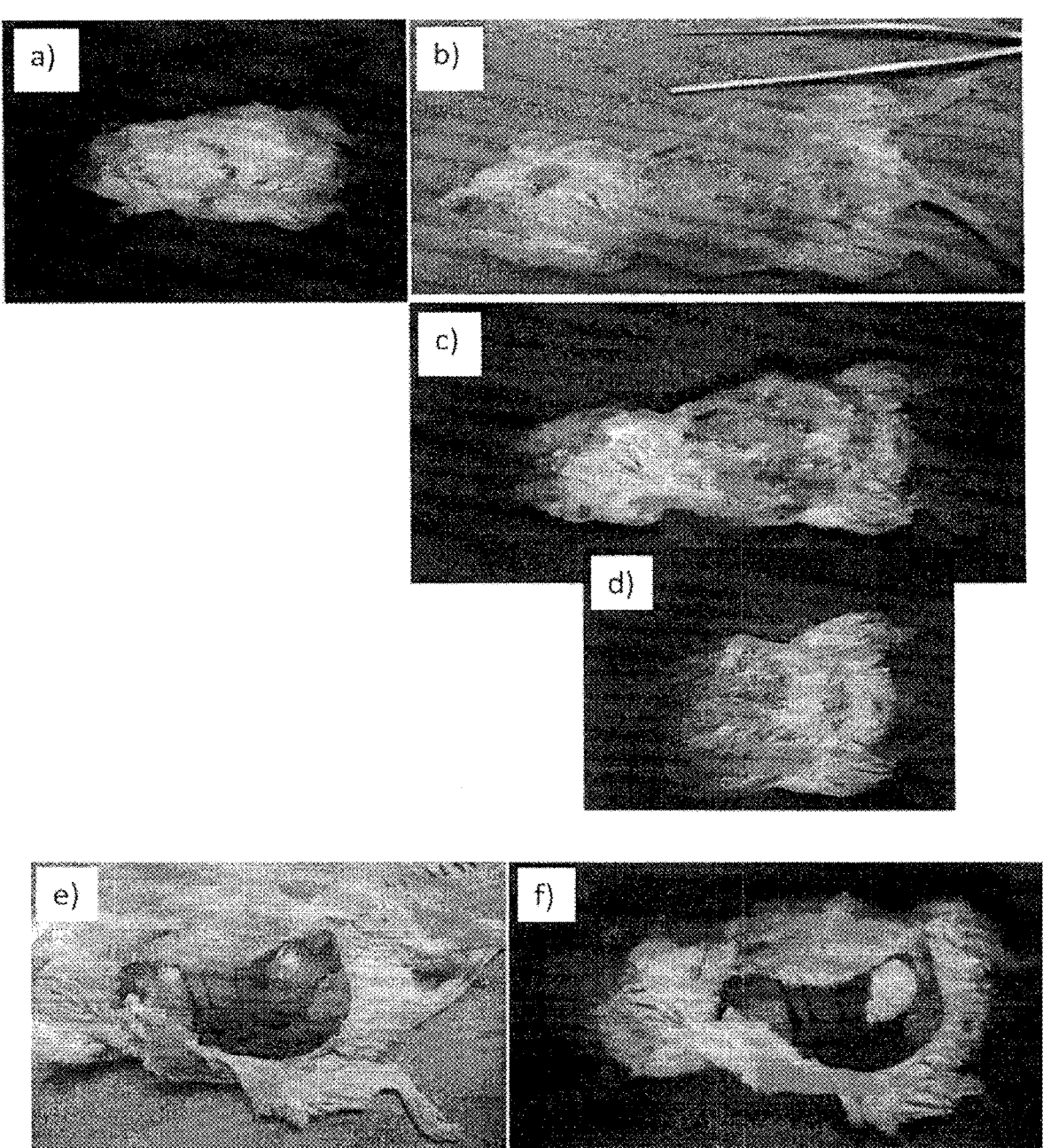
FIG. 20 shows images demonstrating the use of a device for fluorescence-based monitoring in imaging a mouse model.
Figure 20:
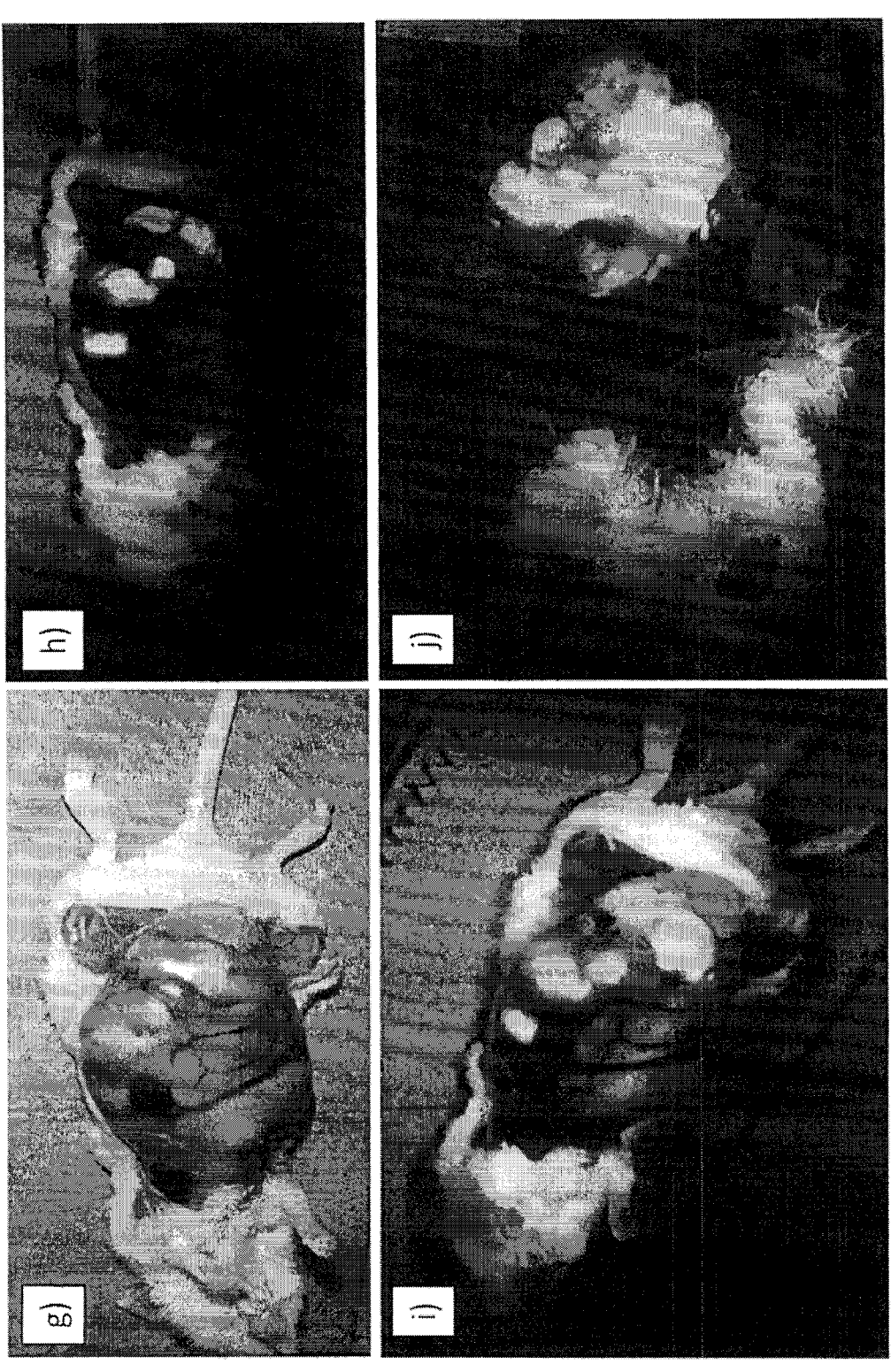

FIG. 20 demonstrates the usefulness of the device for fluorescence imaging-assisted surgery. With the aid of fluorescence imaging using the device, different organs of a mouse model may be more clearly distinguishable than under white light. b, c and g show the mouse model under white light. a, d-f and h-j show the mouse model as imaged with the device.

Figure 20B:
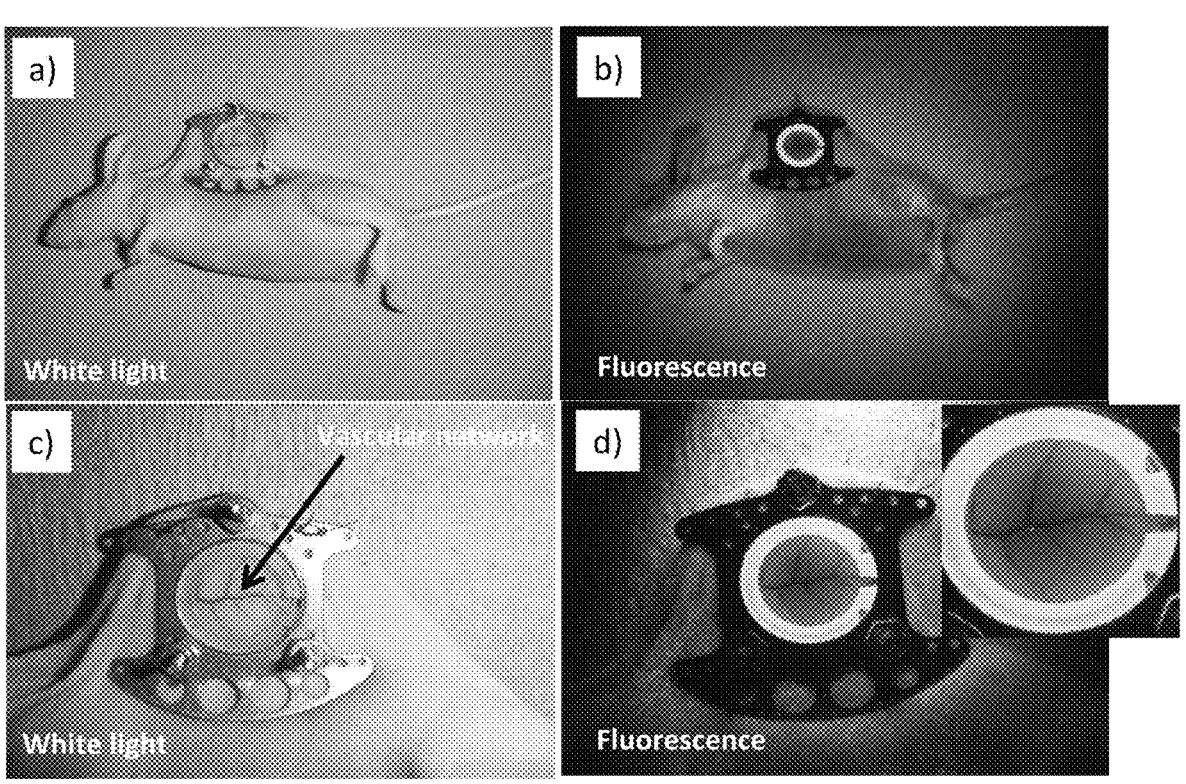
FIG. 20B shows an example of the use of a device for fluorescence-based monitoring for imaging small animal models.

FIG. 20B shows an example of the use of the device for imaging small animal models. Here, the mouse dorsal skin-fold window chamber is imaged under white light (a, c) and fluorescence (b, d). Note the high-resolution white light and fluorescence images obtained by the device. The feet and face appear bright red fluorescent due to endogenous auto-fluorescence from the cage bedding and food dust materials. (405 nm excitation; 490-550 nm and >600 nm emission channels).

Bioengineered Skin

Several bioengineered skin products or skin equivalents have become available commercially for the treatment of acute and chronic wounds, as well as burn wounds. These have been developed and tested in human wounds. Skin equivalents may contain living cells, such as fibroblasts or keratinocytes, or both, while others are made of acellular materials or extracts of living cells (Phillips. *J Dermatol Surg Oncol* 1993; 19(8): 794-800). The clinical effect of these constructs is 15-20% better than conventional 'control' therapy, but there is debate over what constitutes an appropriate control. Bioengineered skin may work by delivering living cells which are known as a 'smart material' because they are capable of adapting to their environment. There is evidence that some of these living constructs are able to release growth factors and cytokines (Falanga et al. *J Invest Dermatol* 2002; 119(3): 653-60). Exogenous fluorescent molecular agents may be used in conjunction with such skin substitutes to determine completeness of engraftment as well as biological response of the wound to the therapy. The healing of full-thickness skin defects may require extensive synthesis and remodeling of dermal and epidermal components. Fibroblasts play an important role in this process and are being incorporated in the latest generation of artificial dermal substitutes.

The imaging device described here may be used to determine the fate of fibroblasts seeded in skin substitute and the influence of the seeded fibroblasts on cell migration and dermal substitute degradation after transplantation to wound site can be determined. Wounds may be treated with either dermal substitutes seeded with autologous fibroblasts or acellular substitutes. Seeded fibroblasts, labeled with a fluorescent cell marker, may then be detected in the wounds with fluorescence imaging device and then quantitatively assessed using image analysis, for example as described above.

Polymer-Based Therapeutic Agents

There are a number of commercially available medical polymer products made for wound care. For example, Rimon Therapeutics produces Theramers™ (www.rimon-therapeutics.com) which are medical polymers that have biological activity in and of themselves, without the use of drugs. Rimon Therapeutics produces the following wound care products, which can be made to be uniquely fluorescent, when excited by 405 nm excitation light: Angiogenic Theramer™, which induces new blood vessel development (i.e., angiogenesis) in wounds or other ischemic tissue; MI Theramer™, which inhibits the activity of matrix metallopro-teases (MMPs), a ubiquitous group of enzymes that are implicated in many conditions in which tissue is weakened or destroyed; AM Theramer™, a thermoplastic that kills gram +ve and gram −ve bacteria without harming mammalian cells; and ThermaGel™, a polymer that changes from a liquid to a strong gel reversibly around body temperature. These can each be made to be fluorescent by addition of fluorescent dyes or fluorescent nanoparticles selected to be excited, for example, at 405 nm light with longer wavelength fluorescence emission.

By using the imaging device, the application of such fluorescent polymer agents may be guided by fluorescent imaging in real-time. This may permit the Theramer agent to be accurately delivered/applied (e.g., topically) to the wound site. Following application of the agent to the wound, the fluorescent imaging device may then be used to quantitatively determine the therapeutic effects of the Theramers on the wound as well as track the biodistribution of these in the wound over time, in vivo and non-invasively. It may also be possible to add a molecular beacon, possibly having another fluorescent emission wavelength, to the MI Theramer™ that can fluoresce in the presence of wound enzymes (e.g., MMPs), and this may indicate in real-time the response of the wound to the MI Theramer™. It may be possible to use one fluorescence emission for image-guided Theramer application to the wound site and another different fluorescence emission for therapeutic response monitoring, and other fluorescence emissions for other measurements. The relative effectiveness of MMP inhibition and antimicrobial treatments may be determined simultaneously over time. Using image analysis, real-time comparison of changes in fluorescence of these signals in the wound may be possible. This adds a quantitative aspect to the device, and adds to its clinical usefulness.

It should be noted that other custom bio-safe fluorescence agents may be added to the following materials which are currently used for wound care. The fluorescent material may then be imaged and monitored using the device.

Moist Wound Dressings: This provides a moist conducive environment for better healing rates as compared to traditional dressings. The primary consumer base that manufacturers target for these dressings is people over the age of 65 years, suffering from chronic wounds such as pressure ulcers and venous stasis ulcers. Those suffering from diabetes and as a result, developed ulcers form a part of the target population.

Hydrogels: This adds moisture to dry wounds, creating a suitable environment for faster healing. Their added feature is that they may be used on infected wounds. These are also designed for dry to lightly exudative wounds.

Hydrocolloid Dressings: Hydrocolloids seal the wound bed and prevent loss of moisture. They form a gel upon absorbing exudates to provide a moist healing environment. These are used for light to moderately exudative wounds with no infection.

Alginate Dressings: These absorb wound exudates to form a gel that provides a moist environment for healing. They are used mainly for highly exudative wounds.

Foam Dressing: These absorb wound drainage and maintain a moist wound surface, allowing an environment conducive for wound healing. They are used on moderately exudative wounds.

Transparent Film Dressing: These are non-absorptive, but allow moisture vapor permeability, thereby ensuring a moist wound surface. They are intended for dry to lightly exudative wounds. Examples include alginate foam transparent film dressings.

Antimicrobials: These provide antibacterial action to disinfect the wound. Of particular interest is the use of nanocrystalline silver dressings. The bio burden, particularly accumulated proteases and toxins released by bacteria that hampers healing and causes pain and exudation, is reduced significantly with the extended release of silver.

Active Wound Dressings: These comprise highly evolved tissue engineered products. Biomaterials and skin substitutes fall under this category; these are composed entirely of biopolymers such as hyaluronic acid and collagen or biopolymers in conjunction with synthetic polymers like nylon. These dressings actively promote wound healing by interacting either directly or indirectly with the wound tissues. Skin substitutes are bioengineered devices that impersonate the structure and function of the skin.

Hyaluronic Acid: This is a natural component of the extra cellular matrix, and plays a significant role in the formation of granular tissue, re-epithelization and remodeling. It provides hydration to the skin and acts as an absorbent.

Other wound care products that may be imaged using the disclosed device include Theramers, silver-containing gels (e.g., hydrogels), artificial skin, ADD stem cells, anti-matrix metalloproteinases, and hyaluronic acid. Fluorescent agents may be added to other products to allow for imaging using the device. In some cases, the products may already be luminescent and may not require the addition of fluorescent agents.

The device may be used also to monitor the effects of such treatments over time.

Application for Food Products

The imaging device may also be useful for monitoring food products (e.g., meat products) for contamination. This may be useful, for example, in food/animal product preparation in the meat, poultry, dairy, fish, and agricultural industries. The device may be used as part of an integrated multi-disciplinary approach to analytical laboratory services within this sector, which may provide capabilities including image-based detection of contamination and guidance for obtaining samples for testing. The device may be used for real-time detection, identification and monitoring of level of bacterial and other microbial meat contamination/adulteration of food products. It may be used for bacterial contamination tracking in the food processing plant environment, and thus may provide an image-based method for determining food safety and quality. In embodiments where the device is hand-held, compact and portable, the imaging device may be useful in food preparation areas to determine safety of food products from bacterial/microbial contamination. The device may also be used for relatively rapid detection and analysis of bacteria/microbes in meat samples (and on preparation surfaces) collected or sampled, for example as part of food-safety and quality regulated inspection process, during processing and in finished food products. This device may be used in the meat, horticulture and aquaculture industries in implementing food safety inspection/detection procedures that meet the requirements for food safety and quality. The device may be used to detect food contaminants, for example contaminants found in the meat, poultry, dairy and fish industries. This technology may be useful for as a fecal contaminant detection system, since fecal bacteria produce porphyrins which may be readily detected by the device.

Detection and accurate identification of foodborne pathogens, such as Listeria monocytogenes (LM), in food samples and processing lines may be critical both for ensuring food quality assurance and tracing of bacterial pathogen outbreaks within the food supply. Current detection methods employed in food production and processing facilities typically rely on multiple random surface sampling of equipment (e.g., swabbing), and subsequent molecular-based diagnostic assays (e.g., real-time polymerase chain reaction, RT-PCR) which may provide quantitative confirmation of the presence of LM, typically within 24-72 h. However, given time and cost restraints, typically only randomized selected zones of a given food production facility are tested for pathogen contamination at a time, and the significant potential of under-sampling during the "first pass" surface swabbing of equipment may result in undetected pathogens causing catastrophic health and economic consequences. In addition, the inability to i) rapidly sample all surface areas during the "first pass" swabbing to identify areas with high infection probability, ii) to visually document this initial screening process (e.g. no imaging methods available to date), iii) the delay in obtaining laboratory results, iv) the high-costs associated with current methods, and v) more importantly, the potential of missing deadly pathogen infections have prompted efforts to improve the early and accurate detection of food-born pathogens cost-effectively.

The device may be useful in providing a relatively rapid and accurate way of detecting such pathogens. The device may be used with an assay of a multi-coloured fluorescence probe 'cocktail' (e.g., a combination of two or more contrast agents) which may unequivocally identify (and may make visible) only viable *Listeria monocytogenes* from other *Listeria* species using highly-specific gene probe technology. This may allow specific detection of living LM in real-time, potentially minimizing the need for standard time-consuming enrichment methods. This method may also be expanded to include detection of other pathogens of interest, including *Enterobacter sakazakii, Campylobacter* species (*C. coli, C. jejuni* and *C. lari*), coliform bacteria and bacteria of the species *E. coli* (including lactose- and indol-negative *Escherichia coli*-strains), *Salmonella*, all bacteria belonging to the species *Staphylococcus aureus* and separately all bacteria belonging to the genus *Staphylococcus*, and *Pseudomonas aeruginosa*. Other bacteria may be detectable by selecting a suitable probe or combination of probes. For example a combination of two or more contrast agents may be designed to be specific to a certain bacteria, and may result in a unique detectable fluorescent signature when imaged using the imaging device.

The imaging device may be used (e.g., when combined with applied exogenous bacteria-specific contrast agents, including a multi-targeted probe or a combination of probes) for relatively rapid "first pass" screening of food-preparation and handling surfaces for targeted swabbing and microbiological testing. This device may allow relatively rapid image-based surveillance of any surface of equipment and food products and may capture the fluorescence signature of food-borne bacteria/pathogens in real-time. The device may be used in combination with, for example, an assay of a multi-coloured fluorescence probe 'cocktail' (and combinations thereof) which may unequivocally identify (and may make visible) only viable *Listeria monocytogenes* from other *Listeria* species using highly-specific gene probe technology, as described above. Such a probe 'cocktail' may be designed to specifically target certain pathogens based on a specific combination of probes known to be sensitive to such pathogens, and known to give a signature fluorescence response. In addition to detection of such pathogens, the device may allow for the presence and/or location of different strains to be differentiated, based on their different signature fluorescence response.

Figure 26:
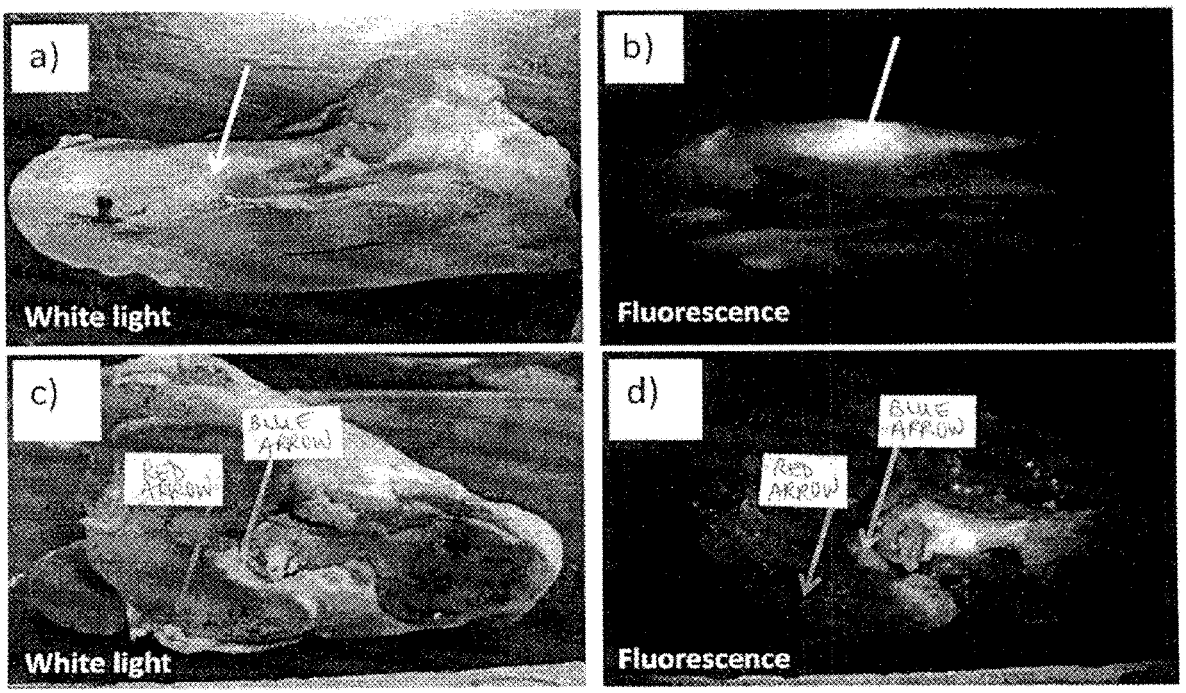
FIGS. 26 and 27 show examples of the use of a device for fluorescence-based monitoring for detecting contamination in food products.

FIG. 26 shows an example of the use of the imaging device for real-time examination of meat products in the food supply. Here, a) white light and b) corresponding autofluorescence imaging of a piece of pork meat shows the difference between various tissues including bone and tendon (white arrow), fat, and muscle. c) White light and b) corresponding autofluorescence imaging of a 'cut-on edge' of bone, where cartilage (blue arrow) appears bright green under fluorescence light due to collagen autofluorescence, while various types of inner bone tissues including bone marrow (red arrow) can be differentiated using fluorescence. The latter observation may additionally suggest the use of the handheld optical imaging device for real-time fluorescence image-guidance during orthopedic surgery in human and veterinary patients, as discussed above. (405 nm excitation, 500-550 nm emission (green), >600 nm emission (red)).

Figure 27:
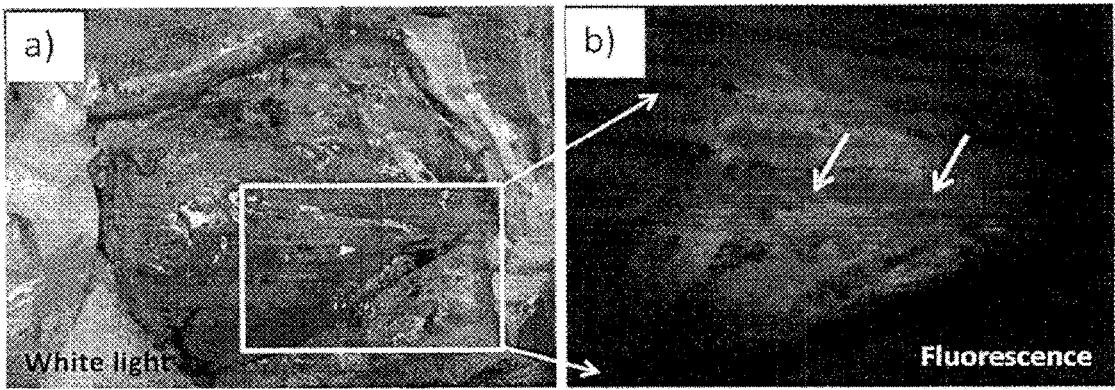

FIG. 27 shows another example of the use of the imaging device for real-time examination of meat products in the food supply. Here, a) white light and b) corresponding autofluorescence imaging of a piece of pork meat that has been maintained for 2 days at 37° C. Autofluorescence imaging shows the presence of a mixed bacterial contamination on the meat surface (red fluorescence areas; yellow arrows) including, for example, *Staphylococcus aureus* and *E. Coli*. (405 nm excitation, 500-550 nm emission (green), >600 nm emission (red)).

Surface Contamination

The imaging device may be useful for detection of surface contamination, such as for detection of 'surface bacterial contamination' in health care settings. This device may be used for detecting and imaging of the presence of bacteria/microbes and other pathogens on a variety of surfaces/materials/instruments (in particular those related to surgery) in hospitals, chronic care facilities, and old age homes, where contamination is the leading source of infection. The device may be used in conjunction with standard detection, identification and enumeration of indicator organisms and pathogens strategies.

Figure 28:
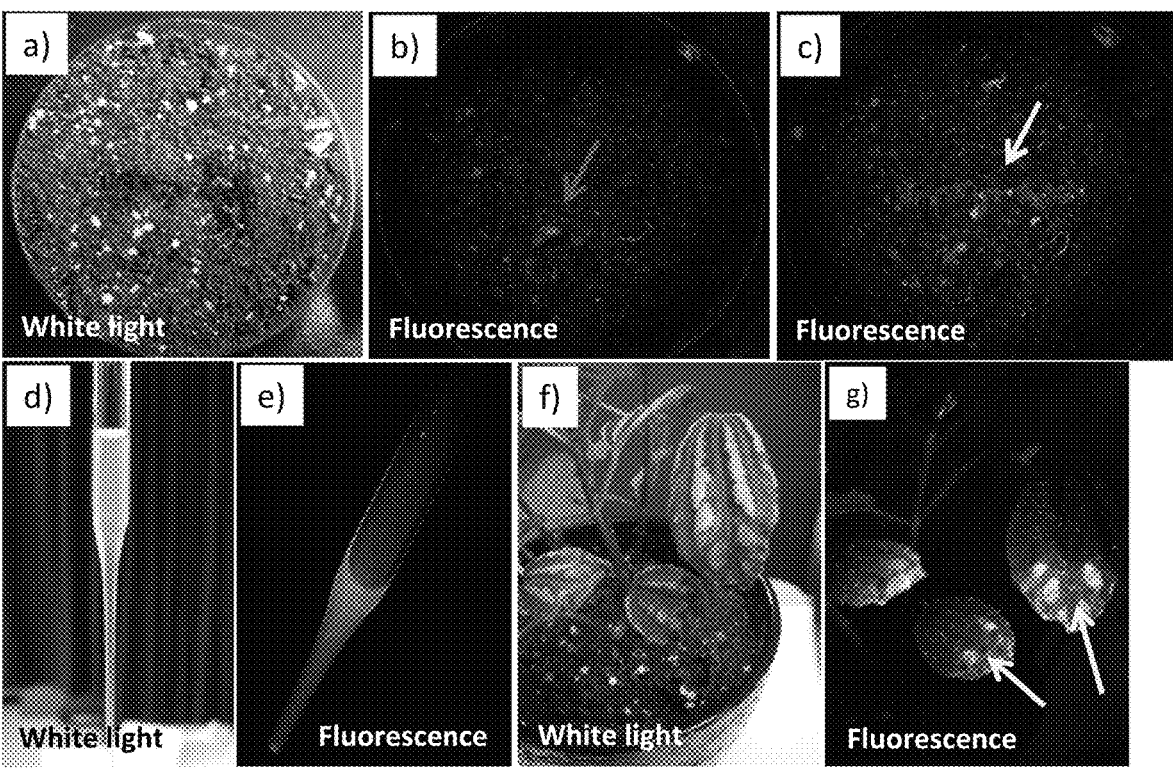
FIGS. 28-28C show examples of the use of a device for fluorescence-based monitoring for detecting surface contamination.

FIG. 28 shows an example of the use of the imaging device for real-time examination of soil and algae samples, in an example of environmental sampling/detection of contaminants. A) White light and b) corresponding autofluorescence images of a Petri dish containing a soil and mineral sample. c) An example of the imaging device used to detect fluorescent soil contaminants/hazardous materials. Here, for example, a fluorescein-labeled fluid was added to the soil prior to fluorescence imaging to illustrate the potential use of the imaging device for detection and monitoring of environmental pollutants and contaminants. d) An example of the imaging device used to obtain white light and e) autofluorescence images of a green algae culture grown under laboratory conditions, illustrating the potential utility of the imaging device for real-time fluorescence image-based monitoring of water conditions (e.g., drinking water purification/safety testing, or algae growth in large-scale production plants). As an example of the imaging device used to detect disease in plants, f) shows a white light image of a common house plant while g) shows the corresponding autofluorescence image of a fungal infection appearing bright green (yellow arrows) affecting the plants leaves, compared to healthy leaf tissue which appears bright reddish-brown. (405 nm excitation, 500-550 nm emission (green), >600 nm emission (red)). Thus, the device may be useful for imaging plant materials.

Figure 28B:
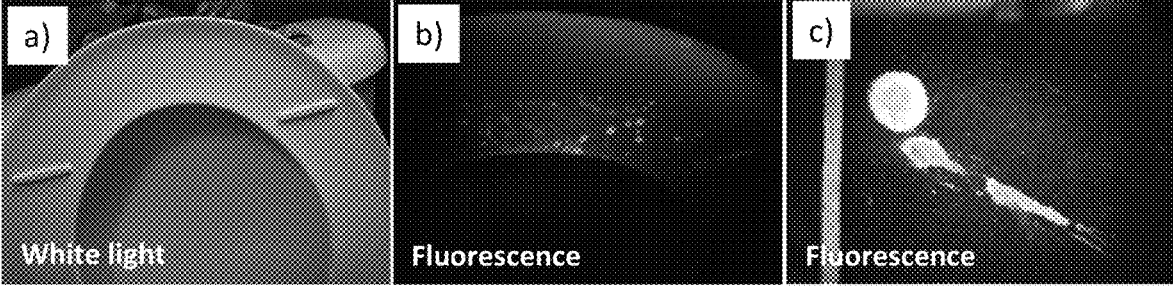

FIG. 28B shows an example of the use of the imaging device used for detection of white light-occult contamination of biological fluids in public and private environments. a) White light and b), c) corresponding autofluorescence of the biological fluids contaminating a toilet seat and a bathroom vanity countertop. These data suggest that the imaging device may be used for detecting surface contamination by potentially hazardous biological/infectious fluids/samples for image-guided targeted sampling, cleaning or monitoring. (405 nm excitation, 500-550 nm emission (green), >600 nm emission (red)).

Figure 28C:
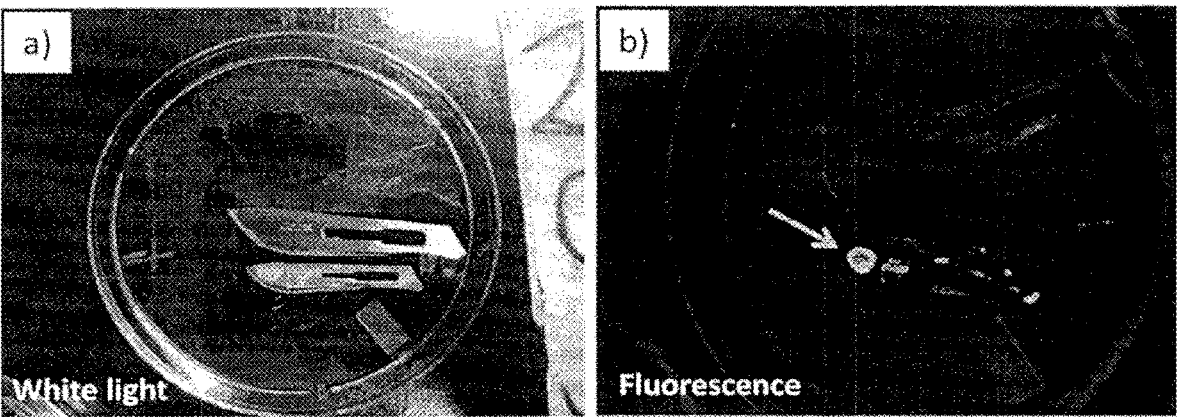

FIG. 28C shows an example of the use of the device for detection of bacterial contamination of surgical instrumentation (b; green arrow) using fluorescence imaging. (405 nm excitation; 490-550 nm and >600 nm emission channels).

Forensic Uses

Figure 29:
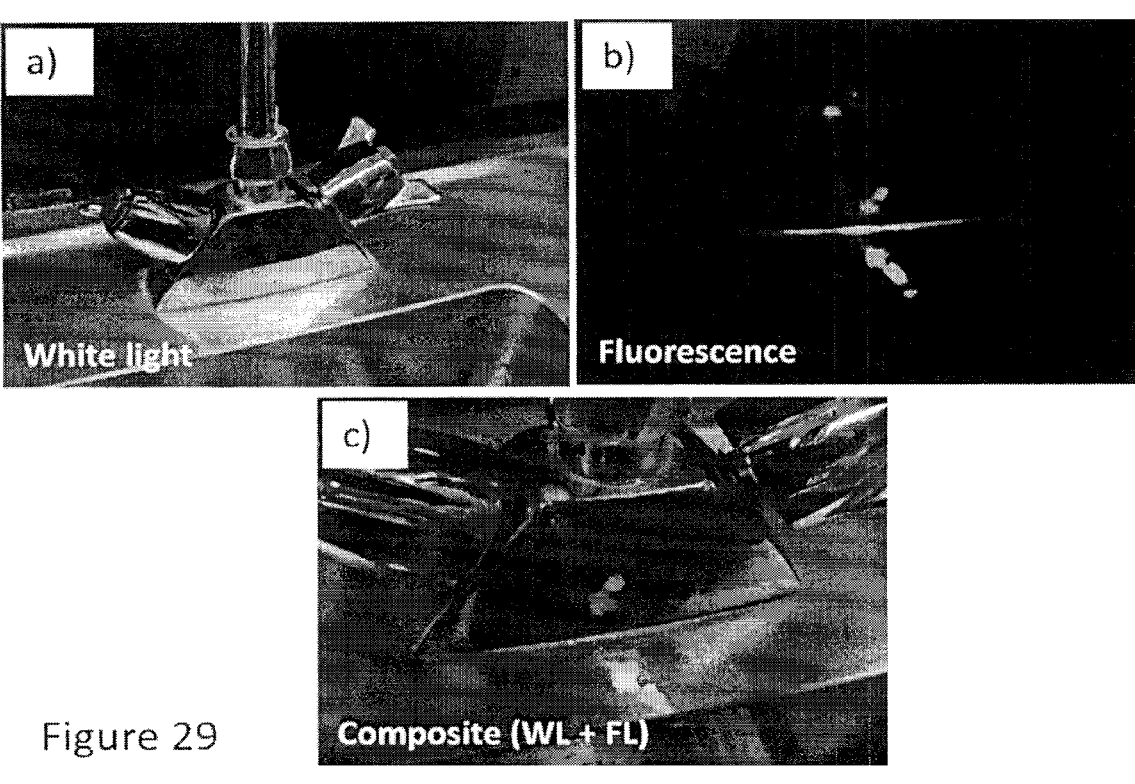
FIGS. 29-31 show examples of the use of a device for fluorescence-based monitoring for forensic applications.

The use of the imaging device to image surface contaminants and targets may be useful in forensic applications. For example, the device may be useful for forensic detection of latent finger prints and biological fluids on non-biological surfaces. The device may offer a relatively inexpensive, compact and portable means of digitally imaging (e.g., with white light, fluorescence and/or reflectance) latent finger prints and biological fluids, and other substances of forensic interest. The former may be made fluorescent using commercially available finger print fluorescence dyes, and the latter may be detected either using autofluorescence of the fluids or exogenously applied 'targeted' fluorescent dye agents (such as Luminol). Images may be recorded digitally. The device may also be used during autopsy procedures to detect bruising FIG. 29 shows an example of the use of the imaging device for real-time fluorescence detection of liquid leaks using a exogenous fluorescent leak-tracer dye. a) White light image of a typical faucet, b) corresponding fluorescence image (showing the presence of the leaking fluid (with fluorescence dye added), and composite image of white light and fluorescence. Note that the leak (in this example, water) is not visible under white light, but is easily detected using fluorescence. These data suggest the imaging device may be useful for relatively rapid image-based tracing and detection of leaks of liquids/fluids (405 nm excitation, 500-550 nm emission (green), >600 nm emission (red)).

Figure 30:
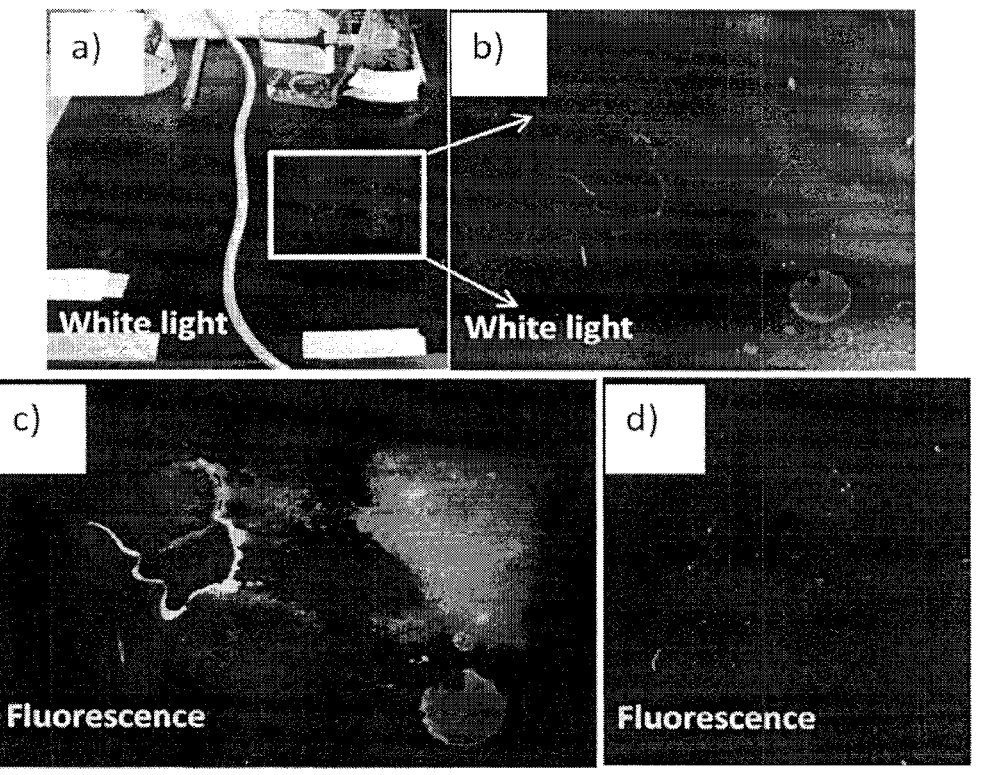

FIG. 30 shows an example of the use of the imaging device for real-time fluorescence detection of surface contaminants). a) White light image of a typical laboratory bench surface and b) an area that is to be imaged using the imaging device. c) Fluorescence imaging may be used to detect contaminants that are not easily visualized under white light (a, b).

The imaging device may also be used to detect latent fingerprints, for example by using a fluorescent dye to enhance the finger print ridges on a table surface. This may be done, for example, by including fluorescent dye combined with superglue (e.g., cyanoacrylate) to develop fingerprint contrast against background surfaces. Far-red and near-infrared fluorescent dyes may be used to reduce the potential of background autofluorescent. These data suggest the use of the imaging device for relatively rapid image-based detection of non-biological and biological contaminants as well as fingerprints, for example, in forensic applications. (405 nm excitation, 500-550 nm emission (green), >600 nm emission (red)).

Figure 31:
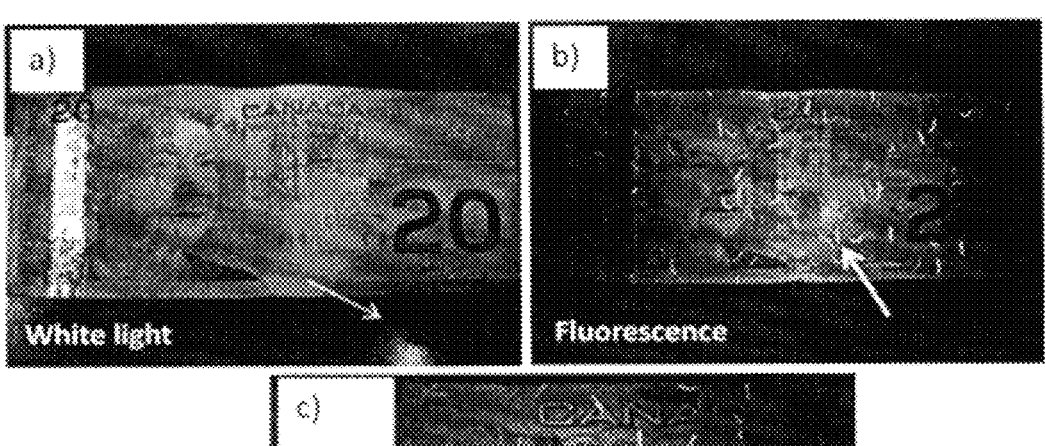

The device may also be useful in anti-counterfeit applications. FIG. 31 shows an example of the imaging device being used for imaging of common currency (in this example, a Canadian $20 bill) under a) white light and b, c) autofluorescence modes. Invisible under white light (a), special anti-counterfeiting measures may be seen under fluorescence: i.e., embedded fluorescence fibers (b) and embedded watermarking of bank notes (c) can be spectrally distinguished (arrows). These data suggest that the device may be used for anti-counterfeiting purposes. (405 nm excitation, 500-550 nm emission (green), >600 nm emission (red)).

Cataloguing

Figure 32:
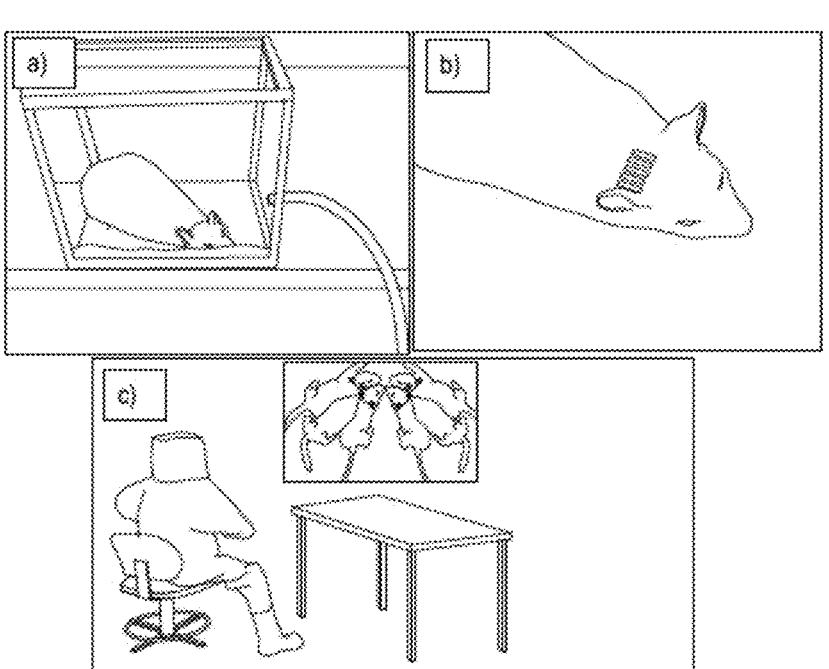
FIG. 32 shows an example of the use of a device for fluorescence-based monitoring for cataloguing animals.

The imaging device may be allow for fluorescent-based cataloguing of animals, such as laboratory animals. FIG. 32 shows an example of the use of the imaging device for real-time fluorescence detection of identification "barcode" tagging for laboratory animals. The figure shows a) white light image of a typical laboratory rat and b) a fluorescence image of the rat tagged with a fluorescent barcode. The use of multiple fluorescent dyes/colors in combination with barcode patterns/bars may be used for 'multiplexed cataloguing' of animals, for example for longitudinal research studies. These data suggest the use of the imaging device for relatively rapid high-throughput image-based barcode cataloguing of laboratory animals for use in c) "pathogen-containment" animal colonies in research laboratories and for animal genotyping (e.g. transgenic animals, inset in c), for examples. (405 nm excitation, 500-550 nm emission (green), >600 nm emission (red)). The device may also be used for imaging of fluorescence-based barcoding or other coding systems in other applications, such as inventory tracking and point-of-sale tracking.

Kits for Device

The imaging device may be provided in a kit, for example including the device and a fluorescing contrast agent. The contrast agent may be any one or more of those described above. For example, the contrast agent may be for labeling a biomarker in a wound, where the kit is for wound monitoring applications.

Figure 33:
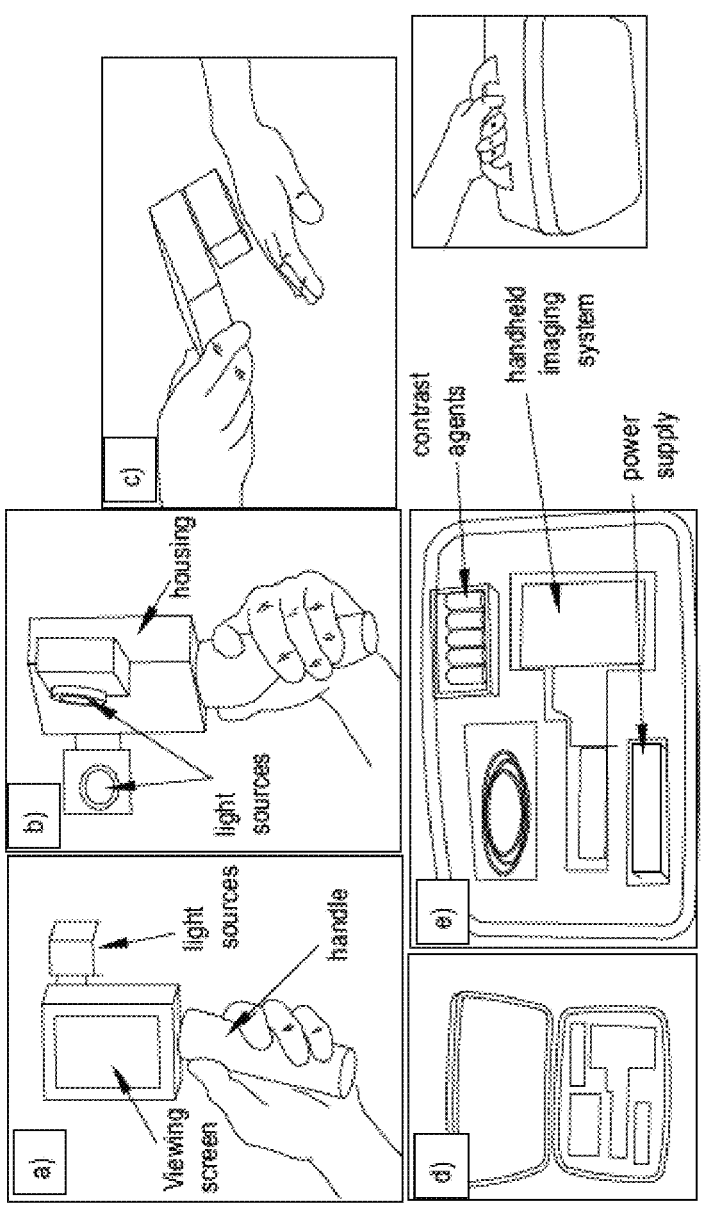
FIG. 33 shows an example of a kit including a device for fluorescence-based monitoring.

FIG. 33 shows an example of a kit including the imaging device. a) shows the handle and the touch-sensitive viewing screen, and b) shows external housing and excitation light sources. The imaging device may be used to scan the body surface of both human and veterinary patients for image-based wound assessment, or for non-wound imaging applications. The device and any accessories (e.g., electrical/ battery power supplies), potential exogenous fluorescence contrast agents, etc.) may be conveniently placed into hard-case containers for transport within clinical and non-clinical environments (including remote sites, home care and research laboratory settings).

Cosmetic or Dermatology Uses

The imaging device may also be used for imaging cosmetic or dermatological products.

Figure 34:
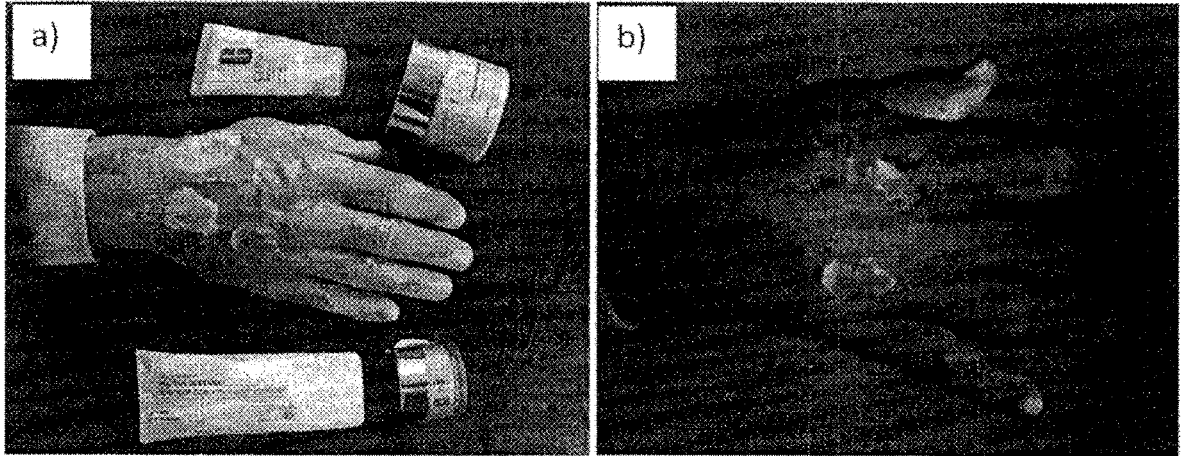
FIG. 34 shows an example of the use of a device for fluorescence-based monitoring for imaging cosmetic or dermatological substances.

FIG. 34 shows an example of the use of the device for imaging of cosmetic products. For example, four commercially available cosmetic creams are shown under a) white light and b) fluorescence imaging modes, showing fluorescence contrast between the creams and the background skin. These data illustrate the potential use of the handheld imaging device for use in imaging the presence and potential biological effects of cosmetic (e.g. rehydration of skin, collagen remodeling, repairing sunburn damage, skin exfoliation) and/or dermatological agents or drugs (405 nm excitation; 490-550 nm and >600 nm emission channels)).

The imaging device may be used in white light and fluorescence modes to improve the administration of these treatments as well as monitor their effectiveness over time non-invasively and quantitatively. The device may be used in combination with other imaging modalities, for example thermal imaging methods, among others.

This device may also be used to test anti-bacterial, anti-biotic, or disinfectant agents. Fluorescence imaging provided by this device may be used, for example in combination with white light imaging, to quantitatively detect the effectiveness of pharmaceutical treatments in bacterial cultures and other model systems, during drug discovery, optimization, and evaluation, for example for wound treatment.

All examples and embodiments described herein are for the purpose of illustration only and are not intended to be limiting. A person skilled in the art would understand that other variations are possible. All references mentioned are hereby incorporated by reference in their entirety.

We claim:

1. A method for fluorescence-based imaging of a target to detect biological contamination of the target, comprising:

applying at least one fluorescing contrast agent to a target, wherein the at least one fluorescing contrast agent includes an exogenous, bacteria-specific contrast agent and is configured to label one or more pre-selected biomarkers at the target;

subsequent to application of the at least one fluorescing contrast agent, illuminating the target with excitation light emitted by an excitation light source of a handheld imaging device and having at least one wavelength or wavelength band configured to cause the one or more pre-selected biomarkers to fluoresce;

detecting fluorescence emissions from the one or more pre-selected biomarkers with an image detector of the handheld imaging device;

illuminating the target with white light emitted by a white light source of the handheld imaging device;

detecting reflections from the target in response to illumination of the target with the white light;

comparing fluorescence emission band(s) of the one or more pre-selected biomarkers to a predetermined look-up table of fluorescence emission spectra or fluorescence emission band(s) of biomarkers;

identifying one or more of a presence, a location, and a quantity of biological contamination on or in the target based, at least in part, on the detected fluorescence emissions of the one or more pre-selected biomarkers, wherein the biological contamination comprises one or more of colonies of bacteria and biological fluids; and displaying a representation of the target indicative of one or more of the presence, the location, and the quantity of the biological contamination on or in the target, wherein the representation of the target spatially co-registers fluorescence emission data from the detected fluorescence emissions of the one or more pre-selected biomarkers and reflection data from the target and comprises fluorescence red-blue-green (RBG) ratio data displayed in combination with reflectance RBG ratio data.

2. The method of claim 1, wherein applying the at least one fluorescing contrast agent to the target comprises applying a combination of two or more contrast agents to the target, wherein the combination is specific to the one or more pre-selected biomarkers.

3. The method as claimed in claim 1, wherein the exogenous, bacteria-specific contrast agent is configured to make visible biological contamination comprising colonies of one or more of *Listeria monocytogenes, Enterobacter sakazakii, Campylobacter coli, Campylobacter jejuni, Campylobacter lari,* coliform bacteria, bacteria of the *E. coli* species, *Salmonella,* bacteria of the *Staphylococcus aureus* species, bacteria of the *Staphylococcus* genus, and *Pseudomonas aeruginosa* in or on the target.

4. The method of claim 1, wherein identifying one or more of the presence, the location, and the quantity of the biological contamination on or in the target includes detecting one or more of a presence, a location, and a quantity of a bacterial strain based on the fluorescence emissions of the one or more pre-selected biomarkers.

5. The method as claimed in claim 4, wherein the bacterial strain is at least one selected from the group consisting of *Staphylococcus* bacteria, *Staphylococcus aureus, Pseudomonas aeruginosa, Listeria monocytogenes, Enterobacter sakazakii, Campylobacter* species of bacteria, coliform bacteria, *Escherichia coli* bacteria, *Propionibacterium acnes* and *Salmonella.*

6. The method of claim 4, wherein detecting the one or more of the presence, the location, and the quantity of the bacterial strain based on the fluorescence emissions of the one or more pre-selected biomarkers includes differentiating one or more of the presence, the location, and the quantity of two or more different bacterial strains based on the fluorescence emissions of the one or more pre-selected biomarkers.

7. The method of claim 6, wherein the different bacterial strains include *Staphylococcus aureus* and *Pseudomonas aeruginosa*, and the different bacterial strains are differentiated based on their respective fluorescence emission signatures.

8. The method of claim 1, wherein the one or more pre-selected biomarkers are chosen from the group consisting of: bacteria, fungi, yeast, spores, virus, microbes, parasites, connective tissues, tissue components, exudates, pH, blood vessels, reduced nicotinamide adenine dinucleotide (NADH), flavin adenine dinucleotide (FAD), microorganisms, vascular endothelial growth factor (VEGF), endothelial growth factor (EGF), epithelial growth factor, epithelial cell membrane antigen (ECMA), hypoxia inducible factor (HIF-1), carbonic anhydrase IX (CAIX), laminin, fibrin, fibronectin, fibroblast growth factor, transforming growth factors (TGF), fibroblast activation protein (FAP), tissue inhibitors of metalloproteinases (TIMPs), nitric oxide synthase (NOS), inducible and endothelial NOS, lysosomes in cells, macrophages, neutrophils, lymphocytes, hepatocyte growth factor (HGF), anti-neuropeptides, neutral endopeptidase (NEP), granulocyte-macrophage colony stimulating factor (GMCSF), neutrophil elastases, cathepsins, arginases, fibroblasts, endothelial cells and keratinocytes, keratinocyte growth factor (KGF), macrophage inflammatory protein-2 (MIP-2), macrophage inflammatory protein-2 (MIP-2), and macrophage chemoattractant protein-1 (MCP-1), polymorphonuclear neutrophils (PMN), macrophages, myofibroblasts, interleukin-1 (IL-1), tumour necrosis factor (TNF), nitric oxide (NO), c-myc, beta-catenin, endothelial progenitor cells (EPCs), matrix metalloproteinases (MMPs) and MMP inhibitors.

9. The method of claim 1, wherein illuminating the target with excitation light having at least one wavelength or wavelength band causing the one or more pre-selected biomarkers to fluoresce comprises illuminating the target with excitation light having a wavelength between 400 nm and 450 nm.

10. The method of claim 1, wherein detecting fluorescence emissions of the one or more pre-selected biomarkers with the image detector of the handheld imaging device includes filtering emissions responsive to illumination of the target with one or more filters configured to permit optical signals having wavelengths corresponding to bacterial fluorescence to pass through the one or more filters to the image detector of the handheld device.

11. The method of claim 10, wherein the wavelengths corresponding to bacterial fluorescence include one or more of wavelengths of 490 nm to 550 nm and wavelengths above 600 nm.

12. The method of claim 1, wherein identifying the one or more of the presence, the location, and the quantity of the biological contamination on or in the target comprises displaying the detected fluorescence emissions on a display of the handheld imaging device.

13. The method of claim 12, further comprising displaying an image of one or more of colonies of bacteria and biological fluids detected on or in the target.

14. The method as claimed in claim 13, wherein displaying the image of the one or more of colonies of bacteria and biological fluids detected on or in the target includes displaying the image on a display of the handheld device.

15. The method of claim 13, wherein displaying the image of the one or more of colonies of bacteria and biological fluids detected on the target comprises displaying an image of a location or a biodistribution of the one or more of the colonies of bacteria and biological fluids on the target.

16. The method of claim 1, wherein the target is contained in one or more of a public setting, a health care setting, a forensic setting, a clinical setting, a sterile setting, a laboratory setting, a surgical setting, an environmental setting, a hospital, a clinic, a nursing home, a home for aging adults, a surgical suite, and a bathroom.

17. The method of claim 1, wherein the target is selected from the group consisting of a surgical field, a skin target, an environmental target, a forensic target, a laboratory target, a surgical instrumentation target, a biological target, and a non-biological target.

18. The method of claim 1, further comprising, when one or more of the presence, the location, and the quantity of the biological contamination er on or in the target is identified, removing the identified biological contamination from the target.

19. The method of claim 18, further comprising, subsequent to removing the identified biological contamination from the target:

illuminating the target with excitation light emitted by the excitation light source of the handheld imaging device;

detecting fluorescence emissions of the one or more pre-selected biomarkers with the image detector of the handheld imaging device;

illuminating the target with white light emitted by the white light source of the handheld imaging device;

detecting reflection from the target in response to illumination of the target with the white light; and displaying a new representation of the target based on the detected fluorescence emissions and detected reflection.

20. The method of claim 1, further comprising storing, archiving, cataloguing, or retrieving from storage the displayed representation of the target.

21. The method of claim 1, further comprising comparing previously calculated fluorescence intensities of the target stored on a memory of the handheld imaging device and an external database to newly calculated fluorescence intensities of the target.

22. The method of claim 1, further comprising:

cleaning the target, and subsequent to the cleaning of the target, identifying and displaying one or more of a presence, a location, and a quantity of remaining biological contamination on the cleaned target based on the detected fluorescence emissions of the one or more pre-selected biomarkers.

23. The method of claim 21, further comprising identifying a change in one or more of the presence, the location, and the quantity of one or more of the colonies of bacteria and the biological fluid contaminating the target based at least in part on a comparison of the previously calculated fluorescence intensities of the target and the newly calculated fluorescence intensities of the target.

24. The method of claim 1, wherein the representation of the target comprises fluorescence intensity data displayed in combination with reflectance data.

\*    \*    \*    \*    \*